US009156829B2

(12) United States Patent
Fieldhouse et al.

(10) Patent No.: US 9,156,829 B2
(45) Date of Patent: Oct. 13, 2015

(54) CYCLOALKYL AND HETEROCYCLOALKYL COMPOUNDS AS OREXIN RECEPTOR ANTAGONISTS

(71) Applicant: Takeda Pharmaceutical Company Limited, Osaka (JP)

(72) Inventors: Charlotte Fieldhouse, Cambridge (GB); Angela Glen, Cambridge (GB); Stephanie Maine, Cambridge (GB); Tatsuhiko Fujimoto, Kanagawa (JP); John Stephen Robinson, Cambridge (GB)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 14/625,812

(22) Filed: Feb. 19, 2015

(65) Prior Publication Data
US 2015/0232460 A1 Aug. 20, 2015

(30) Foreign Application Priority Data

Feb. 20, 2014 (EP) ..................... 14156011

(51) Int. Cl.
| A61K 31/4965 | (2006.01) |
| C07D 401/00 | (2006.01) |
| C07D 405/00 | (2006.01) |
| C07D 213/46 | (2006.01) |
| C07D 413/12 | (2006.01) |
| C07D 213/74 | (2006.01) |
| A61K 31/44 | (2006.01) |
| C07D 239/42 | (2006.01) |
| A61K 31/505 | (2006.01) |
| C07D 403/12 | (2006.01) |
| A61K 31/506 | (2006.01) |
| C07D 401/12 | (2006.01) |
| A61K 31/4439 | (2006.01) |
| A61K 31/497 | (2006.01) |
| C07D 241/20 | (2006.01) |
| A61K 45/06 | (2006.01) |

(52) U.S. Cl.
CPC .............. *C07D 413/12* (2013.01); *A61K 31/44* (2013.01); *A61K 31/4439* (2013.01); *A61K 31/497* (2013.01); *A61K 31/4965* (2013.01); *A61K 31/505* (2013.01); *A61K 31/506* (2013.01); *A61K 45/06* (2013.01); *C07D 213/74* (2013.01); *C07D 239/42* (2013.01); *C07D 241/20* (2013.01); *C07D 401/12* (2013.01); *C07D 403/12* (2013.01)

(58) Field of Classification Search
None
See application file for complete search history.

(56) References Cited

U.S. PATENT DOCUMENTS 7,312,214 B2    12/2007    Qiao et al.
2014/0228322 A1*  8/2014    Haq et al. ..................... 514/86

FOREIGN PATENT DOCUMENTS

| WO | WO 96/06098 | 2/1996 |
| WO | WO 97/23466 | 7/1997 |
| WO | WO 97/30998 | 8/1997 |
| WO | WO 99/03859 | 1/1999 |
| WO | WO 99/05134 | 2/1999 |
| WO | WO 00/42044 | 7/2000 |
| WO | WO 01/29034 | 1/2001 |
| WO | WO 01/36417 | 5/2001 |
| WO | WO 01/60821 | 8/2001 |
| WO | WO 02/08212 | 1/2002 |
| WO | WO 02/094794 | 11/2002 |
| WO | WO 02/096912 | 12/2002 |
| WO | WO 03/087102 | 10/2003 |
| WO | WO 03/087103 | 10/2003 |
| WO | WO 03/087104 | 10/2003 |
| WO | WO 2004/016616 | 2/2004 |
| WO | WO 2004/016617 | 2/2004 |
| WO | WO 2004/019947 | 3/2004 |
| WO | WO 2008/038841 | 4/2008 |

OTHER PUBLICATIONS

Chemelli, et al., "Narcolepsy in orexin knockout mice: molecular genetics of sleep regulation", Cell, No. 98, 1999, pp. 437-451.
De Lecea, et al., "The hypocretins: Hypothalamus-specific peptides with neuroexcitatoryactivity", Proc. Nat. Acad. Sci., No. 95(1), 1998, pp. 322-327.
Harris, et al., "Arousal and reward: a dichotomy in orexin function", Trends Neurosci, No. 29, 2006, pp. 571-577.
Sakurai, et al., "Orexins and orexin receptors: a family of hypothalamic neuropeptides and G protein-coupled receptors that regulate feeding behavior", Cell, No. 92, 1998, pp. 573-585.
Extended European Search Report from related application EP 14156011.0, dated Jun. 17, 2014, 9 pages.
Christopher, Pharma Patent Analyst, vol. 1, No. 3, 2012, pp. 329-346.
Jiang, et al., Bioorganic and Medicinal Chemistry Letters, vol. 22, 2012, pp. 3890-3894.
Palomba, et al., Anti-Inflamatory and analgesic amides. New Developments, Arch Pharm (Weinheim, Germany), 2000, XP-002724962 Chemical Abstracts Service, 2 pages.
Sifferlen, et al., Bioorganic and Medicinal Chemistry Letters, vol. 24, 2014, pp. 1201-1208.
Winrow, et al., British Journal of Pharmacology, vol. 171, 2014, pp. 283-293.

* cited by examiner

*Primary Examiner* — Heidi Reese
(74) *Attorney, Agent, or Firm* — Norton Rose Fulbright US LLP; Scott D. Rothenberger

(57) ABSTRACT

The present invention provides compounds of formula (I) and pharmaceutically acceptable salts thereof,

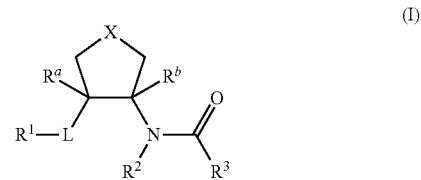

wherein L, X, $R^a$, $R^b$, $R^1$, $R^2$ and $R^3$ are as defined in the specification, processes for their preparation, pharmaceutical compositions containing them and their use in therapy.

20 Claims, No Drawings

CYCLOALKYL AND HETEROCYCLOALKYL COMPOUNDS AS OREXIN RECEPTOR ANTAGONISTS

The present invention relates to amide derivatives, processes for their preparation, pharmaceutical compositions containing them and their use in therapy, particularly in the treatment or prevention of conditions having an association with the orexin sub-type 1 receptor.

The orexin peptides (orexin A and orexin B, OxA and OxB), also known as hypocretins, were discovered in 1998 bp two groups (Sakurai et al., *Cell*, 1998, 92, 573 and De Lecea et al., *Proc. Nat. Acad. Sci.*, 1998, 95, 322). These neuropeptides are both derived from the common precursor pre-pro-orexin and are produced in the lateral hypothalamus. OxA is a 33 amino acid residue which has similar potency at both the Ox1R (orexin 1 receptors) and Ox2R (orexin 2 receptors) whereas OxB is made up of 28 amino acids and binds selectively to the Ox2R.

Orexin receptors are believed to be implicated in both feeding behaviour (Sakurai et al., *Cell*, 1998, 92, 573) and also in regulating sleep architecture (Chemelli et al., *Cell*, 1999, 98, 437). More recently, it has been shown that orexin receptors are implicated in arousal, reward, learning and memory (Harris et al., *Trends Neurosci.*, 2006, 29, 571).

WO 2003/099276 describes a broad class of compounds, including certain amides, which are useful as factor Xa inhibitors for treating thromboembolic disorders.

We have now discovered a class of compounds that are orexin receptor antagonists. Furthermore, certain compounds of the invention show selectivity for the orexin 1 receptor over the orexin 2 receptor.

In accordance with the present invention, there is therefore provided a compound of formula

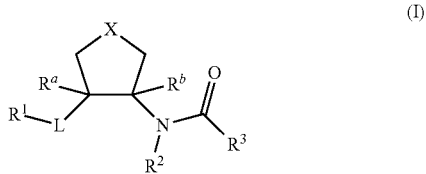

(I)

wherein $R^1$ represents a 5- or 6-membered heteroaryl group optionally substituted by at least one substituent independently selected from halogen, cyano, hydroxyl, $C_3$-$C_6$ cycloalkyl, $C_1$-$C_3$ alkyl, $C_1$-$C_3$ alkoxy, $C_1$-$C_3$ alkoxycarbonyl, $C_1$-$C_3$ alkoxycarbonylamino, $C_1$-$C_3$ haloalkyl, $C_1$-$C_3$ haloalkoxy, —$NR^4R^5$, $C_3$-$C_6$ cycloalkylamino, $C_1$-$C_3$ alkylcarbonyloxy, $C_1$-$C_3$ alkylcarbonylamino, sulphonamido (—$SO_2NH_2$), $C_1$-$C_3$ alkylsulphonyl, $C_1$-$C_3$ alkylsulphonylamino and —$C(O)NR^6R^7$;

L represents a bond, $CH_2$, O or $NR^{12}$;

$R^a$ represents a hydrogen atom or a $C_1$-$C_3$ alkyl or $C_1$-$C_3$ haloalkyl group;

$R^b$ represents a hydrogen atom or a $C_1$-$C_3$ alkyl or $C_1$-$C_3$ haloalkyl group;

X represents $CH_2$, CHF or $CF_2$;

$R^2$ represents a hydrogen atom or a $C_1$-$C_6$ alkyl or $C_3$-$C_6$ cycloalkyl group;

$R^3$ represents a phenyl group or a 5- or 6-membered heteroaryl group, all optionally substituted by at least one substituent independently selected from halogen, hydroxyl, cyano, $C_1$-$C_3$ alkyl, $C_1$-$C_3$ haloalkyl, $C_1$-$C_3$ hydroxyalkyl, $C_1$-$C_3$ alkoxy, $C_1$-$C_3$ haloalkoxy, $C_2$-$C_4$ alkenyl, $C_1$-$C_3$ alkylcarbonyloxy, $C_1$-$C_3$ alkoxycarbonyl, —$NR^8R^9$, —$C(O)NR^{10}R^{11}$, $C_3$-$C_6$ cycloalkyl, $C_3$-$C_6$ cycloalkyloxy, $C_3$-$C_6$ cycloalkylmethyl or a 5- or 6-membered heteroaryl group, the heteroaryl group itself being optionally substituted by at least one substituent independently selected from $C_1$-$C_6$ alkyl, $C_1$-$C_6$ alkoxy and $C_1$-$C_6$ haloalkoxy;

$R^4$ and $R^5$ each independently represent a hydrogen atom or a $C_1$-$C_3$ alkyl or $C_3$-$C_6$ cycloalkyl group, or $R^4$ and $R^5$ may together with the nitrogen atom to which they are attached form a 4- to 7-membered saturated heterocyclic ring optionally substituted by at least one substituent independently selected from halogen, hydroxyl and $C_1$-$C_3$ alkoxy;

$R^6$ and $R^7$ each independently represent a hydrogen atom or a $C_1$-$C_3$ alkyl or $C_3$-$C_6$ cycloalkyl group, or $R^6$ and $R^7$ may together with the nitrogen atom to which they are attached form a 4- to 7-membered saturated heterocyclic ring optionally substituted by at least one substituent independently selected from halogen and hydroxyl;

$R^8$ and $R^9$ each independently represent a hydrogen atom or a $C_1$-$C_3$ alkyl or $C_3$-$C_6$ cycloalkyl group, or $R^8$ and $R^9$ may together with the nitrogen atom to which they are attached form a 4- to 7-membered saturated heterocyclic ring optionally substituted by at least one substituent independently selected from halogen, hydroxyl and $C_1$-$C_3$ alkoxy;

$R^{10}$ and $R^{11}$ each independently represent a hydrogen atom or a $C_1$-$C_3$ alkyl or $C_3$-$C_6$ cycloalkyl group, or $R^{10}$ and $R^{11}$ may together with the nitrogen atom to which they are attached form a 4- to 7-membered saturated heterocyclic ring optionally substituted by at least one substituent independently selected from halogen and hydroxyl; and $R^{12}$ represents a hydrogen atom, methyl group or a $C_2$-$C_3$ alkylene chain that links to $R^1$ to form a 5- or 6-membered ring;

or a pharmaceutically acceptable salt thereof.

In the context of the present specification, unless otherwise stated, an "alkyl" substituent group or an alkyl moiety in a substituent group may be linear or branched. Examples of $C_1$-$C_8$ alkyl groups/moieties include methyl, ethyl, propyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, tert-butyl, n-pentyl, isopentyl, neopentyl, n-hexyl, n-heptyl and n-octyl.

An "alkenyl" substituent group or an alkenyl moiety in a substituent group refers to an unsaturated alkyl group having one or more double bonds. Examples of $C_2$-$C_6$ alkenyl groups/moieties include ethenyl, propenyl, 1-butenyl, 2-butenyl, 1-pentenyl, 1-hexenyl, 1,3-butadienyl, 1,3-pentadienyl, 1,4-pentadienyl and 1,4-hexadienyl.

A "cycloalkyl" substituent group/moiety is a saturated hydrocarbyl ring containing, for example, from 3 to 8 carbon atoms, examples of which include cyclopropyl, cyclobutyl, cyclopentyl and cyclohexyl.

A "haloalkyl" or "haloalkoxy" substituent group/moiety comprises at least one halogen atom, e.g. one, two, three, four or five halogen atoms. Examples of $C_1$-$C_6$ haloalkyl and $C_1$-$C_6$ haloalkoxy groups/moieties include fluoromethyl, difluoromethyl, trifluoromethyl, 2,2,2-trifluoroethyl, pentafluoroethyl, fluoromethoxy, difluoromethoxy and trifluoromethoxy.

It will be understood that if $R^4$ and $R^5$ together with the nitrogen atom to which they are attached form a 4- to 7-membered saturated heterocyclic ring, the heterocyclic ring may contain one or more (e.g. one or two) further ring heteroatoms (e.g. nitrogen, oxygen or sulphur atoms) in addition to the nitrogen atom to which $R^4$ and $R^5$ are attached. However, it will be appreciated that the invention does not encompass any unstable ring structures or any O—O, O—S or S—S bonds. If a substituent is present on the ring, it may be attached to any suitable ring atom. Examples of such heterocyclic rings include azetidinyl, pyrrolidinyl, piperidinyl, morpholinyl, thiomorpholinyl, piperazinyl, 1,4-azathianyl, azepanyl and 1,4-oxaazepanyl moieties. Similar comments apply with respect to $R^6$ and $R^7$, $R^8$ and $R^9$, and $R^{10}$ and $R^{11}$ when they form a 4- to 7-membered saturated heterocyclic ring.

A "heteroaryl" group is a 5- or 6-membered aryl group in which from 1 to 4 ring carbon atoms are replaced by heteroatoms independently selected from nitrogen, oxygen and sulphur. The heteroaryl group can be bonded at any suitable ring atom (i.e. at any carbon or heteroatom of the heteroaryl ring system).

When any chemical moiety or group in formula (I) is described as being optionally substituted, it will be appreciated that the moiety or group may be either unsubstituted or substituted by one or more of the specified substituents. It will be appreciated that the number and nature of substituents will be selected so as to avoid sterically undesirable combinations.

$R^1$ represents a 5- or 6-membered heteroaryl group optionally substituted by at least one substituent, e.g. one, two, three or four substituents, independently selected from halogen (e.g. fluorine, chlorine, bromine or iodine), cyano, hydroxyl, $C_3$-$C_6$ cycloalkyl (cyclopropyl, cyclobutyl, cyclopentyl or cyclohexyl), $C_1$, $C_2$ or $C_3$ alkyl, $C_1$, $C_2$ or $C_3$ alkoxy, $C_1$, $C_2$ or $C_3$ alkoxycarbonyl, $C_1$, $C_2$ or $C_3$ alkoxycarbonylamino, $C_1$, $C_2$ or $C_3$ haloalkyl, $C_1$, $C_2$ or $C_3$ haloalkoxy, —$NR^4R^5$, $C_3$-$C_6$ cycloalkylamino (cyclopropylamino, cyclobutylamino, cyclopentylamino or cyclohexylamino), $C_1$, $C_2$ or $C_3$ alkylcarbonyloxy, $C_1$, $C_2$ or $C_3$ alkylcarbonylamino, sulphonamido, $C_1$, $C_2$ or $C_3$ alkylsulphonyl, $C_1$, $C_2$ or $C_3$ alkylsulphonylamino and —$C(O)NR^6R^7$.

$R^1$ represents a 5- or 6-membered heteroaryl group. This $R^1$ heteroaryl group comprises one or more, e.g. one, two, three or four, ring heteroatoms independently selected from nitrogen, oxygen and sulphur. Examples of such 5- or 6-membered monocyclic heteroaromatic groups include pyrrolyl, imidazolyl, pyrazolyl, triazolyl, tetrazolyl, pyridinyl, pyrazinyl, pyrimidinyl, pyridazinyl, triazinyl, thienyl, furyl, furazanyl, oxazolyl, thiazolyl, oxadiazolyl, isothiazolyl, isoxazolyl, thiadiazolyl and tetrazinyl.

In an embodiment of the invention, $R^1$ represents a 5- or 6-membered heteroaryl group containing one or two ring heteroatoms independently selected from nitrogen, oxygen and sulphur (such as pyridinyl, pyrimidinyl and pyrazinyl), the heteroaryl group being optionally substituted by at least one substituent, e.g. one, two, three or four substituents, independently selected from halogen (e.g. fluorine, chlorine, bromine or iodine), cyano, hydroxyl, $C_3$-$C_6$ cycloalkyl (cyclopropyl, cyclobutyl, cyclopentyl or cyclohexyl), $C_1$, $C_2$ or $C_3$ alkyl, $C_1$, $C_2$ or $C_3$ alkoxy, $C_1$, $C_2$ or $C_3$ alkoxycarbonyl, $C_1$, $C_2$ or $C_3$ alkoxycarbonylamino, $C_1$, $C_2$ or $C_3$ haloalkyl, $C_1$, $C_2$ or $C_3$ haloalkoxy, —$NR^4R^5$, $C_3$-$C_6$ cycloalkylamino (cyclopropylamino, cyclobutylamino, cyclopentylamino or cyclohexylamino), $C_1$, $C_2$ or $C_3$ alkylcarbonyloxy, $C_1$, $C_2$ or $C_3$ alkylcarbonylamino, sulphonamido, $C_1$, $C_2$ or $C_3$ alkylsulphonyl, $C_1$, $C_2$ or $C_3$ alkylsulphonylamino and —$C(O)NR^6R^7$.

In another embodiment, $R^1$ represents a 5- or 6-membered heteroaryl group containing one or two ring heteroatoms independently selected from nitrogen and oxygen (such as pyridinyl, pyrimidinyl and pyrazinyl), the heteroaryl group being optionally substituted by one, two, three or four substituents independently selected from halogen (e.g. fluorine, chlorine, bromine or iodine), cyano, hydroxyl, $C_3$-$C_6$ cycloalkyl, $C_1$, $C_2$ or $C_3$ alkyl, $C_1$, $C_2$ or $C_3$ alkoxy, $C_1$, $C_2$ or $C_3$ alkoxycarbonyl, $C_1$, $C_2$ or $C_3$ alkoxycarbonylamino, $C_1$, $C_2$ or $C_3$ haloalkyl, $C_1$, $C_2$ or $C_3$ haloalkoxy, —$NR^4R^5$, $C_5$-$C_6$ cycloalkylamino, $C_1$, $C_2$ or $C_3$ alkylcarbonyloxy, $C_1$, $C_2$ or $C_3$ alkylcarbonylamino, sulphonamido, $C_1$, $C_2$ or $C_3$ alkylsulphonyl, $C_1$, $C_2$ or $C_3$ alkylsulphonylamino and —$C(O)NR^6R^7$.

In a further embodiment, $R^1$ represents a 6-membered heteroaryl group containing as the only ring heteroatoms one or two ring nitrogen atoms (such as pyridinyl, pyrimidinyl and pyrazinyl), the heteroaryl group being optionally substituted by one, two, three or four (particularly one or two) substituents independently selected from halogen (particularly fluorine, chlorine and bromine), cyclopropyl, $C_1$, $C_2$ or $C_3$ alkyl (particularly methyl, ethyl and isopropyl), $C_1$, $C_2$ or $C_3$ alkoxy (particularly methoxy), $C_1$, $C_2$ or $C_3$ haloalkyl (particularly trifluoromethyl) and $C_1$, $C_2$ or $C_3$ haloalkoxy (particularly trifluoromethoxy).

In a still further embodiment, $R^1$ represents any one of the following moieties or is selected from a group containing two or more of such moieties in any combination:
(i) 4-(trifluoromethyl)pyridin-2-yl,
(ii) 5-(trifluoromethyl)pyridin-2-yl,
(iii) 5-(trifluoromethoxy)pyridin-2-yl,
(iv) 6-(trifluoromethyl)pyridin-2-yl,
(v) 6-(trifluoromethyl)pyridin-3-yl,
(vi) 5-chloropyridin-2-yl,
(vii) 5-bromopyridin-2-yl,
(viii) 3-fluoro-5-(trifluoromethyl)pyridin-2-yl,
(ix) 3-chloro-5-(trifluoromethyl)pyridin-2-yl,
(x) 3-bromo-5-(trifluoromethyl)pyridin-2-yl,
(xi) 5-bromo-3-methoxypyridin-2-yl,
(xii) 3-methyl-5-(trifluoromethyl)pyridin-2-yl,
(xiii) 5-(trifluoromethyl)pyrimidin-2-yl,
(xiv) 5-ethylpyrimidin-2-yl,
(xv) 5-(trifluoromethyl)pyrazin-2-yl,
(xvi) 5-chloropyrazin-2-yl,
(xvii) 5-(ethyl)pyrazin-2-yl,
(xviii) 5-(cyclopropyl)pyrazin-2-yl,
(xix) 5-(isopropyl)pyrazin-2-yl,
(xx) 3-methyl-5-(trifluoromethyl)pyrazin-2-yl,
(xxi) 3-ethyl-5-(trifluoromethyl)pyrazin-2-yl,
(xxii) 3-cyclopropyl-5-(trifluoromethyl)pyrazin-2-yl, and
(xxiii) 3-isopropyl-5-(trifluoromethyl)pyrazin-2-yl.

In one embodiment, $R^1$ represents a mono-substituted 6-membered heteroaryl group, the substituent being preferably attached in the para-position relative to the point of attachment of the moiety -L-, or, the five-membered ring in the case where the moiety -L- represents a bond.

In an embodiment of the invention, L represents $CH_2$, O or $NR^{12}$.

In a further embodiment, L represents $NR^{12}$.

$R^a$ and $R^b$ each independently represent a hydrogen atom or a $C_1$, $C_2$ or $C_3$ alkyl or $C_1$, $C_2$ or $C_3$ haloalkyl group.

In one embodiment, $R^a$ and $R^b$ each represent a hydrogen atom.

In another embodiment, one of $R^a$ and $R^b$ represents a hydrogen atom and the other of $R^a$ and $R^b$ represents a $C_1$ alkyl (i.e. methyl) or haloalkyl (e.g. trifluoromethyl) group.

In a further embodiment, $R^a$ represents a hydrogen atom or a methyl group and $R^b$ represents a hydrogen atom.

X represents $CH_2$, CHF or $CF_2$.

In one embodiment, X represents $CH_2$.

$R^2$ represents a hydrogen atom or a $C_1$-$C_6$, or $C_1$-$C_4$, or $C_1$-$C_2$ alkyl or $C_3$-$C_6$ cycloalkyl (cyclopropyl, cyclobutyl, cyclopentyl or cyclohexyl) group.

In one embodiment, $R^2$ represents a hydrogen atom or $C_3$-$C_6$ cycloalkyl group. In another embodiment, $R^2$ represents a hydrogen atom.

$R^3$ represents a phenyl group or a 5- or 6-membered heteroaryl group, all optionally substituted by at least one substituent, e.g. one, two, three or four substituents, independently selected from halogen (e.g. fluorine, chlorine, bromine or iodine), hydroxyl, cyano, $C_1$, $C_2$ or $C_3$ alkyl, $C_1$, $C_2$ or $C_3$ haloalkyl, $C_1$, $C_2$ or $C_3$ hydroxyalkyl, $C_1$, $C_2$ or $C_3$ alkoxy, $C_1$, $C_2$ or $C_3$ haloalkoxy, $C_2$, $C_3$ or $C_4$ alkenyl, $C_1$, $C_2$ or $C_3$ alkylcarbonyloxy, $C_1$, $C_2$ or $C_3$ alkoxycarbonyl, —$NR^8R^9$, —$C(O)NR^{10}R^{11}$, $C_3$-$C_6$ cycloalkyl (cyclopropyl, cyclobutyl, cyclopentyl or cyclohexyl), $C_3$-$C_6$ cycloalkyloxy (cyclopropyloxy, cyclobutyloxy, cyclopentyloxy or cyclohexyloxy), $C_3$-$C_6$ cycloalkylmethyl (cyclopropylmethyl, cyclobutylmethyl, cyclopentylmethyl or cyclohexylmethyl) or a 5- or 6-membered heteroaryl group, the heteroaryl group itself being optionally substituted by at least one substituent, e.g. one, two, three or four substituents, independently selected from $C_1$-$C_6$, or $C_1$-$C_4$, or $C_1$-$C_2$ alkyl, $C_1$-$C_6$, or $C_1$-$C_4$, or $C_1$-$C_2$ alkoxy and $C_1$-$C_6$, or $C_1$-$C_4$, or $C_1$-$C_2$ haloalkoxy.

$R^3$ represents a phenyl group or a 5- or 6-membered heteroaryl group. This $R^3$ heteroaryl group comprises one or more, e.g. one, two, three or four, ring heteroatoms independently selected from nitrogen, oxygen and sulphur. Examples of such 5- or 6-membered heteroaryl groups include pyrrolyl, imidazolyl, pyrazolyl, triazolyl, tetrazolyl, pyridinyl, pyrazinyl, pyrimidinyl, pyridazinyl, triazinyl, thienyl, furyl, furazanyl, oxazolyl, thiazolyl, oxadiazolyl, isothiazolyl, isoxazolyl, thiadiazolyl and tetrazinyl.

The $R^3$ phenyl or heteroaryl group may optionally be substituted with at least one 5- or 6-membered heteroaryl substituent group. The "heteroaryl" substituent group, as used in this context, comprises a total of 5 or 6 ring atoms, of which one, two, three or four ring atoms are heteroatoms independently selected from nitrogen, oxygen and sulphur atoms. Examples of such heteroaryl substituent groups include pyrrolyl, imidazolyl, pyrazolyl, triazolyl, tetrazolyl, pyridinyl, pyrazinyl, pyrimidinyl, pyridazinyl, triazinyl, thienyl, furyl, furazanyl, oxazolyl, thiazolyl, oxadiazolyl, isothiazolyl, isoxazolyl, thiadiazolyl and tetrazinyl.

In an embodiment of the invention, $R^3$ represents a phenyl group or a 5- or 6-membered heteroaryl group containing one or two ring heteroatoms independently selected from nitrogen, oxygen and sulphur (such as pyridinyl, pyrimidinyl and pyrazinyl), all optionally substituted by at least one substituent, e.g. one, two, three or four substituents, independently selected from halogen (e.g. fluorine, chlorine, bromine or iodine), hydroxyl, cyano, $C_1$, $C_2$ or $C_3$ alkyl, $C_1$, $C_2$ or $C_3$ haloalkyl, $C_1$, $C_2$ or $C_3$ hydroxyalkyl, $C_1$, $C_2$ or $C_3$ alkoxy, $C_1$, $C_2$ or $C_3$ haloalkoxy, $C_2$, $C_3$ or $C_4$ alkenyl, $C_1$, $C_2$ or $C_3$ alkylcarbonyloxy, $C_1$, $C_2$ or $C_3$ alkoxycarbonyl, —$NR^8R^9$, —$C(O)NR^{10}R^{11}$, $C_3$-$C_5$ cycloalkyl, $C_3$-$C_5$ cycloalkyloxy, $C_3$-$C_5$ cycloalkylmethyl or a 5- or 6-membered heteroaryl group (such as triazolyl, pyrazolyl, oxadiazolyl, pyrimidinyl and imidazolyl), the heteroaryl group itself being optionally substituted by at least one substituent, e.g. one, two, three or four substituents, independently selected from $C_1$-$C_6$, or $C_1$-$C_4$, or $C_1$-$C_2$ alkyl, $C_1$-$C_6$, or $C_1$-$C_4$, or $C_1$-$C_2$ alkoxy and $C_1$-$C_6$, or $C_1$-$C_4$, or $C_1$-$C_2$ haloalkoxy.

In another embodiment, $R^3$ represents a phenyl group or a 5- or 6-membered heteroaryl group containing one or two ring heteroatoms independently selected from nitrogen, oxygen and sulphur (such as pyridinyl, pyrimidinyl and pyrazinyl), all optionally substituted by at least one substituent, e.g. one, two, three or four substituents, independently selected from fluorine, chlorine, bromine, $C_1$, $C_2$ or $C_3$ alkyl, $C_1$, $C_2$ or $C_3$ haloalkyl, $C_1$, $C_2$ or $C_3$ alkoxy, $C_1$, $C_2$ or $C_3$ haloalkoxy, cyclopropyl, —$NR^8R^9$ (e.g. piperidinyl), or a 5- or 6-membered heteroaryl group (such as triazolyl, pyrazolyl, oxadiazolyl, pyrimidinyl and imidazolyl), the heteroaryl group itself being optionally substituted by at least one substituent, e.g. one, two, three or four substituents, independently selected from $C_1$-$C_2$ alkyl, $C_1$-$C_2$ alkoxy and $C_1$-$C_2$ haloalkoxy.

In a further embodiment, $R^3$ represents a phenyl group optionally substituted by one, two or three (particularly one or two) substituents independently selected from fluorine, chlorine, $C_1$, $C_2$ or $C_3$ alkyl, $C_1$, $C_2$ or $C_3$ alkoxy or a 5- or 6-membered heteroaryl group (such as triazolyl, pyrazolyl, oxadiazolyl and pyrimidinyl), the heteroaryl group itself being optionally substituted by one or two substituents independently selected from $C_1$-$C_2$ alkyl, $C_1$-$C_2$ alkoxy and $C_1$-$C_2$ haloalkoxy, preferably methyl.

In a still further embodiment, $R^3$ represents any one of the following moieties or is selected from a group containing two or more of such moieties in any combination:

(i) 2-fluorophenyl,
(ii) 2-chlorophenyl,
(iii) 2-methylphenyl,
(iv) 2-cyclopropylphenyl,
(v) 2-methoxyphenyl,
(vi) 2-ethoxyphenyl,
(vii) 2-(difluoromethoxy)phenyl,
(viii) 3-methylphenyl,
(ix) 3-methoxyphenyl,
(x) 2,6-difluorophenyl,
(xi) 2,6-dichlorophenyl,
(xii) 2,6-dimethoxyphenyl,
(xiii) 2,6-diethoxyphenyl,
(xiv) 2-ethoxy-5-methylphenyl,
(xv) 2,5-dimethoxyphenyl,
(xvi) 2-fluoro-6-methoxyphenyl,
(xvii) 5-fluoro-2-methoxyphenyl,
(xviii) 3-fluoro-2-methoxyphenyl,
(xix) 2-(1H-1,2,4-triazol-1-yl)phenyl,
(xx) 2-(2H-1,2,3-triazol-2-yl)phenyl,
(xxi) 5-methyl-2-(1H-1,2,3-triazol-1-yl)phenyl,
(xxii) 5-methyl-2-(2H-1,2,3-triazol-2-yl)phenyl,
(xxiii) 5-fluoro-2-(1H-1,2,3-triazol-1-yl)phenyl,
(xxiv) 5-fluoro-2-(2H-1,2,3-triazol-2-yl)phenyl,
(xxv) 2-(3-methyl-1,2,4-oxadiazol-5-yl)phenyl,
(xxvi) 2-(pyrimidin-2-yl)phenyl,
(xxvii) 5-fluoro-2-(pyrimidin-2-yl)phenyl,
(xxviii) 2-(1H-pyrazol-1-yl)phenyl,
(xxix) 2-(1H-imidazol-1-yl)phenyl,
(xxx) 2-(1H-1,2,3-triazol-1-yl)phenyl,
(xxxi) 2-(pyrimidin-2-yl)-5-fluorophenyl,
(xxxii) 2-fluoro-6-(2H-1,2,3-triazol-2-yl)phenyl,
(xxxiii) 2-methoxy-5-methylphenyl,
(xxxiv) 2-chloro-6-(2H-1,2,3-triazol-2-yl)phenyl,
(xxxv) 2-(5-methyl-1,3,4-oxadiazol-2-yl)phenyl,
(xxxvi) 5-trifluoromethyl-2-(2H-1,2,3-triazol-2-yl)phenyl,
(xxxvii) 2-fluoro-6-(pyrazol-1-yl)phenyl,
(xxxviii) 5-fluoro-2-(pyrazol-1-yl)phenyl,
(xxxix) 5-methyl-2-(pyrazol-1-yl)phenyl,
(xl) 2-bromo-6-methoxyphenyl,
(xli) 2-methoxy-6-(pyrazol-1-yl)phenyl,
(xlii) 5-chloro-2-(2H-1,2,3-triazol-2-yl)phenyl,
(xliii) 3-fluoro-2-(2H-1,2,3-triazol-2-yl)phenyl,
(xliv) 5-trifluoromethyl-2-(1H-1,2,3-triazol-1-yl)phenyl,
(xlv) 5-chloro-2-(1H-1,2,3-triazol-1-yl)phenyl, (xlvi) 2,3-difluoro-6-(2H-1,2,3-triazol-2-yl)phenyl,
(xlvii) 5-cyclopropyl-2-(2H-1,2,3-triazol-2-yl)phenyl,
(xlviii) 5-chloro-2-(pyrazol-1-yl)phenyl,
(xlix) 3,5-difluoro-2-(2H-1,2,3-triazol-2-yl)phenyl,
(l) 2-(difluoromethyl)phenyl,
(li) 2-(trifluoromethyl)phenyl,
(lii) 3,6-difluoro-2-(2H-1,2,3-triazol-2-yl)phenyl,
(liii) 2-cyclopropyl-6-fluorophenyl,
(liv) 2-(5-ethoxypyrimidin-2-yl)phenyl,
(lv) 3-(pyrimidin-2-yl)pyridin-2-yl,
(lvi) 3-ethoxy-6-methylpyridin-2-yl,
(lvii) 3-(pyrazol-1-yl)pyridin-2-yl,
(lviii) 3-(piperidin-1-yl)pyridin-2-yl,
(lix) 3-(trifluoromethoxy)pyridin-2-yl,
(lx) 3-(ethoxy)pyridin-2-yl,
(lxi) 3-(cyclopropyl)pyridin-2-yl,
(lxii) 3-chloropyridin-2-yl,
(lxiii) 3-bromopyridin-2-yl,
(lxiv) 3-methoxypyridin-2-yl,
(lxv) 3-(propan-2-yloxy)pyridin-2-yl,
(lxvi) 6-bromo-3-methoxypyridin-2-yl,
(lxvii) 3-methoxy-6-methylpyridin-2-yl, and
(lxviii) 3-(2H-1,2,3-triazol-2-yl)pyridin-2-yl.

In a still further embodiment, when $R^3$ represents a substituted phenyl group or a substituted 5- or 6-membered heteroaryl group (such as pyridinyl, pyrimidinyl and pyrazinyl), the substituent(s) is/are independently any one of the following moieties or is/are independently selected from a group containing two or more of such moieties in any combination:
(i) methyl,
(ii) methoxy,
(iii) ethoxy,
(iv) isopropyloxy,
(v) difluoromethoxy,
(vi) trifluoromethoxy,
(vii) fluorine,
(viii) chlorine,
(ix) bromine,
(x) difluoromethyl,
(xi) trifluoromethyl,
(xii) piperidinyl (e.g. piperidin-1-yl),
(xiii) triazolyl (e.g. 1,2,3-triazol-2-yl, 1,2,3-triazol-1-yl or 1,2,4-triazol-1-yl),
(xiv) pyrazolyl (e.g. pyrazol-1-yl),
(xv) oxadiazolyl,
(xvi) 3-methyl-1,2,4-oxadiazol-5-yl,
(xvii) 5-methyl-1,3,4-oxadiazol-2-yl,
(xviii) pyrimidinyl (e.g. pyrimidin-2-yl),
(xix) 5-ethoxypyrimidin-2-yl,
(xx) imidazolyl (e.g. imidazol-1-yl), and
(xxi) cyclopropyl.

When $R^3$ represents a substituted phenyl group or a substituted 6-membered heteroaryl group, the substituent(s) is/are preferably attached in the ortho- and/or meta-positions relative to the point of attachment of the amide moiety, —$NR^2C(O)$—.

$R^4$ and $R^5$ each independently represent a hydrogen atom or a $C_1$, $C_2$ or $C_3$ alkyl or $C_3$-$C_6$ cycloalkyl (cyclopropyl, cyclobutyl, cyclopentyl or cyclohexyl) group, or $R^4$ and $R^5$ may together with the nitrogen atom to which they are attached form a 4-, 5-, 6- or 7-membered saturated heterocyclic ring optionally substituted by at least one substituent, e.g. one or two substituents independently, selected from halogen (e.g. fluorine, chlorine, bromine or iodine), hydroxyl and $C_1$, $C_2$ or $C_3$ alkoxy.

In one aspect, the saturated heterocyclic ring may contain a single ring heteroatom (being the nitrogen atom to which $R^4$ and $R^5$ are attached).

In an alternative aspect, the saturated heterocyclic ring may contain a second ring heteroatom selected from a nitrogen or oxygen atom.

In one embodiment, $R^4$ and $R^5$ each independently represent a hydrogen atom or a $C_1$, $C_2$ or $C_3$ alkyl or $C_3$-$C_6$ or $C_3$—$O_5$ or $C_5$-$C_6$ cycloalkyl, particularly cyclopropyl, group, or $R^4$ and $R^5$ may together with the nitrogen atom to which they are attached form a 4- or 5-membered saturated heterocyclic ring optionally substituted by one or two substituents independently selected from fluorine, chlorine, bromine, hydroxyl and methoxy.

In a second embodiment, $R^4$ and $R^5$ each represent a hydrogen atom.

In a third embodiment, $R^4$ and $R^5$ each represent a $C_1$-$C_3$ alkyl group.

In a fourth embodiment, one of $R^4$ and $R^5$ represents a hydrogen atom and the other of $R^4$ and $R^5$ represents a $C_1$-$C_3$ alkyl group.

In a fifth embodiment, one of $R^4$ and $R^5$ represents a cyclopropyl group and the other of $R^4$ and $R^5$ represents a $C_1$-$C_3$ alkyl group.

In a sixth embodiment, $R^4$ and $R^5$ together with the nitrogen atom to which they are attached form an azetidinyl or pyrrolidinyl ring optionally substituted by one or two substituents independently selected from fluorine, hydroxyl and methoxy.

$R^6$ and $R^7$ each independently represent a hydrogen atom or a $C_1$, $C_2$ or $C_3$ alkyl or $C_3$-$C_6$ cycloalkyl (cyclopropyl, cyclobutyl, cyclopentyl or cyclohexyl) group, or $R^6$ and $R^7$ may together with the nitrogen atom to which they are attached form a 4-, 5-, 6- or 7-membered saturated heterocyclic ring optionally substituted by at least one substituent, e.g. one or two substituents, independently selected from halogen (e.g. fluorine, chlorine, bromine or iodine) and hydroxyl.

In one aspect, the saturated heterocyclic ring may contain a single ring heteroatom (being the nitrogen atom to which $R^6$ and $R^7$ are attached).

In an alternative aspect, the saturated heterocyclic ring may contain a second ring heteroatom selected from a nitrogen or oxygen atom.

In one embodiment, $R^6$ and $R^7$ each independently represent a hydrogen atom or a $C_1$, $C_2$ or $C_3$ alkyl or $C_3$-$C_6$ or $C_3$—$O_5$ or $C_5$-$C_6$ cycloalkyl, particularly cyclopropyl, group, or $R^6$ and $R^7$ may together with the nitrogen atom to which they are attached form a 4- or 5-membered saturated heterocyclic ring optionally substituted by one or two substituents independently selected from fluorine, chlorine, bromine and hydroxyl.

In a second embodiment, $R^6$ and $R^7$ each represent a hydrogen atom.

In a third embodiment, $R^6$ and $R^7$ each represent a $C_1$-$C_3$ alkyl group.

In a fourth embodiment, one of $R^6$ and $R^7$ represents a hydrogen atom and the other of $R^6$ and $R^7$ represents a $C_1$-$C_3$ alkyl group.

In a fifth embodiment, one of $R^6$ and $R^7$ represents a cyclopropyl group and the other of $R^6$ and $R^7$ represents a $C_1$-$C_3$ alkyl group.

In a sixth embodiment, $R^6$ and $R^7$ together with the nitrogen atom to which they are attached form an azetidinyl or pyrrolidinyl ring optionally substituted by one or two substituents independently selected from fluorine and hydroxyl.

$R^8$ and $R^9$ are defined as for $R^4$ and $R^5$ above.

$R^{10}$ and $R^{11}$ are defined as for $R^6$ and $R^7$ above.

$R^{12}$ represents a hydrogen atom, methyl group or a $C_2$-$C_3$ alkylene chain that links to $R^1$ to form a 5- or 6-membered ring. Thus, for example, the following moiety may be formed when $R^{12}$ represents a $C_3$ alkylene chain and $R^1$ represents a pyridin-2-yl group:

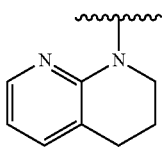

In an embodiment of the invention, $R^{12}$ represents a hydrogen atom or methyl group.

In another embodiment, $R^{12}$ represents a hydrogen atom.

In a preferred embodiment of the invention,
$R^1$ represents a 5- or 6-membered heteroaryl group optionally substituted by at least one substituent independently selected from halogen, cyclopropyl, $C_1$-$C_3$ alkyl, $C_1$-$C_3$ alkoxy, $C_1$-$C_3$ haloalkyl and $C_1$-$C_3$ haloalkoxy;
L represents $CH_2$, O or $NR^{12}$;
$R^a$ represents a hydrogen atom or a methyl group;
$R^b$ represents a hydrogen atom;
X represents $CH_2$ or $CF_2$;
$R^2$ represents a hydrogen atom or cyclobutyl group;
$R^3$ represents a phenyl or pyridinyl group optionally substituted by at least one substituent independently selected from fluorine, chlorine, bromine, $C_1$-$C_3$ alkyl, $C_1$-$C_3$ haloalkyl, $C_1$-$C_3$ alkoxy, $C_1$-$C_3$ haloalkoxy, cyclopropyl, piperidinyl, or a 5- or 6-membered heteroaryl group, the heteroaryl group itself being optionally substituted by at least one $C_1$-$C_2$ alkyl or $C_1$-$C_2$ alkoxy group.

In another preferred embodiment, the invention provides compounds of formula

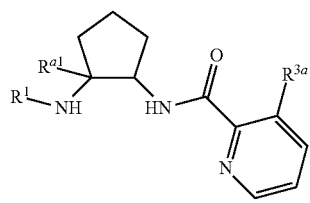

(Ia)

wherein
$R^1$ as defined above;
$R^{a1}$ represents a hydrogen atom or methyl group; and
$R^{3a}$ represents 5- or 6-membered heteroaryl group.

In one aspect, $R^{3a}$ in formula (Ia) represents a triazolyl (e.g. 1,2,3-triazol-2-yl) or pyrimidinyl (e.g. pyrimidin-2-yl) group.

Examples of compounds of the invention include:
2,6-Dimethoxy-N-[(1S,2S)-2-{[5-(trifluoromethyl)pyridin-2-yl]amino}cyclopentyl]benzamide;
2,6-Dimethoxy-N-[(1S,2S)-2-{[5-(trifluoromethyl)pyrimidin-2-yl]amino}cyclopentyl]benzamide;
5-Methyl-2-(2H-1,2,3-triazol-2-yl)-N-[(1S,2S)-2-{[5-(trifluoromethyl)pyrimidin-2-yl]amino}cyclopentyl]benzamide;
N-[(1S,2S)-2-[(5-Ethylpyrimidin-2-yl)amino]cyclopentyl]-5-methyl-2-(2H-1,2,3-triazol-2-yl)benzamide;
N-[(1S,2S)-2-[(5-Chloropyridin-2-yl)amino]cyclopentyl]-5-methyl-2-(2H-1,2,3-triazol-2-yl)benzamide;
5-Methyl-2-(2H-1,2,3-triazol-2-yl)-N-[(1S,2S)-2-{[5-(trifluoromethyl)pyridin-2-yl]amino}cyclopentyl]benzamide;
5-Methyl-2-(2H-1,2,3-triazol-2-yl)-N-[(1S,2S)-2-{[5-(trifluoromethyl)pyrazin-2-yl]amino}cyclopentyl]benzamide;
2-(3-Methyl-1,2,4-oxadiazol-5-yl)-N-[(1S,2S)-2-{[5-(trifluoromethyl)pyridin-2-yl]amino}cyclopentyl]benzamide;
N-[(1S,2S)-2-[(5-Chloropyrazin-2-yl)amino]cyclopentyl]-5-methyl-2-(2H-1,2,3-triazol-2-yl)benzamide;
5-Fluoro-2-(2H-1,2,3-triazol-2-yl)-N-[(1S,2S)-2-{[5-(trifluoromethyl)pyridin-2-yl]amino}cyclopentyl]benzamide;
is 2-(1H-Pyrazol-1-yl)-N-[(1S,2S)-2-{[5-(trifluoromethyl)pyridin-2-yl]amino}cyclopentyl]benzamide;
2-(2H-1,2,3-Triazol-2-yl)-N-[(1S,2S)-2-{[5-(trifluoromethyl)pyridin-2-yl]amino}cyclopentyl]benzamide;
2-(Pyrimidin-2-yl)-N-[(1S,2S)-2-{[5-(trifluoromethyl)pyridin-2-yl]amino}cyclopentyl]benzamide;
5-Fluoro-2-(pyrimidin-2-yl)-N-[(1S,2S)-2-{[5-(trifluoromethyl)pyridin-2-yl]amino}cyclopentyl]benzamide;
2-(3-Methyl-1,2,4-oxadiazol-5-yl)-N-[(1S,2S)-2-{[5-(trifluoromethyl)pyrazin-2-yl]amino}cyclopentyl]benzamide;
2-(3-Methyl-1,2,4-oxadiazol-5-yl)-N-[(1S,2S)-2-{[5-(trifluoromethyl)pyrimidin-2-yl]amino}cyclopentyl]benzamide;
2-(2H-1,2,3-Triazol-2-yl)-N-[(1S,2S)-2-{[5-(trifluoromethyl)pyrazin-2-yl]amino}cyclopentyl]benzamide;
2-(2H-1,2,3-Triazol-2-yl)-N-[(1S,2S)-2-{[5-(trifluoromethyl)pyrimidin-2-yl]amino}cyclopentyl]benzamide;
2-(2H-1,2,3-Triazol-2-yl)-N-[(1S,2R)-2-{[5-(trifluoromethyl)pyrazin-2-yl]oxy}cyclopentyl]benzamide;
2-(2H-1,2,3-Triazol-2-yl)-N-[(1S,2S)-2-{[4-(trifluoromethyl)pyridin-2-yl]oxy}cyclopentyl]benzamide;
2,6-Dimethoxy-N-[(1S,2S)-2-{[4-(trifluoromethyl)pyridin-2-yl]oxy}cyclopentyl]benzamide;
2-(2H-1,2,3-Triazol-2-yl)-N-(2-{[4-(trifluoromethyl)pyridin-2-yl]methyl}cyclopentyl)benzamide;
2-(2H-1,2,3-Triazol-2-yl)-N-(2-{[5-(trifluoromethyl)pyridin-2-yl]methyl}cyclopentyl)benzamide;
5-Methyl-2-(2H-1,2,3-triazol-2-yl)-N-(2-{[5-(trifluoromethyl)pyridin-2-yl]methyl}cyclopentyl)benzamide;
2,6-Dimethoxy-N-[(1S,2S)-2-{[6-(trifluoromethyl)pyridin-2-yl]amino}cyclopentyl]benzamide;
3-Bromo-N-[(1S,2S)-2-{[5-(trifluoromethyl)pyrazin-2-yl]amino}cyclopentyl]pyridine-2-carboxamide;
2-Ethoxy-5-methyl-N-[(1S,2S)-2-{[5-(trifluoromethyl)pyrazin-2-yl]amino}cyclopentyl]benzamide;
3-Ethoxy-6-methyl-N-[(1S,2S)-2-{[5-(trifluoromethyl)pyrazin-2-yl]amino}cyclopentyl]pyridine-2-carboxamide;
2-(1H-Pyrazol-1-yl)-N-[(1S,2S)-2-{[5-(trifluoromethyl)pyrazin-2-yl]amino}cyclopentyl]benzamide;
2-Fluoro-6-(2H-1,2,3-triazol-2-yl)-N-[(1S,2S)-2-{[5-(trifluoromethyl)pyrazin-2-yl]amino}cyclopentyl]benzamide;
2,6-Difluoro-N-[(1S,2S)-2-{[5-(trifluoromethyl)pyrazin-2-yl]amino}cyclopentyl]benzamide;
2,6-Dimethoxy-N-[(1S,2S)-2-{[5-(trifluoromethyl)pyrazin-2-yl]amino}cyclopentyl]benzamide;
2-(1H-1,2,3-Triazol-1-yl)-N-[(1S,2S)-2-{[5-(trifluoromethyl)pyrazin-2-yl]amino}cyclopentyl]benzamide;
5-Fluoro-2-(2H-1,2,3-triazol-2-yl)-N-[(1S,2S)-2-{[5-(trifluoromethyl)pyrazin-2-yl]amino}cyclopentyl]benzamide;

2-Methoxy-5-methyl-N-[(1S,2S)-2-{[5-(trifluoromethyl)pyrazin-2-yl]amino}cyclopentyl]benzamide;
2-(Pyrimidin-2-yl)-N-[(1S,2S)-2-{[5-(trifluoromethyl)pyrazin-2-yl]amino}cyclopentyl]benzamide;
5-Fluoro-2-(pyrimidin-2-yl)-N-[(1S,2S)-2-{[5-(trifluoromethyl)pyrazin-2-yl]amino}cyclopentyl]benzamide;
2-Chloro-6-(2H-1,2,3-triazol-2-yl)-N-[(1S,2S)-2-{[5-(trifluoromethyl)pyrazin-2-yl]amino}cyclopentyl]benzamide;
5-Fluoro-2-(1H-1,2,3-triazol-1-yl)-N-[(1S,2S)-2-{[5-(trifluoromethyl)pyrazin-2-yl]amino}cyclopentyl]benzamide;
5-Methyl-2-(1H-1,2,3-triazol-1-yl)-N-[(1S,2S)-2-{[5-(trifluoromethyl)pyrazin-2-yl]amino}cyclopentyl]benzamide;
3-(1H-Pyrazol-1-yl)-N-[(1S,2S)-2-{[5-(trifluoromethyl)pyrazin-2-yl]amino}cyclopentyl]pyridine-2-carboxamide;
2-(5-Methyl-1,3,4-oxadiazol-2-yl)-N-[(1S,2S)-2-{[5-(trifluoromethyl)pyrazin-2-yl]amino}cyclopentyl]benzamide;
2-(2H-1,2,3-Triazol-2-yl)-5-(trifluoromethyl)-N-[(1S,2S)-2-{[5-(trifluoromethyl)pyrazin-2-yl]amino}cyclopentyl]benzamide;
2-Fluoro-6-(1H-pyrazol-1-yl)-N-[(1S,2S)-2-{[5-(trifluoromethyl)pyrazin-2-yl]amino}cyclopentyl]benzamide;
5-Fluoro-2-(1H-pyrazol-1-yl)-N-[(1S,2S)-2-{[5-(trifluoromethyl)pyrazin-2-yl]amino}cyclopentyl]benzamide;
5-Methyl-2-(1H-pyrazol-1-yl)-N-[(1S,2S)-2-{[5-(trifluoromethyl)pyrazin-2-yl]amino}cyclopentyl]benzamide;
2-Bromo-6-methoxy-N-[(1S,2S)-2-{[5-(trifluoromethyl)pyrazin-2-yl]amino}cyclopentyl]benzamide;
2-Methoxy-6-(1H-pyrazol-1-yl)-N-[(1S,2S)-2-{[5-(trifluoromethyl)pyrazin-2-yl]amino}cyclopentyl]benzamide;
3-(Piperidin-1-yl)-N-[(1S,2S)-2-{[5-(trifluoromethyl)pyrazin-2-yl]amino}cyclopentyl]pyridine-2-carboxamide;
5-Chloro-2-(2H-1,2,3-triazol-2-yl)-N-[(1S,2S)-2-{[5-(trifluoromethyl)pyrazin-2-yl]amino}cyclopentyl]benzamide;
3-Fluoro-2-(2H-1,2,3-triazol-2-yl)-N-[(1S,2S)-2-{[5-(trifluoromethyl)pyrazin-2-yl]amino}cyclopentyl]benzamide;
2-(1H-1,2,3-Triazol-1-yl)-5-(trifluoromethyl)-N-[(1S,2S)-2-{[5-(trifluoromethyl)pyrazin-2-yl]amino}cyclopentyl]benzamide;
5-Chloro-2-(1H-1,2,3-triazol-1-yl)-N-[(1S,2S)-2-{[5-(trifluoromethyl)pyrazin-2-yl]amino}cyclopentyl]benzamide;
2,3-Difluoro-6-(2H-1,2,3-triazol-2-yl)-N-[(1S,2S)-2-{[5-(trifluoromethyl)pyrazin-2-yl]amino}cyclopentyl]benzamide;
5-Cyclopropyl-2-(2H-1,2,3-triazol-2-yl)-N-[(1S,2S)-2-{[5-(trifluoromethyl)pyrazin-2-yl]amino}cyclopentyl]benzamide;
3-(Trifluoromethoxy)-N-[(1S,2S)-2-{[5-(trifluoromethyl)pyrazin-2-yl]amino}cyclopentyl]pyridine-2-carboxamide;
5-Chloro-2-(1H-pyrazol-1-yl)-N-[(1S,2S)-2-{[5-(trifluoromethyl)pyrazin-2-yl]amino}cyclopentyl]benzamide;
3-Ethoxy-N-[(1S,2S)-2-{[5-(trifluoromethyl)pyrazin-2-yl]amino}cyclopentyl]pyridine-2-carboxamide;
3,5-Difluoro-2-(2H-1,2,3-triazol-2-yl)-N-[(1S,2S)-2-{[5-(trifluoromethyl)pyrazin-2-yl]amino}cyclopentyl]benzamide;
2-(Trifluoromethyl)-N-[(1S,2S)-2-{[5-(trifluoromethyl)pyrazin-2-yl]amino}cyclopentyl]benzamide;
3-Cyclopropyl-N-[(1S,2S)-2-{[5-(trifluoromethyl)pyrazin-2-yl]amino}cyclopentyl]pyridine-2-carboxamide;
3,6-Difluoro-2-(2H-1,2,3-triazol-2-yl)-N-[(1S,2S)-2-{[5-(trifluoromethyl)pyrazin-2-yl]amino}cyclopentyl]benzamide;
2-(Difluoromethyl)-N-[(1S,2S)-2-{[5-(trifluoromethyl)pyrazin-2-yl]amino}cyclopentyl]benzamide;
2-Cyclopropyl-6-fluoro-N-[(1S,2S)-2-{[5-(trifluoromethyl)pyrazin-2-yl]amino}cyclopentyl]benzamide;
5-Methyl-2-(2H-1,2,3-triazol-2-yl)-N-[(1S,2S)-2-{[6-(trifluoromethyl)pyridin-3-yl]amino}cyclopentyl]benzamide;
N-Cyclobutyl-2,6-dimethoxy-N-[(1S,2S)-2-{[5-(trifluoromethyl)pyridin-2-yl]amino}cyclopentyl]benzamide;
2-Chloro-N-[(1S,2S)-2-{[5-(trifluoromethyl)pyridin-2-yl]amino}cyclopentyl]benzamide;
2-Chloro-N-[(1S,2S)-2-{[5-(trifluoromethyl)pyrimidin-2-yl]amino}cyclopentyl]benzamide;
2-Fluoro-6-methoxy-N-[(1S,2S)-2-{[5-(trifluoromethyl)pyridin-2-yl]amino}cyclopentyl]benzamide;
2,6-Difluoro-N-[(1S,2S)-2-{[5-(trifluoromethyl)pyridin-2-yl]amino}cyclopentyl]benzamide;
N-[(1S,2S)-2-{Methyl[5-(trifluoromethyl)pyrazin-2-yl]amino}cyclopentyl]-2-(2H-1,2,3-triazol-2-yl)benzamide;
5-Fluoro-N-[(1S,2S)-2-{methyl[5-(trifluoromethyl)pyrazin-2-yl]amino}cyclopentyl]-2-(2H-1,2,3-triazol-2-yl)benzamide;
2-Fluoro-N-[(1S,2S)-2-{methyl[5-(trifluoromethyl)pyrazin-2-yl]amino}cyclopentyl]-6-(2H-1,2,3-triazol-2-yl)benzamide;
N-[(1S,2S)-2-{[3-Methyl-5-(trifluoromethyl)pyrazin-2-yl]amino}cyclopentyl]-3-(2H-1,2,3-triazol-2-yl)pyridine-2-carboxamide;
N-[(1S,2S)-2-Methyl-2-{[5-(trifluoromethyl)pyrazin-2-yl]amino}cyclopentyl]-3-(2H-1,2,3-triazol-2-yl)pyridine-2-carboxamide;
N-[(1S,2S)-2-{[3-Methyl-5-(trifluoromethyl)pyrazin-2-yl]amino}cyclopentyl]-2-(2H-1,2,3-triazol-2-yl)benzamide;
N-[(1S,2S)-2-{[3-Methyl-5-(trifluoromethyl)pyrazin-2-yl]amino}cyclopentyl]-2-(pyrimidin-2-yl)benzamide;
5-Fluoro-N-[(1S,2S)-2-{[3-methyl-5-(trifluoromethyl)pyrazin-2-yl]amino}cyclopentyl]-2-(pyrimidin-2-yl)benzamide;
N-[(1S,2S)-2-Methyl-2-{[5-(trifluoromethyl)pyrazin-2-yl]amino}cyclopentyl]-2-(2H-1,2,3-triazol-2-yl)benzamide;
N-(2-Methyl-2-{[5-(trifluoromethyl)pyrazin-2-yl]amino}cyclopentyl)-2-(2H-1,2,3-triazol-2-yl)benzamide;
N-[(1R,2R)-2-Methyl-2-{[5-(trifluoromethyl)pyrazin-2-yl]amino}cyclopentyl]-2-(2H-1,2,3-triazol-2-yl)benzamide;
5-Fluoro-N-[(1S,2S)-2-methyl-2-{[5-(trifluoromethyl)pyrazin-2-yl]amino}cyclopentyl]-2-(2H-1,2,3-triazol-2-yl)benzamide;
N-[(1S,2S)-2-Methyl-2-{[5-(trifluoromethyl)pyrazin-2-yl]amino}cyclopentyl]-3-(1H-pyrazol-1-yl)pyridine-2-carboxamide;
3-Ethoxy-N-[(1S,2S)-2-methyl-2-{[5-(trifluoromethyl)pyrazin-2-yl]amino}cyclopentyl]pyridine-2-carboxamide,
2-Chloro-N-[(1S,2S)-2-methyl-2-{[5-(trifluoromethyl)pyrazin-2-yl]amino}cyclopentyl]-6-(2H-1,2,3-triazol-2-yl)benzamide;
2,6-Difluoro-N-[(1S,2S)-2-methyl-2-{[5-(trifluoromethyl)pyrazin-2-yl]amino}cyclopentyl]benzamide;
3-Cyclopropyl-N-[(1S,2S)-2-methyl-2-{[5-(trifluoromethyl)pyrazin-2-yl]amino}cyclopentyl]pyridine-2-carboxamide;

N-[(1S,2S)-2-Methyl-2-{[5-(trifluoromethyl)pyrazin-2-yl]amino}cyclopentyl]-3-(trifluoromethoxy)pyridine-2-carboxamide;
N-[(1S,2S)-2-Methyl-2-{[5-(trifluoromethyl)pyrazin-2-yl]amino}cyclopentyl]-2-(pyrimidin-2-yl)benzamide;
5-Chloro-N-[(1S,2S)-2-methyl-2-{[5-(trifluoromethyl)pyrazin-2-yl]amino}cyclopentyl]-2-(2H-1,2,3-triazol-2-yl)benzamide;
N-(2-Methyl-2-{[5-(trifluoromethyl)pyrimidin-2-yl]amino}cyclopentyl)-2-(2H-1,2,3-triazol-2-yl)benzamide;
N-(2-Methyl-2-{[5-(trifluoromethyl)pyridin-2-yl]amino}cyclopentyl)-2-(2H-1,2,3-triazol-2-yl)benzamide;
N-(2-Methyl-2-{[5-(trifluoromethoxy)pyridin-2-yl]amino}cyclopentyl)-2-(2H-1,2,3-triazol-2-yl)benzamide;
5-Chloro-2-(2H-1,2,3-triazol-2-yl)-N-[(1S,2S)-2-{[5-(trifluoromethyl)pyridin-2-yl]amino}cyclopentyl]benzamide;
3-Fluoro-2-(2H-1,2,3-triazol-2-yl)-N-[(1S,2S)-2-{[5-(trifluoromethyl)pyridin-2-yl]amino}cyclopentyl]benzamide;
3,5-Difluoro-2-(2H-1,2,3-triazol-2-yl)-N-[(1S,2S)-2-{[5-(trifluoromethyl)pyridin-2-yl]amino}cyclopentyl]benzamide;
3-(2H-1,2,3-Triazol-2-yl)-N-[(1S,2S)-2-{[5-(trifluoromethyl)pyridin-2-yl]amino}cyclopentyl]pyridine-2-carboxamide;
3-(1H-Pyrazol-1-yl)-N-[(1S,2S)-2-{[5-(trifluoromethyl)pyridin-2-yl]amino}cyclopentyl]pyridine-2-carboxamide;
2-Fluoro-6-(2H-1,2,3-triazol-2-yl)-N-[(1S,2S)-2-{[5-(trifluoromethyl)pyridin-2-yl]amino}cyclopentyl]benzamide;
N-(2-{[3-Fluoro-5-(trifluoromethyl)pyridin-2-yl]amino}-2-methylcyclopentyl)-3-(2H-1,2,3-triazol-2-yl)pyridine-2-carboxamide;
N-[(1S,2S)-2-{[3-Fluoro-5-(trifluoromethyl)pyridin-2-yl]amino}cyclopentyl]-2-(2H-1,2,3-triazol-2-yl)benzamide;
N-[(1S,2S)-2-{[3-Chloro-5-(trifluoromethyl)pyridin-2-yl]amino}cyclopentyl]-2-(2H-1,2,3-triazol-2-yl)benzamide;
N-[(1S,2S)-2-{[3-Bromo-5-(trifluoromethyl)pyridin-2-yl]amino}cyclopentyl]-2-(2H-1,2,3-triazol-2-yl)benzamide;
N-[(1S,2S)-2-{[3-Methyl-5-(trifluoromethyl)pyridin-2-yl]amino}cyclopentyl]-2-(2H-1,2,3-triazol-2-yl)benzamide;
N-[(1S,2S)-2-{[3-Cyclopropyl-5-(trifluoromethyl)pyrazin-2-yl]amino}cyclopentyl]-2-(2H-1,2,3-triazol-2-yl)benzamide;
N-[(1S,2S)-2-{[3-(Propan-2-yl)-5-(trifluoromethyl)pyrazin-2-yl]amino}cyclopentyl]-2-(2H-1,2,3-triazol-2-yl)benzamide;
N-[(1S,2S)-2-{[3-Ethyl-5-(trifluoromethyl)pyrazin-2-yl]amino}cyclopentyl]-2-(2H-1,2,3-triazol-2-yl)benzamide;
N-[(1S,2S)-2-[(5-Cyclopropylpyrazin-2-yl)amino]cyclopentyl]-2-(2H-1,2,3-triazol-2-yl)benzamide;
N-[(1S,2S)-2-{[5-(Propan-2-yl)pyrazin-2-yl]amino}cyclopentyl]-2-(2H-1,2,3-triazol-2-yl)benzamide;
N-[(1S,2S)-2-[(5-Ethylpyrazin-2-yl)amino]cyclopentyl]-2-(2H-1,2,3-triazol-2-yl)benzamide;
2-(2H-1,2,3-Triazol-2-yl)-N-[(1S,2S)-2-{[5-(trifluoromethoxy)pyridin-2-yl]amino}cyclopentyl]benzamide;
5-Chloro-2-(2H-1,2,3-triazol-2-yl)-N-[(1S,2S)-2-{[5-(trifluoromethoxy)pyridin-2-yl]amino}cyclopentyl]benzamide;
N-[(1S,2S)-2-[(5-Bromopyridin-2-yl)amino]cyclopentyl]-2-(2H-1,2,3-triazol-2-yl)benzamide;
N-[(1S,2S)-2-[(5-Bromo-3-methoxypyridin-2-yl)amino]cyclopentyl]-2-(2H-1,2,3-triazol-2-yl)benzamide;
2-(2H-1,2,3-Triazol-2-yl)-N-[(1S,2S)-2-{[4-(trifluoromethyl)pyridin-2-yl]amino}cyclopentyl]benzamide;
N-[(1S,2S)-2-{[3-Chloro-5-(trifluoromethyl)pyridin-2-yl]amino}cyclopentyl]-3-(2H-1,2,3-triazol-2-yl)pyridine-2-carboxamide;
N-[(1S,2S)-2-{[3-Fluoro-5-(trifluoromethyl)pyridin-2-yl]amino}cyclopentyl]-3-(2H-1,2,3-triazol-2-yl)pyridine-2-carboxamide;
N-[(1S,2S)-2-{[3-Methyl-5-(trifluoromethyl)pyridin-2-yl]amino}cyclopentyl]-3-(2H-1,2,3-triazol-2-yl)pyridine-2-carboxamide;
N-[(1S,2S)-2-{[3-Ethyl-5-(trifluoromethyl)pyridin-2-yl]amino}cyclopentyl]-3-(2H-1,2,3-triazol-2-yl)pyridine-2-carboxamide;
N-(4,4-Difluoro-2-{[5-(trifluoromethyl)pyrazin-2-yl]amino}cyclopentyl)-2-(2H-1,2,3-triazol-2-yl)benzamide;
N-(4,4-Difluoro-2-{[5-(trifluoromethyl)pyrimidin-2-yl]amino}cyclopentyl)-2-(2H-1,2,3-triazol-2-yl)benzamide;
N-(4,4-Difluoro-2-{[5-(trifluoromethyl)pyridin-2-yl]amino}cyclopentyl)-2-(2H-1,2,3-triazol-2-yl)benzamide;
N-[(1S,2S)-4,4-Difluoro-2-{[5-(trifluoromethoxy)pyridin-2-yl]amino}cyclopentyl]-2-(2H-1,2,3-triazol-2-yl)benzamide;
N-[(1S,2S)-4,4-Difluoro-2-{[3-fluoro-5-(trifluoromethyl)pyridin-2-yl]amino}cyclopentyl]-2-(2H-1,2,3-triazol-2-yl)benzamide;
2-(5-Ethoxypyrimidin-2-yl)-N-[(1S,2S)-2-{[5-(trifluoromethyl)pyrazin-2-yl]amino}cyclopentyl]benzamide;
2-Fluoro-6-methoxy-N-[(1S,2S)-2-{[5-(trifluoromethyl)pyrazin-2-yl]amino}cyclopentyl]benzamide;
N-[(1S,2S)-2-{[3-Methyl-5-(trifluoromethyl)pyridin-2-yl]amino}cyclopentyl]-3-(pyrimidin-2-yl)pyridine-2-carboxamide;
N-[(1S,2S)-2-{[3-Fluoro-5-(trifluoromethyl)pyridin-2-yl]amino}cyclopentyl]-2-(pyrimidin-2-yl)benzamide;
5-Fluoro-N-[(1S,2S)-2-{[3-fluoro-5-(trifluoromethyl)pyridin-2-yl]amino}cyclopentyl]-2-(pyrimidin-2-yl)benzamide;
is N-[(1S,2S)-2-{[3-Fluoro-5-(trifluoromethyl)pyridin-2-yl]amino}cyclopentyl]-2-(3-methyl-1,2,4-oxadiazol-5-yl)benzamide;
2-(3-Methyl-1,2,4-oxadiazol-5-yl)-N-[(1S,2S)-2-{[3-methyl-5-(trifluoromethyl)pyrazin-2-yl]amino}cyclopentyl]benzamide;
N-[(1S,2S)-2-{[3-Cyclopropyl-5-(trifluoromethyl)pyrazin-2-yl]amino}cyclopentyl]-3-(2H-1,2,3-triazol-2-yl)pyridine-2-carboxamide;
N-[(1S,2S)-2-{[3-Cyclopropyl-5-(trifluoromethyl)pyrazin-2-yl]amino}cyclopentyl]-3-(pyrimidin-2-yl)pyridine-2-carboxamide;
N-[(1S,2S)-2-Methyl-2-{[5-(trifluoromethyl)pyrazin-2-yl]amino}cyclopentyl]-3-(pyrimidin-2-yl)pyridine-2-carboxamide;
2-(3-Methyl-1,2,4-oxadiazol-5-yl)-N-[(1S,2S)-2-methyl-2-{[5-(trifluoromethyl)pyrazin-2-yl]amino}cyclopentyl]benzamide;
N-(2-{[3-Fluoro-5-(trifluoromethyl)pyridin-2-yl]amino}-2-methylcyclopentyl)-3-(pyrimidin-2-yl)pyridine-2-carboxamide;
N-[(1S,2S)-2-{[3-Fluoro-5-(trifluoromethyl)pyridin-2-yl]amino}cyclopentyl]-3-(pyrimidin-2-yl)pyridine-2-carboxamide;
N-[(1S,2S)-2-{[3-Chloro-5-(trifluoromethyl)pyridin-2-yl]amino}cyclopentyl]-3-(pyrimidin-2-yl)pyridine-2-carboxamide;
N-[(1S,2S)-2-{[3-Ethyl-5-(trifluoromethyl)pyrazin-2-yl]amino}cyclopentyl]-2-(3-methyl-1,2,4-oxadiazol-5-yl)benzamide;
N-[(1S,2S)-2-{[3-Ethyl-5-(trifluoromethyl)pyrazin-2-yl]amino}cyclopentyl]-3-(pyrimidin-2-yl)pyridine-2-carboxamide;

N-[(1S,2S)-2-{[3-Ethyl-5-(trifluoromethyl)pyrazin-2-yl]
  amino}cyclopentyl]-2-(pyrimidin-2-yl)benzamide;

N-(2-Methyl-2-{[5-(trifluoromethyl)pyrimidin-2-yl]
  amino}cyclopentyl)-3-(pyrimidin-2-yl)pyridine-2-car-
  boxamide;

N-(2-Methyl-2-{[5-(trifluoromethyl)pyrimidin-2-yl]
  amino}cyclopentyl)-3-(2H-1,2,3-triazol-2-yl)pyridine-2-
  carboxamide;

N-(2-Methyl-2-{[5-(trifluoromethyl)pyridin-2-yl]
  amino}cyclopentyl)-3-(2H-1,2,3-triazol-2-yl)pyridine-2-
  carboxamide;

N-(2-Methyl-2-{[5-(trifluoromethyl)pyridin-2-yl]
  amino}cyclopentyl)-3-(pyrimidin-2-yl)pyridine-2-car-
  boxamide;

N-[(1S,2S)-2-{[5-(Difluoromethoxy)pyridin-2-yl]amino}-
  4,4-difluoro cyclopentyl]-2-(2H-1,2,3-triazol-2-yl)benza-
  mide;

N-[(1S,2S)-2-{[3-Ethyl-5-(trifluoromethyl)pyrazin-2-yl]
  amino}cyclopentyl]-5-fluoro-2-(pyrimidin-2-yl)benza-
  mide;

N-[(1S,2S)-2-{[3-Methyl-5-(trifluoromethyl)pyrazin-2-yl]
  amino}cyclopentyl]-3-(pyrimidin-2-yl)pyridine-2-car-
  boxamide;

2-(5-Methyl-1,3,4-oxadiazol-2-yl)-N-[(1S,2S)-2-methyl-2-
  {[5-(trifluoromethyl)pyrazin-2-yl]amino}cyclopentyl]
  benzamide;

enantiomers thereof and pharmaceutically acceptable salts of
any of the foregoing.

It should be noted that each of the chemical compounds listed above represents a particular and independent aspect of the invention.

The present invention further provides a process for the preparation of a compound of formula (I) or a pharmaceutically acceptable salt thereof as defined above which comprises (i) reacting a compound of formula

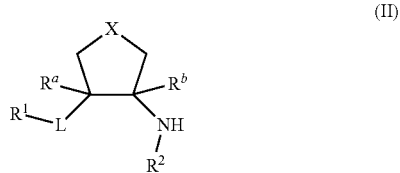

(II)

wherein L, X, $R^a$, $R^b$, $R^1$ and $R^2$ are as defined in formula (I), with a compound of formula

(III)

wherein $R^{20}$ represents a halogen atom (e.g. chlorine atom) or a hydroxyl group and $R^3$ is as defined in formula (I), or a salt (e.g. hydrochloride salt) thereof; or (ii) when L represents NH or N(CH$_3$), reacting a compound of formula

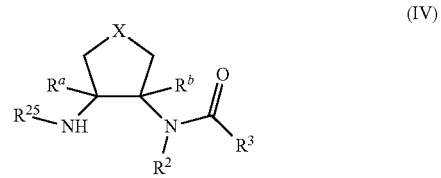

(IV)

wherein $R^{25}$ represents a hydrogen atom or methyl group and X, $R^a$, $R^b$, $R^2$ and $R^3$ are as defined in formula (I), with a compound of formula (V), $R^1$-LG$^1$, wherein LG$^1$ represents a leaving group (e.g. a halogen atom) and $R^1$ is as defined in formula (I);

and optionally thereafter carrying out one or more of the following procedures:

converting a compound of formula (I) into another compound of formula (I)

removing any protecting groups forming a pharmaceutically acceptable salt.

Process (i) may conveniently be carried out by combining the amine of formula (II) with an acid chloride of formula (III) in the presence of a base such as triethyl amine or DIPEA (N,N-diisopropylethylamine) in a solvent such as dichloromethane. Alternatively the reaction can be carried out from the amine of formula (II) and a carboxylic acid of formula (III) using any of the known coupling reagents such as EDC (1-ethyl-3-(3-dimethylaminopropyl)carbodiimide) and HOAt (7-aza-1-hydroxybenzotriazole), with or HATU (1-[bis(dimethylamino)methylene]-1H-1,2,3-triazolo[4,5-b]pyridinium 3-oxide hexafluorophosphate) with a base such as DIPEA. Another method is to activate the carboxylic acid to the corresponding acid chloride in situ for example with oxalyl chloride in the presence of a catalytic amount of DMF.

Process (ii) may conveniently be carried out by mixing the compound of formula (IV) with the compound of formula (V) in a solvent such as DMSO, acetonitrile or toluene and optionally in the presence of a base such as DIPEA, and heating conventionally or using microwave irradiation.

Compounds of formula (II) in which L represents CH$_2$, X represents CH$_2$ and $R^a$ and $R^b$ are each hydrogen may be prepared according to the scheme below. The heterocyclic bromomethylene compound is likely to be commercially available or can be prepared by bromination of the corresponding heterocyclic methyl compound using, for example, N-bromo succinimide and benzoyl peroxide in carbon tetrachloride at elevated temperature. Reaction of the heterocyclic bromomethylene compound with triphenylphosphine in toluene at raised temperature will afford the corresponding phosphonium bromide which on treatment with a base such as n-butyl lithium in the presence of the Boc-protected cyclic ketone will afford the corresponding alkene. The alkene can be reduced by hydrogenation using hydrogen gas in the presence of a catalyst such as palladium on carbon. Finally, the Boc protecting group can be removed using methods known to those skilled in the art, e.g. acid hydrolysis.

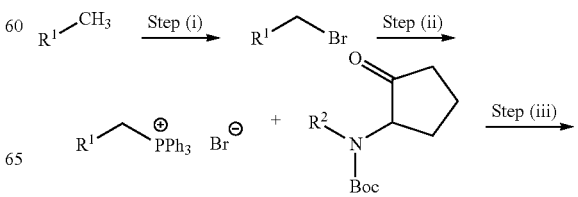

-continued

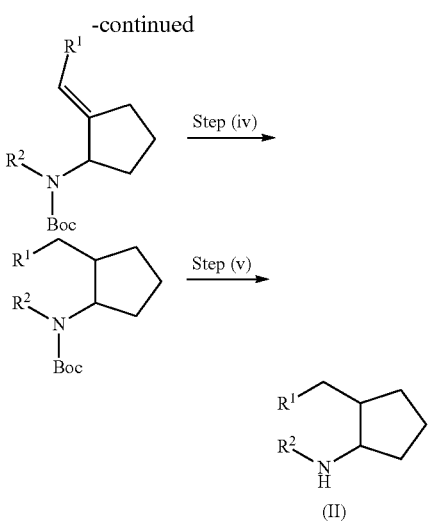

wherein L = CH₂
Boc = tert-butyloxycarbonyl

Compounds of formula (II) in which L represents an oxygen atom may be prepared by reacting a compound of formula

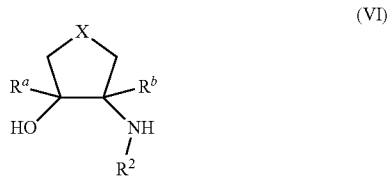

wherein X, $R^a$, $R^b$ and $R^2$ is as defined in formula (II), with a compound of formula (V) as defined above, in the presence of a base such as sodium hydride.

Compounds of formula (II) in which L represents NH or N(CH₃) may be prepared by reacting a compound of formula

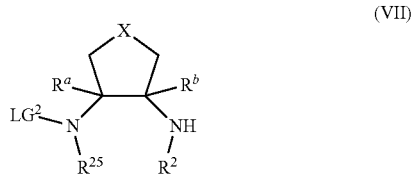

in which $LG^2$ represents a protecting group such as a tert-butyloxycarbonyl group, and X, $R^a$, $R^b$, $R^2$ and $R^{25}$ are as defined in formula (IV) above, with a compound of formula (V) as defined above.

Compounds of formula (IV) may be prepared by reacting a compound of formula (VII) with a compound of formula (III) followed by removal of the protecting group, $LG^2$, by acid treatment using, for example, an acid such as hydrochloric acid.

Compounds of formulae (III), (V), (VI) and (VII) are either commercially available, are well known in the literature or may be prepared using known techniques.

It will be appreciated by those skilled in the art that in the processes of the present invention certain functional groups such as phenol, hydroxyl or amino groups in the reagents may need to be protected by protecting groups. Thus, the preparation of the compounds of formula (I) may involve, at an appropriate stage, the introduction and/or removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 3$^{rd}$ edition, T. W. Greene and P. G. M. Wuts, Wiley-Interscience (1999).

The compounds of formula (I) above may be converted to a pharmaceutically acceptable salt thereof, preferably an acid addition salt such as a formate, hemi-formate, hydrochloride, hydrobromide, benzenesulphonate (besylate), saccharin (e.g. monosaccharin), trifluoroacetate, sulphate, nitrate, phosphate, acetate, fumarate, maleate, tartrate, lactate, citrate, pyruvate, succinate, valerate, propanoate, butanoate, malonate, oxalate, 1-hydroxy-2-napthoate (xinafoate), methanesulphonate or p-toluenesulphonate salt.

In one aspect of the invention, compounds of formula (I) may bear one or more radiolabels. Such radiolabels may be introduced by using radiolabel-containing reagents in the synthesis of the compounds of formula (I), or may be introduced by coupling the compounds of formula (I) to chelating moieties capable of binding to a radioactive metal atom. Such radiolabeled versions of the compounds may be used, for example, in diagnostic imaging studies.

Unless stated otherwise, any atom specified herein may also be an isotope of said atom. For example, the term "hydrogen" encompasses $^1H$, $^2H$ and $^3H$. Similarly carbon atoms are to be understood to include $^{12}C$, $^{13}C$ and $^{14}C$, nitrogen atoms are to be understood to include $^{14}N$ and $^{15}N$, and oxygen atoms are to be understood to include $^{16}O$, $^{17}O$ and $^{18}O$.

In a further aspect of the invention, compounds of formula (I) may be isotopically labelled. As used herein, an "isotopically labelled" compound is one in which the abundance of a particular nuclide at a particular atomic position within the molecule is increased above the level at which it occurs in nature.

Compounds of formula (I) and their salts may be in the form of hydrates or solvates which form an aspect of the present invention. Such solvates may be formed with common organic solvents, including but not limited to, alcoholic solvents e.g. methanol, ethanol or isopropanol.

Where compounds of formula (I) are capable of existing in stereoisomeric forms, it will be understood that the invention encompasses the use of all geometric and optical isomers (including atropisomers) of the compounds of formula (I) and mixtures thereof including racemates. The use of tautomers and mixtures thereof also forms an aspect of the present invention. Enantiomerically pure forms are particularly desired.

Compounds of formula (I) and their salts may be amorphous or in a polymorphic form or a mixture of any of these, each of which forms an aspect of the present invention.

The compounds of formula (I) and their pharmaceutically acceptable salts have activity as pharmaceuticals, in particular as orexin receptor antagonists, and may be used in the treatment of schizophrenia and other psychotic disorders (e.g., psychotic disorder, psychosis or schizoaffective disorder); dementia and other cognitive disorders; anxiety disorders (e.g., generalized anxiety disorder, post-traumatic stress disorder, panic disorders, acute stress disorder, social anxiety disorder, phobias including agoraphobia, obsessive compulsive disorder, trichlofillomania or body dismorphic disorder); mood disorders (e.g., depressive disorders, major depressive disorders, bipolar disorders including bipolar I and II, bipolar mania, bipolar depression); addiction including substance dependence (e.g. cocaine, opiates, *cannabis* or prescription drug dependence), alcohol dependence, nicotine dependence or gambling disorder; eating disorders (e.g. binge eating, bulimia nervosa, anorexia nervosa or obesity); sleep disorders (e.g. rapid eye movement sleep disorder); disorders usually first diagnosed in infancy, childhood, or adolescence (e.g., attention-deficit disorder, autistic spectrum disorders, Rett syndrome, Fragile X syndrome, Asperger syndrome and disruptive behaviour disorders); restless leg syndrome; pain (e.g. neuropathic pain including chemotherapy induced pain or migraine); and neurodegenerative disorders (e.g. Parkinson's or Alzheimer's disease).

Thus, the present invention provides a compound of formula (I) or a pharmaceutically acceptable salt thereof as hereinbefore defined for use in therapy, in particular for the treatment of conditions whose development or symptoms are linked to orexin receptor activity.

The present invention also provides the use of a compound of formula (I) or a pharmaceutically acceptable salt thereof as hereinbefore defined for the preparation of a medicament for the treatment of conditions whose development or symptoms are linked to orexin receptor activity.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disorder or condition in question. Persons at risk of developing a particular disorder or condition generally include those having a family history of the disorder or condition, or those who have been identified by genetic testing or screening to be particularly susceptible to developing the disorder or condition or those in the prodromal phase of a disorder.

In particular, the compounds of the invention (including pharmaceutically acceptable salts) may be used in the treatment of the positive symptoms of schizophrenia, schizophreniform disorder or schizoaffective disorder (e.g. voices or hallucinations), cognitive disorders (such as dementia and impaired learning), anxiety disorders (such as post-traumatic stress disorder or panic disorders), or addiction.

The invention also provides a method of treating at least one symptom or condition associated with schizophrenia and other psychotic disorders (e.g., psychotic disorder, psychosis or schizoaffective disorder); dementia and other cognitive disorders; anxiety disorders (e.g., generalized anxiety disorder, post-traumatic stress disorder, panic disorders, acute stress disorder, social anxiety disorder, phobias including agoraphobia, obsessive compulsive disorder, trichlofillomania or body dismorphic disorder); mood disorders (e.g., depressive disorders, major depressive disorders, bipolar disorders including bipolar I and II, bipolar mania, bipolar depression); addiction including substance dependence (e.g. cocaine, opiates, *cannabis* or prescription drug dependence), alcohol dependence, nicotine dependence or gambling disorder; eating disorders (e.g. binge eating, bulimia nervosa, anorexia nervosa or obesity); sleep disorders (e.g. rapid eye movement sleep disorder); disorders usually first diagnosed in infancy, childhood, or adolescence (e.g., attention-deficit disorder, autistic spectrum disorders, Rett syndrome, Fragile X syndrome, Asperger syndrome and disruptive behaviour disorders); restless leg syndrome; pain (e.g. neuropathic pain including chemotherapy induced pain or migraine); and neurodegenerative disorders (e.g. Parkinson's or Alzheimer's disease) which comprises administering to a patient in need thereof a therapeutically effective amount of a compound of formula (I) or a pharmaceutically acceptable salt thereof as hereinbefore defined.

Such symptoms and conditions include, but are not limited to, anxiety, agitation, hostility, panic, an eating disorder, an affective symptom, a mood symptom, a negative and positive psychotic symptom commonly associated with psychosis and neurodegenerative disorder.

For the above-mentioned therapeutic uses the dosage administered will, of course, vary with the compound employed, the mode of administration, the treatment desired and the disorder indicated. For example, the daily dosage of the compound of the invention, if inhaled, may be in the range from 0.05 micrograms per kilogram body weight (μg/kg) to 100 micrograms per kilogram body weight (μg/kg). Alternatively, if the compound is administered orally, then the daily dosage of the compound of the invention may be in the range from 0.01 micrograms per kilogram body weight (μg/kg) to 100 milligrams per kilogram body weight (mg/kg).

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier.

Therefore the present invention further provides a pharmaceutical composition comprising a compound of formula (I) or a pharmaceutically acceptable salt thereof as hereinbefore defined, in association with a pharmaceutically acceptable adjuvant, diluent or carrier.

The invention still further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

Conventional procedures for the selection and preparation of suitable pharmaceutical formulations are described in, for example, "Pharmaceutics—The Science of Dosage Form Design", M. E. Aulton, Churchill Livingstone, 1988.

Pharmaceutically acceptable adjuvants, diluents or carriers that may be used in the pharmaceutical compositions of the invention are those conventionally employed in the field of pharmaceutical formulation, and include, but are not limited to, sugars, sugar alcohols, starches, ion exchangers, alumina, aluminium stearate, lecithin, serum proteins such as human serum albumin, buffer substances such as phosphates, glycerine, sorbic acid, potassium sorbate, partial glyceride mixtures of saturated vegetable fatty acids, water, salts or electrolytes such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the present invention may be administered orally, parenterally, by inhalation spray, rectally, nasally, buccally, vaginally or via an implanted reservoir. Oral administration is preferred. The pharmaceutical compositions of the invention may contain any conventional non-toxic pharmaceutically acceptable adjuvants, diluents or carriers. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. The suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable diluents and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant.

The pharmaceutical compositions of this invention may be orally administered in any orally acceptable dosage form including, but not limited to, capsules, tablets, powders, granules, and aqueous suspensions and solutions. These dosage forms are prepared according to techniques well-known in the art of pharmaceutical formulation. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added.

The pharmaceutical compositions of the invention may also be administered in the form of suppositories for rectal administration. These compositions can be prepared by mixing the active ingredient with a suitable non-irritating excipient which is solid at room temperature but liquid at the rectal temperature and therefore will melt in the rectum to release the active ingredient. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilising or dispersing agents known in the art.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The compounds of the invention (that is, compounds of formula (I) and pharmaceutically acceptable salts thereof) may also be administered in conjunction with other compounds used for the treatment of the above conditions.

The invention therefore further relates to combination therapies wherein a compound of the invention or a pharmaceutical composition or formulation comprising a compound of the invention is administered with another therapeutic agent or agents for the treatment of one or more of the conditions previously indicated. Such therapeutic agents may be selected from the following:

(i) antidepressants such as, for example, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, reboxetine, robaizotan, sertraline, sibutramine, tianeptine, thionisoxetine, tranylcypromaine, trazodone, trimipramine, venlafaxine, vortioxetine and equivalents and pharmaceutically active isomer(s) and/or metabolite(s) thereof;

(ii) antipsychotics including, for example, amisulpride, aripiprazole, asenapine, benzisoxidil, bifeprunox, brexpiprazole, carbamazepine, cariprazine, clozapine, chlorpromazine, debenzapine, divalproex, duloxetine, eszopiclone, haloperidol, iloperidone, lamotrigine, loxapine, lurasidone, mesoridazine, olanzapine, paliperidone, perlapine, perphenazine, phenothiazine, phenylbutlypiperidine, pimozide, prochlorperazine, quetiapine, risperidone, sertindole, sulpiride, suproclone, suriclone, thioridazine, trifluoperazine, trimetozine, valproate, valproic acid, zopiclone, zotepine, zicronapine, ziprasidone, and equivalents and pharmaceutically active isomer(s) and/or metabolite(s) thereof;

(iii) anxiolytics including, for example, alnespirone, azapirones, benzodiazepines, barbiturates, and equivalents and pharmaceutically active isomer(s) and/or metabolite(s) thereof. Example anxiolytics include adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, and zolazepam; and equivalents and pharmaceutically active isomer(s) and/or metabolite(s) thereof;

(iv) anticonvulsants including, for example, carbamazepine, valproate, lamotrigine, levetiracetam and gabapentin, and equivalents and pharmaceutically active isomer(s) and/or metabolite(s) thereof;

(v) Alzheimer's therapies including, for example, donepezil, galantamine, memantine, rivastigmine, tacrine, and equivalents and pharmaceutically active isomer(s) and/or metabolite(s) thereof;

(vi) Parkinson's therapies including, for example, L-dopa, ropinirole, pramipexole, monoamine oxidase type B (MAO-B) inhibitors such as deprenyl, selegiline and rasagiline, catechol-O-methyl transferase (COMT) inhibitors such as entacapone or tolcapone, adenosine A-2 inhibitors, dopamine re-uptake inhibitors, NMDA antagonists, Nicotine agonists, and Dopamine agonists and inhibitors of neuronal nitric oxide synthase, and equivalents and pharmaceutically active isomer(s) and/or metabolite(s) thereof;

(vii) migraine therapies including, for example, almotriptan, amantadine, botulinum toxin A, bromocriptine, butalbital, cabergoline, dichloralphenazone, dihydroergotamine, eletriptan, frovatriptan, lisuride, naratriptan, pergolide, pramipexole, rizatriptan, ropinirole, sumatriptan, topiramate, zolmitriptan, and zomitriptan, and equivalents and pharmaceutically active isomer(s) and/or metabolite(s) thereof;

(viii) stroke therapies including, for example, abciximab, activase, citicoline, desmoteplase, and equivalents and pharmaceutically active isomer(s) and/or metabolite(s) thereof;

(ix) urinary incontinence therapies including, for example, darafenacin, duloxetine, falvoxate, mirabegron, oxybutynin, propiverine, robalzotan, solifenacin, and tolterodine, and equivalents and pharmaceutically active isomer(s) and/or metabolite(s) thereof;

(x) neuropathic pain therapies including, for example, capsaicin, gabapentin, lidoderm, and pregabalin, and equivalents and pharmaceutically active isomer(s) and/or metabolite(s) thereof;

(xi) nociceptive pain therapies such as, for example, celecoxib, etoricoxib, lumiracoxib, rofecoxib, valdecoxib, diclofenac, loxoprofen, naproxen, and paracetamol, and equivalents and pharmaceutically active isomer(s) and/or metabolite(s) thereof;

(xii) insomnia therapies including, for example, allobarbital, alonimid, amobarbital, benzoctamine, butabarbital, capuride, chloral, cloperidone, clorethate, dexclamol, ethchlorvynol, eszopiclone, etomidate, glutethimide, halazepam, hydroxyzine, lorediplon, mecloqualone, melatonin, mephobarbital, methaqualone, midaflur, nisobamate, pentobarbital, phenobarbital, propofol, ralmeteon, roletamide, suvorexant, triclofos, secobarbital, zaleplon, and zolpidem, zopiclone and equivalents and pharmaceutically active isomer(s) and/or metabolite(s) thereof;

(xiii) mood stabilizers including, for example, carbamazepine, divalproex, gabapentin, lamotrigine, lithium, olanzapine, quetiapine, valproate, valproic acid, and verapamil, and equivalents and pharmaceutically active isomer(s) and/or metabolite(s) thereof;

(xiv) 5HT1B ligands such as, for example, compounds disclosed in WO 99/05134 and WO 02/08212;

(xv) mGluR2 agonists;

(xvi) alpha 7 nicotinic agonists such as, for example, compounds disclosed in WO 96/006098, WO 97/030998, WO 99/003859, WO 00/042044, WO 01/029034, WO 01/60821, WO 01/36417, WO 02/096912, WO 03/087102, WO 03/087103, WO 03/087104, WO 2004/016617, WO 2004/016616, and WO 2004/019947;

(xvii) chemokine receptor CCR1 inhibitors; and (xviii) delta opioid agonists such as, for example, compounds disclosed in WO 97/23466 and WO 02/094794.

Such combination products employ the compounds of this invention within the dosage range described herein and the other pharmaceutically active agent within approved dosage ranges and/or the dosage such as described in the publication reference.

In a further aspect the present invention provides a combination (for example for the treatment of schizophrenia, cognitive disorders or pain) of a compound of formula (I) or a pharmaceutically acceptable salt thereof as hereinbefore defined and one or more agents selected from carbamazepine, olanzapine, quetiapine, verapamil, lamotrigine, oxcarbazepine, risperidone, aripiprazole, ziprasidone and lithium.

The invention also provides a pharmaceutical product comprising, in combination, a preparation of a first active ingredient which is a compound of formula (I) or a pharmaceutically acceptable salt thereof as hereinbefore defined, and a preparation of a second active ingredient which is carbamazepine, olanzapine, quetiapine, verapamil, lamotrigine, oxcarbazepine, risperidone, aripiprazole, ziprasidone or lithium, for simultaneous, sequential or separate use in therapy.

In another aspect, the invention provides a kit comprising a preparation of a first active ingredient which is a compound of formula (I) or a pharmaceutically acceptable salt thereof as hereinbefore defined, and a preparation of a second active ingredient which is carbamazepine, olanzapine, quetiapine, verapamil, lamotrigine, oxcarbazepine, risperidone, aripiprazole, ziprasidone or lithium, and instructions for the simultaneous, sequential or separate administration of the preparations to a patient in need thereof.

The present invention will now be further explained by reference to the following illustrative examples.

The methods used for synthesis of the compounds of the invention are illustrated by the general schemes below and the preparative examples that follow. The starting materials and reagents used in preparing these compounds are available from commercial suppliers. These general schemes are merely illustrative of methods by which the compounds of this invention can be synthesised, and various modifications to these schemes can be made and will be suggested to one skilled in the art having referred to this disclosure.

Nuclear magnetic resonance (NMR) spectra were recorded at 400 MHz; the chemical shifts ($\delta$) are reported in parts per million. Spectra were recorded using a Bruker 400 Avance instrument fitted with a 5 mm BBFO probe or DUL probe. Instrument control was by Bruker TopSpin 2.1 software, unless stated otherwise.

Purity was assessed using UPLC with UV (photodiode array) detection over a wide range of wavelengths, normally 220-450 nm, using a Waters Acquity UPLC system equipped with Acquity UPLC BEH or HSS C18 columns (2.1 mm id×50 mm long) operated at 50 or 60° C. Mobile phases typically consisted of acetonitrile or methanol mixed with water containing either 0.05% formic acid or 0.025% ammonia.

Mass spectra were recorded with a Waters SQD single quadrupole mass spectrometer using atmospheric pressure ionisation, unless stated otherwise.

Compounds were purified using normal phase chromatography on silica or alumina, or by reverse phase chromatographic methods, using Biotage or Isolute KPNH Cartridge, SCX cartridge and SCX-2 solid phase extraction cartridges.

Preparative High Performance Liquid Chromatography (HPLC) was performed using an Agilent Technologies 1100 Series system or Waters autopurification system typically using Waters 19 mm id×100 mm or 19 mm id×250 mm C18 columns such as)(Bridge or SunFire 5 µm materials at 20 mL/min. Mobile phases typically consisted of acetonitrile or methanol mixed with water containing either 0.1% formic acid or 0.1% ammonia, unless stated otherwise.

In the following descriptions "room temperature" denotes a temperature in the range from 20° C. to 25° C.

The abbreviations used in the specific examples have the following meanings:

Aza-HOBt (HOAt)=7-Aza-1-hydroxybenzotriazole

BINAP=2,2'-bis(Diphenylphosphino)-1,1'-binaphthyl

Boc=tert-Butyloxycarbonyl

DCM=Dichloromethane

DIAD=Diisopropyl azodicarboxylate

DIPEA=N,N-Diisopropylethylamine

DMF=N,N-Dimethylformamide

DMSO=Dimethyl sulfoxide

EDC=1-Ethyl-3-(3-dimethylaminopropyl)carbodiimide

HATU=1-[Bis(dimethylamino)methylene]-1H-1,2,3-triazolo[4,5-b]pyridinium 3-oxid hexafluorophosphate IPA=propan-2-ol LiHMDS=Lithium bis(trimethylsilyl)amine MTBE=2-methoxy-2-methylpropane NMP=N-Methyl-2-pyrrolidone TBTU=O-(Benzotriazol-1-yl)-N,N,N',N'-tetramethyluronium tetrafluoroborate TOTU=[Bis(dimethylamino)methylene][(Z)-(1-cyano-2-ethoxy-2-oxoethylidene)amino]oxonium tetrafluoroborate 1. Intermediates Intermediate 1: (1S,2S)-1-N-[5-(Trifluoromethyl)pyridin-2-yl]cyclopentane-1,2-diamine hydrochloride

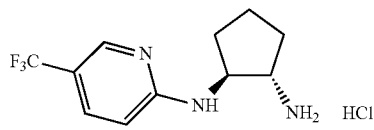 [SMILES: N[C@H]1CCC[C@@H]1Nc1ccc(C(F)(F)F)cn1 ; Cl]

A microwave vial was charged with tert-butyl N-[(1S,2S)-2-aminocyclopentyl]carbamate (CAS number 586961-34-4; 1.0 g, 4.99 mmol), 2-chloro-5-(trifluoromethyl)pyridine (CAS number 52334-81-3; 0.997 g, 5.49 mmol), DIPEA (2.62 ml, 14.98 mmol) and DMSO (16.6 ml). The reaction was heated with microwave irradiation at 140° C. for 2 hours and then partitioned between ethyl acetate and water. The organics were washed with water and brine, dried over magnesium sulfate, filtered and concentrated in vacuo. This was then purified by column chromatography (silica, 0-50% ethyl acetate/petrol) to afford a cream solid to which was then added methanol (10 ml) and HCl in 1,4-dioxane (4M, 6.24 ml, 24.97 mmol) and the reaction was stirred at room temperature for 17 hours. The reaction mixture was concentrated in vacuo and azeotropically distilled with toluene to afford the title compound.

$^1$H NMR (DMSO-$d_6$) δ ppm 1.56-1.83 (m, 4H), 2.02-2.22 (m, 2H), 3.25-3.35 (m, 1H), 4.06-4.18 (m, 1H), 6.68-6.72 (m, 1H), 7.65-7.82 (m, 2H), 8.18 (br. s., 2H), 8.37 (br. s., 1H).
MS ES$^+$: 246

Intermediate 2: N-[(1S,2S)-2-Aminocyclopentyl]-2-(3-methyl-1,2,4-oxadiazol-5-yl)benzamide hydrochloride

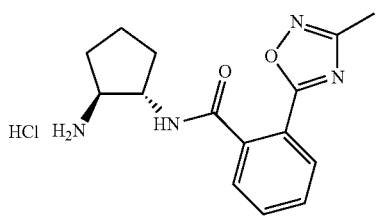 [SMILES: Cl ; Cc1noc(-c2ccccc2C(=O)N[C@H]2CCC[C@@H]2N)n1]

A mixture of 2-(3-methyl-1,2,4-oxadiazol-5-yl)benzoic acid (CAS number 475105-77-2; 0.84 g, 4.12 mmol), tert-butyl N-[(1S,2S)-2-aminocyclopentyl]carbamate (CAS number 586961-34-4; 0.75 g, 3.74 mmol), HATU (2.14 g, 5.62 mmol) and triethylamine (1.57 ml, 11.23 mmol) was stirred in dry DMF (12.5 ml) at room temperature for 17 hours. The reaction mixture was partitioned between ethyl acetate and water, washed with water and brine, dried over magnesium sulfate, filtered and concentrated in vacuo. The crude material was then purified by column chromatography (silica, 0-100% ethyl acetate/petrol). The resulting cream solid was recrystalised from ethyl acetate, to which was then added methanol (10 ml) and HCl in 1,4-dioxane (4M, 4.68 ml, 18.72 mmol) and the reaction was stirred at room temperature for 17 hours. The reaction was concentrated in vacuo and azeotropically distilled with toluene to afford the title compound.

$^1$H NMR (DMSO-$d_6$) δ ppm 1.56-1.82 (m, 4H), 1.94-2.04 (m, 2H), 2.42 (s, 3H), 3.35-3.43 (m, 1H), 4.10-4.26 (m, 1H), 7.12-7.28 (m, 1H), 7.63-7.80 (m, 2H), 7.94-8.00 (m, 1H), 8.08-8.25 (br. s., 2H) and 8.75-8.80 (m, 1H).
MS ES$^+$: 287

Intermediate 3: N-[(1S,2R)-2-Aminocyclopentyl]-2,6-dimethoxybenzamide hydrochloride

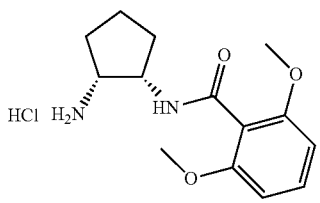 [SMILES: Cl ; COc1cccc(OC)c1C(=O)N[C@H]1CCC[C@H]1N]

To a solution of tert-butyl N-[(1R,2S)-2-aminocyclopentyl]carbamate (CAS number 721395-15-9; 0.50 g, 2.50 mmol) in dry DCM (8.3 ml) was added DIPEA (1.3 ml, 7.49 mmol) and 2,6-dimethoxybenzoyl chloride (CAS number 1989-53-3; 0.75 g, 3.74 mmol). The reaction was stirred at room temperature under an atmosphere of nitrogen for 17 hours and then partitioned between DCM and water, filtered through a hydrophobic frit and concentrated in vacuo. This was purified by column chromatography (silica, 50-100% ethyl acetate/petrol). To the resulting solid was then added 1,4-dioxane (2 ml) and HCl in 1,4-dioxane (4M, 2 ml) and the reaction was stirred at room temperature for 2 hours and then concentrated in vacuo, and azeotropically distilled with toluene to afford the title compound.
MS ES$^+$: 265

Intermediate 4: N-[(1S,2S)-2-Aminocyclopentyl]-2-(2H-1,2,3-triazol-2-yl)benzamide hydrochloride

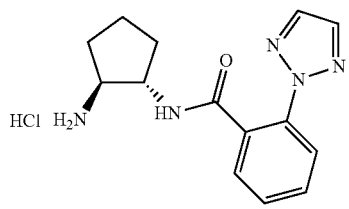 [SMILES: Cl ; N[C@H]1CCC[C@@H]1NC(=O)c1ccccc1-n1nccn1]

Prepared according to the procedure for N-[(1S,2S)-2-aminocyclopentyl]-2-(3-methyl-1,2,4-oxadiazol-5-yl)benzamide hydrochloride (Intermediate 2) from tert-butyl N-[(1S,2S)-2-aminocyclopentyl]carbamate (CAS number 586961-34-4; 1.58 g, 7.94 mmol) and 2-(2H-1,2,3-triazol-2-yl)benzoic acid (CAS number 1001401-62-2; 1.64 g, 8.68 mmol) to afford the title compound.

$^1$H NMR (DMSO-$d_6$) δ ppm 1.48-1.79 (m, 4H), 1.93-2.10 (m, 2H), 3.36-3.42 (m, 1H), 4.06-4.14 (m, 1H), 7.49-7.61 (m, 1H), 7.62-7.69 (m, 2H), 7.81-7.86 (m, 1H), 8.08 (br. s., 2H), 8.18 (br. s., 2H) and 8.62-8.68 (m, 1H).
MS ES$^+$: 272

Intermediate 5: N-[(1S,2S)-2-Aminocyclopentyl]-2,6-dimethoxybenzamide hydrochloride

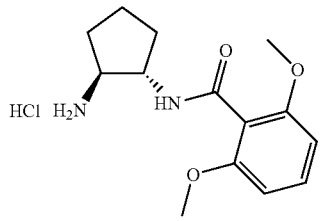 [SMILES: Cl ; COc1cccc(OC)c1C(=O)N[C@H]1CCC[C@@H]1N]

Prepared according to the procedure for N-[(1S,2R)-2-aminocyclopentyl]-2,6-dimethoxybenzamide hydrochloride (Intermediate 3) from tert-butyl N-[(1S,2S)-2-aminocyclopentyl]carbamate (CAS number 586961-34-4; 1.0 g, 4.99 mmol) and 2,6-dimethoxybenzoyl chloride (CAS number 1989-53-3; 1.50 g, 7.99 mmol) except that after the reaction was complete it was partitioned between DCM and a saturated solution of sodium bicarbonate, filtered through a hydrophobic frit and concentrated in vacuo. The Boc protected intermediate was purified by column chromatography (silica, 0-100% ethyl acetate/petrol) to give a white solid. After deprotection with HCl in 1,4-dioxane, azeotropic distillation from toluene afforded the title compound.

MS ES+: 265

Intermediate 6: 5-Methyl-2-(2H-1,2,3-triazol-2-yl)benzoic acid

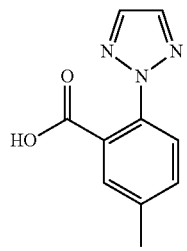

To a solution of 2H-1,2,3-triazole (CAS number 288-36-8; 1.99 g, 28.93 mmol) in DMF (7.0 ml) at 0-10° C. was added cesium carbonate (4.7 g, 14.45 mmol), trans-1-N,2-N-dimethylcyclohexane-1,2-diamine (0.127 g, 1.45 mmol), copper (I) iodide (0.068 g, 0.36 mmol) and 2-iodo-5-methylbenzoic acid (CAS number 52548-14-8; 3.79 g, 14.46 mmol). The reaction was subjected to microwave irradiation at 125° C. for 15 minutes, and then poured into water (20 ml) and extracted with ethyl acetate. The combined organics were washed with brine, dried over sodium sulfate and concentrated in vacuo. The crude product was purified by column chromatography (0-3% methanol/DCM) to afford the title compound.

$^1$H NMR (DMSO-d$_6$) δ ppm 2.42 (s, 3H), 7.49-7.52 (m, 1H), 7.58-7.64 (m, 2H), 8.05 (s, 2H), 13.01 (s, 1H).

MS ES+: 204

Intermediate 7: N-[(1S,2S)-2-Aminocyclopentyl]-5-methyl-2-(2H-1,2,3-triazol-2-yl)benzamide hydrochloride

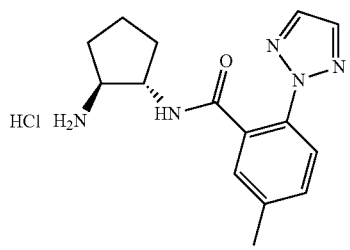 [SMILES: Cl ; Cc1ccc(-n2nccn2)c(C(=O)N[C@H]2CCC[C@@H]2N)c1]

To a solution of 5-methyl-2-(2H-1,2,3-triazol-2-yl)benzoic acid (Intermediate 6; 254 mg, 1.25 mmol) in dry DCM (4.16 ml) was added EDC (359 mg, 1.87 mmol), 3H-[1,2,3]triazolo[4,5-b]pyridin-3-ol (255 mg, 1.87 mmol), triethylamine (6.9 ml, 4.99 mmol) and tert-butyl N-[(1S,2S)-2-aminocyclopentyl]carbamate (CAS number 586961-34-4; 250 mg, 1.25 mmol). The solution was stirred at room temperature under an atmosphere of nitrogen for 72 hours and then partitioned between DCM and water, filtered through a hydrophobic frit and concentrated in vacuo. This was then purified by column chromatography (silica, 0-100% ethyl acetate/petrol) to afford a pale white solid. This Boc protected intermediate was dissolved in HCl in 1,4-dioxane (4M, 3 ml) and stirred at room temperature for 17 hours. The reaction was concentrated in vacuo and azeotropically distilled with toluene to afford the title compound.

MS ES+: 285

Intermediates 8 and 9: 5-Fluoro-2-(2H-1,2,3-triazol-2-yl)benzoic acid (Intermediate 8) and 5-Fluoro-2-(1H-1,2,3-triazol-1-yl)benzoic acid (Intermediate 9)

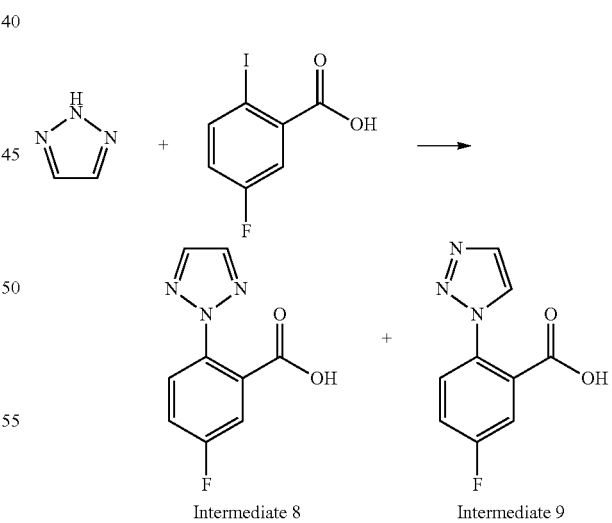

To a solution of 2H-1,2,3-triazole (CAS number 288-36-8; 4.0 g, 57.97 mmol) in DMF (14.0 ml) was added cesium carbonate (18.84 g, 57.97 mmol), trans-1-N,2-N-dimethylcyclohexane-1,2-diamine (0.510 g, 5.797 mmol), copper(I) iodide (0.276 g, 1.449 mmol) and 5-fluoro-2-iodobenzoic acid (CAS number 52548-63-7; 7.71 g, 28.98 mmol) at 0-10° C. The resulting reaction mixture was then heated with microwave irradiation at 125° C. for 15 hours with stirring. The reaction mass was poured into water and the product was extracted into ethyl acetate. The combined organic layers were washed with brine, dried over sodium sulfate and concentrated in vacuo. This was then purified by column chromatography (silica, 0-3% methanol/DCM) to obtain 5-fluoro-2-(2H-1,2,3-triazol-2-yl)benzoic acid (Intermediate 8) (also commercially available CAS number 1186050-64-5) and crude 5-fluoro-2-(1H-1,2,3-triazol-1-yl)benzoic acid (Intermediate 9).

The crude compound (Intermediate 9) obtained was further purified by column chromatography (silica, 0-3% methanol/DCM) and then by reverse phase preparative HPLC (eluted with acetonitrile/water with 0.1% ammonia) to afford the title compound.

Intermediate 9

$^1$H NMR (DMSO-d$_6$) δ ppm 7.41-7.45 (m, 1H), 7.50-7.52 (m, 1H), 7.57-7.60 (m, 1H), 7.83-7.84 (m, 1H), 8.42 (s, 1H).
MS ES$^+$: 208

Intermediates 10: N-[(1S,2R)-2-Hydroxycyclopentyl]-2-(2H-1,2,3-triazol-2-yl)benzamide

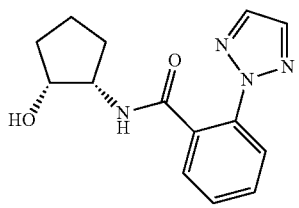 [SMILES: O=C(N[C@H]1CCC[C@H]1O)c1ccccc1-n1nccn1]

Triethylamine (1.52 ml, 10.90 mmol), 3H-[1,2,3]triazolo[4,5-b]pyridin-3-ol (0.59 g, 4.36 mmol) and EDC (0.84 g, 4.36 mmol) were added to a solution of (1R,2S)-2-aminocyclopentan-1-ol hydrochloride (CAS number 137254-03-6; 0.50 g, 3.63 mmol) and 2-(2H-1,2,3-triazol-2-yl)benzoic acid (CAS number 1001401-62-2; 0.76 g, 4.00 mmol) in DCM (10 ml). The reaction was stirred at room temperature for 18 hours and then diluted with DCM (50 ml) and washed with a saturated solution of sodium bicarbonate (2×20 ml). The crude product was purified by column chromatography (silica, 0-100% ethyl acetate/petrol) to afford the title compound.

$^1$H NMR (400 MHz, DMSO-d$_6$) δ ppm 1.36-1.59 (m, 3H), 1.62-1.88 (m, 3H), 3.79-3.93 (m, 1H), 3.94-4.10 (m, 1H), 4.29-4.39 (m, 1H), 7.49-7.58 (m, 1H), 7.58-7.67 (m, 2H), 7.71-7.82 (m, 2H), 8.05 (s, 2H)
MS ES$^+$: 273

Intermediates 11: N-[(1S,2S)-2-Hydroxycyclopentyl]-2-(2H-1,2,3-triazol-2-yl)benzamide

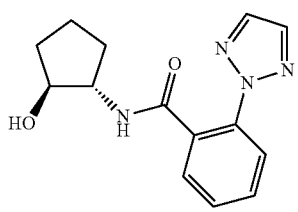 [SMILES: O=C(N[C@H]1CCC[C@@H]1O)c1ccccc1-n1nccn1]

Prepared according to the procedure for N-[(1S,2R)-2-hydroxycyclopentyl]-2-(2H-1,2,3-triazol-2-yl)benzamide (Intermediate 10) from 2-(2H-1,2,3-triazol-2-yl)benzoic acid (CAS number 1001401-62-2; 531 mg, 2.81 mmol), (1S,2S)-2-aminocyclopentan-1-ol hydrochloride (CAS number 68327-04-8; 368 mg, 2.67 mmol) and DIPEA (1401 μl, 8.02 mmol) to afford the title compound.

$^1$H NMR (400 MHz, DMSO-d$_6$) δ ppm 1.33-1.48 (m, 2H), 1.49-1.79 (m, 3H), 1.83-1.97 (m, 1H), 3.80-3.88 (m, 1H), 3.89-3.98 (m, 1H), 4.57-4.67 (m, 1H), 7.43-7.55 (m, 2H), 7.56-7.67 (m, 1H), 7.73-7.83 (m, 1H), 8.03 (s, 2H), 8.09-8.23 (m, 1H)

MS ES$^+$: 273

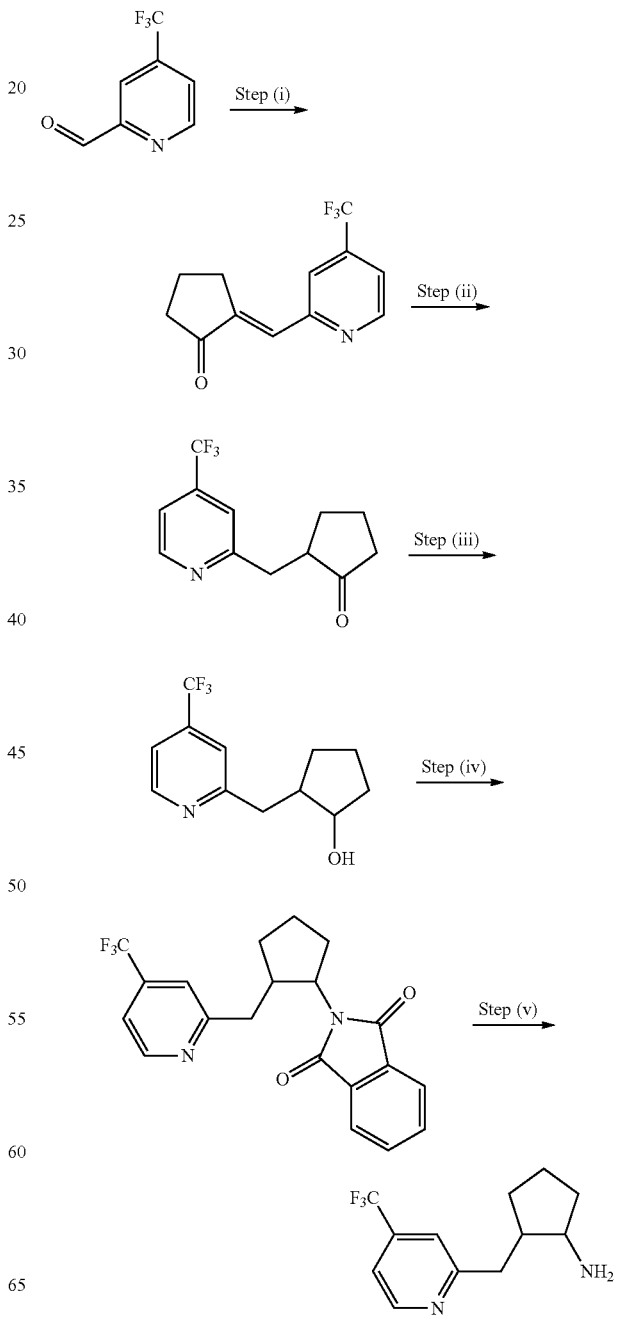

Intermediate 12: 2-{[4-(Trifluoromethyl)pyridin-2-yl]methyl}cyclopentan-1-amine

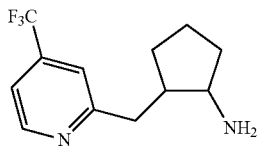

Step (i): 2-{[4-(Trifluoromethyl)pyridin-2-yl]methylidene}cyclopentan-1-one A solution of 4-(trifluoromethyl)pyridine-2-carbaldehyde (CAS number 132470-83-8; 1.00 g, 5.71 mmol) and 4-(cyclopent-1-en-1-yl)morpholine (CAS number 936-52-7; 0.90 ml, 5.60 mmol) in toluene (15 ml) was heated at 90° C. for 18 hours. The reaction was then cooled to room temperature and concentrated HCl (2 ml) and water (2 ml) was added drop wise. The reaction was stirred at room temperature for 20 minutes and then neutralised with a saturated solution of sodium bicarbonate and then basified with 2 M NaOH (aq). The organics were extracted with ethyl acetate (2×40 ml) and the combined organics were washed with brine (10 ml), dried over magnesium sulfate, filtered through a hydrophobic frit and concentrated in vacuo. The crude product was purified by column chromatography (silica, 0-20% ethyl acetate/petrol) to afford the title compound.

$^1$H NMR (400 MHz, DCM-d$_2$) δ ppm 2.01-2.10 (m, 2H), 2.34-2.48 (m, 2H), 3.13-3.26 (m, 2H), 7.23-7.34 (m, 1H), 7.41-7.50 (m, 1H), 7.63-7.71 (m, 1H), 8.83-8.94 (m, 1H)

MS ES$^+$: 242

Step (ii): 2-{[4-(Trifluoromethyl)pyridin-2-yl]methyl}cyclopentan-1-one

A solution of 2-{[4-(trifluoromethyl)pyridin-2-yl]methylidene}cyclopentan-1-one (0.513 g, 2.13 mmol) in ethyl acetate (20 mL) was added palladium on carbon (10% wt, 50% wet, 0.226 g, 0.11 mmol) and the resulting mixture was stirred under a balloon of hydrogen gas for 2 hours. The reaction was filtered through diatomaceous earth (commercially sold under the trade mark "Celite") and concentrated in vacuo. The crude product was purified by column chromatography (silica, 0-30% ethyl acetate/petrol) to afford the title compound.

$^1$H NMR (300 MHz, DCM-d$_2$) δ ppm 1.44-1.67 (m, 1H), 1.68-1.89 (m, 1H), 1.94-2.05 (m, 1H), 2.05-2.25 (m, 2H), 2.25-2.42 (m, 1H), 2.54-2.73 (m, 1H), 2.74-2.95 (m, 1H), 3.21-3.41 (m, 1H), 7.27-7.47 (m, 2H), 8.59-8.80 (m, 1H)

MS ES$^+$: 244

Step (iii): 2-{[4-(Trifluoromethyl)pyridin-2-yl]methyl}cyclopentan-1-ol

Sodium borohydride (0.117 g, 3.08 mmol) was added to a solution of 2-{[4-(trifluoromethyl)pyridin-2-yl]methyl}cyclopentan-1-one (0.375 g, 1.54 mmol) in ethanol (10 ml). The reaction was stirred at room temperature for 3 hours and then quenched with water (5 mL) and 2M HCl (aq., 5 ml). The organics were extracted with ethyl acetate (2×30 ml) and the combined organics were washed with brine (10 ml), dried over magnesium sulfate, filtered through a hydrophobic frit and concentrated in vacuo. The crude product was purified by column chromatography (silica, 0-35% ethyl acetate/petrol) to afford the title compound as two diastereomers.

Diastereomer 1: 2-{[4-(trifluoromethyl)pyridin-2-yl]methyl}cyclopentan-1-ol $^1$H NMR (400 MHz, DCM-d$_2$) δ ppm 1.42-1.70 (m, 3H), 1.72-1.94 (m, 3H), 1.97-2.13 (m, 1H), 2.87-3.00 (m, 1H), 3.02-3.17 (m, 1H), 3.82-4.00 (m, 1H), 7.30-7.49 (m, 2H), 8.59-8.77 (m, 1H)

MS ES$^+$: 246

Diastereomer 2: 2-{[4-(trifluoromethyl)pyridin-2-yl]methyl}cyclopentan-1-ol $^1$H NMR (400 MHz, DCM-d$_2$) δ ppm 1.27-1.43 (m, 1H), 1.51-1.80 (m, 3H), 1.83-2.07 (m, 2H), 2.09-2.25 (m, 1H), 2.94-3.06 (m, 2H), 3.84-3.98 (m, 1H), 7.31-7.47 (m, 2H), 8.63-8.73 (m, 1H)

MS ES$^+$: 246

Step (iv): 2-(2-{[4-(Trifluoromethyl)pyridin-2-yl]methyl}cyclopentyl)-2,3-dihydro-1H-isoindole-1,3-dione DIAD (0.26 ml, 1.36 mmol) was added to a solution of triphenylphosphine (0.350 g, 1.34 mmol), 2,3-dihydro-1H-isoindole-1,3-dione (CAS number 136918-14-4; 0.197 g, 1.34 mmol) and 2-{[4-(trifluoromethyl)pyridin-2-yl]methyl}cyclopentan-1-ol (Diastereomer 2) (0.252 g, 1.03 mmol) in THF (5 ml). The reaction was stirred at room temperature for 24 hours and then further triphenylphosphine (0.175 g, 0.69 mmol) and DIAD (0.130 ml, 0.69 mmol) was added. The reaction was stirred for 72 hours at room temperature and then concentrated in vacuo. The crude product was purified by column chromatography (silica, 0-100% ethyl acetate/petrol) and then by column chromatography (basic silica, 0-100% ethyl acetate/petrol) to afford the title compound.

$^1$H NMR (400 MHz, DCM-d$_2$) δ ppm 1.46-1.65 (m, 2H), 1.78-1.93 (m, 2H), 2.01-2.12 (m, 2H), 2.29-2.46 (m, 1H), 2.76-2.93 (m, 2H), 4.65-4.83 (m, 1H), 7.11-7.26 (m, 2H), 7.63-7.81 (m, 4H), 8.50-8.58 (m, 1H)

MS ES$^+$: 375

Step (v): 2-{[4-(Trifluoromethyl)pyridin-2-yl]methyl}cyclopentan-1-amine

Methanamine (40% aq, 1 ml, 11.55 mmol) was added to a solution of 2-(2-{[4-(trifluoromethyl)pyridin-2-yl]methyl}cyclopentyl)-2,3-dihydro-1H-isoindole-1,3-dione (0.100 g, 0.27 mmol) in ethanol (6 ml) in a microwave vial. The vial was sealed and stirred at room temperature for 18 hours and then heated to 60° C. for 5 hours. The reaction was cooled to room temperature and concentrated in vacuo. This was then purified by SCX chromatography (2M ammonia in methanol) to afford the title compound.

$^1$H NMR (400 MHz, DCM-d$_2$) δ ppm 1.50-1.79 (m, 4H), 1.79-2.02 (m, 2H), 2.18-2.35 (m, 1H), 2.86-3.02 (m, 1H), 3.05-3.21 (m, 1H), 3.26-3.38 (m, 1H), 7.33-7.48 (m, 2H), 8.62-8.74 (m, 1H)

MS ES$^+$: 245

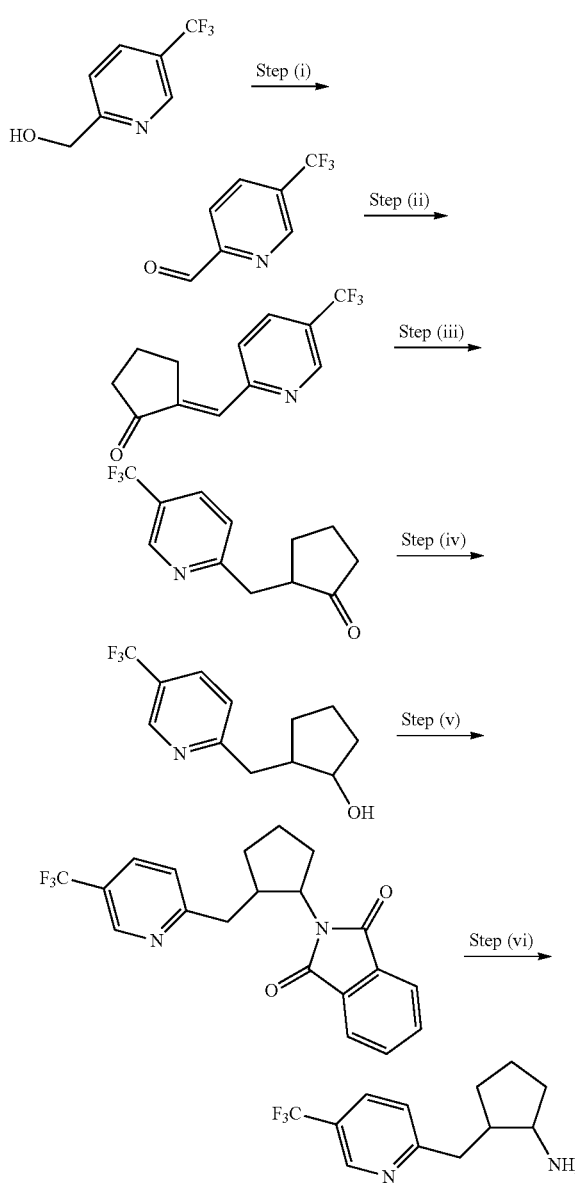

Intermediate 13: 2-{[5-(Trifluoromethyl)pyridin-2-yl]methyl}cyclopentan-1-amine

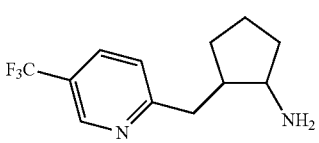 [SMILES: NC1CCCC1Cc1ccc(C(F)(F)F)cn1]

Step (i): 5-(Trifluoromethyl)pyridine-2-carbaldehyde

Dess-Martin periodinane (CAS number 87413-09-0; 13.17 g, 31.10 mmol) was added to a solution of [5-(trifluoromethyl)pyridin-2-yl]methanol (CAS number 31181-84-7; 5.00 g, 28.2 mmol) in DCM (60 ml). The reaction was stirred at room temperature for 18 hours and then a saturated solution of sodium thiosulfate (aq, 100 ml) was added. The reaction was stirred for 45 min at room temperature and then phases separated. The aqueous phase was further extracted with DCM (60 ml) and the combined organics were washed with a saturated solution of sodium bicarbonate (aq, 60 ml), filtered through a hydrophobic frit and concentrated in vacuo. The crude product was purified by column chromatography (silica, 0-20% ethyl acetate/petrol) to afford the title compound.

MS ES+: 176

Step (ii): 2-{[5-(Trifluoromethyl)pyridin-2-yl]methylidene}cyclopentan-1-one

A solution of 5-(trifluoromethyl)pyridine-2-carbaldehyde (3.32 g, 18.96 mmol) and 4-(cyclopent-1-en-1-yl)morpholine (CAS number 936-52-7; 2.97 ml, 18.58 mmol) in toluene (50 ml) was heated to 90° C. for 18 hours. The reaction was then cooled to room temperature and concentrated HCl (2 ml) and water (2 ml) was added drop wise. The reaction was stirred at room temperature for 20 minutes and then neutralised with a saturated solution of sodium bicarbonate and then basified with 2M NaOH (aq). The organics were extracted with ethyl acetate (2×40 ml) and the combined organics were washed with brine (10 ml), dried over magnesium sulfate, filtered through a hydrophobic frit and concentrated in vacuo. The crude product was purified by column chromatography (silica, 0-20% ethyl acetate/petrol) to afford the title compound.

$^1$H NMR (400 MHz, DCM-d$_2$) δ ppm 1.94-2.13 (m, 2H), 2.31-2.51 (m, 2H), 3.11-3.36 (m, 2H), 7.22-7.43 (m, 1H), 7.51-7.72 (m, 1H), 7.87-8.09 (m, 1H), 8.95 (s, 1H)

MS ES+: 242

Step (iii): 2-{[5-(Trifluoromethyl)pyridin-2-yl]methyl}cyclopentan-1-one

A solution of 2-{[5-(trifluoromethyl)pyridin-2-yl]methylidene}cyclopentan-1-one (0.513 g, 2.13 mmol) in ethyl acetate (20 ml) was added palladium on carbon (10% wt, 50% wet, 0.226 g, 0.11 mmol) and the resulting mixture was stirred under a balloon of hydrogen gas for 2 hours. The reaction was filtered through diatomaceous earth (commercially sold under the trade mark "Celite") and concentrated in vacuo. The crude product was purified by column chromatography (silica, 0-40% ethyl acetate/petrol) to afford the title compound.

$^1$H NMR (400 MHz, DCM-d$_2$) δ ppm 1.50-1.67 (m, 1H), 1.71-1.88 (m, 1H), 1.92-2.05 (m, 1H), 2.07-2.24 (m, 2H), 2.26-2.41 (m, 1H), 2.62-2.79 (m, 1H), 2.82-3.02 (m, 1H), 3.16-3.41 (m, 1H), 7.18-7.50 (m, 1H), 7.80-8.00 (m, 1H), 8.80 (br. s., 1H)

MS ES+: 244

Step (iv): 2-{[5-(Trifluoromethyl)pyridin-2-yl]methyl}cyclopentan-1-ol

Sodium borohydride (0.036 g, 0.954 mmol) was added to a solution of 2-{[5-(trifluoromethyl)pyridin-2-yl]methyl}cyclopentan-1-one (0.116 g, 0.48 mmol) in ethanol (5 ml). The reaction was stirred at room temperature for 1 hour and then quenched with water (5 ml) and 2M HCl (aq, 5 ml), basified with 2M NaOH (aq) and extracted with ethyl acetate (2×30 ml). The combined organics were dried over dried over magnesium sulfate, filtered through a hydrophobic frit and concentrated in vacuo. The crude product was purified by column chromatography (silica, 0-30% ethyl acetate/petrol) to afford the title compound as two diastereomers.

Diastereomer 1: 2-{[5-(trifluoromethyl)pyridin-2-yl]methyl}cyclopentan-1-ol $^1$H NMR (400 MHz, DCM-d$_2$) δ ppm 0.79-0.96 (m, 1H), 1.22-1.40 (m, 1H), 1.44-1.59 (m, 2H), 1.60-1.71 (m, 1H), 1.73-1.91 (m, 2H), 1.98-2.13 (m, 1H), 2.89-3.02 (m, 1H), 3.03-3.14 (m, 1H), 3.84-3.98 (m, 1H), 7.26-7.41 (m, 1H), 7.85-7.98 (m, 1H), 8.77 (s, 1H)

MS ES$^+$: 246

Diastereomer 2: 2-{[5-(trifluoromethyl)pyridin-2-yl]methyl}cyclopentan-1-ol $^1$H NMR (400 MHz, DCM-d$_2$) δ ppm 0.80-0.95 (m, 1H), 1.26-1.40 (m, 1H), 1.51-1.78 (m, 3H), 1.84-2.05 (m, 2H), 2.09-2.21 (m, 1H), 2.92-3.11 (m, 2H), 3.84-3.98 (m, 1H), 7.29-7.45 (m, 1H), 7.79-7.94 (m, 1H), 8.78 (s, 1H)

MS ES$^+$: 246

Step (v): 2-(2-{[5-(Trifluoromethyl)pyridin-2-yl]methyl}cyclopentyl)-2,3-dihydro-1H-isoindole-1,3-dione DIAD (0.348 mL, 1.791 mmol) was added to a solution of 2,3-dihydro-1H-isoindole-1,3-dione (CAS number 136918-14-4; 0.263 g, 1.791 mmol), triphenylphosphine (0.470 g, 1.791 mmol) and 2-{[5-(trifluoromethyl)pyridin-2-yl]methyl}cyclopentan-1-ol (Diastereomer 2) (0.366 g, 1.492 mmol) in THF (2 ml) under nitrogen. The reaction was stirred at room temperature for 72 hours and then concentrated. The crude product was purified by column chromatography (silica, 0-20% ethyl acetate/petrol) to afford the title compound.

$^1$H NMR (400 MHz, DCM-d$_2$) δ ppm 1.48-1.66 (m, 1H), 1.74-1.92 (m, 2H), 2.01-2.15 (m, 2H), 2.32-2.53 (m, 1H), 2.68-2.95 (m, 3H), 4.76 (m, 1H), 7.06-7.19 (m, 1H), 7.64-7.81 (m, 5H), 8.59 (s, 1H)

MS ES$^+$: 375

Step (vi): 2-{[5-(Trifluoromethyl)pyridin-2-yl]methyl}cyclopentan-1-amine

Methanamine (40% aq, 3 ml, 34.7 mmol) was added to a solution of 2-(2-{[5-(trifluoromethyl)pyridin-2-yl]methyl}cyclopentyl)-2,3-dihydro-1H-isoindole-1,3-dione (0.316 g, 0.84 mmol) in ethanol (5 ml). The reaction was stirred at room temperature for 24 hours and then further methanamine (40% aq, 3 ml, 34.7 mmol) was added. The reaction was stirred for 24 hours at room temperature and then re-suspended in ethanol (5 ml) and methanamine (40% aq, 3 ml, 34.7 mmol). The reaction stirred for 72 hours at room temperature. The reaction mixture was concentrated in vacuo and was then purified by reverse phase preparative HPLC (eluted with acetonitrile/water with 0.1% ammonia) and then purified by column chromatography (basic silica, 50-100% ethyl acetate/petrol) to afford the title compound.

MS ES$^+$: 245

Intermediate 14: (1S,2S)-1-N-[5-(Trifluoromethyl)pyrazin-2-yl]cyclopentane-1,2-diamine hydrochloride

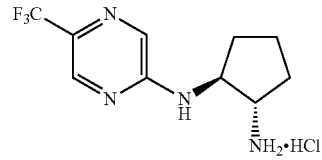

A solution of 2-chloro-5-(trifluoromethyl)pyrazine (CAS number 799557-87-2; 5.01 g, 27.5 mmol), tert-butyl N-[(1S,2S)-2-aminocyclopentyl]carbamate (CAS number 586961-34-4; 5 g, 24.97 mmol) and DIPEA (13.08 ml, 74.9 mmol) in DMSO (50 ml) was heated in a sealed vial at 120° C. for 2 hours and then 140° C. for 2 hours. The reaction mixture was partitioned between ethyl acetate (400 ml) and water (200 ml). The organics were washed with water (3×100 ml) and brine (100 ml), dried over sodium sulfate and concentrated in vacuo. The resulting residue was purified by column chromatography (silica, 5-40% ethyl acetate/petrol). To the resulting solid was then added HCl in 1,4-dioxane (4M, 30 ml, 120 mmol) and the reaction was stirred at room temperature overnight. The reaction was concentrated in vacuo, triturated with diethyl ether and filtered to afford the title compound.

$^1$H NMR (400 MHz, DMSO-d$_6$) δ ppm 1.49-1.88 (m, 4H), 2.02-2.22 (m, 2H), 3.24-3.47 (m, 1H), 4.12-4.28 (m, 1H), 7.99-8.14 (m, 1H), 8.18-8.48 (m, 5H)

MS ES$^+$: 247

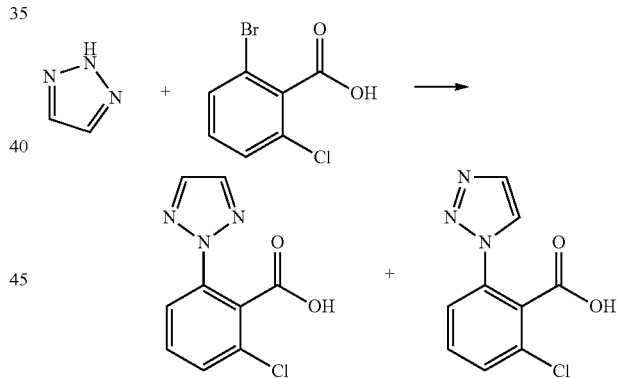

Intermediate 15: 2-Chloro-6-(2H-1,2,3-triazol-2-yl)benzoic acid

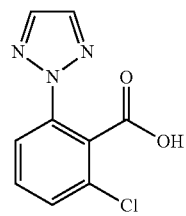 [SMILES: O=C(O)c1c(Cl)cccc1-n1nccn1]

To the solution of 2H-1,2,3-triazole (CAS number 288-36-8; 4.0 g, 57.97 mmol) in DMF (14 ml) was added cesium carbonate (18.84 g, 57.97 mmol), trans-1-N,2-N-dimethylcyclohexane-1,2-diamine (0.510 g, 5.80 mmol), copper(I) iodide (0.276 g, 1.45 mmol) and 2-bromo-6-chlorobenzoic acid (CAS number 93224-85-2; 6.78 g, 28.98 mmol) at 0-10° C. The reaction was subjected to microwave irradiation at 125° C. for 15 minutes and was then partitioned between ethyl acetate (3×100 ml) and water (100 ml). The aqueous layer was acidified with 2M HCl (aq) to give pH 2 and then extracted with ethyl acetate (3×100 ml). The combined organics were washed with brine, dried over sodium sulfate and concentrated in vacuo. This was then purified by column chromatography (0-3% methanol/DCM) to afford the title compound.

$^1$H NMR (400 MHz DMSO-d$_6$) δ ppm 7.62-7.67 (m, 2H), 7.92-7.94 (m, 1H), 8.17 (s, 2H), 13.73 (s, 1H)

MS ES$^+$: 224, 226

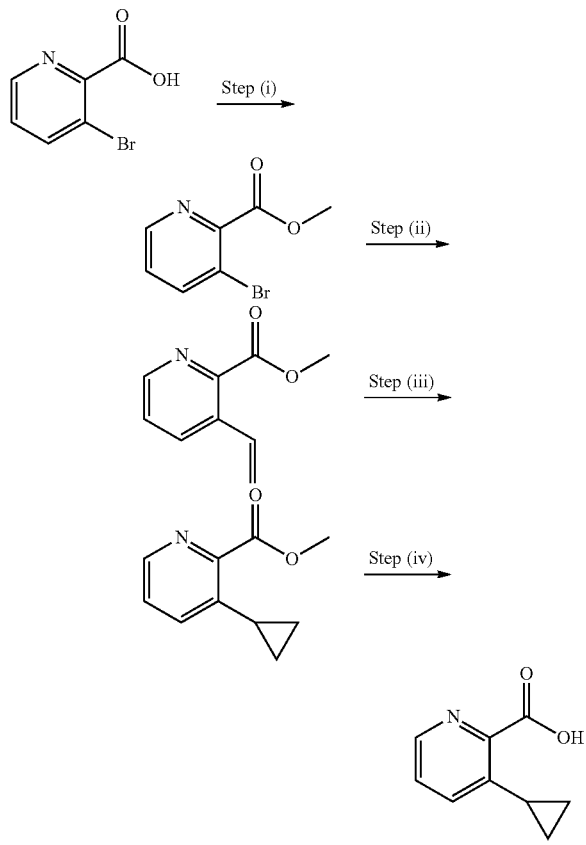

Intermediate 16:
3-Cyclopropylpyridine-2-carboxylic acid

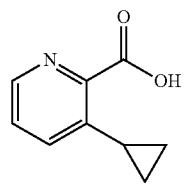 [SMILES: O=C(O)c1ncccc1C1CC1]

Step (i): Methyl 3-bromopyridine-2-carboxylate

To a solution of 3-bromopyridine-2-carboxylic acid (CAS number 30683-23-9; 2.0 g, 9.90 mmol) in methanol (15 ml) was added concentrated H$_2$SO$_4$ (3 ml) and the reaction mixture was refluxed for 2 hours. The reaction was diluted with a saturated solution of sodium bicarbonate and extracted with ethyl acetate (3×75 ml). The organics were washed with water (50 ml), brine (20 ml), dried over sodium sulfate and concentrated in vacuo to afford the title compound.

$^1$H NMR (400 MHz, DMSO-d) δ ppm 3.91 (s, 3H), 7.53-7.56 (m, 1H), 8.25-8.28 (m, 1H) 8.62-8.64 (m, 1H)

MS ES$^+$: 218

Step (ii): Methyl 3-ethenylpyridine-2-carboxylate

Methyl 3-bromopyridine-2-carboxylate (1.0 g, 4.63 mmol) and potassium vinyltrifluoroborate (CAS number 13682-77-4; 0.744 g, 5.56 mmol) were dissolved in IPA (15 ml). To this was then added triethylamine (0.467 g, 4.63 mmol) and the mixture was degassed under nitrogen atmosphere for 15 minutes. [1,1'-Bis(diphenyl phosphino)ferrocene]dichloropalladium(II) (0.075 g, 0.092 mmol) was added and the reaction was stirred at 100° C. for 4 hours. The reaction was diluted with water (75 ml) and filtered through diatomaceous earth (commercially sold under the trade mark "Celite"). The organics were extracted with ethyl acetate (3×50 ml), washed with water (25 ml), brine (20 ml), dried over sodium sulfate and concentrated in vacuo. The resulting residue was purified by column chromatography (silica, 0-18% ethyl acetate/n-hexane to afford the title compound.

$^1$H NMR (400 MHz, DMSO-d) δ ppm 3.88 (s, 3H), 5.49-5.52 (m, 1H), 5.93-5.98 (m, 1H), 7.03-7.10 (m, 1H), 7.58-7.62 (m, 1H), 8.19-8.21 (m, 1H), 8.54-8.56 (m, 1H)

MS ES$^+$: 164

Step (iii): Methyl 3-cyclopropylpyridine-2-carboxylate

To a stirred solution of diiodomethane (2.46 g, 9.20 mmol) in dry DCM (5 ml) at −10° C. was added diethyl zinc in hexane (1 M, 9.2 ml, 9.20 mmol). The reaction was stirred for 30 minutes under nitrogen. To this was then added methyl 3-ethenylpyridine-2-carboxylate (0.30 g, 1.84 mmol) as a solution in DCM (5 ml) over a 15 minute period. The reaction was then allowed to warm to room temperature and was stirred at room temperature for 15 hours. The reaction mixture was diluted with a saturated solution of ammonium chloride (25 ml) and the organics were extracted with ethyl acetate (3×30 ml). The combined organics were washed with water (25 ml), brine (25 ml), dried over sodium sulfate and concentrated in vacuo. The resulting residue was purified by column chromatography (silica, 0-15% ethyl acetate/n-hexane to afford the title compound.

MS ES$^+$: 178

Step (iv): 3-cyclopropylpyridine-2-carboxylic acid

To a solution of methyl 3-cyclopropylpyridine-2-carboxylate (80 mg, 0.45 mmol) in THF (2 ml) and water (2 ml) was added lithium hydroxide (55 mg, 1.36 mmol) and the reaction mixture was refluxed for 2 hours. The reaction was then acidified to pH 2 using 1M HCl (aq) and extracted with DCM (3×50 ml). The combined organics were washed with water (30 ml), brine (30 ml), dried over sodium sulfate and concentrated in vacuo to afford the title compound.

MS ES$^+$: 164

Intermediate 17: 3,6-Difluoro-2-(2H-1,2,3-triazol-2-yl)benzoic acid

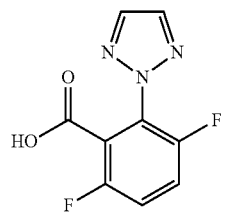 [SMILES: O=C(O)c1c(F)ccc(F)c1-n1nccn1]

To the solution of 2H-1,2,3-triazole (CAS number 288-36-8; 0.23 g, 3.33 mmol) in 1,4-dioxane (4.0 ml) was added cesium carbonate (1.0 g, 3.33 mmol), trans-1-N,2-N-dimethylcyclohexane-1,2-diamine (0.047 g, 0.33 mmol), copper(I) iodide (0.015 g, 0.08 mmol) and 2-bromo-3,6-difluorobenzoic acid (CAS number 124244-65-1; 0.40 g, 1.68 mmol). The reaction was stirred at 120° C. for 30 minutes and was then poured into water (10 ml) and extracted with ethyl acetate (2×30 ml). The organics were washed with brine, dried over sodium sulfate and concentrated in vacuo. The resulting residue was purified by column chromatography (silica, 0-5% methanol/DCM) to afford the title compound.

$^1$H NMR (400 MHz, DMSO-d) 7.63-7.69 (m, 1H), 7.73-7.79 (m, 1H), 8.19 (s, 2H), 13.87 (br. s., 1H)

MS ES$^+$: 225

Intermediate 18: N-[(1S,2S)-2-Aminocyclopentyl]-N-cyclobutyl-2,6-dimethoxybenzamide hydrochloride

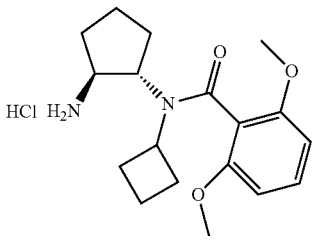 [SMILES: Cl ; COc1cccc(OC)c1C(=O)N(C1CCC1)[C@H]1CCC[C@@H]1N]

Step (i): tert-Butyl N-[(1S,2S)-2-(cyclobutylamino)cyclopentyl]carbamate

To a solution of tert-butyl N-[(1S,2S)-2-aminocyclopentyl]carbamate (CAS number 586961-34-4; 600 mg, 3.00 mmol) in dry DCM (10 ml) was added cyclobutanone (CAS number 1191-95-3; 248 µl, 3.30 mmol), acetic acid (257 µl, 4.49 mmol) and molecular sieves. The reaction was then stirred at room temperature for 1 hour. To this was then added sodium triacetoxyborohydride (952 mg, 4.49 mmol) and the reaction was allowed to stir at room temperature for 17 hours. The reaction was basified by the addition of 2M NaOH (aq) and the organics were extracted DCM, filtered through a hydrophobic frit and concentrated in vacuo.

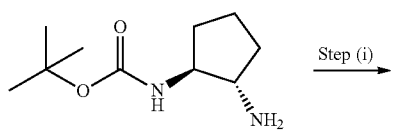

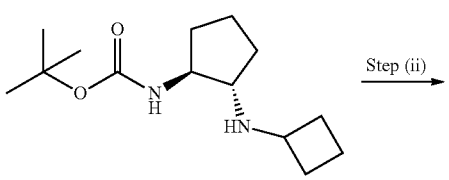

Step (ii): tert-Butyl N-[(1S,2S)-2-(N-cyclobutyl-2,6-dimethoxybenzamido)cyclopentyl]carbamate To a solution of tert-butyl N-[(1S,2S)-2-(cyclobutylamino)cyclopentyl]carbamate (400 mg, 1.573 mmol) in dry DCM (5.3 ml) was added DIPEA (1.3 ml, 7.86 mmol) and 2,6-dimethoxybenzoyl chloride (CAS number 1989-53-3; 473 mg, 2.359 mmol). The reaction was stirred at room temperature for 1 hour and was then partitioned between DCM and water, filtered through a hydrophobic frit and concentrated in vacuo. This was then purified by column chromatography (basic silica, 0-100% ethyl acetate/petrol) to afford the title compound.

MS ES$^+$: 419

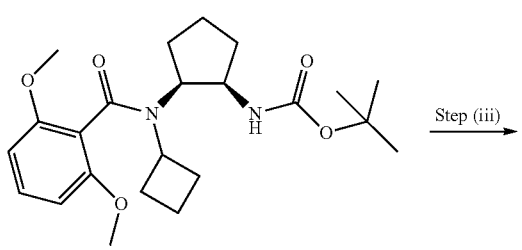

Step (iii): N-[(1S,2S)-2-Aminocyclopentyl]-N-cyclobutyl-2,6-dimethoxybenzamide hydrochloride To a solution of tert-butyl N-[(1S,2S)-2-(N-cyclobutyl2,6-dimethoxybenzamido)cyclopentyl]carbamate (1.34 g, 3.20 mmol) in methanol (11 ml) was added HCl in 1,4-dioxane (4 M, 8.00 ml, 32.0 mmol). The reaction was stirred at room temperature for 17 hours (overnight) and then was concentrated in vacuo, azeotropically distilled with toluene to afford the title compound.

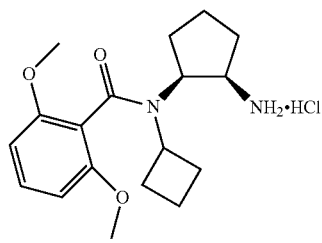

MS ES$^+$: 319

Intermediate 19: N-[(1S,2S)-2-Aminocyclopentyl]-2-chlorobenzamide hydrochloride

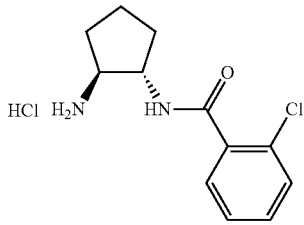 [SMILES: Cl ; N[C@H]1CCC[C@@H]1NC(=O)c1ccccc1Cl]

To a stirred solution of tert-butyl N-[(1S,2S)-2-aminocyclopentyl]carbamate (CAS number 586961-34-4; 500 mg, 2.497 mmol) in dry DCM (8.3 ml) was added triethylamine (1.74 ml, 12.48 mmol) and 2-chlorobenzoyl chloride (CAS number 609-65-4; 476 µl, 3.74 mmol). The reaction was stirred at room temperature for 72 hours. The reaction was partitioned between DCM and a saturated solution of sodium bicarbonate, filtered through a hydrophobic frit and concentrated in vacuo. The resulting residue was purified by column chromatography (silica, 0-100% ethyl acetate/petrol). The Boc protect intermediate was dissolved in 1,4-dioxane (8 ml) and to this was added HCl in 1,4-dioxane (4 M, 6.0 ml, 23.91 mmol). The reaction was stirred at room temperature for 17 hours and then concentrated in vacuo, azeotropically distilled with toluene to afford the title compound.

$^1$H NMR (400 MHz, DMSO-$d_6$) δ ppm 1.50-1.83 (m, 4H), 1.98-2.16 (m, 2H), 3.35-3.45 (m, 1H), 4.06-4.31 (m, 1H), 7.37-7.61 (m, 4H), 8.03-8.25 (m, 2H), 8.62-8.74 (M, 1H)

MS ES$^+$: 239

Intermediate 20: N-[(1S,2S)-2-Aminocyclopentyl]-2-fluoro-6-methoxybenzamide hydrochloride

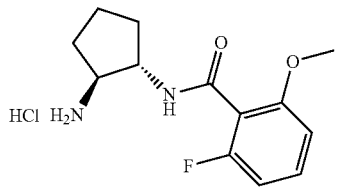 [SMILES: Cl ; COc1cccc(F)c1C(=O)N[C@H]1CCC[C@@H]1N]

Prepared according to the procedure for N-[(1S,2S)-2-aminocyclopentyl]-2-chlorobenzamide hydrochloride (Intermediate 19) from tert-butyl N-[(1S,2S)-2-aminocyclopentyl]carbamate (CAS number 586961-34-4; 500 mg, 2.50 mmol), 2-fluoro-6-methoxybenzoic acid (CAS number 137654-21-8; 637 mg, 3.74 mmol) and 1,3,5,2,4,6-trioxatriphosphorinane, 2,4,6-tripropyl-, 2,4,6-trioxide (CAS number 68957-94-8; 50% in ethyl acetate, 2.2 ml, 3.74 mmol). Subsequent deprotection with HCl afforded the title compound.

$^1$H NMR (400 MHz, DMSO-$d_6$) δ ppm 1.51-1.79 (m, 4H), 1.95-2.14 (m, 2H), 3.34-3.42 (m, 1H), 4.04-4.19 (m, 1H), 6.77-6.99 (m, 2H), 7.33-7.50 (m, 1H), 7.94-8.11 (m, 2H), 8.64-8.78 (m, 1H)

MS ES$^+$: 253

Intermediate 21: N-[(1S,2S)-2-Aminocyclopentyl]-2,6-difluorobenzamide hydrochloride

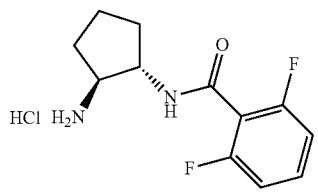 [SMILES: Cl ; N[C@H]1CCC[C@@H]1NC(=O)c1c(F)cccc1F]

Prepared according to the procedure for N-[(1S,2S)-2-aminocyclopentyl]-2-chlorobenzamide hydrochloride (Intermediate 19) from tert-butyl N-[(1S,2S)-2-aminocyclopentyl]carbamate (CAS number 586961-34-4; 500 mg, 2.50 mmol), 2,6-difluorobenzoic acid (CAS number 385-00-2; 592 mg, 3.74 mmol) and 1,3,5,2,4,6-trioxatriphosphorinane, 2,4,6-tripropyl-, 2,4,6-trioxide (CAS number 68957-94-8; 50% in ethyl acetate, 2.2 ml, 3.74 mmol). Subsequent deprotection with HCl afforded the title compound.

$^1$H NMR (400 MHz, DMSO-$d_6$) δ ppm 1.49-1.79 (m, 4H), 1.94-2.13 (m, 2H), 3.34-3.41 (m, 1H), 4.02-4.16 (m, 1H), 6.77-6.98 (m, 2H), 7.34-7.47 (m, 1H), 7.93-8.11 (m, 2H), 8.66-8.78 (m, 1H)

MS ES$^+$: 241

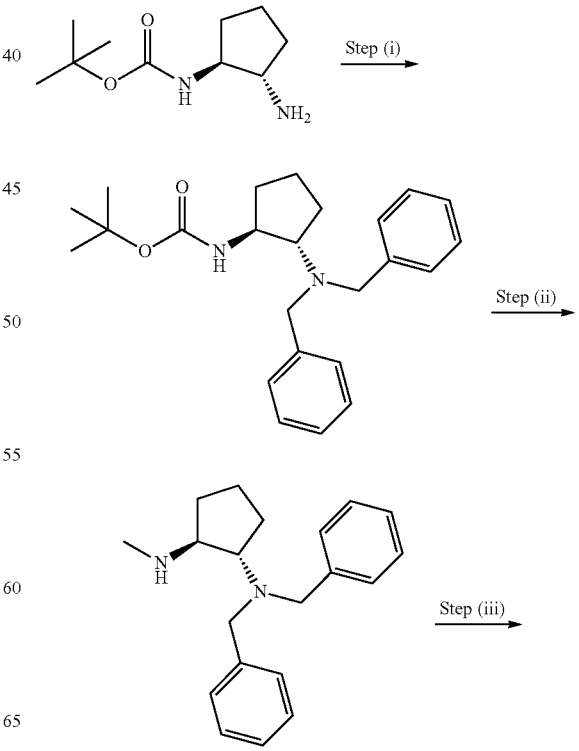

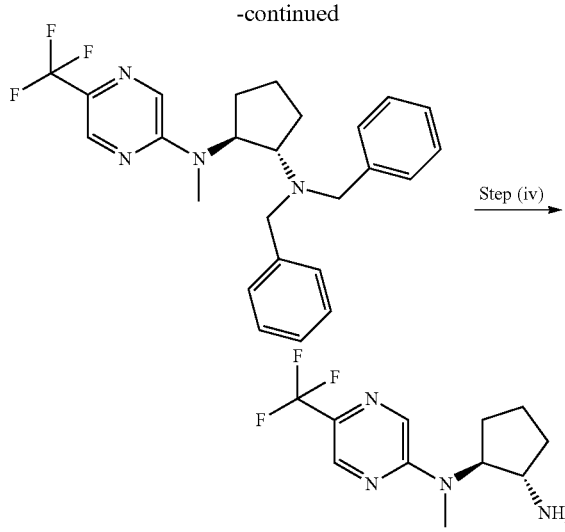

Intermediate 22: (1S,2S)-1-N-Methyl-1-N-[5-(trifluoromethyl)pyrazin-2-yl]cyclopentane-1,2-diamine

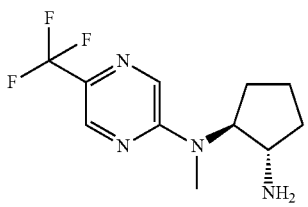 [SMILES: CN(c1cnc(C(F)(F)F)cn1)[C@H]1CCC[C@@H]1N]

Step (i): tert-Butyl N-[(1S,2S)-2-(dibenzylamino)cyclopentyl]carbamate

To a suspension of tert-butyl N-[(1S,2S)-2-aminocyclopentyl]carbamate (CAS number 586961-34-4; 500 mg, 2.50 mmol) and potassium carbonate (518 mg, 3.74 mmol) in DMF (5 ml) was added (bromomethyl)benzene (CAS number 100-39-0; 356 μl, 3.00 mmol). The reaction was stirred at room temperature for 24 hours. To this was then added further (bromomethyl)benzene (CAS number 100-39-0; 356 μl, 3.00 mmol) and stirring was continued for 24 hours. The reaction mixture was diluted with ethyl acetate (40 ml) and washed with water (3×30 ml) and brine (30 ml). The organics were filtered through a hydrophobic frit and concentrated in vacuo. This was then purified by column chromatography (silica, 0-100% ethyl acetate/petrol) to afford the title compound.

$^1$H NMR (400 MHz, DCM-d$_2$) δ ppm 1.16-1.29 (m, 1H), 1.37-1.67 (m, 12H), 1.68-1.82 (m, 1H), 1.92-2.06 (m, 1H), 2.70-2.87 (m, 1H), 3.46 (d, J=13.64 Hz, 2H), 3.77 (d, J=13.64 Hz, 2H), 4.28-4.49 (m, 1H), 7.15-7.47 (m, 11H)

MS ES$^+$: 381

Step (ii): (1S,2S)-1-N,1-N-Dibenzyl-2-N-methylcyclopentane-1,2-diamine

To a solution of tert-butyl N-[(1S,2S)-2-(dibenzylamino)cyclopentyl]carbamate (320 mg, 0.841 mmol) in THF (2.8 ml) at room temperature was added drop wise lithium aluminium hydride in THF (1 M, 1.3 ml, 1.261 mmol). The reaction was stirred for 1 hour and then was heated to 60° C. for 3 hours. The reaction was then cooled to room temperature and quenched by the addition of sodium sulfate decahydrate, filtered and washed with THF and ethyl acetate. The filtrate was concentrated in vacuo to afford the title compound.

$^1$H NMR (400 MHz, DCM-d$_2$) δ ppm 1.16-1.33 (m, 1H), 1.52-1.90 (m, 5H), 2.24-2.33 (m, 3H), 2.72-2.94 (m, 2H), 3.37-3.50 (m, 2H), 3.56-3.66 (m, 1H), 3.69-3.85 (m, 2H), 7.13-7.51 (m, 10H)

Step (iii): (1S,2S)-1-N,1-N-Dibenzyl-2-N-methyl-2-N-[5-(trifluoromethyl)pyrazin-2-yl]cyclopentane-1,2-diamine A solution of 2-chloro-5-(trifluoromethyl)pyrazine (CAS number 799557-87-2; 198 mg, 1.087 mmol), (1S,2S)-1-N,1-N-dibenzyl-2-N-methylcyclopentane-1,2-diamine (291 mg, 0.988 mmol) and DIPEA (518 μl, 2.97 mmol) in DMSO (3.3 ml) was subjected to microwave irradiation at 140° C. for 4 hours. The reaction was diluted with ethyl acetate (20 ml), washed with a saturated solution of sodium bicarbonate (3×20 ml), brine (20 ml), filtered through a hydrophobic frit and concentrated in vacuo. This was then purified by column chromatography (silica, 0-15% ethyl acetate/petrol) to afford the title compound.

$^1$H NMR (400 MHz, DCM-d$_2$) δ ppm 1.43-1.58 (m, 2H), 1.61-1.93 (m, 4H), 2.58 (s, 3H), 3.17-3.33 (m, 1H), 3.41 (d, J=13.64 Hz, 2H), 3.76 (d, J=13.64 Hz, 2H), 5.12-5.29 (m, 1H), 7.03-7.29 (m, 10H), 7.96 (s, 1H), 8.23 (s, 1H)

MS ES$^+$: 441

Step (iv): (1S,2S)-1-N-Methyl-1-N-[5-(trifluoromethyl)pyrazin-2-yl]cyclopentane-1,2-diamine To a solution of (1S,2S)-1-N,1-N-dibenzyl-2-N-methyl-2-N-[5-(trifluoromethyl)pyrazin-2-yl]cyclopentane-1,2-diamine (285 mg, 0.647 mmol) in ethyl acetate (2 ml) and ethanol (1 ml) was added palladium on carbon (10% wt, 50% wet, 100 mg, 0.094 mmol). The resulting mixture was stirred under a balloon of hydrogen gas for 18 hours. The reaction was filtered through diatomaceous earth (commercially sold under the trade mark "Celite") and concentrated in vacuo to afford the title compound.

$^1$H NMR (400 MHz, DCM-d$_2$) δ ppm 1.37-1.56 (m, 1H), 1.61-1.87 (m, 3H), 1.88-2.08 (m, 2H), 3.01 (s, 3H), 3.24-3.42 (m, 1H), 4.52-4.71 (m, 1H), 8.11 (s, 1H), 8.32 (s, 1H)

MS ES$^+$: 261

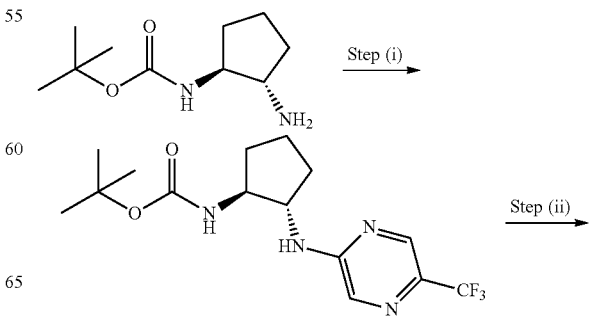

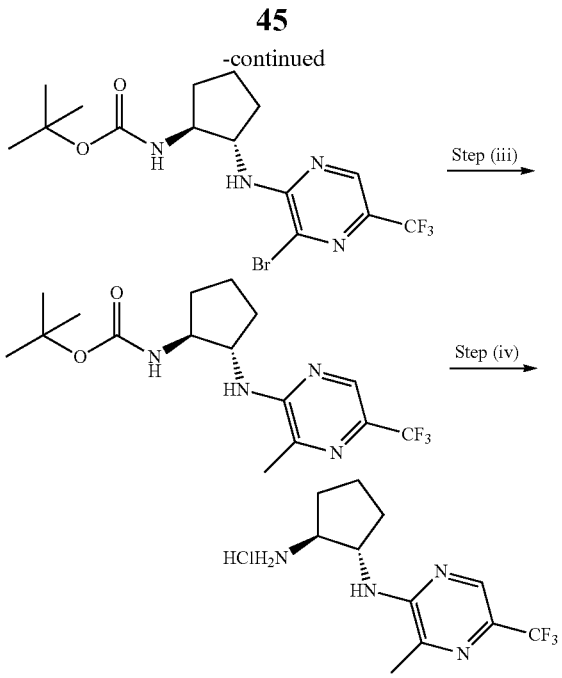

Intermediate 23: (1S,2S)-1-N-Methyl-1-N-[5-(trifluoromethyl)pyrazin-2-yl]cyclopentane-1,2-diamine hydrochloride

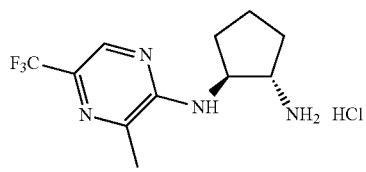 [SMILES: Cc1nc(C(F)(F)F)cnc1N[C@H]1CCC[C@@H]1N ; Cl]

Step (i): tert-Butyl N-[(1S,2S)-2-{[5-(trifluoromethyl)pyrazin-2-yl]amino}cyclopentyl]carbamate A solution of 2-chloro-5-(trifluoromethyl)pyrazine (CAS number 799557-87-2; 2.0 g, 10.98 mmol), tert-butyl N-[(1S,2S)-2-aminocyclopentyl]carbamate (CAS number 586961-34-4; 2 g, 9.99 mmol) and DIPEA (5.23 ml, 30.0 mmol) in DMSO (20 ml) was sealed and heated at 140° C. for 3 hours. The reaction mixture was partitioned between ethyl acetate (200 ml) and water (100 ml). The organics were washed with water (2×100 ml), brine (100 ml), dried over sodium sulfate and concentrated in vacuo. The residue was purified by column chromatography (silica, 10-40% ethyl acetate/petrol) to afford the title compound.

$^1$H NMR (300 MHz, CHLOROFORM-d) δ ppm 1.32-1.66 (m, 11H), 1.71-1.96 (m, 2H), 2.07-2.24 (m, 1H), 2.30-2.51 (m, 1H), 3.76-4.04 (m, 2H), 4.69-4.92 (m, 1H), 6.07-6.24 (m, 1H), 7.91 (s, 1H), 8.30 (s, 1H)

MS ES$^+$: 347

Step (ii): tert-Butyl N-[(1S,2S)-2-{[3-bromo-5-(trifluoromethyl)pyrazin-2-yl]amino}cyclopentyl]carbamate To a solution of tert-butyl ((1S,2S)-2-((5-(trifluoromethyl)pyrazin-2-yl)amino)cyclopentyl)carbamate (3.49 g, 10.08 mmol) in dry DCM (67 ml) at 0° C. was added 1-bromopyrrolidine-2,5-dione (CAS number 128-08-5; 2.15 g, 12.09 mmol). The reaction was allowed to warm to room temperature overnight. A further portion of portion of 1-bromopyrrolidine-2,5-dione (CAS number 128-08-5; 1.70 g, 9.56 mmol) was added and the reaction stirred for an additional 24 hours. The reaction was concentrated in vacuo and then purified by column chromatography (silica, 0-30% ethyl acetate/petrol) to afford the title compound.

$^1$H NMR (300 MHz, CHLOROFORM-d) δ ppm 1.31-1.62 (m, 11H), 1.72-1.92 (m, 2H), 2.08-2.24 (m, 1H), 2.36-2.56 (m, 1H), 3.75-4.14 (m, 2H), 4.63-4.87 (m, 1H), 6.78-6.96 (m, 1H), 8.25 (s, 1H)

MS ES$^+$: 425, 427

Step (iii): tert-Butyl N-[(1S,2S)-2-{[3-methyl-5-(trifluoromethyl)pyrazin-2-yl]amino}cyclopentyl] carbamate A mixture of tert-butyl N-[(1S,2S)-2-{[3-bromo-5-(trifluoromethyl)pyrazin-2-yl]amino}cyclopentyl]carbamate (800 mg, 1.88 mmol), methylboronic acid (CAS number 13061-96-6; 338 mg, 5.64 mmol), tetrakis(triphenylphosphine)palladium (217 mg, 0.19 mmol) and, 2 M potassium carbonate (aq, 3.8 ml, 7.53 mmol) in 1,4-dioxane (6.3 ml) was sealed, evacuated and purged with nitrogen and then subjected to microwave irradiation at 120° C. for 2 hours. The reaction mixture was then diluted with ethyl acetate (40 ml) and water (10 ml). The organics were washed with water and brine, dried over sodium sulfate and concentrated in vacuo. The residue was then purified by column chromatography (silica, 0-50% ethyl acetate/petrol) to afford the title compound.

$^1$H NMR (400 MHz, CHLOROFORM-d) δ ppm 1.34-1.53 (m, 11H), 1.73-1.93 (m, 2H), 2.08-2.20 (m, 1H), 2.43 (s, 3H), 2.48-2.64 (m, 1H), 3.73-3.89 (m, 1H), 3.95-4.09 (m, 1H), 4.75-4.85 (m, 1H), 6.45-6.57 (m, 1H), 8.20 (s, 1H)

MS ES$^+$: 361

Step (iv): (1S,2S)-1-N-Methyl-1-N-[5-(trifluoromethyl)pyrazin-2-yl]cyclopentane-1,2-diamine hydrochloride To a solution of tert-butyl N-[(1S,2S)-2-{[3-methyl-5-(trifluoromethyl)pyrazin-2-yl]amino}cyclopentyl]carbamate (480 mg, 1.332 mmol) in methanol (5 ml) was added HCl in 1,4-dioxane (4 M, 3.33 ml, 13.32 mmol). The reaction was stirred at room temperature overnight and then concentrated in vacuo, azeotropically distilled with toluene to afford the title compound.

$^1$H NMR (400 MHz, DMSO-d$_6$) δ ppm 1.58-1.85 (m, 4H), 1.99-2.23 (m, 2H), 2.43 (s, 3H), 3.46-3.65 (m, 1H), 4.28-4.46 (m, 1H), 7.24-7.41 (m, 1H), 8.13-8.37 (m, 4H)

MS ES$^+$: 261

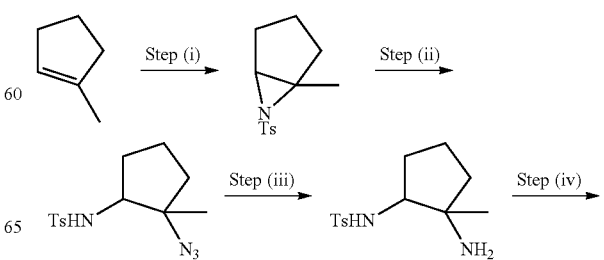

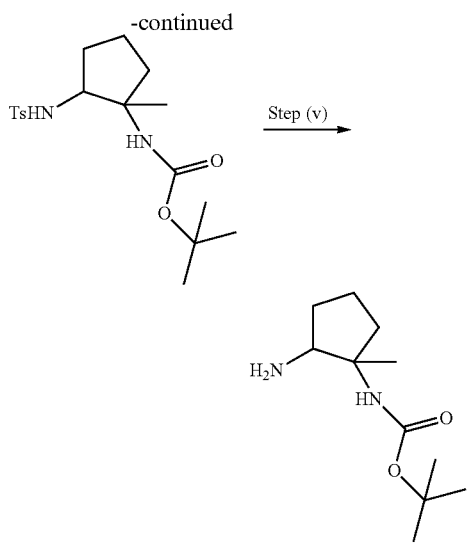

Intermediate 24: tert-Butyl
N-(2-amino-1-methylcyclopentyl)carbamate

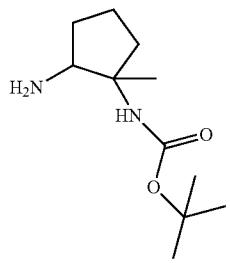

Step (i): 1-Methyl-6-(4-methylbenzenesulfonyl)-6-azabicyclo[3.1.0]hexane

To a solution of 1-methylcyclopent-1-ene (CAS number 693-89-0; 50.0 g, 609.75 mmol) iii and sodium chloro(4-methylbenzenesulfonyl)azanide (CAS number 127-65-1; 192 g, 680.85 mmol) in THF (2500 ml) was added trimethylphenylammonium tribromide (13.3 g, 61.57 mmol). The reaction was stirred vigorously at 25° C. for 12 hours. The reaction mixture was poured into water (1500 ml) and the organics were extracted with ethyl acetate (3×1000 ml). The combined organics were washed with water (500 ml), brine (500 ml), dried over sodium sulfate and concentrated in vacuo. This was then purified by column chromatography (silica, 0-2.5% ethyl acetate/n-hexane) to afford the title compound.

$^1$H NMR (400 MHz, DMSO-d6) δ ppm 1.15-1.25 (m, 1H), 1.46-1.70 (m, 4H), 1.75 (s, 3H), 1.88-1.93 (m, 1H), 2.50 (s, 3H), 3.34-3.35 (m, 1H), 7.40-7.42 (m, 2H), 7.74-7.76 (m, 2H)
MS ES$^+$: 251

Step (ii): N-(2-Azido-2-methylcyclopentyl)-4-methylbenzene-1-sulfonamide

To a solution of 1-methyl-6-(4-methylbenzenesulfonyl)-6-azabicyclo[3.1.0]hexane (55 g, 219.12 mmol) in IPA (1000 ml) and water (1000 ml) was added sodium azide (57.0 g, 876.92 mmol). The reaction mixture was stirred at room temperature for 17 hours. The reaction was cooled to room temperature and water (1000 ml) was added. The aqueous layer was extracted with diethyl ether (3×500 ml). The combined organics were washed with brine (250 ml), dried over sodium sulfate, concentrated in vacuo to afford the title compound.

$^1$H NMR (400 MHz, DMSO-d6) δ ppm 1.20-1.30 (m, 4H), 1.45-1.63 (m, 5H), 2.38 (s, 3H) 3.33-3.39 (m, 1H), 7.38-7.40 (m, 2H), 7.69-7.77 (m, 3H)
MS ES$^+$: 294

Step (iii): N-(2-Amino-2-methylcyclopentyl)-4-methylbenzene-1-sulfonamide

To a solution of N-(2-azido-2-methylcyclopentyl)-4-methylbenzene-1-sulfonamide (52.0 g, 176.87 mmol) in methanol (1100 ml) was added palladium on carbon (10% wt, 10.0 g). The reaction mixture was stirred at room temperature under a balloon of hydrogen gas for 12 hours. The reaction was filtered through diatomaceous earth (commercially sold under the trade mark "Celite") and concentrated in vacuo to afford the title compound.

$^1$H NMR (400 MHz, DMSO-d6) δ ppm 0.93 (s, 3H), 1.20-1.22 (m, 1H), 1.36-1.52 (m, 5H) 2.38 (s, 3H) 2.94-2.98 (m, 1H) 4.11 (br. s, 1H), 7.37-7.39 (m, 2H), 7.69-7.71 (m, 2H)
MS ES$^+$: 268

Step (iv): tert-Butyl N-[1-methyl-2-(4-methylbenzenesulfonamido)-cyclopentyl]carbamate To a solution of N-(2-amino-2-methylcyclopentyl)-4-methylbenzene-1-sulfonamide (48.0 g, 179.10 mmol) in DCM (1400 ml) was added triethylamine (27.13 g, 268.65 mmol) and di-tert-butyl dicarbonate (CAS number 24424-99-5; 46.85 g, 214.92 mmol). The reaction mixture was stirred at room temperature for 15 hours. The reaction mixture was concentrated in vacuo and the resulting residue was partitioned between ethyl acetate (1000 ml) and water (800 ml). The organics were dried over sodium sulfate and concentrated in vacuo. The solid was then triturated with hexane (300 ml) to afford the title compound.

$^1$H NMR (400 MHz, DMSO-d6) δ ppm 1.16 (s, 3H), 1.18-1.57 (m, 14H), 1.92 (m, 1H) 2.67 (s, 3H) 3.53 (m, 1H) 6.24 (br. s, 1H), 7.27-7.39 (m, 2H), 7.60-7.69 (m, 3H)
MS ES$^+$: 368

Step (v): tert-Butyl N-(2-amino-1-methylcyclopentyl)carbamate

A mixture of lithium granules (7.17 g, 1195 mmol) and naphthalene (57.39 g, 448.36 mmol) in dry dimethoxyethane (1900 ml) was stirred at room temperature for 2 hours. The deep blue solution was then cooled to 0° C. and a solution of tert-butyl N-[1-methyl-2-(4-methylbenzenesulfonamido)cyclopentyl]carbamate (55.0 g, 149.45 mmol) in dry dimethoxyethane (300 ml) was added drop wise over 30 minutes. The mixture was stirred at 0° C. for 3 hours. The un-dissolved lithium was removed by filtration and 1M HCl solution (aq, 720 ml) was added to the filtrate. The organic layer was washed with further 1M HCl (aq, 2×600 ml). The combined aqueous layers were washed with diethyl ether (2×600), and then basified with 2M NaOH (aq) to give pH 12-14. The aqueous layer was then extracted with ethyl acetate (5×600 ml). The combined organics were dried over sodium sulfate and then concentrated in vacuo. This was then purified by column chromatography (silica, 0-4% methanol/DCM) to afford the title compound.

¹H NMR (400 MHz, DMSO-d6) δ ppm 1.10 (s, 3H), 1.14-1.27 (m, 2H), 1.40 (s, 9H) 1.44-1.55 (m, 2H) 1.76-1.86 (m, 2H) 2.72 (br. s, 2H), 3.09 (m, 1H) 6.61 (br. s, 1H)

MS ES⁺: 214

Intermediate 25: (1S,2S)-1-Methyl-1-N-[5-(trifluoromethyl)pyrazin-2-yl]cyclopentane-1,2-diamine

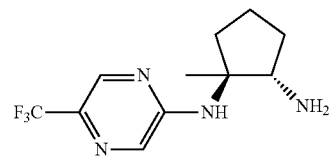 [SMILES: C[C@]1(Nc2cnc(C(F)(F)F)cn2)CCC[C@@H]1N]

Method 1:

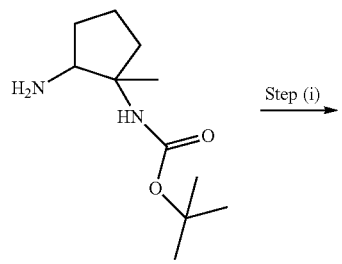

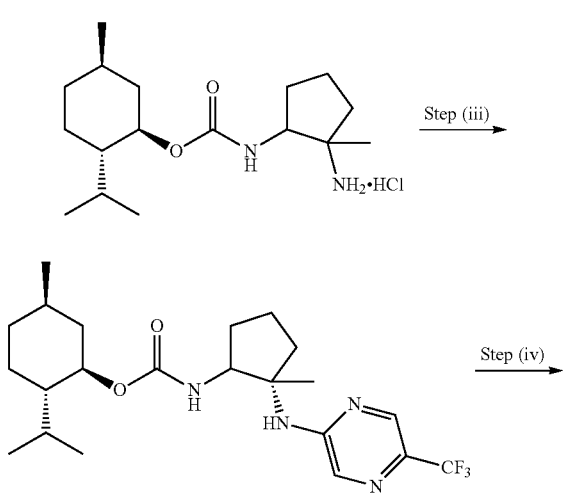

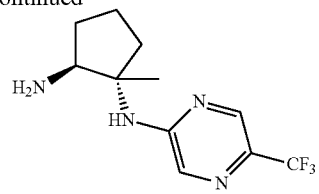

Step (i): (1R,2S,5R)-5-Methyl-2-(propan-2-yl)cyclohexyl N-(2-{[(tert-butoxy)carbonyl]amino}-2-methylcyclopentyl)carbamate To a solution of tert-butyl N-(2-amino-1-methylcyclopentyl)carbamate (Intermediate 24; 5.49 ml, 26.1 mmol) in DCM (87 ml) at 0° C. was added DIPEA (4.56 ml, 26.1 mmol) followed by (1R,2S,5R)-5-methyl-2-(propan-2-yl)cyclohexyl chloroformate (CAS number 14602-86-9; 17.15 g, 78 mmol) drop wise. The reaction mixture was allowed to warm to room temperature and stirred overnight. The reaction was diluted with DCM (150 ml) and a saturated solution of sodium bicarbonate solution (200 ml). The aqueous layer was re-extracted with DCM (100 ml) and the combined organics were washed further with a saturated solution of sodium bicarbonate (100 ml), dried over magnesium sulfate and concentrated in vacuo. The residue was purified by column chromatography (silica, 0-50% ethyl acetate/petrol) to afford the title compound.

¹H NMR (400 MHz, DCM-d₂) δ ppm 0.72-1.79 (m, 30H), 1.81-2.34 (m, 6H), 3.80-4.01 (m, 1H), 4.44-4.90 (m, 2H), 5.98-6.11 (m, 1H)

MS ES⁺: 397

Step (ii): (1R,2S,5R)-5-Methyl-2-(propan-2-yl)cyclohexyl N-(2-amino-2-methylcyclopentyl)carbamate hydrochloride To a solution of (1R,2S,5R)-5-methyl-2-(propan-2-yl)cyclohexyl N-(2-{[(tert-butoxy)carbonyl]amino}-2-methylcyclopentyl)carbamate (6.12 g, 15.43 mmol) in 1,4-dioxane (35 ml) was added HCl in 1,4-dioxane (4 M, 38.6 ml, 154 mmol). The reaction mixture was stirred at room temperature overnight, concentrated in vacuo and azeotropically distilled with toluene to afford the title compound.

¹H NMR (300 MHz, DMSO-d6) δ ppm 0.62-2.09 (m, 27H), 3.75-4.00 (m, 1H), 4.30-4.55 (m, 1H), 7.31-7.46 (m, 1H), 7.96 (br. s., 3H)

MS ES⁺: 297

Step (iii): (1R,2S,5R)-5-Methyl-2-(propan-2-yl)cyclohexyl N-[(1S,2S)-2-methyl-2-{[5-(trifluoromethyl)pyrazin-2-yl]amino}cyclopentyl]carbamate A solution of (1R,2S,5R)-5-methyl-2-(propan-2-yl)cyclohexyl N-(2-amino-2-methylcyclopentyl)carbamate hydrochloride (5.14 g, 15.44 mmol), 2-chloro-5-(trifluoromethyl)pyrazine (CAS number 799557-87-2; 2.097 ml, 16.98 mmol) and DIPEA (8.10 ml, 46.32 mmol) in DMSO (51.5 ml) was heated to 140° C. for 17 hours. The reaction mixture was diluted with water (200 ml) and extracted with ethyl acetate (2×200 ml). The combined organics were washed with brine (3×200 ml), dried over magnesium sulfate and concentrated in vacuo. The residue was purified by column chromatography (silica, 0-15% ethyl acetate/petrol) to afford the title compound as a single diastereomer.

$^1$H NMR (400 MHz, DCM-d$_2$) δ ppm 0.68-2.04 (m, 27H), 2.06-2.20 (m, 1H), 2.41-2.64 (m, 1H), 4.56-4.70 (m, 1H), 4.85-5.03 (m, 1H), 7.64-8.08 (m, 1H), 8.21 (br. s., 1H)

MS ES$^+$: 443

Step (iv): (1S,2S)-1-Methyl-1-N-[5-(trifluoromethyl)pyrazin-2-yl]cyclopentane-1,2-diamine To a solution of (1R,2S,5R)-5-methyl-2-(propan-2-yl)cyclohexyl N-[(1S,2S)-2-methyl-2-{[5-(trifluoromethyl)pyrazin-2-yl]amino}cyclopentyl]carbamate (1.03 g, 2.328 mmol) in acetic acid (8 ml) was added HBr (6 M, 1.940 ml, 11.64 mmol). The reaction was heated to 90° C. for 20 hours in a sealed vial and then cooled. To this was then added further HBr (6 M, 1.00 ml, 6 mmol) and the reaction was heated at 90° C. for 36 hours. The reaction was cooled to room temperature and concentrated in vacuo. The crude product was purified by reverse phase chromatography (C18 silica, 5-100% water (with 0.05% ammonia)/acetonitrile) to afford the title compound.

$^1$H NMR (400 MHz, DCM-d$_2$) δ ppm 1.32 (s, 3H), 1.37-1.51 (m, 1H), 1.63-1.76 (m, 2H), 1.85-2.22 (m, 3H), 3.17-3.35 (m, 1H), 5.44 (br. s., 1H), 7.89 (s, 1H), 8.29 (s, 1H)

MS ES$^+$: 261

Method 2:

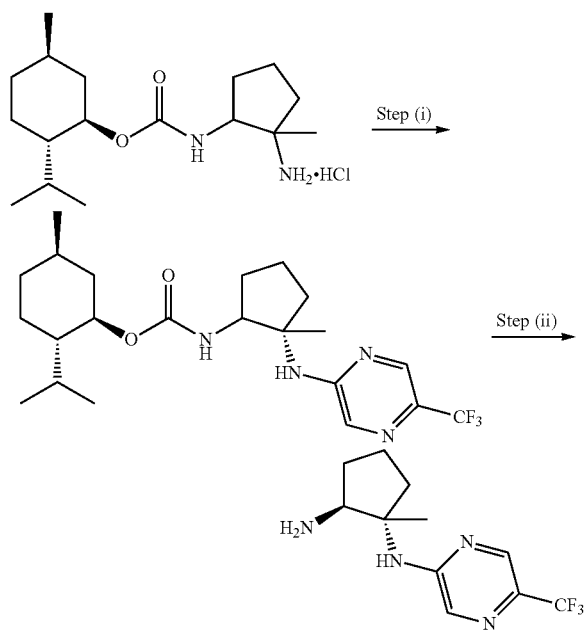

Step (i): (1R,2S,5R)-5-Methyl-2-(propan-2-yl)cyclohexyl N-[(1S,2S)-2-methyl-2-{[5-(trifluoromethyl)pyrazin-2-yl]amino}cyclopentyl]carbamate A solution of 2-chloro-5-(trifluoromethyl)pyrazine (CAS number 799557-87-2; 0.816 ml, 6.61 mmol), (1R,2S,5R)-5-methyl-2-(propan-2-yl)cyclohexyl N-(2-amino-2-methylcyclopentyl)carbamate hydrochloride (Intermediate 27; 2.00 g, 6.01 mmol) and DIPEA (3.15 ml, 18.02 mmol) in DMSO (10 mL) was subjected to microwave irradiation at 140° C. for 5 hours. The reaction was diluted with ethyl acetate (100 ml) and a saturated solution of sodium bicarbonate (50 m). The organics were washed with water (40 ml), brine (40 ml), dried over magnesium sulfate, filtered through a hydrophobic frit and concentrated in vacuo. The crude product was purified by column chromatography (silica, 0-20% ethyl acetate/petrol) to afford the title compound

MS ES$^+$: 443

Step (ii): (1S,2S)-1-Methyl-1-N-[5-(trifluoromethyl)pyrazin-2-yl]cyclopentane-1,2-diamine To a solution of (1R,2S,5R)-5-methyl-2-(propan-2-yl)cyclohexyl N-[(1S,2S)-2-methyl-2-{[5-(trifluoromethyl)pyrazin-2-yl]amino}cyclopentyl]carbamate (1.03 g, 2.33 mmol) in acetic acid (8 ml) was added HBr (6M, 1.94 ml, 11.64 mmol). The reaction was sealed and heated to 90° C. for 20 hours. To this was added further HBr (6M, 1.00 ml, 6.00 mmol) and the reaction was heated at 90° C. for 36 hours and was then concentrated in vacuo. The crude product was purified by reverse phase chromatography (C18 silica, 0-100% water (with 0.05% ammonia)/acetonitrile) to afford the title compound.

$^1$H NMR (400 MHz, DCM-d$_2$) δ ppm 1.32 (s, 3H), 1.33-2.19 (m, 6H), 3.21-3.35 (m, 1H), 5.44 (br. s., 1H), 7.89 (s, 1H), 8.29 (s, 1H)

MS ES$^+$: 261

Intermediate 26: N-(2-Amino-2-methylcyclopentyl)-2-(2H-1,2,3-triazol-2-yl)benzamide hydrochloride

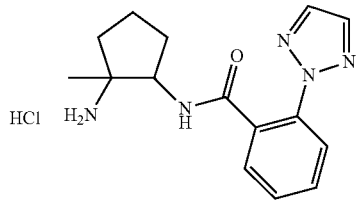 [SMILES: Cl ; CC1(N)CCCC1NC(=O)c1ccccc1-n1nccn1]

To a solution of 2-(2H-1,2,3-triazol-2-yl)benzoyl chloride (213 mg, 1.03 mmol) (which was prepared from 2-(2H-1,2,3-triazol-2-yl)benzoic acid (CAS number 1001401-62-2; 0.194 g, 1.03 mmol) and thionyl chloride (0.112 ml, 1.541 mmol)) in dry DCM (3.1 ml) was added tert-butyl N-(2-amino-1-methylcyclopentyl)carbamate (Intermediate 24; 200 mg, 0.93 mmol) and DIPEA (489 µl, 2.80 mmol). The reaction was stirred at room temperature for 17 hours and was then partitioned between a saturated solution of sodium bicarbonate and DCM, filtered through a hydrophobic frit and concentrated in vacuo. This was then purified by column chromatography (silica, 0-100% ethyl acetate/petrol). The resulting product was then dissolved in 1,4-dioxane (5 ml) and to this was then added HCl in 1,4-dioxane (4 M, 2.3 ml, 9.33 mmol). The reaction was stirred at room temperature for 1 hour and then concentrated in vacuo, azeotropically distilled with toluene to afford the title compound.

$^1$H NMR (400 MHz, DMSO-d$_6$) δ ppm 1.23 (s, 3H), 1.55-1.80 (m, 4H), 1.84-2.01 (m, 2H), 4.10-4.28 (m, 1H), 7.54-7.60 (m, 1H), 7.62-7.70 (m, 2H), 7.81-7.86 (m, 1H), 7.98 (br. s., 3H), 8.07 (s, 2H), 8.60-8.76 (m, 1H)

MS ES$^+$: 286

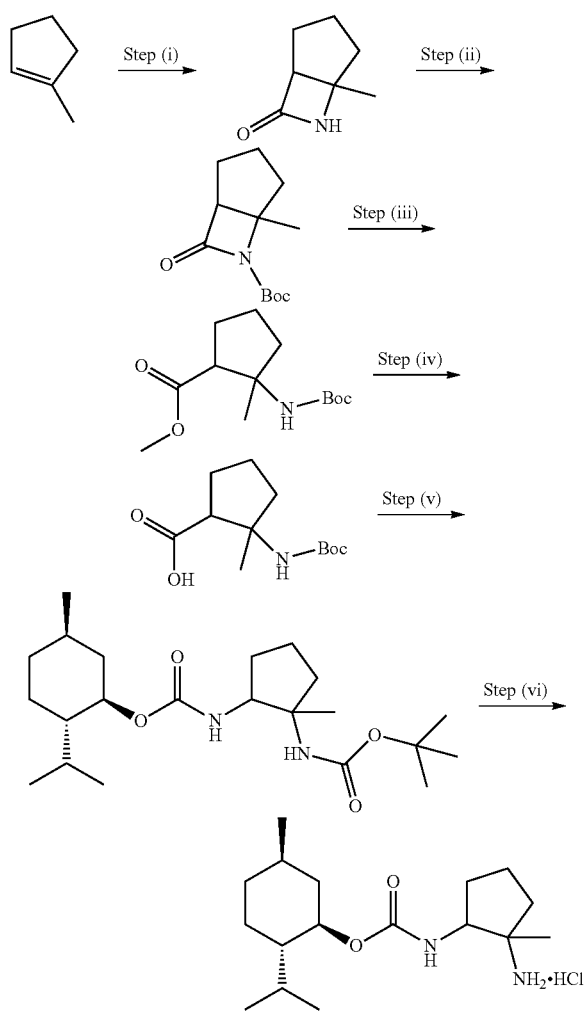

Intermediate 27: (1R,2S,5R)-5-Methyl-2-(propan-2-yl)cyclohexyl N-(2-amino-2-methylcyclopentyl)carbamate hydrochloride

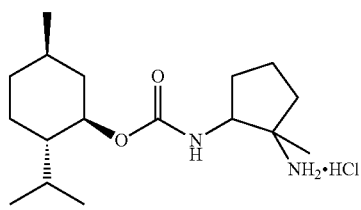

Step (i): 5-Methyl-6-azabicyclo[3.2.0]heptan-7-one

To a solution of 1-methylcyclopent-1-ene (CAS number 693-89-0; 38.5 mL, 365 mmol) in diethyl ether (220 ml) at 0° C. was added drop wise [(chlorosulfonyl)imino]methanone (CAS number 1189-71-5; 33.3 ml, 383 mmol). The reaction was then allowed to warm to room temperature and heated to 36° C. for 72 hours. The reaction was then cooled to room temperature and a solution of sodium sulfite (73.5 g) in water (400 ml) was added drop wise, followed by the addition of 15% w/v potassium hydroxide (500 ml) to obtain pH 7-8. The phases were separated and aqueous phase was extracted with diethyl ether (2×200 ml). The combined organics were dried over magnesium sulfate and concentrated in vacuo to afford the title compound.

$^1$H NMR (400 MHz, DMSO-$d_6$) δ ppm 1.23-1.36 (m, 1H), 1.37-1.81 (m, 8H), 2.82-2.95 (m, 1H), 7.60 (br. s., 1H)

Step (ii): tert-Butyl 5-methyl-7-oxo-6-azabicyclo[3.2.0]heptane-6-carboxylate

To a solution of 5-methyl-6-azabicyclo[3.2.0]heptan-7-one (41.39 g, 331 mmol) in THF (500 ml) was added N,N-dimethylpyridin-4-amine (0.404 g, 3.31 mmol), triethylamine (115 ml, 827 mmol) and di-tert-butyl dicarbonate (81 ml, 347 mmol). The reaction was stirred at room temperature for 20 hours and then concentrated in vacuo. The residue was purified by column chromatography (silica, petrol then 10% ethyl acetate/petrol then 20% ethyl acetate/petrol (step gradient)) to afford the title compound.

$^1$H NMR (400 MHz, DMSO-$d_6$) δ ppm 1.30-1.69 (m, 15H), 1.75-1.88 (m, 2H), 2.07-2.20 (m, 1H), 3.08-3.17 (m, 1H)

Step (iii): Methyl 2-{[(tert-butoxy)carbonyl]amino}-2-methylcyclopentane-1-carboxylate Sodium methoxide (30%, 85 ml, 457 mmol) was added drop wise to a solution of tert-butyl 5-methyl-7-oxo-6-azabicyclo[3.2.0]heptane-6-carboxylate (51.52 g, 229 mmol) in methanol (400 ml) at 0° C. The reaction was stirred at room temperature for 68 hours. The reaction was then concentrated in vacuo, partitioned between ethyl acetate (200 ml) and water (100 ml) and the aqueous phase re-extracted with ethyl acetate (200 ml). The combined organics were dried over magnesium sulfate and concentrated in vacuo to afford the title compound which was used without further purification.

Step (iv): 2-{[(tert-Butoxy)carbonyl]amino}-2-methylcyclopentane-1-carboxylic acid Lithium hydroxide (23.50 g, 981 mmol) was added to a solution of methyl 2-{[(tert-butoxy)carbonyl]amino}-2-methylcyclopentane-1-carboxylate (50.51 g, 196 mmol) in THF (300 ml) and water (150 ml). The reaction was heated at 50° C. for 18 hours and then to 60° C. for 18 hours. The reaction was concentrated in vacuo and then acidified to pH 7 with concentrated HCl and then to pH 3 with 2 M HCl (aq). The organics were extracted with ethyl acetate (3×300 ml) and the combined organics were washed with brine (50 ml), dried over magnesium sulfate and concentrated in vacuo to afford the title compound which was used without further purification.

Step (v): (1R,2S,5R)-5-Methyl-2-(propan-2-yl)cyclohexyl N-(2-{[(tert-butoxy)carbonyl]amino}-2-methylcyclopentyl)carbamate To a solution of 2-{[(tert-butoxy)carbonyl]amino}-2-methylcyclopentane-1-carboxylic acid (42.68 g, 175 mmol) and triethylamine (25.7 ml, 184 mmol) in toluene (250 ml) at room temperature was added {[azido(phenoxy)phosphoryl]oxy}benzene (CAS number 26386-88-9; 37.8 ml, 175 mmol) as a solution in toluene (100 ml). The reaction was heated to 60° C. for 2 hours, then (1R,2S,5R)-5-methyl-2-(propan-2-yl)cyclohexan-1-ol (CAS number 2216-51-5; 14.25 g, 91 mmol) was added. The reaction was heated at 90° C. for 20

Intermediate 28: 1-N-[3-Fluoro-5-(trifluoromethyl) pyridin-2-yl]-1-methylcyclopentane-1,2-diamine

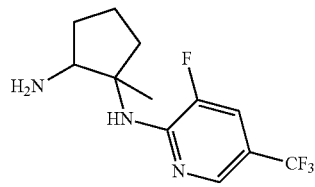 [SMILES: CC1(Nc2ncc(C(F)(F)F)cc2F)CCCC1N]

Step (i): (1R,2S,5R)-5-Methyl-2-(propan-2-yl)cyclohexyl N-(2-{[3-fluoro-5-(trifluoromethyl)pyridin-2-yl]amino}-2-methylcyclopentyl)carbamate A solution of (1R,2S,5R)-5-methyl-2-(propan-2-yl)cyclohexyl N-(2-amino-2-methylcyclopentyl)carbamate hydrochloride (Intermediate 27; 1.00 g, 3.00 mmol), 2,3-difluoro-5-(trifluoromethyl)pyridine (CAS number 89402-42-6; 0.412 ml, 3.30 mmol) and DIPEA (1.57 ml, 9.01 mmol) in DMSO (10 ml) was subjected to microwave irradiation at 140° C. for 3 hours. The reaction was then partitioned between ethyl acetate (10 ml) and water (10 ml), filtered through a hydrophobic frit and concentrated in vacuo. The residue was purified by column chromatography (silica, 0-12% diethyl ether/petrol) to afford the title compound as a single trans-enantiomer.

$^1$H NMR (400 MHz, DCM-d$_2$) δ ppm 0.68-2.17 (m, 26H), 2.51-2.72 (m, 1H), 4.02-4.23 (m, 1H), 4.53-4.69 (m, 1H), 4.92 (br. s., 1H), 7.15-7.32 (m, 2H), 8.03-8.19 (m, 1H)

MS ES$^+$: 460

Step (ii): 1-N-[3-Fluoro-5-(trifluoromethyl)pyridin-2-yl]-1-methylcyclopentane-1,2-diamine To a solution (1R,2S,5R)-5-methyl-2-(propan-2-yl)cyclohexyl N-(2-{[3-fluoro-5-(trifluoromethyl)pyridin-2-yl]amino}-2-methylcyclopentyl)carbamate (0.533 g, 1.16 mmol) in acetic acid (4 ml) was added HBr (6 M, 0.98 ml, 5.80 mmol). The reaction was sealed and heated at 90° C. for 24 hours. To this was then added further HBr (6 M, 0.50 ml, 3.00 mmol) and the reaction was heated at 90° C. for a further 6 hours. The reaction was cooled to room temperature and concentrated in vacuo. The residue was purified by SCX chromatography (2M ammonia in methanol) and then concentrated in vacuo. The crude product was further purified by reverse phase chromatography (C18 silica, 0-100% water (with 0.05% ammonia)/acetonitrile) to afford the title compound as a single trans-enantiomer.

$^1$H NMR (300 MHz, DCM-d$_2$) δ ppm 1.28-1.50 (m, 4H), 1.59-1.79 (m, 4H), 1.88-2.25 (m, 3H), 3.25-3.45 (m, 1H), 5.25 (br. s., 1H), 7.21-7.36 (m, 1H), 8.08-8.19 (m, 1H)

MS ES$^+$: 278 hours and then cooled to room temperature, quenched by the addition of water (50 ml) and diluted with ethyl acetate (200 ml). The organics were washed with a saturated solution of sodium bicarbonate (2×100 ml), brine (100 ml), dried over magnesium sulfate, filtered through a hydrophobic frit and concentrated in vacuo. The residue was purified by column chromatography (silica, petrol—10% ethyl acetate/petrol—20% ethyl acetate/petrol (step gradient)) to afford the title compound (a mixture of trans-amino compounds) which was taken on to next stage without further purification.

Step (vi): (1R,2S,5R)-5-Methyl-2-(propan-2-yl)cyclohexyl N-(2-amino-2-methylcyclopentyl)carbamate hydrochloride To a solution of (1R,2S,5R)-5-methyl-2-(propan-2-yl)cyclohexyl N-(2-{[(tert-butoxy)carbonyl]amino}-2-methylcyclopentyl)carbamate (25.2 g, 63.5 mmol) in DCM (100 ml) was added HCl in 1,4-dioxane (4 M, 60 ml, 240 mmol). The reaction mixture was stirred at room temperature for 18 hours and then further HCl in 1,4-dioxane (4 M, 20 ml, 80 mmol) was added and the stirred for an additional 24 hours at room temperature. The reaction was concentrated in vacuo and purified by SCX chromatography (2M ammonia in methanol). The resulting residue was suspended in DCM/methanol and to this was added HCl in 1,4-dioxane (4 M, 10 ml, 40 mmol) and stirred for 2 hours. The reaction was concentrated in vacuo and further evaporated from diethyl ether and then methanol to afford the title compound as a mixture of trans-amino compounds.

$^1$H NMR (400 MHz, DMSO-d$_6$) δ ppm 0.68-1.76 (m, 22H), 1.77-2.09 (m, 5H), 3.81-4.00 (m, 1H), 4.35-4.54 (m, 1H), 7.29-7.46 (m, 1H), 7.88-8.10 (m, 3H)

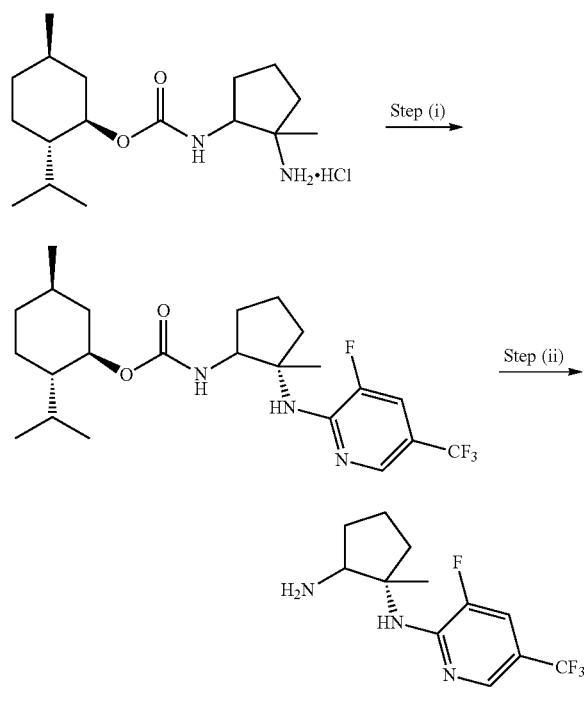

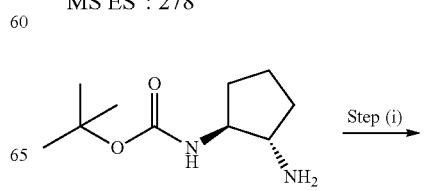

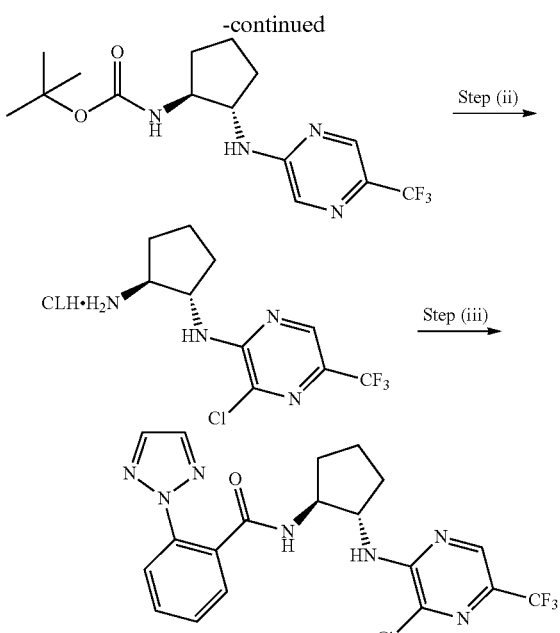

Intermediate 29: N-[(1S,2S)-2-{[3-Chloro-5-(trifluoromethyl)pyrazin-2-yl]amino}cyclopentyl]-2-(2H-1,2,3-triazol-2-yl)benzamide

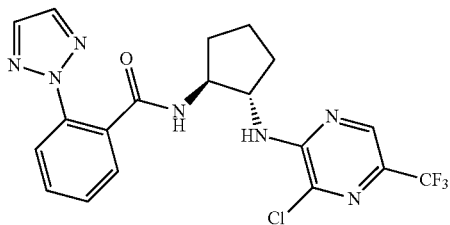 [SMILES: O=C(N[C@H]1CCC[C@@H]1Nc1ncc(C(F)(F)F)nc1Cl)c1ccccc1-n1nccn1]

Step (i): tert-Butyl N-[(1S,2S)-2-{[5-(trifluoromethyl)pyrazin-2-yl]amino}cyclopentyl]carbamate A solution of tert-butyl N-[(1S,2S)-2-aminocyclopentyl]carbamate (CAS number 586961-34-4; 1 g, 4.99 mmol), 2-chloro-5-(trifluoromethyl)pyrazine (CAS number 799557-87-2; 1.09 g, 5.99 mmol) and DIPEA (2.62 ml, 14.98 mmol) in DMSO (17 ml) was subjected to microwave irradiation at 140° C. for 1 hour. The reaction was partitioned between ethyl acetate and water, washed with water, brine, dried over magnesium sulfate and concentrated in vacuo. The resulting residue was purified by column chromatography (silica, 0-100% ethyl acetate/petrol) to afford the title compound.

$^1$H NMR (400 MHz, METHANOL-$d_4$) δ ppm 1.35 (s, 9H), 1.48-1.64 (m, 2H), 1.71-1.85 (m, 2H), 2.03-2.23 (m, 2H), 3.72-3.86 (m, 1H), 4.14-4.25 (m, 1H), 7.84-7.98 (m, 1H), 8.18-8.29 (m, 1H)

MS ES$^+$: 347

Step (ii): (1S,2S)-1-N-[3-Chloro-5-(trifluoromethyl)pyrazin-2-yl]cyclopentane-1,2-diamine hydrochloride To a solution of tert-butyl N-[(1S,2S)-2-{[5-(trifluoromethyl)pyrazin-2-yl]amino}cyclopentyl]carbamate (1.04 g, 3.00 mmol) in dry DCM (10 ml) at 0° C. under an atmosphere of nitrogen was added 1-bromopyrrolidine-2,5-dione (CAS number 128-08-5; 0.80 g, 4.50 mmol). The reaction was allowed to warm to room temperature and stirred for 17 hours and then was concentrated in vacuo. The resulting residue was purified by column chromatography (basic silica, 0-50% ethyl acetate/petrol). To this was then added HCl in 1,4-dioxane (4 M, 7.51 ml, 30.0 mmol) and stirred at room temperature for 72 hours. The reaction mixture was concentrated in vacuo and azeotropically distilled with toluene to afford the title compound.

$^1$H NMR (400 MHz, DMSO-$d_6$) δ ppm 1.58-1.83 (m, 4H), 2.00-2.16 (m, 2H), 3.54-3.66 (m, 1H), 4.39-4.57 (m, 1H), 7.80-8.04 (m, 4H), 8.42-8.53 (m, 1H)

MS ES$^+$: 281

Step (iii): N-[(1S,2S)-2-{[3-Chloro-5-(trifluoromethyl)pyrazin-2-yl]amino}cyclopentyl]-2-(2H-1,2,3-triazol-2-yl)benzamide To a solution of (1S,2S)-1-N-[3-chloro-5-(trifluoromethyl)pyrazin-2-yl]cyclopentane-1,2-diamine hydrochloride (530 mg, 1.67 mmol) in dry DMF (5.6 ml) was added 2-(2H-1,2,3-triazol-2-yl)benzoic acid (CAS number 1001401-62-2; 348 mg, 1.84 mmol), HATU (953 mg, 2.51 mmol) and triethylamine (699 µl, 5.01 mmol) and then stirred at room temperature for 17 hours. The reaction was partitioned between ethyl acetate and a saturated solution of sodium bicarbonate. The organics were washed with water, brine, dried over magnesium sulfate and concentrated in vacuo. The resulting residue was purified by column chromatography (basic silica, 0-100% ethyl acetate/petrol) to afford the title compound.

$^1$H NMR (400 MHz, DMSO-$d_6$) δ ppm 1.49-1.77 (m, 4H), 1.93-2.05 (m, 1H), 2.06-2.17 (m, 1H), 4.18-4.29 (m, 1H), 4.33-4.44 (m, 1H), 7.40-7.46 (m, 1H), 7.46-7.53 (m, 1H), 7.56-7.64 (m, 1H), 7.72-7.78 (m, 1H), 7.79-7.87 (m, 3H), 8.41-8.57 (m, 2H)

MS ES$^+$: 452

Intermediate 30a and 30b: N-[(1S,2S)-2-[(5-Bromopyrazin-2-yl)amino]cyclopentyl]-2-(2H-1,2,3-triazol-2-yl)benzamide (Intermediate 30a) and N-[(1S,2S)-2-[(5-Chloropyrazin-2-yl)amino]cyclopentyl]-2-(2H-1,2,3-triazol-2-yl)benzamide (Intermediate 30b)

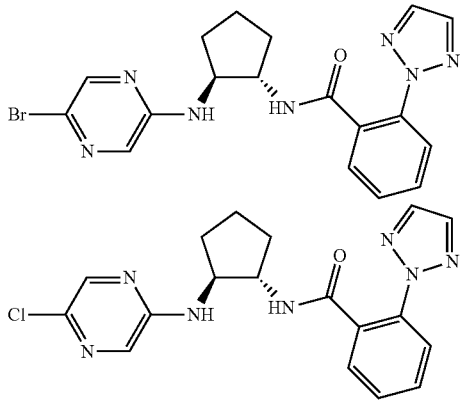

A solution of N-[(1S,2S)-2-aminocyclopentyl]-2-(2H-1,2,3-triazol-2-yl)benzamide hydrochloride (Intermediate 4; 1.00 g, 3.25 mmol), 2-bromo-5-chloropyrazine (CAS number 912773-21-8; 0.691 g, 3.57 mmol) and DIPEA (1.7 ml, 9.75 mmol) in DMSO (11 ml) was subjected to microwave irradiation at 140° C. for 3 hours. The reaction was partitioned between ethyl acetate and water, washed with water, brine, dried over magnesium sulfate and concentrated in vacuo. This was then purified by column chromatography (silica, 0-100% ethyl acetate/petrol then 0-20% methanol/ethyl acetate) to afford title compound as a mixture of both products.

5-chloro-2-(2H-1,2,3-triazol-2-yl)benzoic acid (Intermediate 38a; CAS number 1293284-54-4; 134 mg, 0.60 mmol), TBTU (231 mg, 0.72 mmol) and DIPEA (0.116 g, 0.9 mmol) in DMF (3 ml) was stirred at room temperature for 2 hours. The reaction was diluted with water (30 ml) and extracted with ethyl acetate (3×30 ml). The combined organics were washed with water (20 ml), brine (20 ml), dried over sodium sulfate and concentrated in vacuo. The residue was purified by column chromatography (silica, 0-30% ethyl acetate/n-hexane) to afford the title compound.

<sup>1</sup>H NMR (400 MHz, DMSO-d) δ ppm 1.20-1.42 (m, 11H), 1.55-1.60 (m, 2H), 1.83-1.86 (m, 2H), 3.73-3.77 (m, 1H), 3.92-3.96 (m, 1H), 6.85-6.87 (m, 1H), 7.58 (s, 1H), 7.67-7.70 (m, 1H), 7.81-7.83 (m, 1H), 8.05 (s, 2H), 8.45-8.47 (m, 1H)

MS ES<sup>+</sup>: 406

Step (ii): N-[(1S,2S)-2-Aminocyclopentyl]-5-chloro-2-(2H-1,2,3-triazol-2-yl)benzamide hydrochloride To a solution of tert-butyl N-[(1S,2S)-2-[5-chloro-2-(2H-1,2,3-triazol-2-yl)benzamido]cyclopentyl]carbamate (170 mg, 0.418 mmol) in DCM (5 ml) was added HCl in 1,4-dioxane (4 M, 3 ml). The reaction was stirred at room temperature overnight and then concentrated in vacuo. The solid was triturated with diethyl ether (3×1 ml) to afford the title compound.

<sup>1</sup>H NMR (400 MHz, DMSO-d) δ ppm 1.55-1.73 (m, 4H), 1.92-2.10 (m, 2H), 3.40-3.42 (m, 1H), 4.06-4.13 (m, 1H), 7.72-7.75 (m, 1H), 7.79-7.80 (m, 1H), 7.87-7.90 (m, 1H), 8.10-8.14 (m, 4H), 8.76-8.78 (m, 2H)

MS ES<sup>+</sup>: 306

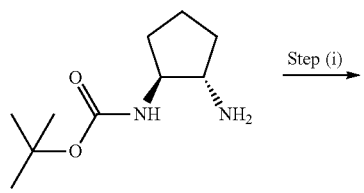

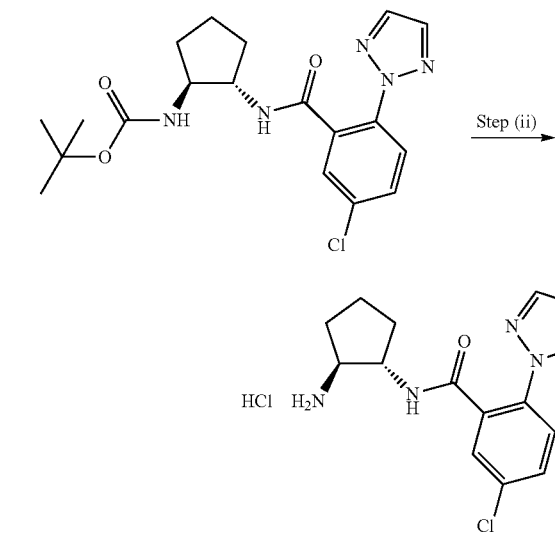

Intermediate 31: N-[(1S,2S)-2-Aminocyclopentyl]-5-chloro-2-(2H-1,2,3-triazol-2-yl)benzamide hydrochloride

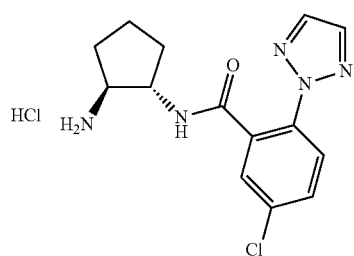 [SMILES: Cl ; N[C@H]1CCC[C@@H]1NC(=O)c1cc(Cl)ccc1-n1nccn1]

Step (i): tert-Butyl N-[(1S,2S)-2-[5-chloro-2-(2H-1,2,3-triazol-2-yl)benzamido]cyclopentyl]carbamate A solution of tert-butyl N-[(1S,2S)-2-aminocyclopentyl]carbamate (CAS number 586961-34-4; 120 mg, 0.60 mmol),

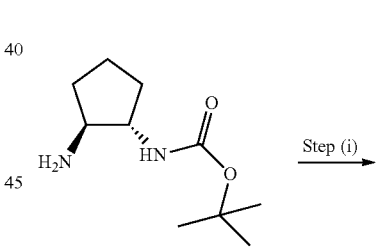

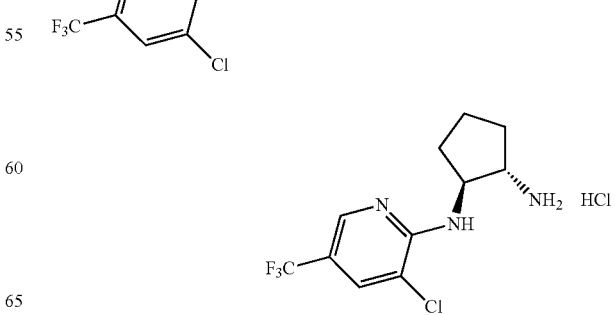

Intermediate 33: (1S,2S)-1-N-[3-Chloro-5-(trifluoromethyl)pyridin-2-yl]cyclopentane-1,2-diamine hydrochloride

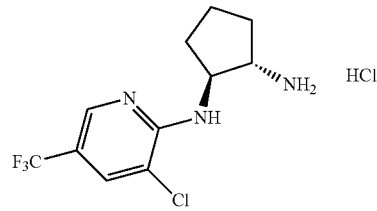 [SMILES: N[C@H]1CCC[C@@H]1Nc1ncc(C(F)(F)F)cc1Cl ; Cl]

Step (i): tert-Butyl N-[(1S,2S)-2-{[3-chloro-5-(trifluoromethyl)pyridin-2-yl]amino}cyclopentyl]carbamate A solution of tert-butyl N-[(1S,2S)-2-aminocyclopentyl]carbamate (CAS number 586961-34-4; 2 g, 9.99 mmol), 3-chloro-2-fluoro-5-(trifluoromethyl)pyridine (CAS number 72537-17-8; 1.44 ml, 10.98 mmol), DIPEA (1.744 ml, 9.99 mmol) in DMSO (35 ml) was heated at 140° C. for 5 hours. The reaction was partitioned between ethyl acetate and water. The phases were separated and the aqueous layer was re-extracted with ethyl acetate (2×50 ml). The combined organics were washed with brine (50 ml), filtered through a hydrophobic frit and concentrated in vacuo. The crude product was purified by column chromatography (silica, 0-15% ethyl acetate/petrol) and then by column chromatography (silica, 0-10% ethyl acetate/petrol) to afford the title compound.

$^1$H NMR (400 MHz, DMSO-d) δ ppm 1.31 (s, 9H), 1.39-1.77 (m, 4H), 1.81-1.95 (m, 1H), 2.03-2.21 (m, 1H), 3.86-3.98 (m, 1H), 4.09-4.20 (m, 1H), 6.78-7.10 (m, 2H), 7.95 (s, 1H), 8.31 (s, 1H)

MS ES$^+$: 380

Step (ii): (1S,2S)-1-N-[3-Chloro-5-(trifluoromethyl)pyridin-2-yl]cyclopentane-1,2-diamine hydrochloride To a solution of tert-butyl N-[(1S,2S)-2-{[3-chloro-5-(trifluoromethyl)pyridin-2-yl]amino}cyclopentyl]carbamate (2.23 g, 5.87 mmol) in 1,4-dioxane (20 ml) was added HCl in 1,4-dioxane (4 M, 15 ml, 60.0 mmol). The reaction was stirred at room temperature for 18 hours. The reaction mixture was concentrated in vacuo to afford the title compound.

$^1$H NMR (400 MHz, DMSO-d$_6$) δ ppm 1.57-1.83 (m, 4H), 1.98-2.19 (m, 2H), 4.35-4.53 (m, 1H), 7.17-7.36 (m, 1H), 7.95-8.05 (m, 1H), 8.15 (br. s., 3H), 8.31-8.44 (m, 1H)

MS ES$^+$: 280

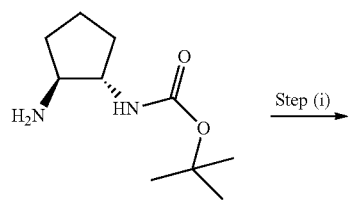

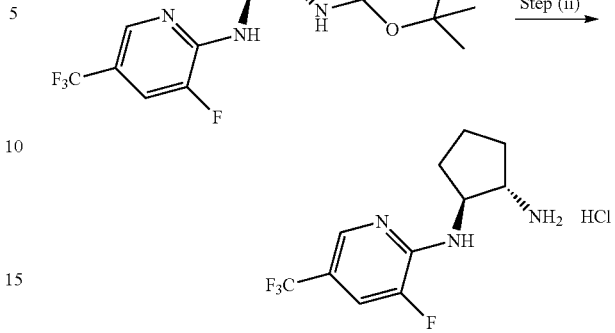

Intermediate 34: (1S,2S)-1-N-[3-Fluoro-5-(trifluoromethyl)pyridin-2-yl]cyclopentane-1,2-diamine hydrochloride

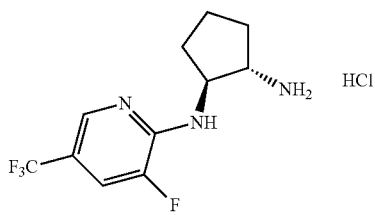 [SMILES: N[C@H]1CCC[C@@H]1Nc1ncc(C(F)(F)F)cc1F ; Cl]

Step (i): tert-Butyl N-[(1S,2S)-2-{[3-fluoro-5-(trifluoromethyl)pyridin-2-yl]amino}cyclopentyl]carbamate A solution of tert-butyl N-[(1S,2S)-2-aminocyclopentyl]carbamate (CAS number 586961-34-4; 2 g, 9.99 mmol), 2,3-difluoro-5-(trifluoromethyl)pyridine (CAS number 89402-42-6; 2.011 g, 10.98 mmol) and DIPEA (1.744 ml, 9.99 mmol) in DMSO (35 ml) was heated at 140° C. for 5 hours. The reaction was partitioned between ethyl acetate and water. The phases were separated and the aqueous layer was re-extracted with ethyl acetate (2×50 ml). The combined organics were washed with brine (50 ml), filtered through a hydrophobic frit and concentrated in vacuo. The crude product was purified by column chromatography (0-15% ethyl acetate/petrol) to afford the title compound.

$^1$H NMR (400 MHz, DCM-d$_2$) δ ppm 1.41 (s, 9H), 1.47-1.65 (m, 2H), 1.73-1.92 (m, 2H), 2.08-2.24 (m, 1H), 2.29-2.48 (m, 1H), 3.78-4.17 (m, 2H), 4.93-5.15 (m, 1H), 5.86-6.03 (m, 1H), 7.26-7.39 (m, 1H), 8.08-8.21 (m, 1H)

MS ES$^+$: 364

Step (ii): (1S,2S)-1-N-[3-Fluoro-5-(trifluoromethyl)pyridin-2-yl]cyclopentane-1,2-diamine hydrochloride To a solution of tert-butyl N-[(1S,2S)-2-{[3-fluoro-5-(trifluoromethyl)pyridin-2-yl]amino}cyclopentyl]carbamate (2.57 g, 7.08 mmol) in 1,4-dioxane (25 ml) was added HCl in 1,4-dioxane (4 M, 20 ml, 80 mmol). The reaction was stirred at room temperature for 20 hours. The reaction mixture was concentrated in vacuo and azeotropically distilled with toluene to afford the title compound.

¹H NMR (300 MHz, DMSO-d₆) δ ppm 1.51-1.83 (m, 4H), 1.99-2.20 (m, 2H), 3.39-3.53 (m, 1H), 4.29-4.47 (m, 1H), 7.54-7.69 (m, 1H), 7.73-7.89 (m, 1H), 8.11-8.33 (m, 4H)

MS ES⁺: 264

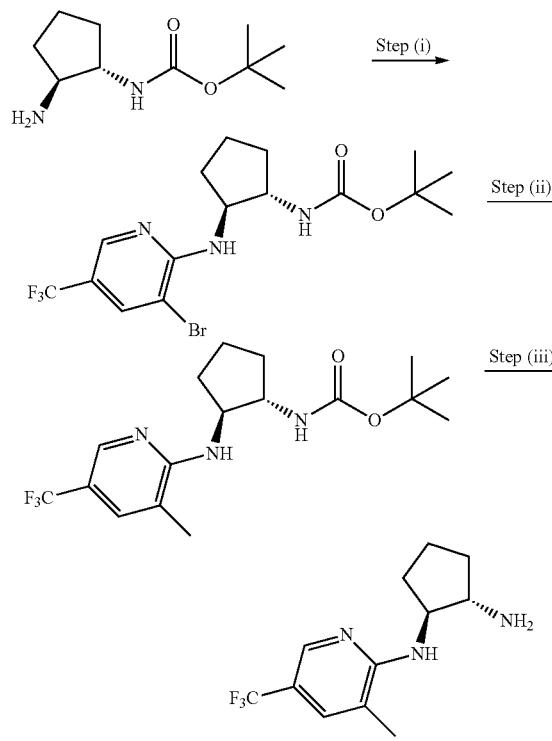

Intermediate 35: (1S,2S)-1-N-[3-Methyl-5-(trifluoromethyl)pyridin-2-yl]cyclopentane-1,2-diamine hydrochloride

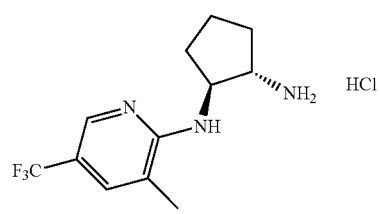 [SMILES: Cc1cc(C(F)(F)F)cnc1N[C@H]1CCC[C@@H]1N ; Cl]

Step (i): tert-Butyl N-[(1S,2S)-2-{[3-bromo-5-(trifluoromethyl)pyridin-2-yl]amino}cyclopentyl]carbamate A solution of tert-butyl N-[(1S,2S)-2-aminocyclopentyl]carbamate (CAS number 586961-34-4; 2 g, 9.99 mmol), 3-bromo-2-chloro-5-(trifluoromethyl)pyridine (CAS number 71701-92-3; 2.86 g, 10.98 mmol), DIPEA (1.74 ml, 9.99 mmol) in DMSO (35 ml) was heated at 140° C. for 5 hours. The reaction was partitioned between ethyl acetate and water. The phases were separated and the aqueous layer was re-extracted with ethyl acetate (2×50 ml). The combined organics were washed with brine (50 ml), filtered through a hydrophobic frit and concentrated in vacuo. The crude product was purified by column chromatography (silica, 0-50% ethyl acetate/petrol), then by column chromatography (silica, 0-15% ethyl acetate/petrol) and then by column chromatography (silica, 0-10% ethyl acetate/petrol) to afford the title compound.

¹H NMR (400 MHz, DCM-d₂) δ ppm 1.42 (s, 9H), 1.45-1.56 (m, 2H), 1.75-1.92 (m, 2H), 2.09-2.53 (m, 2H), 3.77-4.19 (m, 2H), 4.80-5.09 (m, 1H), 6.20-6.37 (m, 1H), 7.72-7.89 (m, 1H), 8.21-8.38 (m, 1H)

MS ES⁺: 425

Step (ii): tert-Butyl N-[(1S,2S)-2-{[3-methyl-5-(trifluoromethyl)pyridin-2-yl]amino}cyclopentyl]carbamate A mixture of tert-butyl N-[(1S,2S)-2-{[3-bromo-5-(trifluoromethyl)pyridin-2-yl]amino}cyclopentyl]carbamate (1.26 g, 2.96 mmol), methylboronic acid (CAS number 13061-96-6; 0.532 g, 8.88 mmol), tetrakis(triphenylphosphine)palladium (0.342 g, 0.296 mmol) and potassium carbonate (1.303 g, 9.43 mmol) in 1,4-dioxane (10 ml) and water (1.5 ml) was sealed, evacuated and purged with nitrogen and subjected to microwave irradiation at 140° C. for 1 hour. The mixture was partitioned between ethyl acetate (10 ml) and water (10 ml). The organics were extracted with ethyl acetate (2×20 ml). The combined organics were washed with brine (20 ml), filtered through a hydrophobic frit and concentrated in vacuo. The crude product was purified by column chromatography (silica, 0-60% ethyl acetate/petrol) to afford the title compound.

¹H NMR (400 MHz, DMSO-d₆) δ ppm 1.31 (s, 9H), 1.37-1.57 (m, 2H), 1.58-1.71 (m, 2H), 1.82-1.95 (m, 1H), 2.08-2.19 (m, 4H), 3.81-3.97 (m, 1H), 4.07-4.19 (m, 1H), 6.31-6.47 (m, 1H), 6.86-7.00 (m, 1H), 7.43-7.54 (m, 1H), 8.11-8.21 (m, 1H)

MS ES⁺: 360

Step (iii): (1S,2S)-1-N-[3-Methyl-5-(trifluoromethyl)pyridin-2-yl]cyclopentane-1,2-diamine hydrochloride To a solution of tert-butyl N-[(1S,2S)-2-{[3-methyl-5-(trifluoromethyl)pyridin-2-yl]amino}cyclopentyl]carbamate (580 mg, 1.614 mmol) in 1,4-dioxane (5 ml) was added HCl in 1,4-dioxane (4M, 4 ml, 16.00 mmol). The reaction was stirred at room temperature for 18 hours. The reaction mixture was concentrated in vacuo and azeotropically distilled with toluene to afford the title compound.

¹H NMR (400 MHz, DCM-d₂) δ ppm 1.74-1.96 (m, 4H), 2.17-2.32 (m, 1H), 2.37-2.57 (m, 1H), 3.63 (s, 3H), 4.30-4.50 (m, 1H), 4.77-4.94 (m, 1H), 7.63 (s, 1H), 8.10 (s, 1H), 8.53-8.86 (m, 4H)

MS ES⁺: 260

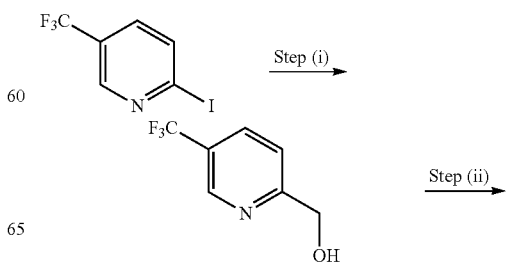

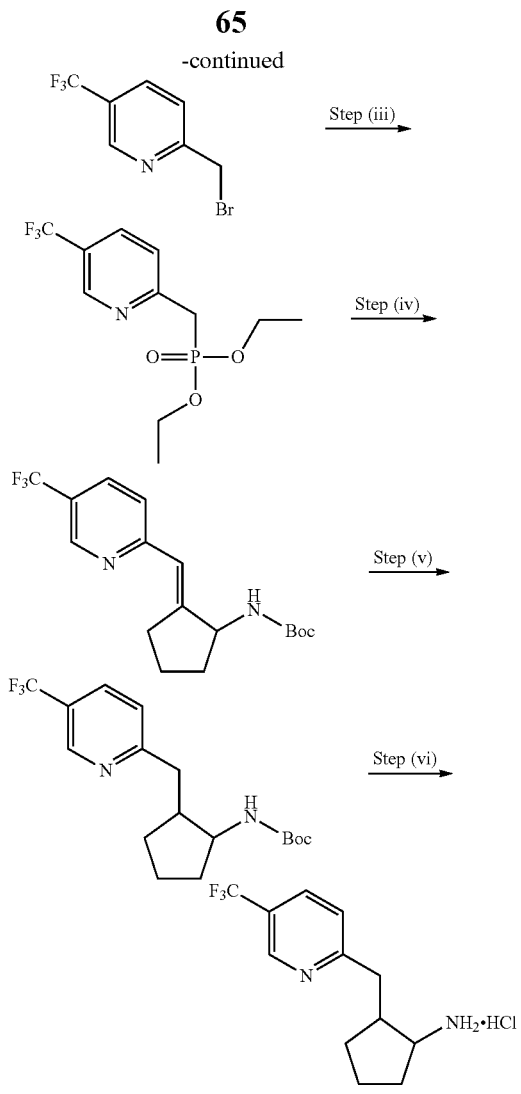

Intermediate 36: 2-{[5-(Trifluoromethyl)pyridin-2-yl]methyl}cyclopentan-1-amine hydrochloride

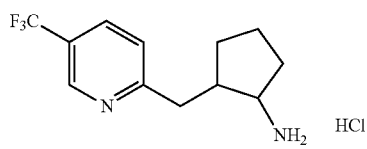 [SMILES: NC1CCCC1Cc1ccc(C(F)(F)F)cn1 ; Cl]

Step (i): [5-(Trifluoromethyl)pyridin-2-yl]methanol

To the solution of 2-iodo-5-(trifluoromethyl)pyridine (CAS number 100366-75-4; 10 g, 69.4 mmol) in toluene (250 ml) at −78° C. was added n-BuLi in hexane (2.5 M, 15.0 mL, 37.5 mmol). The reaction was stirred at −78° C. for 15 minutes. To this was then added drop wise DMF (3.5 ml) and then stirred at −78° C. for 1 hour. Sodium borohydride (2.74 g, 72.0 mmol) and methanol (50 ml) were added and the resulting reaction mixture was stirred for 30 minutes and then allowed to warm to room temperature. The reaction was cooled to −10° C. and to this was then added a saturated solution of ammonium chloride. The organics were extracted with ethyl acetate (2×200 ml) and the combined organics were washed with brine, dried over sodium sulfate and concentrated in vacuo to afford the title compound which was used without further purification.

$^1$H NMR (400 MHz, DMSO) δ ppm 4.66-4.65 (m, 2H), 5.69-5.66 (m, 1H), 7.71-7.69 (m, 1H), 8.23-8.21 (m, 1H), 8.87 (s, 1H)

MS ES$^+$: 178

Step (ii): 2-(Bromomethyl)-5-(trifluoromethyl)pyridine

To a solution of [5-(trifluoromethyl)pyridin-2-yl]methanol (5.0 g, 28.24 mmol) in DCM (50 ml) was added tribromophosphane (0.58 g, 3.50 mmol) at 0° C. The reaction was allowed to warm to room temperature and stirred for 3 hours. The reaction was then poured into water (50 ml) and the organics were extracted with DCM (2×50 ml), washed with brine, dried over sodium sulfate and concentrated in vacuo to afford the title compound which was used without further purification.

MS ES$^+$: 240, 242

Step (iii): Diethyl {[5-(trifluoromethyl)pyridin-2-yl]methyl}phosphonate

To a solution of 2-(bromomethyl)-5-(trifluoromethyl)pyridine (3.0 g, 12.5 mmol) in toluene (100 ml) was added triethyl phosphite (6.2 g, 37.0 mmol). The reaction was refluxed for 17 hours and was then concentrated in vacuo. The resulting residue was purified by column chromatography (silica, 0-50% ethyl acetate/n-hexane) to afford the title compound.

$^1$H NMR (400 MHz, DMSO) δ ppm 1.06-1.27 (m, 6H), 3.57-3.65 (m, 2H), 3.95-4.08 (m, 4H), 7.61-7.59 (m, 1H), 8.20-8.18 (m, 1H), 8.90-8.89 (m, 1H)

MS ES$^+$: 298

Step (iv): tert-Butyl N-[(2E)-2-{[5-(trifluoromethyl)pyridin-2-yl]methylidene}cyclopentyl]carbamate To the suspension of diethyl ((5-(trifluoromethyl)pyridin-2-yl)methyl)phosphonate (2.0 g, 6.71 mmol) in THF (50 ml) at 0° C. was added potassium tert-butoxide (1.5 g, 13.42 mmol) and then stirred at room temperature for 30 minutes. To this was then added a solution of tert-butyl N-(2-oxocyclopentyl)carbamate (CAS number 477585-30-1; 1.62 g, 8.05 mmol) in THF (20 ml) and the resulting reaction was stirred at room temperature for 1 hour and then heated at reflux overnight. The reaction was quenched with water (50 ml) and extracted with ethyl acetate (3×100 ml). The combined organics were washed with brine, dried over sodium sulfate and concentrated in vacuo. The resulting residue was purified by column chromatography (silica, 0-15% ethyl acetate/n-hexane) to afford the title compound.

MS ES$^+$: 343

Step (v): tert-Butyl N-(2-{[5-(trifluoromethyl)pyridin-2-yl]methyl}cyclopentyl)carbamate To a solution of tert-butyl N-[(2E)-2-{[5-(trifluoromethyl)pyridin-2-yl]methylidene}cyclopentyl]carbamate (1.5 g, 4.38 mmol) in methanol (5 ml) was added palladium on carbon (10% wt, 50% wet, 300 mg) and 2M NaOH (5 ml). The resulting reaction was stirred under a balloon of hydrogen gas for 2 hours. The reaction was filtered through diatomaceous earth (commercially sold under the trade mark "Celite") and concentrated in vacuo to afford the title compound. The resulting residue was purified by column chromatography (silica, 0-70% ethyl acetate/n-hexane) to afford the title compound.

MS ES+: 345

Step (vi): 2-{[5-(Trifluoromethyl)pyridin-2-yl]methyl}cyclopentan-1-amine hydrochloride To a solution of tert-butyl N-(2-{[5-(trifluoromethyl)pyridin-2-yl]methyl}cyclopentyl)carbamate (1.0 g, 2.9 mmol) in 1,4-dioxane (5 ml) at 0° C. was added drop wise HCl in 1,4-dioxane (12%, 15.0 ml). The reaction was stirred at room temperature for 1 hour, then concentrated in vacuo. To this was then added DCM (50 ml) and a solution of sodium bicarbonate (aq, 7.5%, 15 ml). The organics were dried over sodium sulfate and concentrated in vacuo. The resulting residue was purified by column chromatography (0-2% methanol/DCM) and then treated with HCl in 1,4-dioxane (12%, 5 ml), stirred for 2 hours, concentrated in vacuo, triturated with diethyl ether to afford the title compound as a single diastereomer.

$^1$H NMR (400 MHz, DMSO) δ ppm 1.40-1.76 (m, 5H), 1.95-1.99 (m, 1H), 2.79-2.85 (m, 1H), 3.05-3.15 (m, 1H), 3.55-3.59 (m, 1H), 7.54-7.56 (m, 1H), 7.75 (bs, 3H), 8.15-8.17 (m, 1H), 8.90 (s, 1H)

MS ES+: 245

Intermediate 37a and 37b: 2-(2H-1,2,3-Triazol-2-yl)-5-(trifluoromethyl)benzoic acid (Intermediate 37a) and 2-(1H-1,2,3-Triazol-1-yl)-5-(trifluoromethyl)benzoic acid (Intermediate 37b)

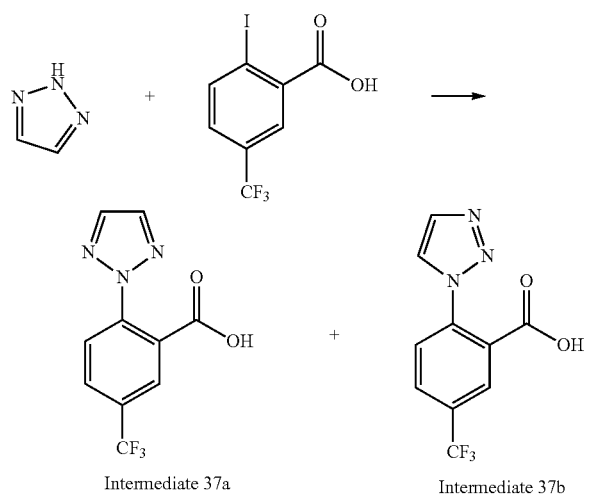

To a solution of 2H-1,2,3-triazole (CAS number 288-36-8; 1.0 g, 10.86 mmol) in DMF (4 ml) at 0-10° C. was added cesium carbonate (4.71 g, 14.49 mmol), copper (I) iodide (68 mg, 0.36 mmol), trans-1-N,2-N-dimethylcyclohexane-1,2-diamine (200 mg, 1.44 mmol) and 2-iodo-5-(trifluoromethyl)benzoic acid (CAS number 702641-04-1; 2.28 g, 7.24 mmol). The reaction was subjected to microwave irradiation at 120° C. for 15 minutes and was then partitioned between ethyl acetate (2×100 ml) and water (50 ml). The aqueous layer was acidified with HCl (aq, 2M) to give pH 2 and the organics were extracted with ethyl acetate (3×100 ml). The combined organics were washed with brine, dried over sodium sulfate and concentrated in vacuo. The resulting residue was purified by column chromatography (silica, 0-3% methanol/DCM) to afford 2-(2H-1,2,3-triazol-2-yl)-5-(trifluoromethyl)benzoic acid (Intermediate 37a; also commercially available CAS number 1384066-81-2). The mixed fractions were further purified by column chromatography (silica, 0-3% methanol/DCM) followed by reverse phase preparative HPLC (eluted with acetonitrile/water containing 0.1% formic acid) to afford 2-(1H-1,2,3-triazol-1-yl)-5-(trifluoromethyl)benzoic acid (Intermediate 37b).

Intermediate 37a $^1$H NMR (400 MHz, DMSO) δ ppm 8.07-8.08 (m, 3H), 8.20 (s, 2H), 13.57 (bs, 1H)

MS ES+: 258

Intermediate 37b $^1$H NMR (400 MHz, DMSO) δ ppm 7.90-7.97 (m, 2H), 8.16-8.21 (m, 2H), 8.65 (s, 1H), 13.65 (bs, 1H)

MS ES+: 258

Intermediate 38a and 38b: 5-Chloro-2-(2H-1,2,3-triazol-2-yl)benzoic acid (Intermediate 38a) and 5-Chloro-2-(1H-1,2,3-triazol-1-yl)benzoic acid (Intermediate 38b)

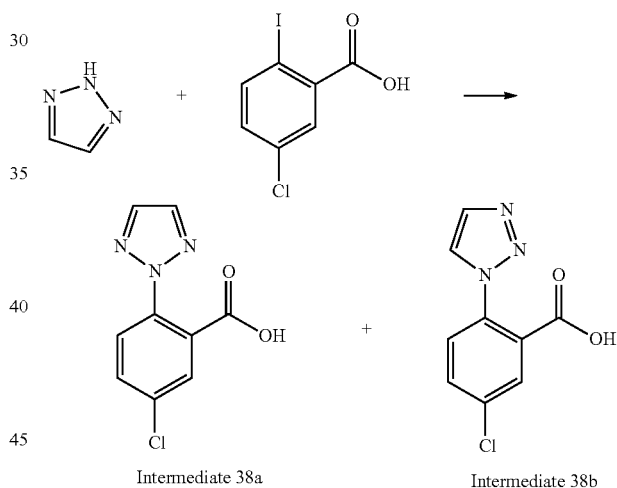

Prepared according to the procedure for 2-(2H-1,2,3-triazol-2-yl)-5-(trifluoromethyl)benzoic acid (Intermediate 37a) and 2-(1H-1,2,3-triazol-1-yl)-5-(trifluoromethyl)benzoic acid (Intermediate 37b) from 2H-1,2,3-triazole (CAS number 288-36-8; 1.0 g, 10.86 mmol) and 5-chloro-2-iodobenzoic acid (CAS number 13421-00-6; 2.00 g, 7.24 mmol). The crude solid was purified by column chromatography (silica, 0-3% methanol/DCM) to afford 5-chloro-2-(2H-1,2,3-triazol-2-yl)benzoic acid (Intermediate 38a; also commercially available CAS number 1293284-54-4). The mixed fractions were further purified by column chromatography (silica, 0-3% methanol/DCM) to afford 5-chloro-2-(1H-1,2,3-triazol-1-yl)benzoic acid (Intermediate 38b).

Intermediate 38a $^1$H NMR (400 MHz, DMSO) δ ppm 7.76-7.83 (m, 3H), 8.12 (s, 2H), 13.42 (bs, 1H)

MS ES+: 224

Intermediate 38b

¹H NMR (400 MHz, DMSO) δ ppm 7.66-7.68 (m, 1H), 7.84-7.93 (m, 3H), 8.54 (s, 1H), 13.50 (bs, 1H)

MS ES⁺: 224

Intermediate 39a and 39b: 2,3-Difluoro-6-(2H-1,2,3-triazol-2-yl)benzoic acid (Intermediate 39a) and 2,3-Difluoro-6-(1H-1,2,3-triazol-1-yl)benzoic acid (Intermediate 39b)

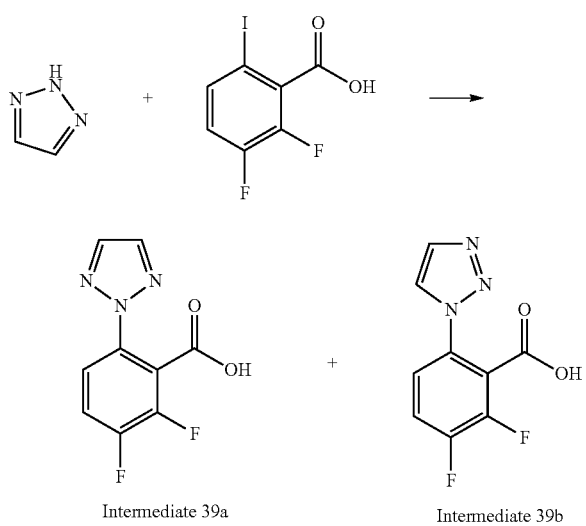

Intermediate 39a        Intermediate 39b

Prepared according to the procedure for 2-(2H-1,2,3-triazol-2-yl)-5-(trifluoromethyl)benzoic acid (Intermediate 37a) and 2-(1H-1,2,3-triazol-1-yl)-5-(trifluoromethyl)benzoic acid (Intermediate 37b) from 2H-1,2,3-triazole (CAS number 288-36-8; 0.75 g, 10.86 mmol) and 2,3-difluoro-6-iodobenzoic acid (CAS number 333780-75-9; 1.54 g, 5.43 mmol) in 1,4-dioxane (10 ml) and water (0.2 ml). The crude solid was purified by column chromatography (silica, 0-3% methanol/DCM) to afford 2,3-difluoro-6-(2H-1,2,3-triazol-2-yl)benzoic acid (Intermediate 39a). The mixed fractions were further purified by column chromatography (silica, 0-3% methanol/DCM) followed by reverse phase preparative HPLC (eluted with acetonitrile/water containing 0.1% formic acid) to afford 2,3-difluoro-6-(1H-1,2,3-triazol-1-yl)benzoic acid (Intermediate 39b).

Intermediate 39a

¹H NMR (400 MHz, DMSO) δ ppm 7.73-7.79 (m, 2H), 8.16 (s, 2H), 14.05 (bs, 1H)

MS ES⁺: 226

Intermediate 39b

¹H NMR (400 MHz, DMSO) δ ppm 7.60-7.63 (m, 1H), 7.79-7.86 (m, 1H), 7.96 (s, 1H), 8.61 (s, 1H), 14.17 (bs, 1H)

MS ES⁺: 226

Intermediate 40a and 40b: 3,5-Difluoro-2-(2H-1,2,3-triazol-2-yl)benzoic acid (Intermediate 40a) and 3,5-Difluoro-2-(1H-1,2,3-triazol-1-yl)benzoic acid (Intermediate 40b)

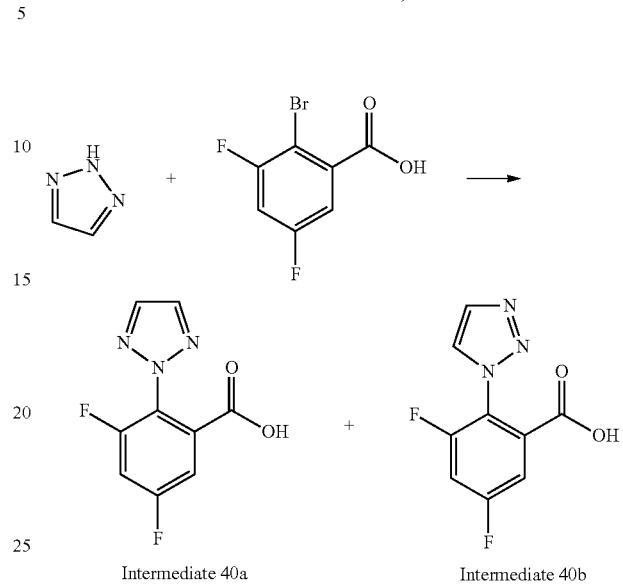

Intermediate 40a        Intermediate 40b

Prepared according to the procedure for 2-(2H-1,2,3-triazol-2-yl)-5-(trifluoromethyl)benzoic acid (Intermediate 37a) and 2-(1H-1,2,3-triazol-1-yl)-5-(trifluoromethyl)benzoic acid (Intermediate 37b) from 2H-1,2,3-triazole (CAS number 288-36-8; 1.0 g, 10.86 mmol) and 2-bromo-3,5-difluorobenzoic acid (CAS number 651027-01-9; 1.27 g, 5.43 mmol) in 1,4-dioxane (5 ml) and water (1 ml). The crude solid was purified by using column chromatography (silica, 0-3% methanol/DCM) to afford 3,5-difluoro-2-(2H-1,2,3-triazol-2-yl)benzoic acid (Intermediate 40a). The mixed fractions were further purified by column chromatography (silica, 0-3% methanol/DCM) followed by reverse phase preparative HPLC (eluted with acetonitrile/water containing 0.1% formic acid) to afford 3,5-difluoro-2-(1H-1,2,3-triazol-1-yl)benzoic acid (Intermediate 40b).

Intermediate 40a

¹H NMR (400 MHz, DMSO) δ ppm 7.63-7.66 (m, 1H), 7.86-7.92 (m, 1H), 8.12 (s, 2H), 13.63 (bs, 1H)

MS ES⁺: 226

Intermediate 40b

¹H NMR (400 MHz, DMSO) δ ppm 7.68-7.71 (m, 1H), 7.90-7.95 (m, 2H), 8.54 (s, 1H), 13.70 (bs, 1H)

MS ES⁺: 226

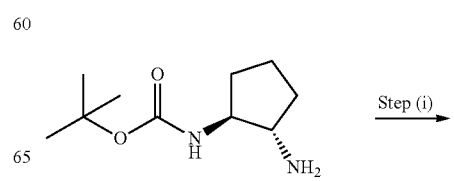

Step (i) →

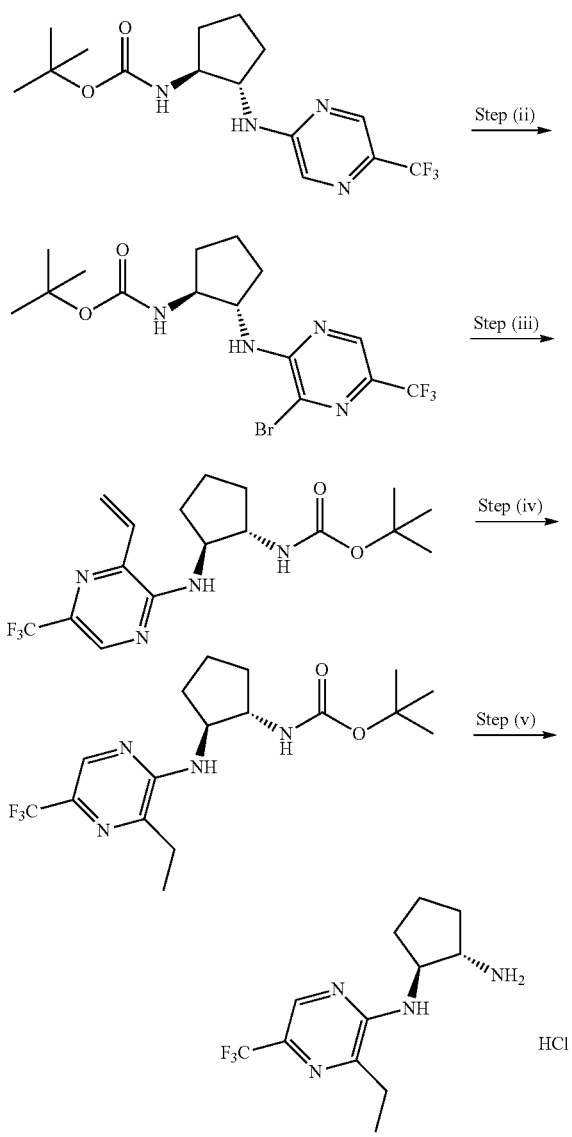

Intermediate 41: (1S,2S)-1-N-[3-Ethyl-5-(trifluoromethyl)pyrazin-2-yl]cyclopentane-1,2-diamine hydrochloride

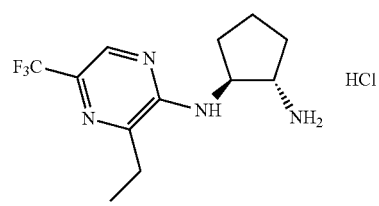 [SMILES: CCc1nc(C(F)(F)F)cnc1N[C@H]1CCC[C@@H]1N ; Cl]

Step (i): tert-Butyl N-[(1S,2S)-2-{[5-(trifluoromethyl)pyrazin-2-yl]amino}cyclopentyl]carbamate A solution of 2-chloro-5-(trifluoromethyl)pyrazine (CAS number 799557-87-2; 2.0 g, 10.98 mmol), tert-butyl N-[(1S, 2S)-2-aminocyclopentyl]carbamate (CAS number 586961-34-4; 2 g, 9.99 mmol) and DIPEA (5.23 ml, 30.0 mmol) in DMSO (20 ml) was sealed and heated at 140° C. for 3 hours. The reaction mixture was partitioned between ethyl acetate (200 ml) and water (100 ml). The organics were washed with water (2×100 ml), brine (100 ml), dried over sodium sulfate and concentrated in vacuo. The residue was purified by column chromatography (silica, 10-40% ethyl acetate/petrol) to afford the title compound.

$^1$H NMR (300 MHz, CHLOROFORM-d) δ ppm 1.32-1.66 (m, 11H), 1.71-1.96 (m, 2H), 2.07-2.24 (m, 1H), 2.30-2.51 (m, 1H), 3.76-4.04 (m, 2H), 4.69-4.92 (m, 1H), 6.07-6.24 (m, 1H), 7.91 (s, 1H), 8.30 (s, 1H)

MS ES$^+$: 347

Step (ii): tert-Butyl N-[(1S,2S)-2-{[3-bromo-5-(trifluoromethyl)pyrazin-2-yl]amino}cyclopentyl]carbamate To a solution of tert-butyl ((1S,2S)-2-((5-(trifluoromethyl)pyrazin-2-yl)amino)cyclopentyl)carbamate (3.49 g, 10.08 mmol) in dry DCM (67 ml) at 0° C. was added 1-bromopyrrolidine-2,5-dione (CAS number 128-08-5; 2.15 g, 12.09 mmol). The reaction was allowed to warm to room temperature overnight. A further portion of portion of 1-bromopyrrolidine-2,5-dione (CAS number 128-08-5; 1.70 g, 9.56 mmol) was added and the reaction stirred for an additional 24 hours. The reaction was concentrated in vacuo and then purified by column chromatography (silica, 0-30% ethyl acetate/petrol) to afford the title compound.

$^1$H NMR (300 MHz, CHLOROFORM-d) δ ppm 1.31-1.62 (m, 11H), 1.72-1.92 (m, 2H), 2.08-2.24 (m, 1H), 2.36-2.56 (m, 1H), 3.75-4.14 (m, 2H), 4.63-4.87 (m, 1H), 6.78-6.96 (m, 1H), 8.25 (s, 1H)

MS ES$^+$: 425, 427

Step (iii): tert-Butyl N-[(1S,2S)-2-{[3-ethenyl-5-(trifluoromethyl)pyrazin-2-yl]amino}cyclopentyl]carbamate A suspension of tert-butyl N-[(1S,2S)-2-{[3-bromo-5-(trifluoromethyl)pyrazin-2-yl]amino}cyclopentyl]carbamate (650 mg, 1.53 mmol), 2-ethenyl-4,4,5,5-tetramethyl-1,3,2-dioxaborolane (CAS number 75927-49-0; 942 mg, 6.11 mmol), tetrakis(triphenylphosphine)palladium (177 mg, 0.15 mmol) and potassium carbonate (845 mg, 6.11 mmol) in 1,4-dioxane (5 ml) and water (0.8 ml) was subjected to microwave irradiation at 120° C. for 1 hour. The reaction was partitioned between ethyl acetate (10 ml) and water (10 ml). The aqueous layer was further extracted with ethyl acetate (3×20 ml). The combined organics were washed with brine (20 ml), filtered through a hydrophobic frit and concentrated in vacuo. The resulting residue was purified by column chromatography (silica, 0-50% ethyl acetate/petrol) to afford the title compound.

$^1$H NMR (400 MHz, DICHLOROMETHANE-d$_2$) δ ppm 1.30-1.62 (m, 11H), 1.74-1.87 (m, 2H), 2.02-2.17 (m, 1H), 2.41-2.61 (m, 1H), 3.73-3.85 (m, 1H), 3.91-4.04 (m, 1H), 4.81-4.95 (m, 1H), 5.62-5.74 (m, 1H), 6.30-6.42 (m, 1H), 6.71-6.90 (m, 2H), 8.21 (s, 1H)

MS ES$^+$: 373

Step (iv): tert-Butyl N-[(1S,2S)-2-{[3-ethyl-5-(trifluoromethyl)pyrazin-2-yl]amino}cyclopentyl]carbamate To a solution of tert-butyl N-[(1S,2S)-2-{[3-ethenyl-5-(trifluoromethyl)pyrazin-2-yl]amino}cyclopentyl]carbamate (460 mg, 1.24 mmol) in methanol (12 ml) was added palladium on carbon (10% wt, 50% wet) (131 mg, 0.124 mmol) and the resulting mixture was stirred under a balloon of hydrogen gas for 2 hours. The reaction was filtered through diatomaceous earth (commercially sold under the trade mark "Celite"). To this was then added further palladium on carbon (10% wt, 50% wet) (131 mg, 0.124 mmol) and the resulting mixture was stirred under a balloon of hydrogen gas for 72 hours. The reaction was filtered through diatomaceous earth (commercially sold under the trade mark "Celite") and concentrated in vacuo to afford the title compound.

$^1$H NMR (400 MHz, DCM-d$_2$) δ ppm 1.24-1.64 (m, 14H), 1.71-1.89 (m, 2H), 2.01-2.19 (m, 1H), 2.37-2.57 (m, 1H), 2.61-2.80 (m, 2H), 3.77-3.90 (m, 1H), 3.91-4.09 (m, 1H), 4.82-4.97 (m, 1H), 6.36-6.55 (m, 1H), 8.16 (s, 1H)

MS ES$^+$: 375

Step (v): (1S,2S)-1-N-[3-Ethyl-5-(trifluoromethyl)pyrazin-2-yl]cyclopentane-1,2-diamine hydrochloride To a solution of tert-butyl N-[(1S,2S)-2-{[3-ethyl-5-(trifluoromethyl)pyrazin-2-yl]amino}cyclopentyl]carbamate (366 mg, 0.98 mmol) in 1,4-dioxane (3 ml) was added HCl in 1,4-dioxane (4M, 3 ml, 12.0 mmol). The reaction was stirred at room temperature for 18 hours and was then concentrated in vacuo and azeotropically distilled with toluene to afford the title compound.

$^1$H NMR (400 MHz, DMSO-d$_6$) δ ppm 1.16-1.29 (m, 3H), 1.53-1.84 (m, 4H), 1.95-2.20 (m, 2H), 2.66-2.82 (m, 2H), 3.43-3.71 (m, 1H), 4.28-4.47 (m, 1H), 8.16 (br. s., 3H), 8.30 (s, 1H)

MS ES$^+$: 275

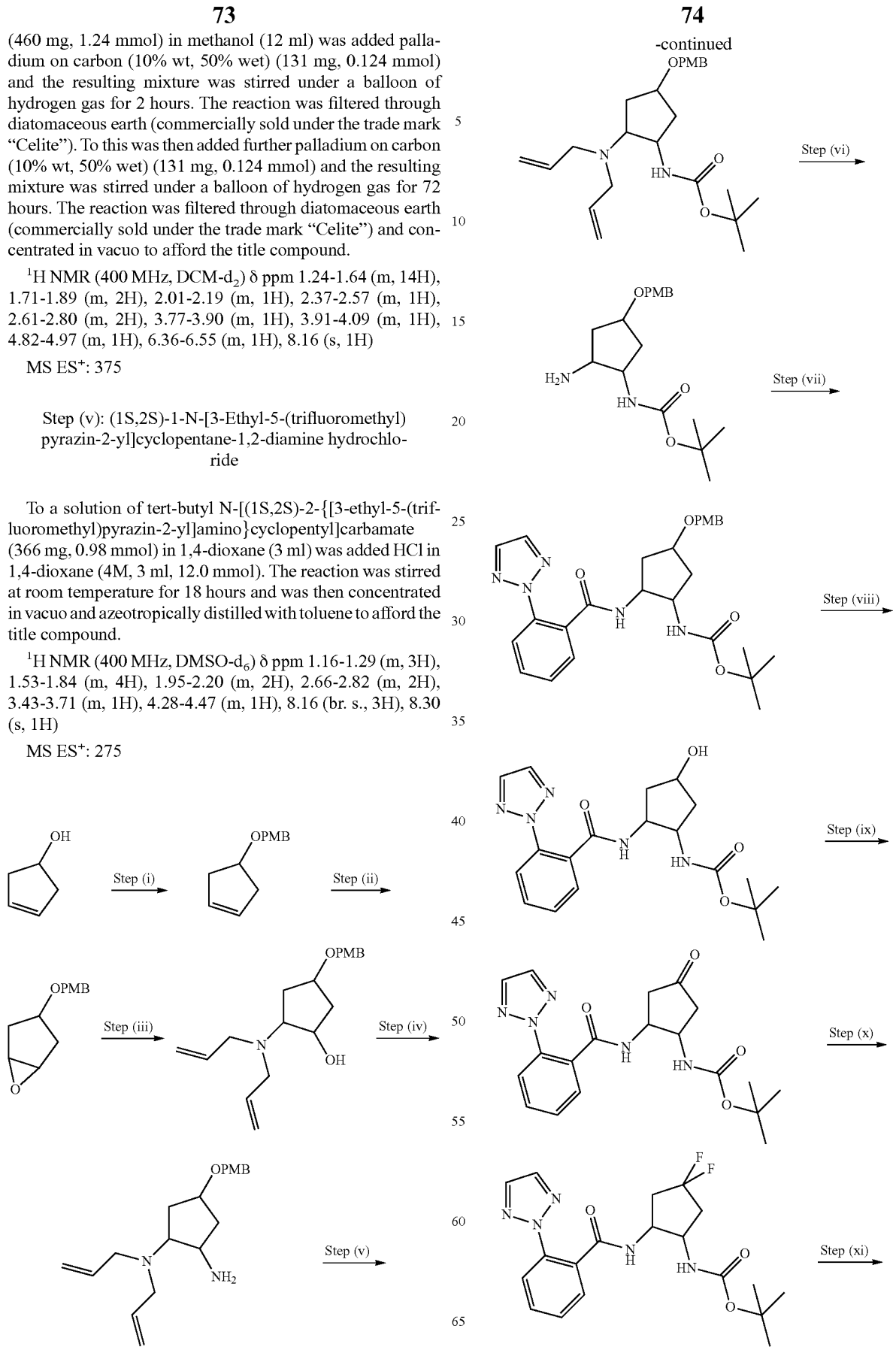

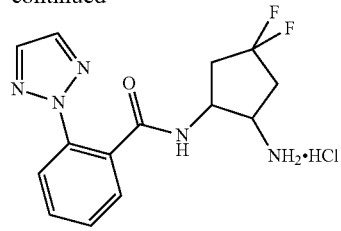

Intermediate 42: N-(2-Amino-4,4-difluorocyclopentyl)-2-(2H-1,2,3-triazol-2-yl)benzamide hydrochloride

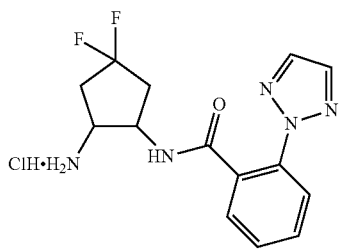

Step (i): 1-[(Cyclopent-3-en-1-yloxy)methyl]-4-methoxybenzene

To a solution of cyclopent-3-en-1-ol (CAS number 14320-38-8; 15 g, 178 mmol) in dry THF (357 ml) at 0° C. under nitrogen was added sodium hydride (60%, 9.27 g, 232 mmol). After fizzing had ceased, to this was then added drop wise 1-(chloromethyl)-4-methoxybenzene (CAS number 824-94-2; 31.4 ml, 232 mmol). The reaction was allowed to warm to room temperature and stirred for 17 hours then quenched by the addition of methanol and concentrated in vacuo. The residue was partitioned between ethyl acetate and water. The organics were dried over magnesium sulfate, filtered and concentrated in vacuo. The crude material was purified by column chromatography (silica, 0-50% DCM/petrol) to afford the title compound.

$^1$H NMR (400 MHz, DCM-d$_2$) δ ppm 2.33-2.47 (m, 2H), 2.49-2.66 (m, 2H), 3.79 (s, 3H), 4.20-4.32 (m, 1H), 4.40 (s, 2H), 5.62-5.75 (m, 2H), 6.86 (d, J=8.59 Hz, 2H), 7.24 (d, J=8.59 Hz, 2H)

Step (ii): 3-[(4-Methoxyphenyl)methoxy]-6-oxabicyclo[3.1.0]hexane

To a solution of 1-[(cyclopent-3-en-1-yloxy)methyl]-4-methoxybenzene (9.64 g, 47.2 mmol) in dry DCM (52 ml) at 0° C. under an atmosphere of nitrogen was added 3-chlorobenzene-1-carboperoxoic acid (CAS number 937-14-4; 16.29 g, 94 mmol). The reaction mixture was warmed to room temperature for 17 hours then filtered. The filtrate was washed with a saturated solution of sodium thiosulfate and then with a saturated solution of sodium bicarbonate. The organics were dried over magnesium sulfate, filtered and concentrated in vacuo. The crude material was purified by column chromatography (silica, 0-50% ethyl acetate/petrol) to afford the title compound.

$^1$H NMR (400 MHz, DCM-d$_2$) δ ppm 1.86-2.17 (m, 4H), 3.39-3.50 (m, 2H), 3.78 (s, 3H), 3.99-4.14 (m, 1H), 4.32 (s, 2H), 6.85 (d, J=8.60 Hz, 2H), 7.22 (d, J=8.59 Hz, 2H)

Step (iii): 2-[Bis(prop-2-en-1-yl)amino]-4-[(4-methoxyphenyl)methoxy]cyclopentan-1-ol To a solution of 3-[(4-methoxyphenyl)methoxy]-6-oxabicyclo[3.1.0]hexane (10.21 g, 46.4 mmol) in ethanol (66 ml) was added bis(prop-2-en-1-yl)amine (CAS number 124-02-7; 13.51 g, 139 mmol). The reaction was heated in a sealed vial at 105° C. for 72 hours. The reaction mixture was concentrated in vacuo then purified by column chromatography (silica, 0-50% ethyl acetate/petrol then 0-30% (0.1% ammonia/methanol)/ethyl acetate) to afford the title compound.

$^1$H NMR (400 MHz, DMSO-d$_6$) δ ppm 1.33-1.54 (m, 1H), 1.56-1.73 (m, 1H), 1.73-1.88 (m, 1H), 2.06-2.25 (m, 1H), 2.78-2.95 (m, 1H), 2.99-3.23 (m, 4H), 3.74 (s, 3H), 3.78-3.94 (m, 1H), 3.95-4.09 (m, 1H), 4.27-4.36 (m, 2H), 4.57-4.67 (m, 1H), 5.02-5.25 (m, 4H), 5.71-5.90 (m, 2H), 6.89 (d, J=8.59 Hz, 2H), 7.22 (d, J=8.60 Hz, 2H)

MS ES$^+$: 318

Step (iv): 4-[(4-Methoxyphenyl)methoxy]-1-N,1-N-bis(prop-2-en-1-yl)cyclopentane-1,2-diamine To a solution of 2-[bis(prop-2-en-1-yl)amino]-4-[(4-methoxyphenyl)methoxy]cyclopentan-1-ol (8.75 g, 27.6 mmol) in dry MTBE (92 ml) at 0° C. under nitrogen was added triethylamine (7.68 ml, 55.1 mmol) and methanesulfonyl chloride (2.58 ml, 33.1 mmol). The reaction mixture was stirred at 0° C. for 30 minutes. To this was then added further triethylamine (7.68 ml, 55.1 mmol) and the reaction was stirred at 0° C. for 30 minutes followed by the addition of ammonium hydroxide (25% aq, 82 ml, 590 mmol). The reaction was warmed to room temperature for 17 hours then partitioned between MTBE and water. The aqueous layer was re-extracted with MTBE. The combined organics were dried over magnesium sulphate, filtered and concentrated in vacuo to afford the title compound.

$^1$H NMR (400 MHz, DMSO-d$_6$) δ ppm 1.28-2.21 (m, 4H), 2.72-3.29 (m, 6H), 3.66-3.78 (m, 3H), 3.81-3.99 (m, 1H), 4.25-4.43 (m, 2H), 5.00-5.32 (m, 4H), 5.65-5.93 (m, 2H), 6.82-6.98 (m, 2H), 7.14-7.29 (m, 2H)

MS ES$^+$: 317

Step (v): tert-Butyl N-{2-[bis(prop-2-en-1-yl)amino]-4-[(4-methoxyphenyl)methoxy]cyclopentyl}carbamate To a solution of 4-[(4-methoxyphenyl)methoxy]-1-N,1-N-bis(prop-2-en-1-yl)cyclopentane-1,2-diamine (9.79 g, 30.9 mmol) in THF (56 ml) at 0° C. under nitrogen was added a saturated solution of sodium carbonate (46.4 ml, 46.4 mmol) and di-tert-butyl dicarbonate (CAS number 24424-99-5; 10.77 ml, 46.4 mmol). The reaction was warmed to room temperature for 72 hours then partitioned between ethyl acetate and water. The organics were washed with water and brine, dried over magnesium sulfate, filtered and concentrated in vacuo. The crude material was purified by reverse phase column chromatography (C18 silica, 5-95% water (0.05% ammonia)/acetonitrile) to afford the title compound.

$^1$H NMR (400 MHz, DMSO-d$_6$) δ ppm 1.38 (s, 9H), 1.47-1.59 (m, 1H), 1.61-1.79 (m, 1H), 1.79-1.93 (m, 1H), 1.93-2.21 (m, 1H), 2.91-3.07 (m, 3H), 3.07-3.24 (m, 2H), 3.74 (s, 3H), 3.79-3.98 (m, 2H), 4.24-4.41 (m, 2H), 4.93-5.26 (m, 4H), 5.66-5.89 (m, 2H), 6.89 (d, J=8.34 Hz, 2H), 7.22 (d, J=8.34 Hz, 2H)

MS ES+: 417

Step (vi): tert-Butyl N-{2-amino-4-[(4-methoxyphenyl)methoxy]cyclopentyl}-carbamate To a solution of tert-butyl N-{2-[bis(prop-2-en-1-yl)amino]-4-[(4-methoxyphenyl)methoxy]cyclopentyl}carbamate (1.77 g, 4.25 mmol) in dry DCM (21 ml) was added 1,3-dimethyl-1,3-diazinane-2,4,6-trione (CAS number 769-42-6; 1.161 g, 7.44 mmol) and tetrakis(triphenylphosphane) palladium (0.113 g, 0.098 mmol). The reaction was stirred at 45° C. under an atmosphere of nitrogen for 3 hours. The reaction mixture was concentrated in vacuo and purified by SCX chromatography (2M ammonia in methanol) to afford the title compound.

$^1$H NMR (400 MHz, DMSO-d$_6$) δ ppm 1.28-1.42 (m, 10H), 1.44-1.61 (m, 1H), 1.81-2.07 (m, 1H), 2.12-2.37 (m, 1H), 2.72-3.09 (m, 1H), 3.18-3.52 (m, 1H), 3.73 (s, 3H), 3.81-3.95 (m, 1H), 4.22-4.38 (m, 2H), 6.89 (d, J=8.34 Hz, 2H), 7.22 (d, J=8.30 Hz, 2H)

MS ES+: 337

Step (vii): tert-Butyl N-{4-[(4-methoxyphenyl)methoxy]-2-[2-(2H-1,2,3-triazol-2-yl)benzamido]cyclopentyl}carbamate To a solution of tert-butyl N-{2-amino-4-[(4-methoxyphenyl)methoxy]cyclopentyl}-carbamate (1.71 g, 5.08 mmol) in dry DMF (17 ml) was added 2-(2H-1,2,3-triazol-2-yl)benzoic acid (CAS number 1001401-62-2; 1.06 g, 5.59 mmol), HATU (2.90 g, 7.62 mmol) and triethylamine (2.13 ml, 15.25 mmol). The reaction was stirred at room temperature for 72 hours then partitioned between ethyl acetate and water. The organics were washed with brine, dried over magnesium sulfate, filtered and concentrated in vacuo. The crude material was purified by column chromatography (silica, 0-100% ethyl acetate/petrol) to afford the title compound.

$^1$H NMR (400 MHz, DMSO-d$_6$) δ ppm 1.37 (s, 9H), 1.46-1.59 (m, 1H), 1.58-1.77 (m, 1H), 1.86-1.97 (m, 1H), 2.18-2.37 (m, 1H), 3.67-3.79 (m, 4H), 3.83-4.01 (m, 2H), 4.32 (s, 2H), 6.85-6.95 (m, 2H), 7.17-7.31 (m, 2H), 7.44-7.54 (m, 2H), 7.55-7.66 (m, 1H), 7.76 (s, 1H), 7.96-8.05 (m, 2H)

MS ES+: 508

Step (viii): tert-Butyl N-{4-hydroxy-2-[2-(2H-1,2,3-triazol-2-yl)benzamido]cyclopentyl}carbamate To a solution of tert-butyl N-{4-[(4-methoxyphenyl)methoxy]-2-[2-(2H-1,2,3-triazol-2-yl)benzamido]cyclopentyl}carbamate (1.85 g, 3.64 mmol) in DCM (36 ml) and water (0.364 ml) at 0° C. under an atmosphere of nitrogen was added 4,5-dichloro-3,6-dioxocyclohexa-1,4-diene-1,2-dicarbonitrile (CAS number 84-58-2; 1.655 g, 7.29 mmol). The reaction was stirred at 0° C. for 1 hour, then was partitioned between a saturated solution of sodium bicarbonate and DCM. The organics were filtered through a hydrophobic frit and concentrated in vacuo. The crude material was purified by column chromatography (silica, 0-100% ethyl acetate/petrol then 0-30% methanol/ethyl acetate) to afford the title compound.

$^1$H NMR (400 MHz, DMSO-d$_6$) δ ppm 1.25-1.48 (m, 10H), 1.55-1.86 (m, 2H), 2.11-2.27 (m, 1H), 3.90-3.94 (m, 1H), 3.99-4.11 (m, 1H), 4.57-4.71 (m, 1H), 6.64-6.86 (m, 1H), 7.41-7.56 (m, 2H), 7.57-7.66 (m, 1H), 7.71-7.83 (m, 1H), 7.95-8.06 (m, 2H), 8.19-8.36 (m, 1H)

MS ES+: 388

Step (ix): tert-Butyl N-{4-oxo-2-[2-(2H-1,2,3-triazol-2-yl)benzamido]cyclopentyl}carbamate To a solution of tert-butyl N-{4-hydroxy-2-[2-(2H-1,2,3-triazol-2-yl)benzamido]cyclopentyl}carbamate (910 mg, 2.35 mmol) in dry DCM (12 ml) at 0° C. under an atmosphere of nitrogen was added Dess-Martin periodinane (3.4 g, 7.99 mmol). The reaction was warmed to room temperature for 2 hours then concentrated in vacuo. The crude material was purified by column chromatography (silica, 0-100% ethyl acetate/petrol) to afford the title compound.

$^1$H NMR (400 MHz, DMSO-d$_6$) δ ppm 1.28-1.47 (m, 10H), 1.56-1.87 (m, 2H), 2.07-2.27 (m, 1H), 3.82-4.00 (m, 1H), 4.00-4.12 (m, 1H), 6.58-6.79 (m, 1H), 7.41-7.54 (m, 2H), 7.55-7.71 (m, 1H), 7.73-7.85 (m, 1H), 7.93-8.06 (m, 2H), 8.17-8.40 (m, 1H)

MS ES+: 386

Step (x): tert-Butyl N-{4,4-difluoro-2-[2-(2H-1,2,3-triazol-2-yl)benzamido]cyclopentyl}carbamate To a solution of tert-butyl N-{4-oxo-2-[2-(2H-1,2,3-triazol-2-yl)benzamido]cyclopentyl}carbamate (950 mg, 2.47 mmol) in dry DCM (12.3 ml) at 0° C. under an atmosphere of nitrogen was added drop wise diethylaminosulfur trifluoride (CAS number 38078-09-0; 1.63 ml, 12.32 mmol) as a solution in dry DCM (12.3 ml). The reaction mixture was warmed to room temperature for 2 hours then cooled to 0° C. To this was added further diethylaminosulfur trifluoride (CAS number 38078-09-0; 1.63 ml, 12.32 mmol). The reaction was then allowed to warm to room temperature for 17 hours. The reaction was then cooled to 0° C. and basified by the cautious addition of sodium carbonate (2M, aq). The reaction mixture was extracted with DCM, filtered through a hydrophobic frit and concentrated in vacuo. The crude material was purified by column chromatography (silica, 0-100% ethyl acetate in petrol) to afford the title compound.

$^1$H NMR (400 MHz, DMSO-d$_6$) δ ppm 1.37 (s, 9H), 1.88-2.17 (m, 2H), 2.36-2.48 (m, 2H), 3.93-4.09 (m, 1H), 4.14-4.30 (m, 1H), 6.97-7.15 (m, 1H), 7.45-7.56 (m, 2H), 7.57-7.70 (m, 1H), 7.75-7.86 (m, 1H), 8.03 (s, 2H), 8.46-8.60 (m, 1H)

MS ES+: 408

Step (xi): N-(2-Amino-4,4-difluorocyclopentyl)-2-(2H-1,2,3-triazol-2-yl)benzamide hydrochloride To a solution of tert-butyl N-{4,4-difluoro-2-[2-(2H-1,2,3-triazol-2-yl)benzamido]cyclopentyl}carbamate (640 mg, 1.57 mmol) in dry 1,4-dioxane (5 ml) was added HCl in 1,4-dioxane (4M, 3.9 ml, 15.71 mmol). The reaction was stirred at room temperature for 6 hours then concentrated in vacuo and azeotropically distilled with toluene to afford the title compound.

$^1$H NMR (400 MHz, DMSO-d$_6$) δ ppm 2.01-2.42 (m, 2H), 2.55-2.78 (m, 2H), 3.30-3.54 (m, 1H), 3.60-3.75 (m, 1H), 7.50-7.61 (m, 1H), 7.62-7.77 (m, 2H), 7.80-7.91 (m, 1H), 8.08 (s, 2H), 8.51 (br. s, 3H), 8.72-8.88 (m, 1H)

MS ES$^+$: 308

Intermediate 43:
N-Chloro-2-methyl-N-sodiopropane-2-sulfonamide

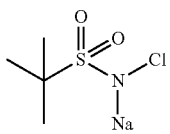

To a rapidly stirred sodium hypochlorite solution (25 ml, 12.76 mmol), with the temperature maintained below 10° C. and in the dark was added a solution of acetic acid (1.85 ml, 12.76 mmol) and 2-methylpropan-2-ol (1.22 ml, 12.76 mmol) in a single portion and the reaction mixture stirred for 3 minutes. The reaction mixture was partitioned and the organics washed with 10% aqueous sodium carbonate and water, dried over calcium chloride and filtered to afford tert-butyl hypochlorite (845 mg, 7.78 mmol). This was slowly added to a stirred solution of 2-methylpropane-2-sulfonamide (2 g, 14.58 mmol) in sodium hydroxide solution (1M, 20.60 ml, 20.6 mmol) at room temperature. The resulting mixture was stirred at room temperature for 1 hour then concentrated in vacuo. The resultant solid was triturated with diethyl ether, filtered and dried in vacuo to afford the title compound.

Prepared as detailed in *Organic Letters* 1999, 1, 783-786

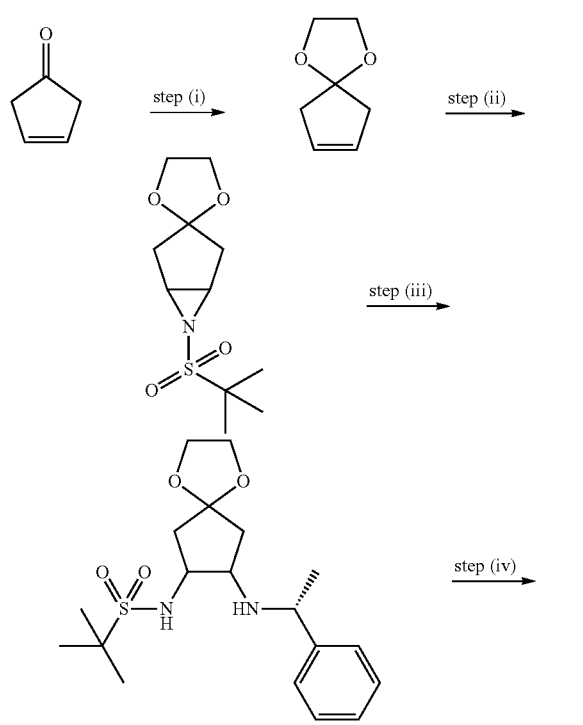

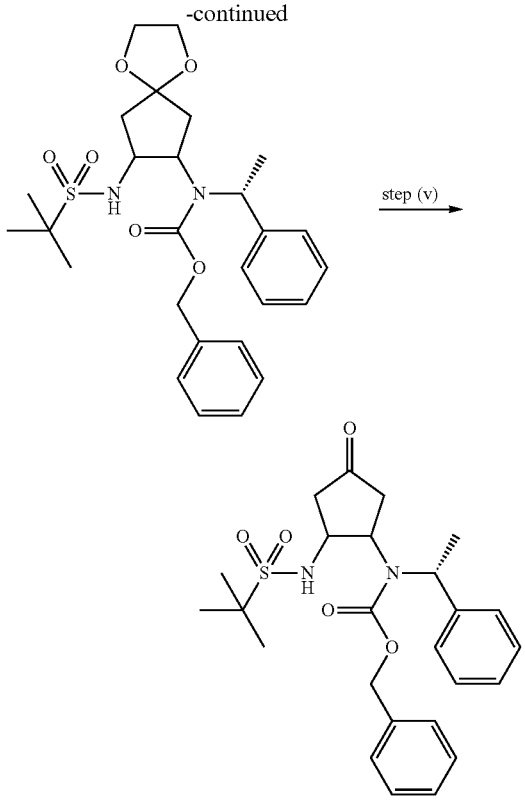

Intermediate 44: Benzyl N-[2-(2-methylpropane-2-sulfonamido)-4-oxocyclopentyl]-N-[(1R)-1-phenyl-ethyl]carbamate

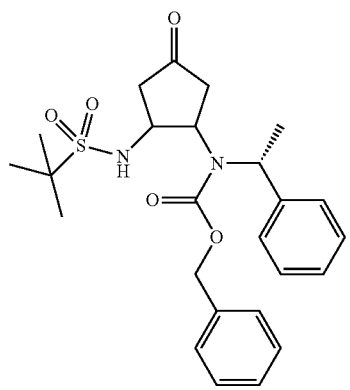 [SMILES: C[C@H](c1ccccc1)N(C(=O)OCc1ccccc1)C1CC(=O)CC1NS(=O)(=O)C(C)(C)C]

Step (i): 1,4-Dioxaspiro[4.4]non-7-ene

To a solution of trimethylsilyl trifluoromethanesulfonate (CAS number 27607-77-8; 0.22 ml, 1.22 mmol) in DCM (12 ml) at −78° C. was successively added 2,2,7,7-tetramethyl-3,6-dioxa-2,7-disilaoctane (CAS number 7381-30-8; 2.51 g, 12.18 mmol) and cyclopent-3-en-1-one (CAS number 14320-37-7; 1 g, 12.18 mmol). The reaction mixture was stirred at −78° C. for 3 hours, quenched with triethylamine (2 ml, 14.35 mmol), poured into a saturated solution of sodium bicarbonate and extracted with diethyl ether. The organics were dried over sodium sulfate, filtered and concentrated in vacuo to afford the title compound.

$^1$H NMR (300 MHz, CHLOROFORM-d) δ ppm 2.59 (s, 4H), 3.96 (s, 4H), 5.71 (s, 2H)

Step (ii): 6-(2-Methylpropane-2-sulfonyl)-6-azaspiro[bicyclo[3.1.0]hexane-3,2'-[1,3]dioxolane]

To a solution of 1,4-dioxaspiro[4.4]non-7-ene (370 mg, 2.93 mmol) and N-chloro-2-methyl-N-sodiopropane-2-sulfonamide (Intermediate 43; 965 mg, 4.99 mmol) in acetonitrile (16 ml) was added trimethylphenylammonium tribromide (CAS number 4207-56-1; 110 mg, 0.29 mmol) under an atmosphere of nitrogen. The reaction mixture was stirred at room temperature for 2 hours then heated to 40° C. for 18 hours. The reaction mixture was filtered through a plug of silica, washed with diethyl ether and the filtrate concentrated in vacuo. The crude material was purified column chromatography (silica, 0-50% diethyl ether/petroleum) to afford the title compound.

$^1$H NMR (400 MHz, CHLOROFORM-d) δ ppm 1.45-1.53 (m, 9H), 2.16-2.23 (m, 4H), 3.34 (s, 2H), 3.77-3.86 (m, 2H), 3.88-3.93 (m, 2H)

Step (iii): 2-Methyl-N-(8-{[(M)-1-phenylethyl]amino}-1,4-dioxaspiro[4.4]nonan-7-yl)propane-2-sulfonamide To a solution of 6-(2-methylpropane-2-sulfonyl)-6-azaspiro[bicyclo[3.1.0]hexane-3,2'-[1,3]dioxolane] (477 mg, 1.83 mmol) in acetonitrile (10 ml) was added lithium perchlorate (20 mg, 0.19 mmol) and (R)-1-phenylethanamine (CAS number 3886-69-9; 0.29 ml, 2.28 mmol). The reaction was heated to reflux for 24 hours. Further portions of lithium perchlorate (12 mg, 0.11 mmol) and (R)-1-phenylethanamine (0.20 ml, 1.57 mmol) were added and the reaction mixture heated to 100° C. overnight. The reaction mixture was transferred to a microwave vial and was then subjected to microwave irradiation at 120° C. for 3 hours. To this was then added water (1 ml) and the volume reduced to a third by concentrating in vacuo. The resultant mixture was partitioned between ethyl acetate and water. The organics were washed with water and brine, dried over sodium sulfate, filtered and concentrated in vacuo. The crude material was purified by column chromatography (silica, 0-70% ethyl acetate/petrol) to afford the title compound.

MS ES$^+$: 383

Step (iv): Benzyl N-[8-(2-methylpropane-2-sulfonamido)-1,4-dioxaspiro[4.4]nonan-7-yl]-N-[(1R)-1-phenylethyl]carbamate To a solution of 2-methyl-N-(8-{[(1R)-1-phenylethyl]amino}-1,4-dioxaspiro[4.4]nonan-7-yl)propane-2-sulfonamide (274 mg, 0.72 mmol) and sodium carbonate (114 mg, 1.074 mmol) in 1,4-dioxane (2 ml) and water (0.4 ml) at 0° C. was added drop wise benzyl chloroformate (CAS number 501-53-1; 0.13 ml, 0.90 mmol). The reaction mixture was allowed to warm to room temperature for 2 hours then concentrated in vacuo. The residue was diluted with ethyl acetate and washed with water and brine, dried over sodium sulfate, filtered and concentrated in vacuo. The crude material was purified by column chromatography (silica, 0-70% ethyl acetate/petrol) to afford the title compound.

MS ES$^-$: 515

Step (v): Benzyl N-[2-(2-methylpropane-2-sulfonamido)-4-oxocyclopentyl]-N-[(1R)-1-phenylethyl]carbamate To a solution of benzyl N-[8-(2-methylpropane-2-sulfonamido)-1,4-dioxaspiro[4.4]nonan-7-yl]-N-[(1R)-1-phenylethyl]carbamate (331 mg, 0.64 mmol) in THF (1.1 ml) was added HCl (aq, 2M, 1.65 ml, 3.30 mmol) was stirred at room temperature for 18 hours. The reaction mixture was concentrated in vacuo and azeotropically distilled with toluene to afford the title compound.

MS ES$^+$: 473

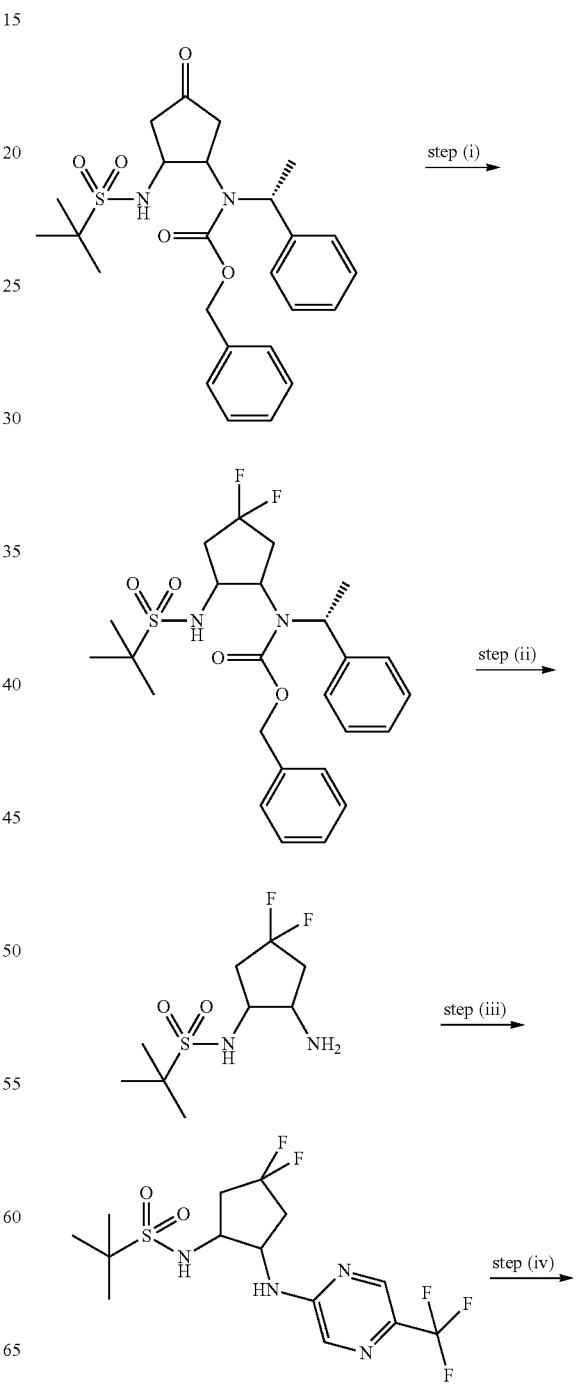

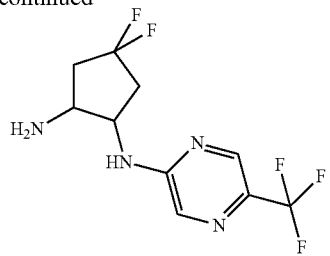

Intermediate 45: 4,4-Difluoro-1-N-[5-(trifluoromethyl)pyrazin-2-yl]cyclopentane-1,2-diamine

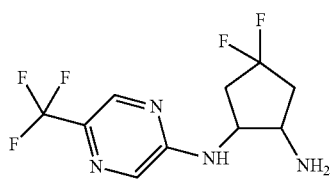 [SMILES: NC1CC(F)(F)CC1Nc1cnc(C(F)(F)F)cn1]

Step (i): Benzyl N-[4,4-difluoro-2-(2-methylpropane-2-sulfonamido)cyclopentyl]-N-[(1R)-1-phenylethyl]carbamate To a solution of benzyl N-[2-(2-methylpropane-2-sulfonamido)-4-oxocyclopentyl]-N-[(JR)-1-phenylethyl]carbamate (Intermediate 44; 330 mg, 0.70 mmol) in DCM (3.5 ml) at 0° C. was added diethylaminosulfur trifluoride (CAS number 38078-09-0; 0.92 ml, 6.98 mmol). The mixture was stirred at 0° C. for 20 minutes and then at room temperature for 5 hours. The reaction mixture was quenched at 0° C. with a saturated solution of sodium u) bicarbonate and extracted with DCM. The organics were dried over sodium sulfate, filtered and concentrated in vacuo. The crude material was purified by column chromatography (silica, 0-50% ethyl acetate/petrol) to afford the title compound.
MS ES⁻: 493

Step (ii): N-(2-Amino-4,4-difluorocyclopentyl)-2-methylpropane-2-sulfonamide

A solution of benzyl N-[4,4-difluoro-2-(2-methylpropane-2-sulfonamido)cyclopentyl]-N-[(1R)-1-phenylethyl]carbamate (130 mg, 0.26 mmol) and palladium hydroxide on carbon (20%, 100 mg, 0.14 mmol) in methanol (3.5 ml) was stirred under a balloon of hydrogen gas for 2 hours. The reaction was filtered through diatomaceous earth (commercially sold under the trade mark "Celite") and concentrated in vacuo to afford the title compound.
MS ES⁺: 257

Step (iii): N-(4,4-Difluoro-2-{[5-(trifluoromethyl)pyrazin-2-yl]amino}cyclopentyl)-2-methylpropane-2-sulfonamide To a solution of N-(2-amino-4,4-difluorocyclopentyl)-2-methylpropane-2-sulfonamide (66 mg, 0.26 mmol) in DMSO (650 µl) was added DIPEA (135 µl, 0.77 mmol) and 2-chloro-5-(trifluoromethyl)pyrazine (CAS number 799557-87-2; 47 mg, 0.26 mmol). The reaction mixture was sealed and heated at 120° C. for 18 hours then partitioned between ethyl acetate and water. The organics were washed with water and brine, dried over sodium sulfate, filtered and concentrated in vacuo. The crude material was purified by column chromatography (silica, 10-60% ethyl acetate/petrol) to afford the title compound.
¹H NMR (400 MHz, CHLOROFORM-d) δ ppm 1.42 (s, 9H), 1.92-2.04 (m, 1H), 2.12-2.30 (m, 1H), 2.68-2.85 (m, 1H), 2.96-3.12 (m, 1H), 3.86-4.03 (m, 1H), 4.18-4.27 (m, 1H), 4.43-4.54 (m, 1H), 5.90-6.04 (m, 1H), 8.02 (s, 1H), 8.34 (s, 1H)
MS ES⁺: 403

Step (iv): 4,4-Difluoro-1-N-[5-(trifluoromethyl)pyrazin-2-yl]cyclopentane-1,2-diamine To a solution of N-(4,4-difluoro-2-{[5-(trifluoromethyl)pyrazin-2-yl]amino}cyclopentyl)-2-methylpropane-2-sulfonamide (45 mg, 0.11 mmol) in DCM (3 ml) at 0° C. was added anisole (CAS number 100-66-3; 0.22 ml, 2.01 mmol) followed by the drop wise addition of trifluoromethanesulfonic acid in DCM (0.2M, 2.5 ml, 0.500 mmol). The reaction mixture was stirred at 0° C. for 1 hour then at room temperature for 2 hours. A further portion of trifluoromethanesulfonic acid in DCM (0.2M, 0.5 ml, 0.100 mmol) was added, the reaction mixture stirred for another hour at room temperature then quenched with sodium hydroxide (0.1M) until pH 11 was obtained. The reaction mixture was then extracted with DCM. The organics were filtered through a hydrophobic frit and concentrated in vacuo. The crude material was purified by SCX chromatography (2M ammonia in methanol) to afford the title compound.
MS ES⁺: 283

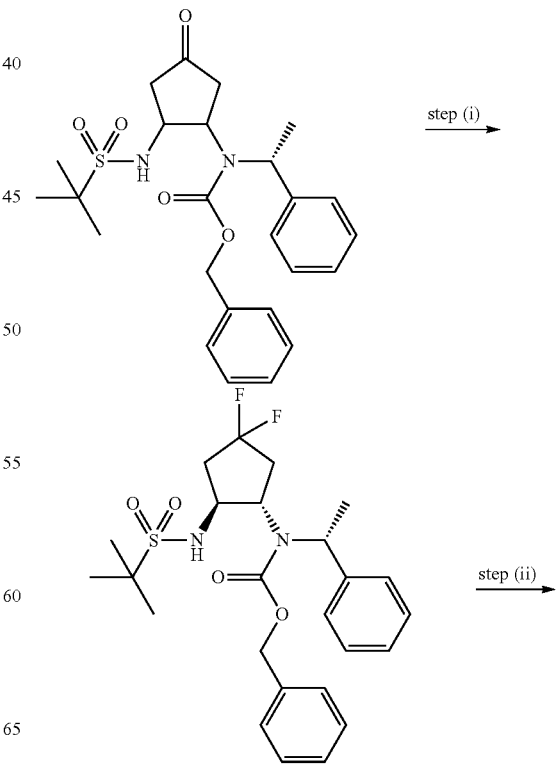

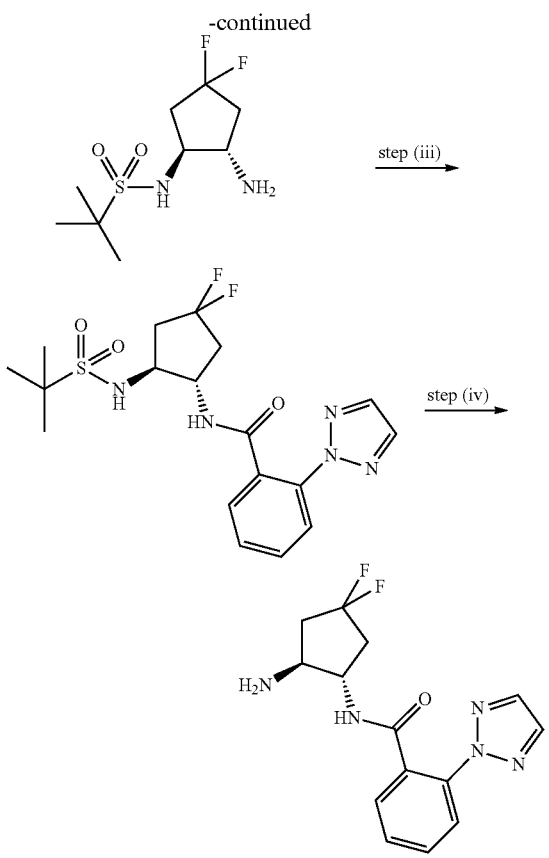

Intermediate 46: N-[(1S,2S)-2-Amino-4,4-difluoro-cyclopentyl]-2-(2H-1,2,3-triazol-2-yl)benzamide Step (i): Benzyl N-[(1S,2S)-4,4-difluoro-2-(2-methylpropane-2-sulfonamido)cyclopentyl]-N-[(1R)-1-phenylethyl]carbamate To a solution of benzyl N-[2-(2-methylpropane-2-sulfonamido)-4-oxocyclopentyl]-N-[(1R)-1-phenylethyl]carbamate (Intermediate 44; 6.39 g, 13.52 mmol) in DCM (67.6 ml) at 0° C. was added diethylaminosulfur trifluoride (CAS number 38078-09-0; 8.93 ml, 67.6 mmol). The mixture was stirred at 0° C. for 15 minutes then at room temperature for 3.5 hours. A further portion of diethylaminosulfur trifluoride (3 ml, 22.71 mmol) was added and the mixture stirred at room temperature for a further 2 hours. The reaction mixture was then quenched at 0° C. by the addition of a saturated solution of sodium bicarbonate until pH7 was achieved. The reaction mixture was then extracted with DCM. The combined organics were washed with brine, dried over sodium sulfate, filtered and concentrated in vacuo. The crude material was purified by column chromatography (silica, 35-60% diethyl ether/petrol) to afford the title compound.

MS ES⁻: 493

Step (ii): N-[(1S,2S)-2-Amino-4,4-difluorocyclopentyl]-2-methylpropane-2-sulfonamide A solution of benzyl N-[(1S,2S)-4,4-difluoro-2-(2-methylpropane-2-sulfonamido)cyclopentyl]-N-[(1R)-1-phenylethyl]carbamate (2.24 g, 4.53 mmol) and palladium hydroxide on carbon (20%, 1.59 g, 2.26 mmol) in methanol (65 ml) was stirred under a balloon of hydrogen gas for 17 hours. The reaction was filtered through diatomaceous earth (commercially sold under the trade mark "Celite") and concentrated in vacuo to afford the title compound.

$^1$H NMR (400 MHz, CHLOROFORM-d) δ ppm 1.44 (s, 9H), 1.84-2.17 (m, 2H), 2.52-2.67 (m, 1H), 2.68-2.85 (m, 1H), 3.26-3.38 (m, 1H), 3.57-3.68 (m, 1H)

MS ES⁺: 257

Step (iii): N-[(1S,2S)-4,4-Difluoro-2-(2-methylpropane-2-sulfonamido)cyclopentyl]-2-(2H-1,2,3-triazol-2-yl)benzamide To a solution of N-[(1S,2S)-2-amino-4,4-difluorocyclopentyl]-2-methylpropane-2-sulfonamide (1.03 g, 4.02 mmol) in dry DCM (13.4 ml) was added 2-(2H-1,2,3-triazol-2-yl)benzoic acid (CAS number 1001401-62-2; 0.91 g, 4.82 mmol), EDC (2.31 g, 12.06 mmol), 3H-[1,2,3]triazolo[4,5-b]pyridin-3-ol (1.64 g, 12.06 mmol) and DIPEA (2.11 ml, 12.06 mmol). The reaction was stirred at room temperature overnight then partitioned between ethyl acetate and water. The organics were washed with water and brine, dried over sodium sulfate, filtered and concentrated in vacuo. The crude material was purified by column chromatography (silica, 30-80% ethyl acetate/petrol) to afford the title compound.

$^1$H NMR (400 MHz, DCM-d$_2$) δ ppm 1.36-1.44 (m, 9H), 1.93-2.08 (m, 1H), 2.10-2.28 (m, 1H), 2.65-2.84 (m, 2H), 3.75-3.96 (m, 1H), 4.24-4.41 (m, 1H), 4.89-5.06 (m, 1H), 6.35-6.52 (m, 1H), 7.51-7.57 (m, 1H), 7.61-7.70 (m, 2H), 7.83-7.88 (m, 1H), 7.90 (s, 2H)

MS ES⁺: 428

Step (iv): N-[(1S,2S)-2-Amino-4,4-difluorocyclopentyl]-2-(2H-1,2,3-triazol-2-yl)benzamide To a solution of N-[(1S,2S)-4,4-difluoro-2-(2-methylpropane-2-sulfonamido)cyclopentyl]-2-(2H-1,2,3-triazol-2-yl)benzamide (1.7 g, 3.98 mmol) in DCM (100 ml) at 0° C. was added anisole (CAS number 100-66-3; 7.82 ml, 71.6 mmol) followed by the drop wise addition of trifluoromethanesulfonic acid in DCM (0.2M, 1.55 ml, 17.5 mmol). The reaction mixture was stirred at 0° C. for 1 hour and then at room temperature for 18 hours. The reaction mixture was quenched with sodium hydroxide (0.2M) until pH 11 obtained then extracted with DCM. The organics were filtered through a hydrophobic frit and concentrated in vacuo. The crude material was purified by SCX chromatography (2M ammonia in methanol) to afford the title compound.

MS ES⁺: 308

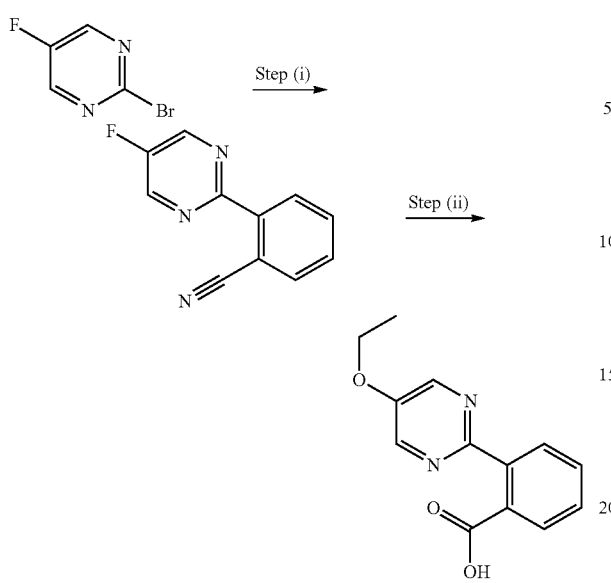

Intermediate 47: 2-(5-Ethoxypyrimidin-2-yl)benzoic acid

Step (i): 2-(5-Fluoropyrimidin-2-yl)benzonitrile

A suspension of 2-bromo-5-fluoropyrimidine (CAS number 947533-45-1; 301 mg, 1.70 mmol), potassium carbonate (705 mg, 5.10 mmol) and [1,1'-bis(diphenylphosphino)ferrocene]dichloropalladium(II) (62 mg, 0.085 mmol) in DMF (5 ml) was purged and evacuated with nitrogen. To this was then added (2-cyanophenyl)boronic acid (CAS number 138642-62-3; 300 mg, 2.04 mmol) and the reaction was subjected to microwave irradiation at 140° C. for 10 minutes and then at 130° C. for 35 minutes. The reaction was partitioned between ethyl acetate (50 ml) and water (50 ml) and filtered through diatomaceous earth (commercially sold under the trade mark "Celite"). The organics were washed with brine, dried over magnesium sulfate and concentrated in vacuo. The resulting residue was purified column chromatography (silica, 0-100% ethyl acetate/petrol) to afford the title compound.

$^1$H NMR (300 MHz, DCM-d$_2$) δ ppm 7.54-7.65 (m, 1H), 7.67-7.79 (m, 1H), 7.81-7.92 (m, 1H), 8.27-8.40 (m, 1H), 8.78 (s, 2H)

MS ES$^+$: 200

Step (ii): 2-(5-Ethoxypyrimidin-2-yl)benzoic acid

To a solution of 2-(5-fluoropyrimidin-2-yl)benzonitrile (40 mg, 0.20 mmol) in ethanol (1 ml) was added sodium hydroxide (3M, 3 ml, 9.0 mmol). The reaction was heated to reflux for 20 hours and then was concentrated in vacuo. The reaction was diluted with water and concentrated HCl was added drop wise until pH2 was reached. The aqueous layer was concentrated in vacuo and the resulting residue was dissolved in methanol, filtered through a hydrophobic frit and concentrated in vacuo to afford the title compound.

MS ES$^-$: 243

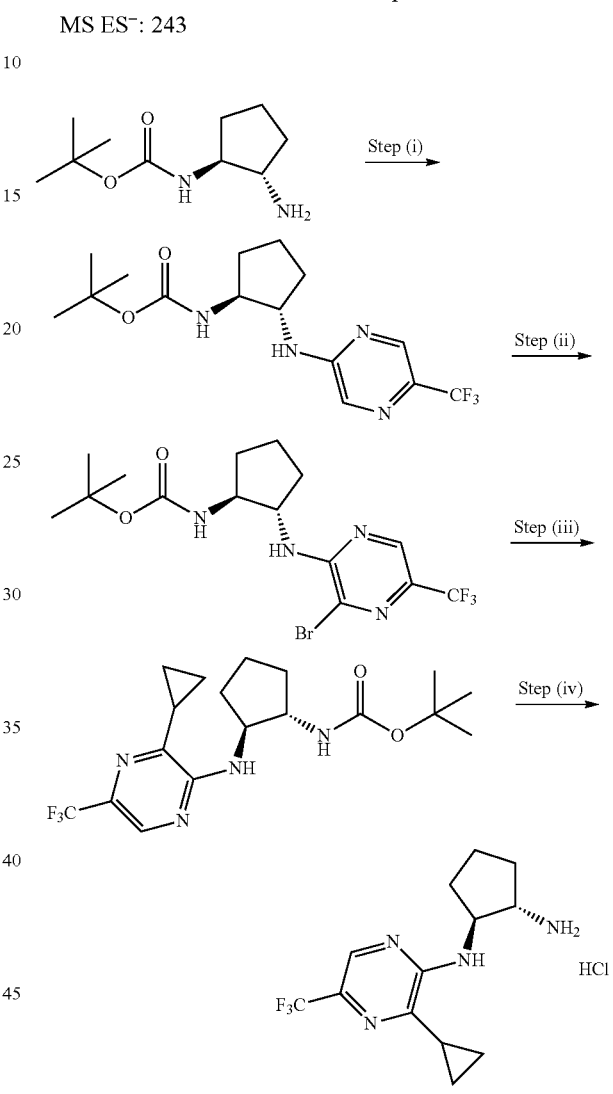

Intermediate 48: (1S,2S)-1-N-[3-Cyclopropyl-5-(trifluoromethyl)pyrazin-2-yl]cyclopentane-1,2-diamine hydrochloride

Step (i): tert-Butyl N-[(1S,2S)-2-{[5-(trifluoromethyl)pyrazin-2-yl]amino}cyclopentyl]carbamate A solution of 2-chloro-5-(trifluoromethyl)pyrazine (CAS number 799557-87-2; 6.78 ml, 54.9 mmol), tert-butyl N-[(1S,2S)-2-aminocyclopentyl]carbamate (CAS number 586961-34-4; 10 g, 49.9 mmol) and DIPEA (26.2 ml, 150 mmol) in DMSO (160 ml) was heated at 140° C. for 18 hours. The reaction mixture was partitioned between ethyl acetate (200 ml) and water (200 ml). The aqueous layer was extracted with ethyl acetate (2×100 ml). The combined organics were washed with brine (3×100 ml), filtered through a hydrophobic frit, further dried over magnesium sulphate and then concentrated in vacuo. The resulting residue was purified by column chromatography (silica, 0-40% ethyl acetate/petrol). Impure fractions were further purified by column chromatography (silica, 10-40% ethyl acetate/petrol) and combined to afford the title compound.

$^1$H NMR (400 MHz, DMSO-$d_6$) δ ppm 1.29 (s, 9H), 1.40-1.54 (m, 2H), 1.58-1.73 (m, 2H), 1.86-2.10 (m, 2H), 3.68-3.83 (m, 1H), 4.07-4.17 (m, 1H), 6.83-6.96 (m, 1H), 7.84-7.95 (m, 1H), 7.99 (br. s., 1H), 8.28-8.37 (m, 1H)

MS ES$^+$: 347

Step (ii): tert-Butyl N-[(1S,2S)-2-{[3-bromo-5-(trifluoromethyl)pyrazin-2-yl]amino}cyclopentyl]carbamate To a solution of tert-butyl N-[(1S,2S)-2-{[5-(trifluoromethyl)pyrazin-2-yl]amino}cyclopentyl]carbamate (11.61 g, 33.5 mmol) in DCM (70 ml) and acetonitrile (35 ml) at 0° C. under was added 1-bromopyrrolidine-2,5-dione (12.53 g, 70.4 mmol). The reaction was allowed to warm to room temperature and stirred for 20 hours. The mixture was concentrated in vacuo and then purified by column chromatography (silica, 0-50% ethyl acetate/petrol) to afford the title compound.

$^1$H NMR (400 MHz, DMSO-$d_6$) δ ppm 1.29 (s, 9H), 1.42-1.73 (m, 4H), 1.82-1.96 (m, 1H), 1.98-2.13 (m, 1H), 3.92-4.17 (m, 2H), 6.90-7.01 (m, 1H), 7.39-7.48 (m, 1H), 8.43 (s, 1H)

MS ES$^+$: 425, 427

Step (iii): tert-Butyl N-[(1S,2S)-2-{[3-cyclopropyl-5-(trifluoromethyl)pyrazin-2-yl]amino}cyclopentyl]carbamate A suspension of tert-butyl N-[(1S,2S)-2-{[3-bromo-5-(trifluoromethyl)pyrazin-2-yl]amino}cyclopentyl]carbamate (2.44 g, 5.73 mmol), cyclopropylboronic acid (2.46 g, 28.6 mmol), potassium carbonate (3.17 g, 22.9 mmol) and tetrakis(triphenylphosphine)palladium (0.662 g, 0.57 mmol) in 1,4-dioxane (15 ml) and water (4 ml) was subjected to microwave irradiation at 140° C. for 2 hours. The reaction was partitioned between ethyl acetate (20 ml) and water (20 ml). The aqueous layer was extracted with ethyl acetate (2×50 ml) and combined organics were washed with brine (50 ml), filtered through a hydrophobic frit and concentrated in vacuo. The crude product was purified by column chromatography (silica, 0-50% ethyl acetate/petrol) to afford the title compound.

$^1$H NMR (400 MHz, DMSO-$d_6$) δ ppm 0.83-0.91 (m, 2H), 0.96-1.03 (m, 2H), 1.29 (s, 9H), 1.44-1.58 (m, 2H), 1.59-1.73 (m, 2H), 1.85-1.96 (m, 1H), 2.03-2.13 (m, 1H), 2.15-2.24 (m, 1H), 3.89-4.00 (m, 1H), 4.11-4.27 (m, 1H), 6.88-7.00 (m, 1H), 7.23-7.38 (m, 1H), 8.14 (s, 1H)

MS ES$^+$: 387

Step (iv): (1S,2S)-1-N-[3-Cyclopropyl-5-(trifluoromethyl)pyrazin-2-yl]cyclopentane-1,2-diamine hydrochloride To a solution of tert-butyl N-[(1S,2S)-2-{[3-cyclopropyl-5-(trifluoromethyl)pyrazin-2-yl]amino}cyclopentyl]carbamate (1.54 g, 3.99 mmol) in 1,4-dioxane (14 ml) was added HCl in 1,4-dioxane (4M, 10 ml, 40 mmol). The reaction was stirred at room temperature for 20 hours and was then concentrated in vacuo and azeotropically distilled with toluene to afford the title compound.

$^1$H NMR (400 MHz, DMSO-$d_6$) δ ppm 0.80-0.92 (m, 1H), 0.94-1.12 (m, 3H), 1.57-1.89 (m, 4H), 2.03-2.26 (m, 2H), 2.36-2.48 (m, 1H), 3.52-3.69 (m, 1H), 4.30-4.48 (m, 1H), 7.67-7.80 (m, 1H), 8.15-8.40 (m, 4H)

MS ES$^+$: 287

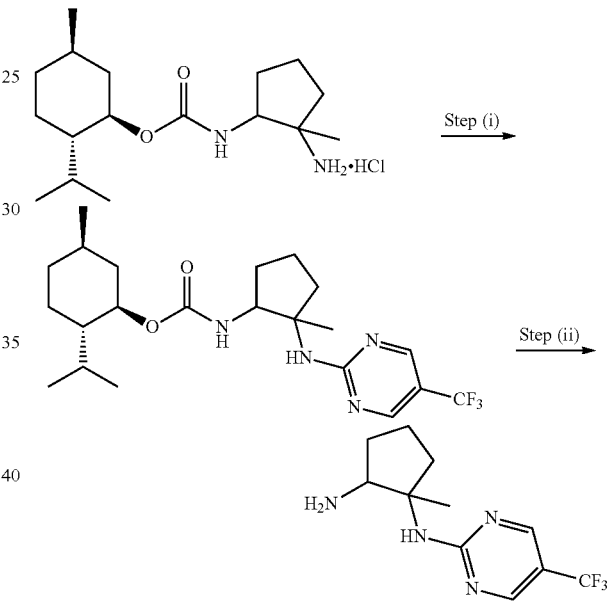

Intermediate 50: 1-Methyl-1-N-[5-(trifluoromethyl)pyrimidin-2-yl]cyclopentane-1,2-diamine

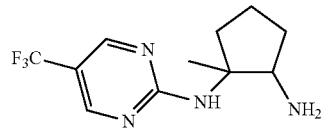 [SMILES: CC1(Nc2ncc(C(F)(F)F)cn2)CCCC1N]

Step (i): (1R,2S,5R)-5-Methyl-2-(propan-2-yl)cyclohexyl N-(2-methyl-2-{[5-(trifluoromethyl)pyrimidin-2-yl]amino}cyclopentyl)carbamate A solution of (1R,2S,5R)-5-methyl-2-(propan-2-yl)cyclohexyl N-(2-amino-2-methylcyclopentyl)carbamate hydrochloride (Intermediate 27; 2.0 g, 6.01 mmol), 2-chloro-5-(trifluoromethyl)pyrimidine (CAS number 69034-12-4; 1.21 g, 6.61 mmol) and DIPEA (3.15 ml, 18.02 mmol) in dry DMSO (15 ml) was subjected to microwave irradiation at 140° C. for 4 hours. The reaction was partitioned between ethyl acetate and brine. The aqueous layer was extracted further with ethyl acetate (2×100 ml). The combined organics were washed with brine (3×125 ml), dried over magnesium sulfate and concentrated in vacuo. The resulting residue was purified by column chromatography (silica, 0-30% diethyl ether/petrol) to afford the title compound as a single trans-enantiomer.

MS ES+: 443

Step (ii): 1-Methyl-1-N-[5-(trifluoromethyl)pyrimidin-2-yl]cyclopentane-1,2-diamine To a solution of (1R,2S,5R)-5-methyl-2-(propan-2-yl)cyclohexyl N-(2-methyl-2-{[5-(trifluoromethyl)pyrimidin-2-yl]amino}cyclopentyl)carbamate (1.04 g, 2.35 mmol) in acetic acid (8 ml) was added HBr (1.28 ml, 23.48 mmol). The reaction was heated sealed and heated at 90° C. overnight. To this was then added further HBr (1.28 ml, 23.48 mmol) and the reaction mixture heated at 90° C. for 24 hours. Further acetic acid (5 ml) and HBr (5 ml) was added and the reaction mixture heated to 90° C. for 5 hours. The reaction mixture was concentrated in vacuo and azeotropically distilled with toluene. The resulting residue was purified by SCX chromatography (2M ammonia in methanol) to afford the title compound as a single trans-enantiomer.

$^1$H NMR (400 MHz, DCM-$d_2$) δ ppm 1.25-1.43 (m, 4H), 1.60-1.73 (m, 2H), 1.86-2.00 (m, 1H), 2.00-2.16 (m, 2H), 3.30-3.37 (m, 1H), 5.84 (br. s., 1H), 8.32-8.56 (m, 2H)

MS ES+: 261

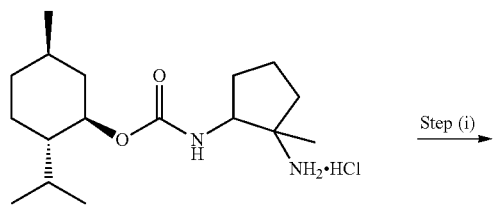

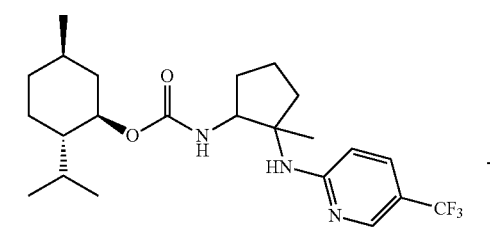

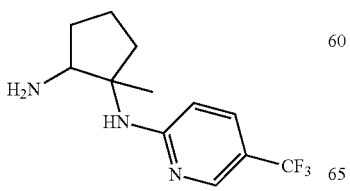

Intermediate 51: 1-Methyl-1-N-[5-(trifluoromethyl)pyridin-2-yl]cyclopentane-1,2-diamine

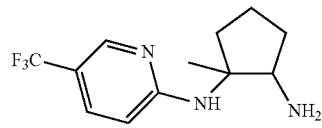 [SMILES: CC1(Nc2ccc(C(F)(F)F)cn2)CCCC1N]

Step (i): (1R,2S,5R)-5-Methyl-2-(propan-2-yl)cyclohexyl N-(2-methyl-2-{[5-(trifluoromethyl)pyridin-2-yl]amino}cyclopentyl)carbamate A solution of (1R,2S,5R)-5-methyl-2-(propan-2-yl)cyclohexyl N-(2-amino-2-methylcyclopentyl)carbamate hydrochloride (Intermediate 27; 1.50 g, 4.51 mmol), 2-fluoro-5-(trifluoromethyl)pyridine (CAS number 69045-82-5; 0.652 mL, 5.41 mmol) and DIPEA (2.36 ml, 13.5 mmol) in DMSO (10 ml) was subjected to microwave irradiation at 140° C. for 4 hours. The reaction was diluted with ethyl acetate (200 ml) and a saturated solution of sodium bicarbonate (100 ml). The aqueous layer was further extracted with ethyl acetate (100 ml). The combined organics were washed with water (50 ml), brine (50 ml), dried over magnesium sulfate, filtered through a hydrophobic frit and concentrated in vacuo. The crude product was purified by column chromatography (silica, 10-20% diethyl ether/petrol) to afford the title compound as a single trans-enantiomer.

MS ES+: 442

Step (ii): 1-Methyl-1-N-[5-(trifluoromethyl)pyridin-2-yl]cyclopentane-1,2-diamine To a solution of (1R,2S,5R)-5-methyl-2-(propan-2-yl)cyclohexyl N-(2-methyl-2-{[5-(trifluoromethyl)pyridin-2-yl]amino}cyclopentyl)carbamate in acetic acid (3 ml) was added HBr (6 M, 1.68 ml, 10.10 mmol). The reaction was sealed and heated at 90° C. for 24 hours. To this was then added further HBr (6 M, 1.68 ml, 10.10 mmol) and the reaction was heated at 90° C. for 24 hours. The reaction was concentrated in vacuo and the resulting residue was purified by SCX chromatography (2M ammonia in methanol). The product was purified by reverse phase chromatography (C18 silica, 5-100% water (with 0.05% ammonia)/acetonitrile) to afford the title compound as a single trans-enantiomer.

$^1$H NMR (400 MHz, DCM-$d_2$) δ ppm 1.33 (s, 3H), 1.43-1.58 (m, 1H), 1.66-1.78 (m, 2H), 1.84-1.97 (m, 1H), 2.04-2.16 (m, 2H), 3.21-3.36 (m, 1H), 5.14-5.21 (m, 1H), 6.43-6.55 (m, 1H), 7.47-7.60 (m, 1H), 8.25-8.33 (m, 1H)

MS ES+: 260

2. Examples

Example 1

2,6-Dimethoxy-N-[(1S,2S)-2-{[5-(trifluoromethyl)pyridin-2-yl]amino}cyclopentyl]benzamide

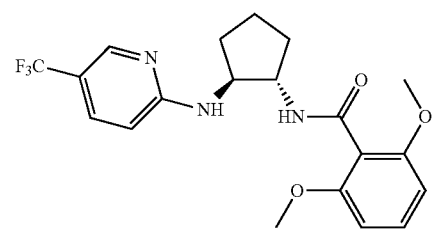

A mixture of 2-chloro-5-(trifluoromethyl)pyridine (CAS number 52334-81-3; 266 mg, 1.46 mmol), N-[(1S,2S)-2-aminocyclopentyl]-2,6-dimethoxybenzamide hydrochloride (Intermediate 5; 400 mg, 1.33 mmol), DIPEA (0.70 ml, 3.99 mmol) and DMSO (4.8 ml) was subjected to microwave irradiation at 140° C. for 2 hours. Upon cooling, the resulting mixture was partitioned between ethyl acetate (10 ml) and water (10 ml) and the combined organics were washed with brine (10 ml), dried over magnesium sulfate, filtered and concentrated in vacuo. The crude product was further purified by trituration with di-isopropylether to afford the title compound.

$^1$H NMR (DMSO-d$_6$) δ ppm 1.39-1.60 (m, 2H), 1.70 (m, 2H), 1.95-2.11 (m, 2H), 3.32 (s, 6H), 4.03-4.20 (m, 2H), 6.59-6.78 (m, 3H), 7.21-7.34 (m, 2H), 7.63-7.70 (m, 1H), 7.65 7.69 (m, 1H) and 8.08 (m, 1H)

MS ES$^+$: 410

Example 2

2,6-Dimethoxy-N-[(1S,2S)-2-{[5-(trifluoromethyl)pyrimidin-2-yl]amino}cyclopentyl]benzamide

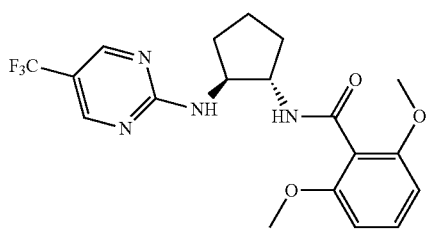

A microwave vial was charged with N-[(1S,2S)-2-aminocyclopentyl]-2,6-m dimethoxybenzamide hydrochloride (Intermediate 5; 80 mg, 0.27 mmol), DIPEA (0.139 ml, 0.80 mmol), 2-chloro-5-(trifluoromethyl)pyrimidine (CAS number 69034-12-4; 0.058 mg, 0.32 mmol) and dry NMP (0.9 ml). The resulting mixture was subjected to microwave irradiation at 250° C. for 20 minutes. The crude material was purified by reverse phase preparative HPLC (eluted with acetonitrile/water with 0.1% ammonia) to afford the title compound.

$^1$H NMR (DMSO-d$_6$) δ ppm 1.45-1.75 (m, 4H), 1.96-2.14 (m, 2H), 3.61 (s, 6H), 4.18-4.33 (m, 2H), 6.51-6.69 (m, 2H), 7.16-7.38 (m, 1H), 8.03 (m, 2H) and 8.60 (s, 2H).

MS ES$^+$: 411

Example 3

5-Methyl-2-(2H-1,2,3-triazol-2-yl)-N-[(1S,2S)-2-{[5-(trifluoromethyl)pyrimidin-2-yl]amino}cyclopentyl]benzamide

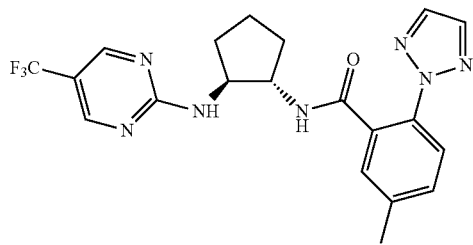 [SMILES: Cc1ccc(-n2nccn2)c(C(=O)N[C@H]2CCC[C@@H]2Nc2ncc(C(F)(F)F)cn2)c1]

To a mixture of N-[(1S,2S)-2-aminocyclopentyl]-5-methyl-2-(2H-1,2,3-triazol-2-yl)benzamide hydrochloride (Intermediate 7; 100 mg, 0.31 mmol) and NMP (1 ml) was added DIPEA (0.200 mg, 1.56 mmol) and 2-bromo-5-(trifluoromethyl)pyrimidine (70 mg, 0.31 mmol). The mixture was subjected to microwave irradiation at 150° C. for 1 hour. Upon cooling, the reaction mass was poured into water (5 ml) and extracted with ethyl acetate (2×10 ml). The combined organics were dried over sodium sulfate and concentrated in vacuo. The crude product was purified by reverse phase preparative HPLC (eluted with acetonitrile/water containing 0.1% ammonia) to afford the title compound.

$^1$H NMR (CD$_3$CN) δ ppm 1.52-1.59 (m, 2H), 1.74-1.80 (m, 2H), 2.09-2.19 (m, 2H), 2.42 (s, 3H), 4.06-4.18 (m, 2H), 6.65-6.67 (m, 1H), 6.90-6.92 (m, 1H), 7.30-7.30 (m, 1H), 7.40-7.42 (m, 1H), 7.63-7.65 (m, 1H), 7.73 (s, 2H), 8.52 (s, 2H).

MS ES$^+$: 432

Example 4

N-[(1S,2S)-2-[(5-Ethylpyrimidin-2-yl)amino]cyclopentyl]-5-methyl-2-(2H-1,2,3-triazol-2-yl)benzamide

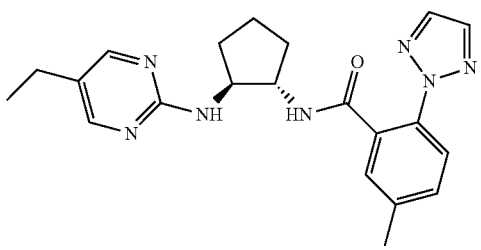 [SMILES: CCc1cnc(N[C@H]2CCC[C@@H]2NC(=O)c2cc(C)ccc2-n2nccn2)nc1]

A mixture of N-[(1S,2S)-2-aminocyclopentyl]-5-methyl-2-(2H-1,2,3-triazol-2-yl)benzamide hydrochloride (Intermediate 7; 100 mg, 0.31 mmol), toluene (1 ml), BINAP (19 mg, 0.03 mmol), cesium carbonate (404 mg, 0.12 mmol) and 2-chloro-5-ethylpyrimidine (CAS number 111196-81-7; 48 mg, 0.34 mmol) was purged with nitrogen gas for 5 minutes before tris(dibenzylideneacetone)dipalladium(0) (14 mg, 0.02 mmol) was added. The reaction mixture was stirred at 100° C. for 15 hours and upon cooling poured into water (3 ml) and extracted with ethyl acetate (3×10 ml). The combined organics were dried over sodium sulfate and concentrated in vacuo. The crude product was purified by reverse phase preparative HPLC (eluted with acetonitrile/water containing 0.1% ammonia) to afford the title compound.

$^1$H NMR (DMSO-d$_6$) δ ppm 1.02-1.15 (m, 3H), 1.45-1.49 (m, 2H), 1.50-1.58 (m, 2H), 1.60-1.65 (m, 2H), 2.32 (s, 3H), 2.33-2.39 (m, 2H), 4.03-4.10 (m, 2H), 6.84-6.86 (m, 1H), 7.22-7.22 (m, 1H), 7.38-740 (m, 1H), 7.61-7.63 (m, 1H), 7.90 (s, 2H), 8.15 (m, 1H), 8.30 (m, 1H), 8.33-8.35 (m, 1H)

MS ES$^+$: 392

Example 5

N-[(1S,2S)-2-[(5-Chloropyridin-2-yl)amino]cyclopentyl]-5-methyl-2-(2H-1,2,3-triazol-2-yl)benzamide

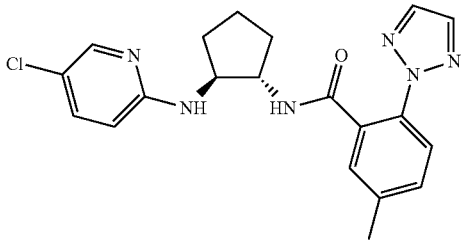 [SMILES: Cc1ccc(-n2nccn2)c(C(=O)N[C@H]2CCC[C@@H]2Nc2ccc(Cl)cn2)c1]

To a solution of N-[(1S,2S)-2-aminocyclopentyl]-5-methyl-2-(2H-1,2,3-triazol-2-yl)benzamide hydrochloride (Intermediate 7; 100 mg, 0.31 mmol) in toluene (1.0 ml) was added BINAP (19 mg, 0.03 mmol), cesium carbonate (405 mg, 1.25 mmol) and 2-bromo-5-chloropyridine (CAS number 40473-01-6; 72 mg, 0.38 mmol). The mixture was purged with nitrogen for 5 minutes and then tris(dibenzylideneacetone)dipalladium(0) (14 mg, 0.02 mmol) was added and the resulting mixture was stirred at 100° C. for 15 hours. The resulting mass was poured into water (3 ml) and extracted into ethyl acetate (3×10 ml). The combined organics were dried over sodium sulfate and concentrated in vacuo. The crude product was purified by reverse phase preparative HPLC (eluted with acetonitrile/water containing 0.1% ammonia) to afford the title compound.

$^1$H NMR (DMSO-d$_6$) δ ppm 1.40-1.52 (m, 2H), 1.63-1.64 (m, 2H), 1.93-2.01 (m, 2H), 2.37 (s, 3H), 3.97-4.06 (m, 2H), 6.56-6.58 (m, 1H), 6.73-6.75 (m, 1H), 7.19 (m, 1H), 7.38-7.44 (m, 2H), 7.62-7.64 (m, 2H), 7.93 (m, 1H), 7.94 (m, 1H), 8.34-8.36 (m, 1H).

MS ES$^+$: 396

Example 6

5-Methyl-2-(2H-1,2,3-triazol-2-yl)-N-[(1S,2S)-2-{[5-(trifluoromethyl)pyridin-2-yl]amino}cyclopentyl]benzamide

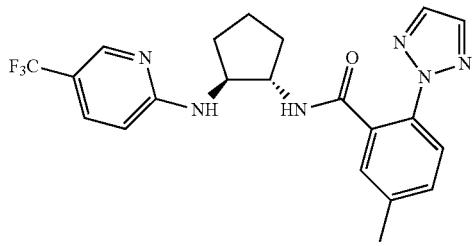

A microwave vial was charged N-[(1S,2S)-2-aminocyclopentyl]-5-methyl-2-(2H-1,2,3-triazol-2-yl)benzamide hydrochloride (Intermediate 7; 650 mg, 2.02 mmol), 2-chloro-5-(trifluoromethyl)pyridine (CAS number 52334-81-3; 403 mg, 2.22 mmol) and DIPEA (1058 µl, 6.06 mmol) in dry DMSO (6.7 ml). The reaction was subjected to microwave irradiation at 120° C. for 2 hours and then at 140° C. for 5 hours. Upon cooling the mixture was partitioned between ethyl acetate and water, washing with water and brine, dried over magnesium sulfate, filtered through a hydrophobic frit and concentrated in vacuo. This was then purified by column chromatography (silica, 0-100% ethyl acetate/petrol) and then further purified by column chromatography (basic silica 0-100% DCM/petrol) to afford the title compound.

$^1$H NMR (DMSO-d$_6$) δ ppm 1.43-1.59 (m, 2H), 1.62-1.73 (m, 2H), 1.92-2.08 (m, 2H), 2.39 (s, 3H), 4.00-4.45 (m, 2H), 6.62-6.69 (m, 1H), 7.19-7.21 (m, 1H), 7.28-7.32 (m, 1H), 7.38-7.44 (m, 1H), 7.61-7.67 (m, 2H), 7.93 (s, 2H), 7.28-7.32 (m, 1H), 8.33-8.39 (m, 1H).

MS ES$^+$: 431

Example 7

5-Methyl-2-(2H-1,2,3-triazol-2-yl)-N-[(1S,2S)-2-{[5-(trifluoromethyl)pyrazin-2-yl]amino}cyclopentyl]benzamide

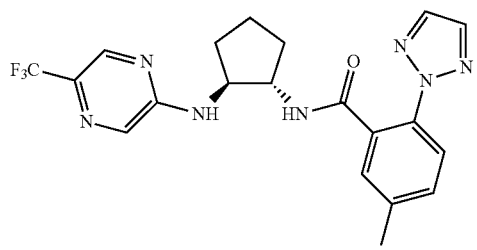 [SMILES: Cc1ccc(-n2nccn2)c(C(=O)N[C@H]2CCC[C@@H]2Nc2cnc(C(F)(F)F)cn2)c1]

A microwave vial was charged with N-[(1S,2S)-2-aminocyclopentyl]-5-methyl-2-(2H-1,2,3-triazol-2-yl)benzamide hydrochloride (Intermediate 7; 450 mg, 1.40 mmol), 2-chloro-5-(trifluoromethyl)pyrazine (CAS number 799557-87-2; 306 mg, 1.68 mmol) and DIPEA (733 µl, 4.20 mmol) in dry DMSO (4.7 ml). The reaction was subjected to microwave irradiation at 140° C. for 2 hours and then partitioned between ethyl acetate and water, washed with water, brine and concentrated in vacuo. The crude product was then purified by column chromatography (basic silica, 0-100% ethyl acetate/petrol) to give a cream solid which was then recrystallised from a mixture of ethyl acetate and pentane to afford the title compound.

$^1$H NMR (DMSO-d$_6$) δ ppm 1.45-1.60 (m, 2H), 1.62-1.72 (m, 2H), 1.93-2.10 (m, 2H), 2.38 (s, 3H), 4.08-4.25 (m, 2H), 7.19 (m, 1H), 7.39-7.42 (m, 1H), 7.63-7.68 (m, 1H), 7.89 (s, 2H), 7.94-7.89 (m, 1H), 8.03-8.08 (br. s., 1H), 8.36 (s, 2H).

MS ES$^+$: 432

Example 8

2-(3-Methyl-1,2,4-oxadiazol-5-yl)-N-[(1S,2S)-2-{[5-(trifluoromethyl)pyridin-2-yl]amino}cyclopentyl]benzamide

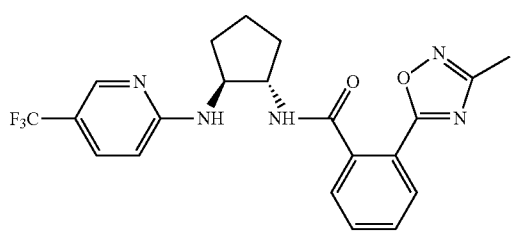 [SMILES: Cc1noc(-c2ccccc2C(=O)N[C@H]2CCC[C@@H]2Nc2ccc(C(F)(F)F)cn2)n1]

A solution of 2-(3-methyl-1,2,4-oxadiazol-5-yl)benzoic acid (CAS number 475105-77-2; 57.4 mg, 0.28 mmol), (1S, 2S)-1-N-[5-(trifluoromethyl)pyridin-2-yl]cyclopentane-1,2-diamine hydrochloride (Intermediate 1; 72 mg, 0.26 mmol), HATU (146 mg, 0.38 mmol) and triethylamine (107 μl, 0.77 mmol) in dry DMF (852 μl) was stirred at room temperature for 72 hours. The reaction was diluted with DMSO and filtered through cotton wool before being purified by reverse phase preparative HPLC (eluted with acetonitrile/water containing 0.1% ammonia) to afford the title compound.

$^1$H NMR (DMSO-d$_6$) δ ppm 1.42-1.78 (m, 4H), 1.98-2.15 (m, 2H), 2.39 (s, 3H), 4.10-4.29 (m, 2H), 6.64-6.69 (m, 1H), 7.36-7.42 (m, 1H), 7.46-7.52 (m, 1H), 7.62-7.72 (m, 3H), 7.91-7.97 (m, 1H), 8.26 (br. s., 1H), 7.56-7.63 (m, 1H).
MS ES$^+$: 432

Example 9

N-[(1S,2S)-2-[(5-Chloropyrazin-2-yl)amino]cyclopentyl]-5-methyl-2-(2H-1,2,3-triazol-2-yl)benzamide

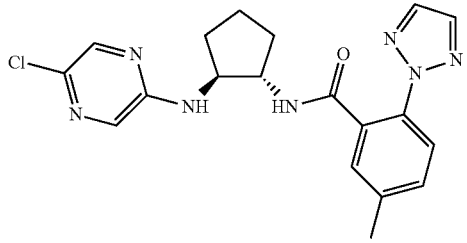 [SMILES: Cc1ccc(-n2nccn2)c(C(=O)N[C@H]2CCC[C@@H]2Nc2cnc(Cl)cn2)c1]

To a solution of N-[(1S,2S)-2-aminocyclopentyl]-5-methyl-2-(2H-1,2,3-triazol-2-yl)benzamide hydrochloride (Intermediate 7; 100 mg, 0.31 mmol) in NMP (1.0 ml) was added DIPEA (160 mg, 1.24 mmol) and 2,5-dichloropyrazine (CAS number 19745-07-4; 92 mg, 0.62 mmol). The resulting reaction mixture was stirred and heated under microwave irradiation at 180° C. for 15 minutes. Upon completion, the reaction mixture was poured into water (3 ml) and extracted with ethyl acetate (3×10 ml). The combined organics were dried over sodium sulfate and concentrated in vacuo. The crude product was purified by reverse phase preparative HPLC (eluted with acetonitrile/water containing 0.1% ammonia) to afford the title compound.

$^1$H NMR (DMSO-d$_6$) δ ppm 1.44-1.56 (m, 2H), 1.62-1.68 (m, 2H), 1.92-2.04 (m, 2H), 2.38 (s, 3H), 4.01-4.10 (m, 2H), 7.19 (s, 1H), 7.28-7.30 (m, 1H), 7.39-7.41 (m, 1H), 7.62-7.64 (m, 1H), 7.80-7.81 (s, 1H), 7.93 (s, 2H), 8.03 (s, 1H), 8.35-8.37 (m, 1H)
MS ES$^+$: 398

Example 10

5-Fluoro-2-(2H-1,2,3-triazol-2-yl)-N-[(1S,2S)-2-{[5-(trifluoromethyl)pyridin-2-yl]amino}cyclopentyl]benzamide

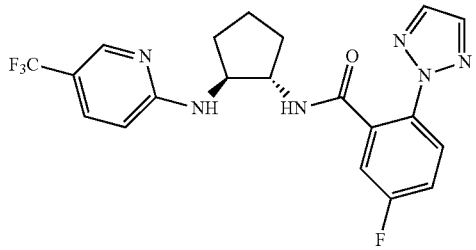 [SMILES: O=C(N[C@H]1CCC[C@@H]1Nc1ccc(C(F)(F)F)cn1)c1cc(F)ccc1-n1nccn1]

Prepared according to the procedure for 2-(3-methyl-1,2,4-oxadiazol-5-yl)-N-[(1S,2S)-2-{[5-(trifluoromethyl)pyridin-2-yl]amino}cyclopentyl]benzamide (Example 8) from 5-fluoro-2-(2H-1,2,3-triazol-2-yl)benzoic acid (Intermediate 8; 72 mg, 0.26 mmol) and (1S,2S)-1-N-[5-(trifluoromethyl)pyridin-2-yl]cyclopentane-1,2-diamine hydrochloride (Intermediate 1; 61 mg, 0.28 mmol) to afford the title compound.

$^1$H NMR (DMSO-d$_6$) δ ppm 1.42-1.59 (m, 2H), 1.60-1.75 (m, 2H), 1.92-2.10 (m, 2H), 4.02-4.23 (m, 2H), 6.64-6.70 (m, 1H), 7.21-7.26 (m, 1H), 7.27-7.30 (m, 1H), 7.42-7.51 (m, 1H), 7.62-7.66 (m, 1H), 7.78-7.84 (m, 1H), 7.96 (s, 2H), 8.26-8.29 (br. s., 1H), 8.46-8.51 (m, 1H)
MS ES$^+$: 435

Example 11

2-(1H-Pyrazol-1-yl)-N-[(1S,2S)-2-{[5-(trifluoromethyl)pyridin-2-yl]amino}cyclopentyl]benzamide

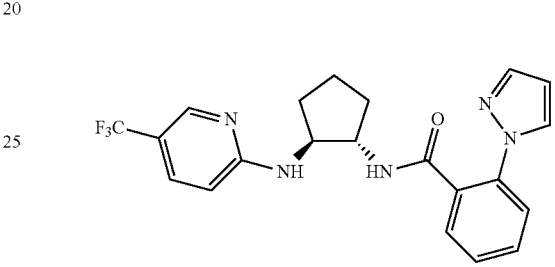

Prepared according to the procedure for 2-(3-methyl-1,2,4-oxadiazol-5-yl)-N-[(1S,2S)-2-{[5-(trifluoromethyl)pyridin-2-yl]amino}cyclopentyl]benzamide (Example 8) from 2-(1H-pyrazol-1-yl)benzoic acid (CAS number 55317-53-8; 53 mg, 0.28 mmol) and (1S,2S)-1-N-[5-(trifluoromethyl)pyridin-2-yl]cyclopentane-1,2-diamine hydrochloride (Intermediate 1; 72 mg, 0.26 mmol) to afford the title compound.

$^1$H NMR (DMSO-d$_6$) δ ppm 1.38-1.53 (m, 2H), 1.60-1.74 (m, 2H), 1.91-2.09 (m, 2H), 3.95-4.18 (m, 2H), 6.28-6.32 (m, 1H), 6.62-6.67 (m, 1H), 7.28-7.36 (m, 1H), 7.46-7.48 (m, 1H), 7.52-7.59 (m, 1H), 7.60-7.68 (m, 3H), 8.09 (s, 1H), 8.29 (br. s., 1H), 8.44-8.50 (m, 1H), 8.74 (s, 1H).
MS ES$^+$: 416

Example 12

2-(2H-1,2,3-Triazol-2-yl)-N-[(1S,2S)-2-{[5-(trifluoromethyl)pyridin-2-yl]amino}cyclopentyl]benzamide

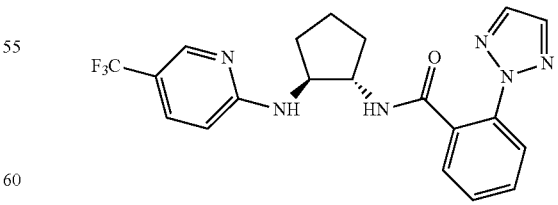

Prepared according to the procedure for 2-(3-methyl-1,2,4-oxadiazol-5-yl)-N-[(1S,2S)-2-{[5-(trifluoromethyl)pyridin-2-yl]amino}cyclopentyl]benzamide (Example 8) from 2-(2H-1,2,3-triazol-2-yl)benzoic acid (CAS number 1001401-62-2; 57 mg, 0.28 mmol) and (1S,2S)-1-N-[5-(trifluoromethyl)pyridin-2-yl]cyclopentane-1,2-diamine hydrochloride (Intermediate 1; 72 mg, 0.26 mmol) to afford the title compound.

$^1$H NMR (DMSO-$d_6$) δ ppm 1.37-1.60 (m, 2H), 1.61-1.86 (m, 2H), 1.92-2.10 (m, 2H), 4.02-4.20 (m, 2H), 6.70-6.80 (m, 1H), 7.26-7.35 (m, 1H), 7.37-7.53 (m, 2H), 7.45-7.54 (m, 2H), 7.73-7.79 (m, 1H), 7.98 (s, 2H), 8.27 (br. s., 1H), 8.37-8.45 (m, 1H).

MS ES$^+$: 417

Example 13

2-(Pyrimidin-2-yl)-N-[(1S,2S)-2-{[5-(trifluoromethyl)pyridin-2-yl]amino}cyclopentyl]benzamide

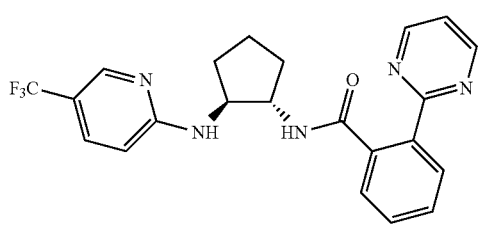 [SMILES: O=C(N[C@H]1CCC[C@@H]1Nc1ccc(C(F)(F)F)cn1)c1ccccc1-c1ncccn1]

Prepared according to the procedure for 2-(3-methyl-1,2,4-oxadiazol-5-yl)-N-[(1S,2S)-2-{[5-(trifluoromethyl)pyridin-2-yl]amino}cyclopentyl]benzamide (Example 8) from 2-(pyrimidin-2-yl)benzoic acid (CAS number 400892-62-8; 56 mg, 0.28 mmol) and (1S,2S)-1-N-[5-(trifluoromethyl)pyridin-2-yl]cyclopentane-1,2-diamine hydrochloride (Intermediate 1; 72 mg, 0.26 mmol) to afford the title compound.

$^1$H NMR (DMSO-$d_6$) δ ppm 1.37-1.73 (m, 4H), 1.94-2.10 (m, 2H), 4.04-4.21 (m, 2H), 6.64-6.69 (m, 1H), 7.33-7.41 (m, 3H), 7.43-7.57 (m, 2H), 7.59-7.64 (m, 1H), 7.95-7.99 (m, 1H), 8.27 (br. s., 2H), 8.83-8.85 (m, 2H).

MS ES$^+$: 428

Example 14

5-Fluoro-2-(pyrimidin-2-yl)-N-[(1S,2S)-2-{[5-(trifluoromethyl)pyridin-2-yl]amino}cyclopentyl]benzamide

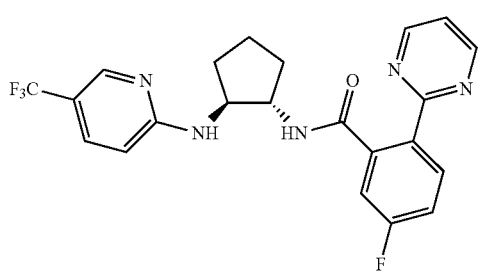 [SMILES: O=C(N[C@H]1CCC[C@@H]1Nc1ccc(C(F)(F)F)cn1)c1cc(F)ccc1-c1ncccn1]

Prepared according to the procedure for 2-(3-methyl-1,2,4-oxadiazol-5-yl)-N-[(1S,2S)-2-{[5-(trifluoromethyl)pyridin-2-yl]amino}cyclopentyl]benzamide (Example 8) from 5-fluoro-2-(pyrimidin-2-yl)benzoic acid (CAS number 1293284-57-7; 61 mg, 0.28 mmol) and (1S,2S)-1-N-[5-(trifluoromethyl)pyridin-2-yl]cyclopentane-1,2-diamine hydrochloride (Intermediate 1; 72 mg, 0.26 mmol) to afford the title compound.

$^1$H NMR (DMSO-$d_6$) δ ppm 1.42-1.75 (m, 4H), 1.95-2.13 (m, 2H), 4.04-4.23 (m, 2H), 6.63-6.69 (m, 1H), 7.12-7.18 (m, 1H), 7.31-7.45 (m, 3H), 7.60-7.67 (m, 1H), 8.03-8.09 (m, 1H), 8.26 (br. s., 1H), 8.32-8.38 (m, 1H), 8.76-8.92 (m, 2H).

MS ES$^+$: 446

Example 15

2-(3-Methyl-1,2,4-oxadiazol-5-yl)-N-[(1S,2S)-2-{[5-(trifluoromethyl)pyrazin-2-yl]amino}cyclopentyl]benzamide

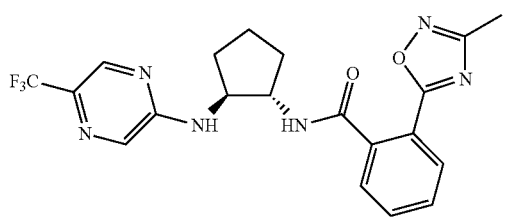 [SMILES: Cc1noc(-c2ccccc2C(=O)N[C@H]2CCC[C@@H]2Nc2cnc(C(F)(F)F)cn2)n1]

Prepared according to the procedure for 2,6-dimethoxy-N-[(1S,2S)-2-{[5-(trifluoromethyl)pyridin-2-yl]amino}cyclopentyl]benzamide (Example 1) from N-[(1S,2S)-2-aminocyclopentyl]-2-(3-methyl-1,2,4-oxadiazol-5-yl)benzamide hydrochloride (Intermediate 2; 100 mg, 0.31 mmol) and 2-chloro-5-(trifluoromethyl)pyrazine (CAS number 799557-87-2; 68 mg, 0.37 mmol). The crude reaction was filtered through cotton wool before being purified by reverse phase preparative HPLC (eluted with acetonitrile/water containing 0.1% ammonia) to afford the title compound.

$^1$H NMR (DMSO-$d_6$) δ ppm 1.45-1.76 (m, 4H), 2.00-2.18 (m, 2H), 2.34 (s, 3H), 4.16-4.32 (m, 2H), 7.47-7.52 (m, 1H), 7.59-7.74 (m, 2H), 7.92-7.96 (m, 1H), 7.99-8.09 (m, 2H), 8.35 (br. s., 1H), 8.56-8.63 (m, 1H).

MS ES$^+$: 433

Example 16

2-(3-Methyl-1,2,4-oxadiazol-5-yl)-N-[(1S,2S)-2-{[5-(trifluoromethyl)pyrimidin-2-yl]amino}cyclopentyl]benzamide

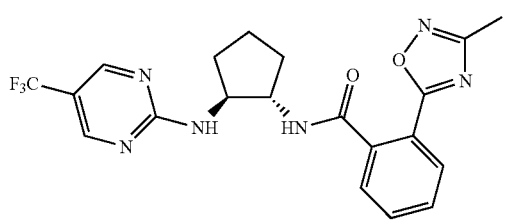 [SMILES: Cc1noc(-c2ccccc2C(=O)N[C@H]2CCC[C@@H]2Nc2ncc(C(F)(F)F)cn2)n1]

Prepared according to the procedure for 2,6-dimethoxy-N-[(1S,2S)-2-{[5-(trifluoromethyl)pyridin-2-yl]amino}cyclopentyl]benzamide (Example 1) from N-[(1S,2S)-2-aminocyclopentyl]-2-(3-methyl-1,2,4-oxadiazol-5-yl)benzamide hydrochloride (Intermediate 2; 100 mg, 0.31 mmol) and 2-chloro-5-(trifluoromethyl)pyrimidine (CAS number 69034-12-4; 68 mg, 0.37 mmol). The crude reaction was filtered through cotton wool before being purified by reverse phase preparative HPLC (eluted with acetonitrile/water containing 0.1% ammonia) to afford the title compound.

¹H NMR (DMSO-d₆) δ ppm 1.45-1.73 (m, 4H), 1.95-2.13 (m, 2H), 2.37 (s, 3H), 4.21-4.37 (m, 2H), 7.45-7.49 (m, 1H), 7.59-7.71 (m, 2H), 7.91-7.95 (m, 1H), 8.09-8.16 (m, 1H), 8.51-8.64 (m, 3H).
MS ES⁺: 433

Example 17

2-(2H-1,2,3-Triazol-2-yl)-N-[(1S,2S)-2-{[5-(trifluoromethyl)pyrazin-2-yl]amino}cyclopentyl]benzamide

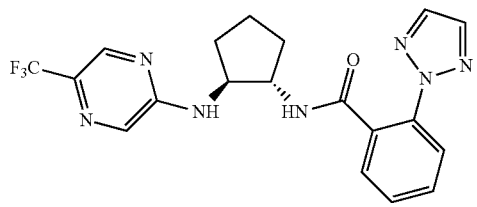 [SMILES: O=C(N[C@H]1CCC[C@@H]1Nc1cnc(C(F)(F)F)cn1)c1ccccc1-n1nccn1]

Prepared according to the procedure for 2,6-dimethoxy-N-[(1S,2S)-2-{[5-(trifluoromethyl)pyridin-2-yl]amino}cyclopentyl]benzamide (Example 1) from N-[(1S,2S)-2-amino cyclopentyl]-2-(2H-1,2,3-triazol-2-yl)benzamide hydrochloride (Intermediate 4; 100 mg, 0.33 mmol) and 2-chloro-5-(trifluoromethyl)pyrazine (CAS number 799557-87-2; 59 mg, 0.33 mmol). The crude reaction was filtered through cotton wool before being purified by reverse phase preparative HPLC (eluted with acetonitrile/water containing 0.1% ammonia) to afford the title compound.
¹H NMR (DMSO-d₆) δ ppm 1.43-1.59 (m, 2H), 1.62-1.74 (m, 2H), 1.95-2.10 (m, 2H), 4.08-4.25 (m, 2H), 7.41-7.44 (m, 1H), 7.46-7.51 (m, 1H), 7.57-7.62 (m, 1H), 7.76-7.79 (m, 1H), 7.92-7.99 (m, 3H), 8.06 (br. s., 1H), 8.36 (s, 1H), 8.39-8.44 (m, 1H).
MS ES⁺: 418

Example 18

2-(2H-1,2,3-Triazol-2-yl)-N-[(1S,2S)-2-{[5-(trifluoromethyl)pyrimidin-2-yl]amino}cyclopentyl]benzamide

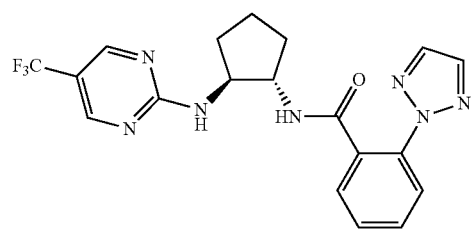 [SMILES: O=C(N[C@H]1CCC[C@@H]1Nc1ncc(C(F)(F)F)cn1)c1ccccc1-n1nccn1]

Prepared according to the procedure for 2,6-dimethoxy-N-[(1S,2S)-2-{[5-(trifluoromethyl)pyridin-2-yl]amino}cyclopentyl]benzamide (Example 1) from N-[(1S,2S)-2-amino cyclopentyl]-2-(2H-1,2,3-triazol-2-yl)benzamide hydrochloride (Intermediate 4; 100 mg, 0.325 mmol) and 2-chloro-5-(trifluoromethyl)pyrimidine (CAS number 69034-12-4; 59.3 mg, 0.325 mmol). The crude reaction was filtered through cotton wool before being purified by reverse phase preparative HPLC (eluted with acetonitrile/water containing 0.1% ammonia) to afford the title compound.
¹H NMR (DMSO-d₆) δ ppm 1.45-1.59 (m, 2H), 1.60-1.73 (m, 2H), 1.94-2.08 (m, 2H), 4.13-4.21 (m, 2H), 7.41-7.44 (m, 1H), 7.46-7.51 (m, 1H), 7.55-7.63 (m, 1H), 7.74-7.79 (m, 1H), 7.92 (s, 2H), 8.03-8.08 (m, 1H), 8.35-8.39 (m, 1H), 8.62 (m, 2H).
MS ES⁺: 418

Example 19

2-(2H-1,2,3-Triazol-2-yl)-N-[(1S,2R)-2-{[5-(trifluoromethyl)pyrazin-2-yl]oxy}cyclopentyl]benzamide

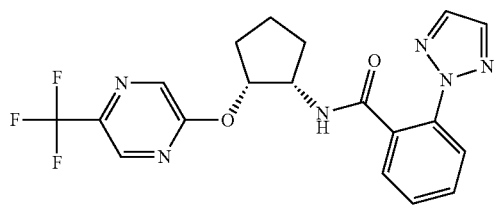 [SMILES: O=C(N[C@H]1CCC[C@H]1Oc1cnc(C(F)(F)F)cn1)c1ccccc1-n1nccn1]

LiHMDS in THF (1.0 M, 0.477 ml, 0.477 mmol) was added to a solution of N-[(1S,2R)-2-hydroxycyclopentyl]-2-(2H-1,2,3-triazol-2-yl)benzamide (Intermediate 10; 0.100 g, 0.37 mmol) in THF (3 ml) at 0° C. under nitrogen. The reaction was stirred at this temperature for 1 hour and then 2-chloro-5-(trifluoromethyl)pyrazine (CAS number 799557-87-2; 0.059 ml, 0.48 mmol) was added. The mixture was allowed to warm to room temperature and stirred for 5 hours. The reaction was then quenched with water (2 ml) and extracted with ethyl acetate (30 ml). The organics were washed with brine (10 ml), dried over magnesium sulfate and concentrated in vacuo. The crude product was purified by column chromatography (silica, 0-50% ethyl acetate/petrol) to afford the title compound.
¹H NMR (400 MHz, DCM-d₂) δ ppm 1.31-1.43 (m, 1H), 1.57-1.80 (m, 2H), 1.82-1.92 (m, 1H), 2.04-2.14 (m, 2H), 4.36-4.45 (m, 1H), 5.39-5.44 (m, 1H), 5.46-5.52 (m, 1H), 7.50-7.56 (m, 1H), 7.63-7.73 (m, 2H), 7.77-7.86 (m, 4H) and 8.30 (s, 1H).
MS ES⁺: 419

Example 20

2-(2H-1,2,3-Triazol-2-yl)-N-[(1S,2S)-2-{[4-(trifluoromethyl)pyridin-2-yl]oxy}cyclopentyl]benzamide

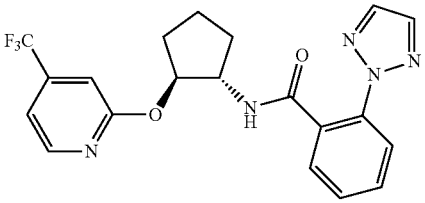 [SMILES: O=C(N[C@H]1CCC[C@@H]1Oc1cc(C(F)(F)F)ccn1)c1ccccc1-n1nccn1]

To a solution of N-[(1S,2S)-2-hydroxycyclopentyl]-2-(2H-1,2,3-triazol-2-yl)benzamide (Intermediate 11; 200 mg, 0.73 mmol) in dry DMF (1.2 ml) was added sodium hydride (60% dispersion in mineral oil, 29.4 mg, 0.73 mmol). To this was then added 2-chloro-4-(trifluoromethyl)pyridine (CAS number 81565-18-6; 133 mg, 0.73 mmol) as a solution in dry DMF (1.2 ml). The reaction was stirred at room temperature for 17 hours and was then partitioned between ethyl acetate and water. The organics were washed with water and brine, dried over magnesium sulfate and concentrated in vacuo. The crude oil was purified by reverse phase preparative HPLC (eluted with acetonitrile/water containing 0.1% ammonia) to afford the title compound.

$^1$H NMR (400 MHz, DMSO-$d_6$) δ ppm 1.52-1.78 (m, 4H), 2.00-2.13 (m, 2H), 4.18-4.30 (m, 1H), 5.30-5.38 (m, 1H), 7.22 (s, 1H), 7.30-7.34 (m, 1H), 7.47-7.56 (m, 2H), 7.59-7.65 (m, 1H), 7.77-7.81 (m, 1H), 7.98 (s, 2H), 8.40-8.48 (m, 2H)

MS ES$^+$: 418

Example 21

2,6-Dimethoxy-N-[(1S,2S)-2-{[4-(trifluoromethyl)pyridin-2-yl]oxy}cyclopentyl]benzamide

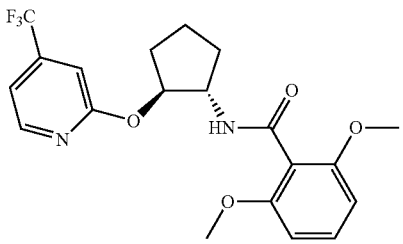 [SMILES: COc1cccc(OC)c1C(=O)N[C@H]1CCC[C@@H]1Oc1cc(C(F)(F)F)ccn1]

Prepared according to the procedure for 2-(2H-1,2,3-triazol-2-yl)-N-[(1S,2S)-2-{[4-(trifluoromethyl)pyridin-2-yl]oxy}cyclopentyl]benzamide (Example 20) from N-[(1S,2S)-2-hydroxycyclopentyl]-2-(2H-1,2,3-triazol-2-yl)benzamide (Intermediate 11; 100 mg, 0.37 mmol) and 2-bromo-4-(trifluoromethyl)pyridine (CAS number 175205-81-9; 100 mg, 0.45 mmol) except that the reaction was stirred at room temperature for 2 hours. After work-up, the resulting residue was purified by reverse phase preparative HPLC (eluted with acetonitrile/water containing 0.1% ammonia) to afford the title compound.

$^1$H NMR (400 MHz, DMSO-d) δ ppm 1.64-1.79 (m, 4H), 2.04-2.14 (m, 2H), 3.68 (s, 6H), 4.25-4.31 (m, 1H), 5.29-5.32 (m, 1H), 6.64-6.66 (m, 2H), 7.24-7.32 (m, 3H), 8.17-8.19 (m, 1H), 8.43-8.44 (m, 1H)

MS ES$^+$: 411

Example 22

2-(2H-1,2,3-Triazol-2-yl)-N-(2-{[4-(trifluoromethyl)pyridin-2-yl]methyl}cyclopentyl)benzamide

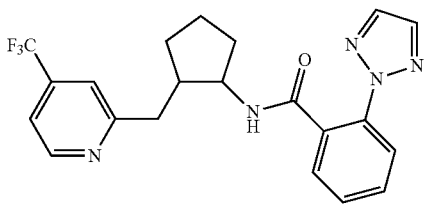 [SMILES: O=C(NC1CCCC1Cc1cc(C(F)(F)F)ccn1)c1ccccc1-n1nccn1]

Triethylamine (0.099 ml, 0.71 mmol), 3H-[1,2,3]triazolo[4,5-b]pyridin-3-ol (0.039 g, 0.29 mmol) and EDC (0.055 g, 0.29 mmol) were added to a solution 2-{[4-(trifluoromethyl)pyridin-2-yl]methyl}cyclopentan-1-amine (Intermediate 12; 0.058 g, 0.24 mmol) and 2-(2H-1,2,3-triazol-2-yl)benzoic acid (CAS number 1001401-62-2; 0.054 g, 0.29 mmol) in DCM (3 ml). The reaction was stirred at room temperature for 24 hours and then diluted with DCM (40 ml) and washed with a saturated solution of sodium bicarbonate (10 ml). The organics were dried over magnesium sulfate, filtered through a hydrophobic frit and concentrated in vacuo. The crude product was purified by column chromatography (silica, 0-80% ethyl acetate/petrol) to afford the title compound.

$^1$H NMR (400 MHz, DCM-$d_2$) δ ppm 1.19-1.31 (m, 1H), 1.39-1.49 (m, 1H), 1.50-1.64 (m, 2H), 1.65-1.75 (m, 1H), 1.91-2.02 (m, 1H), 2.48-2.59 (m, 1H), 2.68-2.76 (m, 1H), 3.00-3.08 (m, 1H), 4.36-4.45 (m, 1H), 6.45-6.53 (m, 1H), 7.30-7.34 (m, 1H), 7.37 (s, 1H), 7.48-7.54 (m, 1H), 7.55-7.61 (m, 1H), 7.62-7.66 (m, 1H), 7.71-7.75 (m, 1H), 7.82 (s, 2H) and 8.59-8.62 (m, 1H).

MS ES$^+$: 416

Example 23

2-(2H-1,2,3-Triazol-2-yl)-N-(2-{[4-(trifluoromethyl)pyridin-2-yl]methyl}cyclopentyl)benzamide

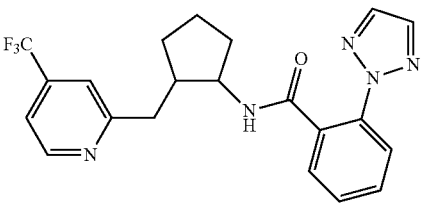 [SMILES: O=C(NC1CCCC1Cc1cc(C(F)(F)F)ccn1)c1ccccc1-n1nccn1]

Prepared according to the procedure for 2-(2H-1,2,3-triazol-2-yl)-N-(2-{[4-(trifluoromethyl)pyridin-2-yl]methyl}cyclopentyl)benzamide (Example 22) except this was then was chirally separated using SFC (Waters prep30/MS system using 20% Ethanol, Daicel IA 10 mm id×250 mm long columns at 30 ml/min, 40° C. and 100 bar) to afford the title compound as a single enantiomer.

$^1$H NMR (300 MHz, DCM-$d_2$) δ ppm 1.15-1.35 (m, 1H), 1.35-1.79 (m, 4H), 1.85-2.06 (m, 1H), 2.42-2.63 (m, 1H), 2.64-2.79 (m, 1H), 2.95-3.16 (m, 1H), 4.28-4.53 (m, 1H), 6.44-6.59 (m, 1H), 7.26-7.43 (m, 2H), 7.43-7.68 (m, 3H), 7.69-7.77 (m, 1H), 7.82 (s, 2H), 8.54-8.68 (m, 1H).

MS ES$^+$: 416

Example 24

2-(2H-1,2,3-Triazol-2-yl)-N-(2-{[5-(trifluoromethyl)pyridin-2-yl]methyl}cyclopentyl)benzamide

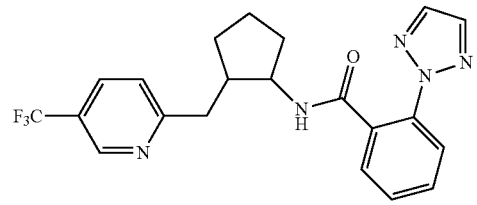 [SMILES: O=C(NC1CCCC1Cc1ccc(C(F)(F)F)cn1)c1ccccc1-n1nccn1]

Prepared according to the procedure for 2-(2H-1,2,3-triazol-2-yl)-N-(2-{[4-(trifluoromethyl)pyridin-2-yl]methyl}cyclopentyl)benzamide (Example 22) from 2-{[5-(trifluoromethyl)pyridin-2-yl]methyl}cyclopentan-1-amine (Intermediate 13; 33 mg, 0.14 mmol) and 2-(2H-1,2,3-triazol-2-yl)benzoic acid (CAS number 1001401-62-2; 31 mg, 0.16 mmol) and then was purified by column chromatography (silica, 0-100% ethyl acetate/petrol) to afford the title compound.

$^1$H NMR (400 MHz, DCM-d$_2$) δ ppm 1.22-1.32 (m, 1H), 1.38-1.48 (m, 1H), 1.50-1.65 (m, 2H), 1.66-1.77 (m, 1H), 1.90-2.01 (m, 1H), 2.47-2.58 (m, 1H), 2.69-2.77 (m, 1H), 3.00-3.08 (m, 1H), 4.36-4.45 (m, 1H), 6.37-6.44 (m, 1H), 7.29-7.34 (m, 1H), 7.49-7.54 (m, 1H), 7.56-7.65 (m, 2H), 7.72-7.76 (m, 1H), 7.83 (s, 2H), 7.84-7.86 (m, 1H) and 8.67-8.71 (m, 1H)

MS ES$^+$: 416

Example 25

2-(2H-1,2,3-Triazol-2-yl)-N-(2-{[5-(trifluoromethyl) pyridin-2-yl]methyl}cyclopentyl)benzamide

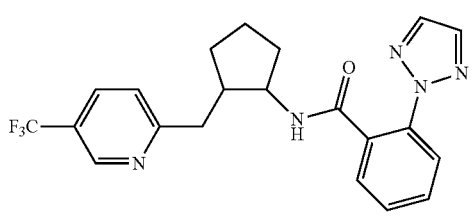 [SMILES: O=C(NC1CCCC1Cc1ccc(C(F)(F)F)cn1)c1ccccc1-n1nccn1]

Prepared according to the procedure for 2-(2H-1,2,3-triazol-2-yl)-N-(2-{[5-(trifluoromethyl)pyridin-2-yl] methyl}cyclopentyl)benzamide (Example 24) except this was then was chirally separated using SFC (Waters prep30/MS system using 20% Ethanol, Daicel IA 10 mm id×250 mm long columns at 30 ml/min, 40° C. and 100 bar) to afford the title compound as a single enantiomer.

$^1$H NMR (300 MHz, DCM-d$_2$) δ ppm 1.14-1.35 (m, 1H), 1.35-1.81 (m, 4H), 1.86-2.08 (m, 1H), 2.41-2.60 (m, 1H), 2.62-2.81 (m, 1H), 2.95-3.13 (m, 1H), 4.29-4.50 (m, 1H), 6.35-6.49 (m, 1H), 7.23-7.35 (m, 1H), 7.44-7.67 (m, 3H), 7.68-7.77 (m, 1H), 7.77-7.88 (m, 3H), 8.69 (s, 1H)

MS ES$^+$: 416

Example 26

5-Methyl-2-(2H-1,2,3-triazol-2-yl)-N-(2-{[5-(trifluoromethyl)pyridin-2-yl]methyl}cyclopentyl)benzamide

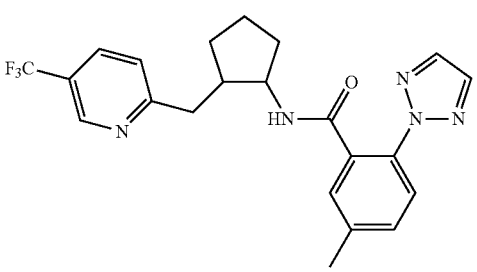 [SMILES: Cc1ccc(-n2nccn2)c(C(=O)NC2CCCC2Cc2ccc(C(F)(F)F)cn2)c1]

To a solution of 2-{[5-(trifluoromethyl)pyridin-2-yl] methyl}cyclopentan-1-amine hydrochloride (Intermediate 36; 0.60 g, 2.44 mmol) in DMF (5 ml) was added DIPEA (0.63 g, 4.80 mmol), TBTU (0.94 g, 2.93 mmol) and added 5-methyl-2-(2H-1,2,3-triazol-2-yl)benzoic acid (Intermediate 6; 0.49 g, 2.44 mmol). The reaction was stirred at room temperature for 1 hour and then partitioned between ethyl acetate (50 ml) and water (10.0 ml). The aqueous layer was further extracted with ethyl acetate (50 ml) and the combined organics were concentrated in vacuo. The resulting residue was purified by column chromatography (silica, 0-2% methanol/DCM) to afford the title compound.

$^1$H NMR (400 MHz, DMSO) δ ppm 1.61-1.38 (m, 6H), 2.33 (s, 3H), 2.68-2.74 (m, 1H), 3.04-3.09 (m, 1H), 4.24-4.26 (m, 1H), 7.30 (s, 1H), 7.41-7.43 (m, 1H), 7.47-7.49 (m, 1H), 7.64-7.66 (m, 1H), 7.98 (m, 2H), 8.09-8.11 (m, 1H), 8.28-8.30 (m, 1H), 8.87 (s, 1H)

MS ES$^+$: 430

Example 27

2,6-Dimethoxy-N-[(1S,2S)-2-{[6-(trifluoromethyl) pyridin-2-yl]amino}cyclopentyl]benzamide

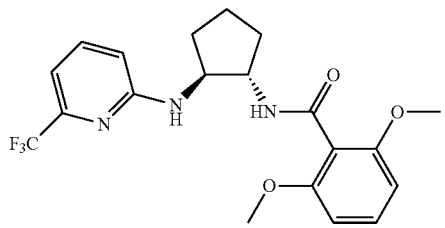 [SMILES: COc1cccc(OC)c1C(=O)N[C@H]1CCC[C@@H]1Nc1cccc(C(F)(F)F)n1]

To a microwave vial were charged N-[(1S,2S)-2-Aminocyclopentyl]-2,6-dimethoxybenzamide hydrochloride (Intermediate 5; 80 mg, 0.266 mmol) in dry NMP (1 ml). To this was then added DIPEA (138 μl, 0.798 mmol) and 2-fluoro-6-(trifluoromethyl)pyridine (CAS number 94239-04-0; 53 mg, 0.319 mmol). The reaction was subjected to microwave irradiation at 200° C. for 30 minutes and then at 250° C. for 20 minutes. The reaction mixture was directly purified by reverse phase preparative HPLC (eluted with acetonitrile/water containing 0.1% ammonia) to afford the title compound.

$^1$H NMR (400 MHz, DMSO-d$_6$) δ ppm 1.44-1.58 (m, 2H), 1.65-1.76 (m, 2H), 1.97-2.10 (m, 2H), 3.63 (s, 6H), 3.95-4.04 (m, 1H), 4.04-4.13 (m, 1H), 6.55-6.67 (m, 2H), 6.84-6.92 (m, 2H), 7.05-7.11 (m, 1H), 7.21-7.29 (m, 1H), 7.55-7.62 (m, 1H), 8.02-8.09 (m, 1H)

MS ES$^+$: 410

Example 28

3-Bromo-N-[(1S,2S)-2-{[5-(trifluoromethyl)pyrazin-2-yl]amino}cyclopentyl]pyridine-2-carboxamide

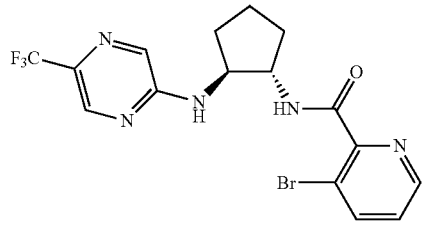 [SMILES: O=C(N[C@H]1CCC[C@@H]1Nc1cnc(C(F)(F)F)cn1)c1ncccc1Br]

EDC (509 mg, 2.65 mmol) was added to a solution of 3-bromopyridine-2-carboxylic acid (429 mg, 2.12 mmol), 3H-[1,2,3]triazolo[4,5-b]pyridin-3-ol (361 mg, 2.65 mmol), (1S,2S)-1-N-[5-(trifluoromethyl)pyrazin-2-yl]cyclopentane-1,2-diamine hydrochloride (Intermediate 14, 500 mg, 1.77 mmol) and triethylamine (0.74 ml, 5.31 mmol) in DCM (5.9 ml). The reaction was stirred at room temperature overnight. The reaction was diluted with DCM, washed with water, brine, filtered through a hydrophobic frit and concentrated in vacuo. The crude product was purified by column chromatography (silica 0-100% ethyl acetate/petrol) to afford the title compound.

$^1$H NMR (400 MHz, DCM-$d_2$) δ ppm 1.57-1.82 (m, 2H), 1.82-2.04 (m, 2H), 2.19-2.35 (m, 1H), 2.35-2.47 (m, 1H), 4.06-4.23 (m, 1H), 4.24-4.39 (m, 1H), 6.99 (br. s., 1H), 7.27-7.32 (m, 1H), 8.02-8.06 (m, 1H), 8.11-8.21 (m, 1H), 8.22 (s, 1H), 8.46-8.52 (m, 1H)

MS ES$^+$: 432

Example 29

2-Ethoxy-5-methyl-N-[(1S,2S)-2-{[5-(trifluoromethyl)pyrazin-2-yl]amino}cyclopentyl]benzamide

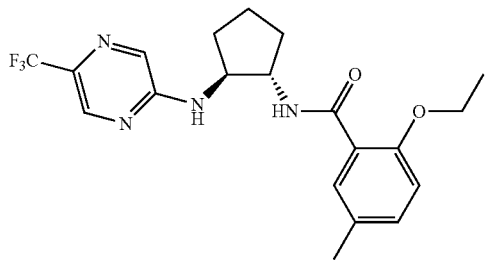

Prepared according to the procedure for 3-bromo-N-[(1S,2S)-2-{[5-(trifluoromethyl)pyrazin-2-yl]amino}cyclopentyl]pyridine-2-carboxamide (Example 28) from (1S,2S)-1-N-[5-(trifluoromethyl)pyrazin-2-yl]cyclopentane-1,2-diamine hydrochloride (Intermediate 14, 75 mg, 0.27 mmol) and 2-ethoxy-5-methylbenzoic acid (CAS number 854645-34-4; 57 mg, 0.32 mmol) and was then purified by column chromatography (silica, 40-100% ethyl acetate/petrol) to afford the title compound.

$^1$H NMR (400 MHz, DCM-$d_2$) δ ppm 1.47 (t, J=6.95 Hz, 3H), 1.57-1.71 (m, 2H), 1.82-1.97 (m, 2H), 2.14-2.28 (m, 1H), 2.31 (s, 3H), 2.41-2.54 (m, 1H), 3.84-3.94 (m, 1H), 4.15 (q, J=6.95 Hz, 2H), 4.35-4.49 (m, 1H), 6.85-6.90 (m, 1H), 7.22-7.28 (m, 1H), 7.92-7.96 (m, 1H), 8.08 (br. s., 1H), 8.23 (s, 1H), 8.38-8.47 (m, 1H)

MS ES$^+$: 409

Example 30

3-Ethoxy-6-methyl-N-[(1S,2S)-2-{[5-(trifluoromethyl)pyrazin-2-yl]amino}cyclopentyl]pyridine-2-carboxamide

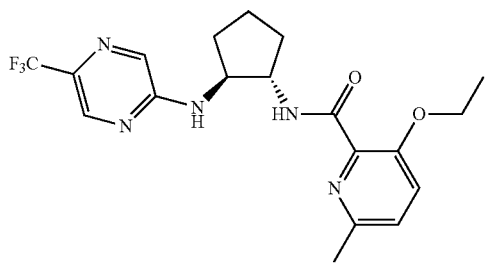 [SMILES: CCOc1ccc(C)cc1C(=O)N[C@H]1CCC[C@@H]1Nc1cnc(C(F)(F)F)cn1]

Prepared according to the procedure for 3-bromo-N-[(1S,2S)-2-{[5-(trifluoromethyl)pyrazin-2-yl] amino}cyclopentyl]pyridine-2-carboxamide (Example 28) from (1S,2S)-1-N-[5-(trifluoromethyl)pyrazin-2-yl]cyclopentane-1,2-diamine hydrochloride (Intermediate 14, 75 mg, 0.27 mmol) and 3-ethoxy-6-methylpyridine-2-carboxylic acid (CAS number 1228188-14-4; 58 mg, 0.32 mmol) and was then purified by column chromatography (silica, 40-100% ethyl acetate/petrol) followed by partitioning between ethyl acetate and a saturated solution of sodium bicarbonate. The organics were filtered through a hydrophobic frit and concentrated in vacuo to afford the title compound.

$^1$H NMR (400 MHz, DCM-$d_2$) δ ppm 1.39-1.47 (m, 3H), 1.51-1.63 (m, 1H), 1.63-1.76 (m, 1H), 1.82-1.95 (m, 2H), 2.17-2.30 (m, 1H), 2.39-2.49 (m, 1H), 2.50 (s, 3H), 3.95-4.06 (m, 1H), 4.07-4.14 (m, 2H), 4.32-4.47 (m, 1H), 6.64-7.05 (m, 1H), 7.20-7.36 (m, 2H), 7.97-8.10 (m, 2H), 8.23-8.25 (m, 1H)

MS ES$^+$: 410

Example 31

2-(1H-Pyrazol-1-yl)-N-[(1S,2S)-2-{[5-(trifluoromethyl)pyrazin-2-yl]amino}cyclopentyl]benzamide

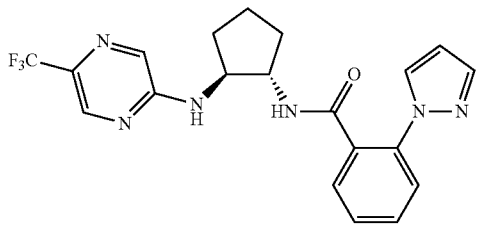

A solution of (1S,2S)-1-N-[5-(trifluoromethyl)pyrazin-2-yl]cyclopentane-1,2-diamine hydrochloride (Intermediate 14, 213 mg, 0.75 mmol), HATU (430 mg, 1.13 mmol), triethylamine (0.315 ml, 2.26 mmol) and 2-(1H-pyrazol-1-yl)benzoic acid (CAS number 55317-53-8; 156 mg, 0.83 mmol) was stirred at room temperature overnight. This was then partitioned between DCM and a saturated solution of sodium bicarbonate, filtered through a hydrophobic frit and concentrated in vacuo. The resulting residue was purified by reverse phase preparative HPLC (eluted with acetonitrile/water containing 0.1% ammonia) to afford the title compound.

$^1$H NMR (400 MHz, DMSO-$d_6$) δ ppm 1.39-1.53 (m, 2H), 1.60-1.72 (m, 2H), 1.92-2.07 (m, 2H), 4.09-4.20 (m, 2H), 6.27-6.31 (m, 1H), 7.35-7.44 (m, 2H), 7.51-7.60 (m, 3H), 7.88-7.92 (m, 1H), 7.94-8.00 (m, 1H), 8.03 (s, 1H), 8.34 (s, 1H), 8.36-8.41 (m, 1H)

MS ES$^+$: 417

Example 32

2-Fluoro-6-(2H-1,2,3-triazol-2-yl)-N-[(1S,2S)-2-{[5-(trifluoromethyl)pyrazin-2-yl]amino}cyclopentyl]benzamide

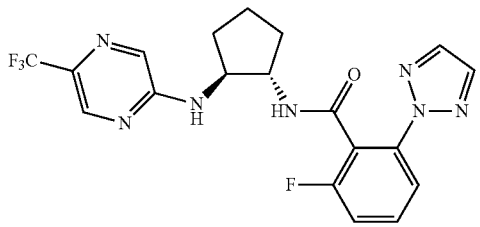

Prepared according to the procedure for 2-(1H-pyrazol-1-yl)-N-[(1S,2S)-2-{[5-(trifluoromethyl)pyrazin-2-yl]amino}cyclopentyl]benzamide (Example 31) from (1S,2S)-1-N-[5-(trifluoromethyl)pyrazin-2-yl]cyclopentane-1,2-diamine hydrochloride (Intermediate 14, 213 mg, 0.75 mmol) and 2-fluoro-6-(2H-1,2,3-triazol-2-yl)benzoic acid (CAS number 1186050-58-7; 172 mg, 0.83 mmol) to afford the title compound.

$^1$H NMR (400 MHz, DMSO-$d_6$) δ ppm 1.43-1.59 (m, 2H), 1.60-1.75 (m, 2H), 1.96-2.08 (m, 2H), 4.12-4.24 (m, 2H), 7.32-7.38 (m, 1H), 7.58-7.65 (m, 1H), 7.70-7.74 (m, 1H), 7.94-8.00 (m, 3H), 8.06 (br. s., 1H), 8.35 (s, 1H) and 8.60-8.65 (m, 1H)

MS ES$^+$: 436

Example 33

2,6-Difluoro-N-[(1S,2S)-2-{[5-(trifluoromethyl)pyrazin-2-yl]amino}cyclopentyl]benzamide

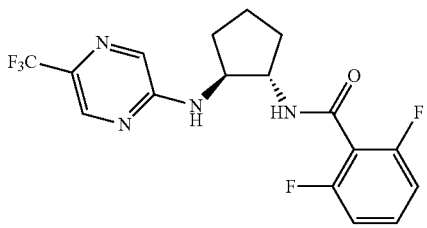 [SMILES: O=C(N[C@H]1CCC[C@@H]1Nc1cnc(C(F)(F)F)cn1)c1c(F)cccc1F]

Prepared according to the procedure for 2-(1H-pyrazol-1-yl)-N-[(1S,2S)-2-{[5-(trifluoromethyl)pyrazin-2-yl]amino}cyclopentyl]benzamide (Example 31) from (1S,2S)-1-N-[5-(trifluoromethyl)pyrazin-2-yl]cyclopentane-1,2-diamine hydrochloride (Intermediate 14, 213 mg, 0.75 mmol) and 2,6-difluorobenzoic acid (CAS number 385-00-2; 131 mg, 0.83 mmol) to afford the title compound.

$^1$H NMR (400 MHz, DMSO-$d_6$) δ ppm 1.44-1.60 (m, 2H), 1.68-1.77 (m, 2H), 2.01-2.14 (m, 2H), 4.18-4.29 (m, 2H), 7.07-7.15 (m, 2H), 7.43-7.52 (m, 1H), 7.99-8.09 (m, 2H), 8.33 (s, 1H), 8.79-8.87 (m, 1H)

MS ES$^+$: 387

Example 34

2,6-Dimethoxy-N-[(1S,2S)-2-{[5-(trifluoromethyl)pyrazin-2-yl]amino}cyclopentyl]benzamide

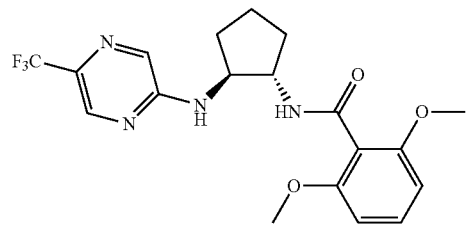 [SMILES: COc1cccc(OC)c1C(=O)N[C@H]1CCC[C@@H]1Nc1cnc(C(F)(F)F)cn1]

Prepared according to the procedure for 2-(1H-pyrazol-1-yl)-N-[(1S,2S)-2-{[5-(trifluoromethyl)pyrazin-2-yl]amino}cyclopentyl]benzamide (Example 31) from (1S,2S)-1-N-[5-(trifluoromethyl)pyrazin-2-yl]cyclopentane-1,2-diamine hydrochloride (Intermediate 14, 213 mg, 0.75 mmol) and 2,6-dimethoxybenzoic acid (CAS number 1466-76-8; 151 mg, 0.83 mmol) except this was then purified by column chromatography (silica, 0-100% ethyl acetate/petrol) to afford the title compound.

$^1$H NMR (400 MHz, DMSO-$d_6$) δ ppm 1.43-1.60 (m, 2H), 1.64-1.75 (m, 2H), 1.95-2.09 (m, 2H), 3.61 (s, 6H), 4.13-4.24 (m, 2H), 6.60-6.64 (m, 2H), 7.21-7.28 (m, 1H), 7.93-8.01 (m, 1H), 8.03-8.12 (m, 2H) and 8.34 (s, 1H).

MS ES$^+$: 411

Example 35

2-(1H-1,2,3-Triazol-1-yl)-N-[(1S,2S)-2-{[5-(trifluoromethyl)pyrazin-2-yl]amino}cyclopentyl]benzamide

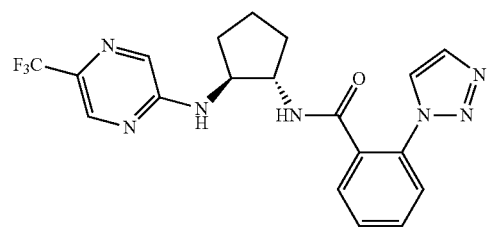 [SMILES: O=C(N[C@H]1CCC[C@@H]1Nc1cnc(C(F)(F)F)cn1)c1ccccc1-n1ccnn1]

Prepared according to the procedure for 2-(1H-pyrazol-1-yl)-N-[(1S,2S)-2-{[5-(trifluoromethyl)pyrazin-2-yl]amino}cyclopentyl]benzamide (Example 31) from (1S,2S)-1-N-[5-(trifluoromethyl)pyrazin-2-yl]cyclopentane-1,2-diamine hydrochloride (Intermediate 14, 213 mg, 0.75 mmol) and 2-(1H-1,2,3-triazol-1-yl)benzoic acid (CAS number 1085458-53-2; 157 mg, 0.83 mmol) except this was then purified by column chromatography (silica, 0-100% ethyl acetate/petrol) to afford the title compound.

$^1$H NMR (400 MHz, DMSO-$d_6$) δ ppm 1.35-1.49 (m, 2H), 1.58-1.72 (m, 2H), 1.87-2.09 (m, 2H), 4.01-4.19 (m, 2H), 7.47-7.54 (m, 1H), 7.55-7.69 (m, 3H), 7.76 (s, 1H), 7.89-7.98 (m, 1H), 7.98-8.07 (m, 1H), 8.27 (s, 1H), 8.35 (s, 1H), 8.43-8.53 (m, 1H)

MS ES$^+$: 418

Example 36

5-Fluoro-2-(2H-1,2,3-triazol-2-yl)-N-[(1S,2S)-2-{[5-(trifluoromethyl)pyrazin-2-yl]amino}cyclopentyl]benzamide

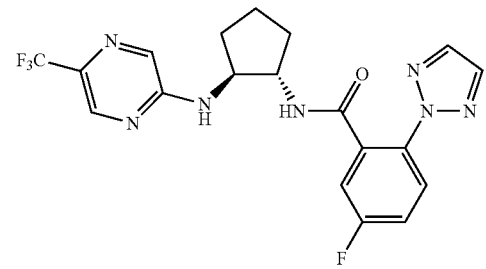 [SMILES: O=C(N[C@H]1CCC[C@@H]1Nc1cnc(C(F)(F)F)cn1)c1cc(F)ccc1-n1nccn1]

Prepared according to the procedure for 2-(1H-pyrazol-1-yl)-N-[(1S,2S)-2-{[5-(trifluoromethyl)pyrazin-2-yl]amino}cyclopentyl]benzamide (Example 31) from (1S,2S)-1-N-[5-(trifluoromethyl)pyrazin-2-yl]cyclopentane-1,2-diamine hydrochloride (Intermediate 14, 213 mg, 0.75 mmol) and 5-fluoro-2-(2H-1,2,3-triazol-2-yl)benzoic acid (Intermediate 8; 172 mg, 0.83 mmol) except this was then purified by column chromatography (silica, 0-100% ethyl acetate/petrol) to afford the title compound.

$^1$H NMR (400 MHz, DMSO-d$_6$) δ ppm 1.41-1.60 (m, 2H), 1.61-1.77 (m, 2H), 1.93-2.10 (m, 2H), 4.02-4.26 (m, 2H), 7.22-7.33 (m, 1H), 7.42-7.53 (m, 1H), 7.75-7.85 (m, 1H), 7.90-8.00 (m, 3H), 8.00-8.08 (m, 1H), 8.36 (s, 1H), 8.45-8.54 (m, 1H)

MS ES$^+$: 436

Example 37

2-Methoxy-5-methyl-N-[(1S,2S)-2-{[5-(trifluoromethyl)pyrazin-2-yl]amino}cyclopentyl]benzamide

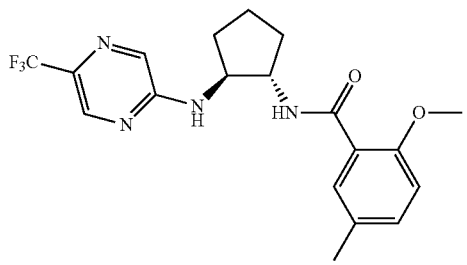 [SMILES: COc1ccc(C)cc1C(=O)N[C@H]1CCC[C@@H]1Nc1cnc(C(F)(F)F)cn1]

A solution of (1S,2S)-1-N-[5-(trifluoromethyl)pyrazin-2-yl]cyclopentane-1,2-diamine hydrochloride (Intermediate 14, 75 mg, 0.27 mmol), 2-methoxy-5-methylbenzoic acid (CAS number 25045-36-7; 53 mg, 0.32 mmol), 3H-[1,2,3]triazolo[4,5-b]pyridin-3-ol (61 mg, 0.40 mmol), EDC (76 mg, 0.40 mmol) and triethylamine (111 µl, 0.80 mmol) in dry DCM (1 ml) was stirred at room temperature for 24 hours. The reaction mixture was partitioned between DCM (3 ml) and water (2 ml), filtered through a hydrophobic frit and concentrated in vacuo. The resulting residue was purified by reverse phase preparative HPLC (eluted with acetonitrile/water containing 0.1% ammonia) to afford the title compound.

$^1$H NMR (400 MHz, DCM-d$_2$) δ ppm 1.49-1.74 (m, 2H), 1.83-1.94 (m, 2H), 2.16-2.27 (m, 1H), 2.31 (s, 3H), 2.41-2.54 (m, 1H), 3.86-4.01 (m, 4H), 4.40-4.53 (m, 1H), 6.82-7.04 (m, 2H), 7.24-7.30 (m, 1H), 7.86-8.00 (m, 2H), 8.08-8.21 (m, 1H), 8.24 (s, 1H)

MS ES$^+$: 395

Example 38

2-(Pyrimidin-2-yl)-N-[(1S,2S)-2-{[5-(trifluoromethyl)pyrazin-2-yl]amino}cyclopentyl]benzamide

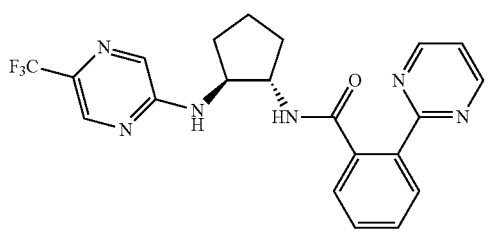 [SMILES: O=C(N[C@H]1CCC[C@@H]1Nc1cnc(C(F)(F)F)cn1)c1ccccc1-c1ncccn1]

Prepared according to the procedure for 2-methoxy-5-methyl-N-[(1S,2S)-2-{[5-(trifluoromethyl)pyrazin-2-yl]amino}cyclopentyl]benzamide (Example 37) from (1S,2S)-1-N-[5-(trifluoromethyl)pyrazin-2-yl]cyclopentane-1,2-diamine hydrochloride (Intermediate 14, 75 mg, 0.27 mmol) and 2-(pyrimidin-2-yl)benzoic acid (CAS number 400892-62-8; 64 mg, 0.32 mmol) to afford the title compound.

$^1$H NMR (400 MHz, DCM-d$_2$) δ ppm 1.44-1.59 (m, 2H), 1.75-1.89 (m, 2H), 2.11-2.24 (m, 1H), 2.32-2.45 (m, 1H), 3.86-3.98 (m, 1H), 4.20-4.34 (m, 1H), 6.40-6.44 (m, 1H), 6.53-6.71 (m, 1H), 7.03-7.10 (m, 1H), 7.44-7.59 (m, 3H), 7.85 (s, 1H), 7.97-8.08 (m, 1H), 8.21 (s, 1H), 8.51-8.60 (m, 2H)

MS ES$^+$: 429

Example 39

5-Fluoro-2-(pyrimidin-2-yl)-N-[(1S,2S)-2-{[5-(trifluoromethyl)pyrazin-2-yl]amino}cyclopentyl]benzamide

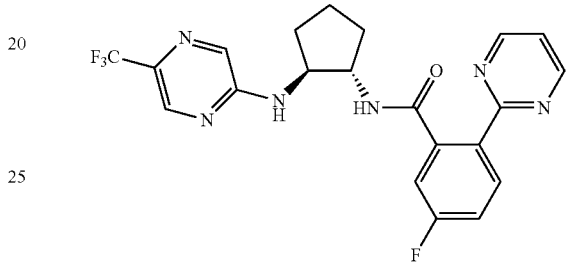

Prepared according to the procedure for 2-methoxy-5-methyl-N-[(1S,2S)-2-{[5-(trifluoromethyl)pyrazin-2-yl]amino}cyclopentyl]benzamide (Example 37) from (1S,2S)-1-N-[5-(trifluoromethyl)pyrazin-2-yl]cyclopentane-1,2-diamine hydrochloride (Intermediate 14, 75 mg, 0.27 mmol) and 5-fluoro-2-(pyrimidin-2-yl)benzoic acid (CAS number 1293284-57-7; 69 mg, 0.32 mmol) to afford the title compound.

$^1$H NMR (400 MHz, DCM-d$_2$) δ ppm 1.48-1.70 (m, 2H), 1.74-1.98 (m, 2H), 2.17-2.43 (m, 2H), 3.94-4.09 (m, 1H), 4.17-4.28 (m, 1H), 6.47-6.61 (m, 1H), 6.83-7.05 (m, 1H), 7.07-7.13 (m, 1H), 7.17-7.28 (m, 2H), 7.96-8.08 (m, 1H), 8.09-8.19 (m, 2H), 8.53-8.62 (m, 2H)

MS ES$^+$: 447

Example 40

2-Chloro-6-(2H-1,2,3-triazol-2-yl)-N-[(1S,2S)-2-{[5-(trifluoromethyl)pyrazin-2-yl]amino}cyclopentyl]benzamide

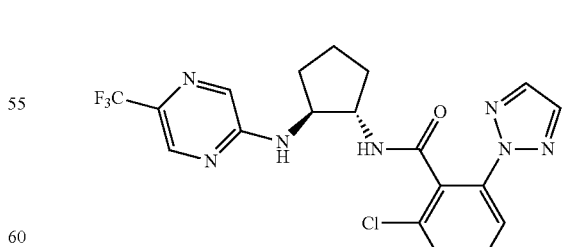

Prepared according to the procedure for 2-methoxy-5-methyl-N-[(1S,2S)-2-{[5-(trifluoromethyl)pyrazin-2-yl]amino}cyclopentyl]benzamide (Example 37) from (1S,2S)-1-N-[5-(trifluoromethyl)pyrazin-2-yl]cyclopentane-1,2-diamine hydrochloride (Intermediate 14; 75 mg, 0.265 mmol)

and 2-chloro-6-(2H-1,2,3-triazol-2-yl)benzoic acid (Intermediate 15; 71 mg, 0.318 mmol) to afford the title compound.

$^1$H NMR (400 MHz, DCM-$d_2$) δ ppm 1.52-1.67 (m, 2H), 1.81-1.95 (m, 2H), 2.21-2.41 (m, 2H), 4.04-4.15 (m, 1H), 4.24-4.38 (m, 1H), 6.14-6.29 (m, 1H), 6.47-6.62 (m, 1H), 7.46-7.55 (m, 2H), 7.61 (s, 2H), 7.88-7.96 (m, 2H), 8.17 (s, 1H)

MS ES$^+$: 452

Example 41

5-Fluoro-2-(1H-1,2,3-triazol-1-yl)-N-[(1S,2S)-2-{[5-(trifluoromethyl)pyrazin-2-yl]amino}cyclopentyl]benzamide

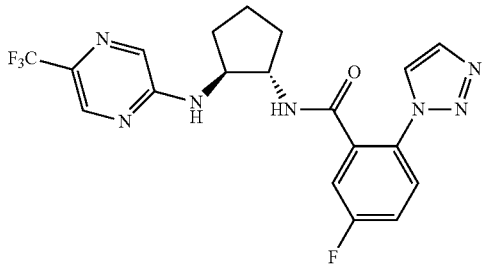

Prepared according to the procedure for 2-methoxy-5-methyl-N-[(1S,2S)-2-{[5-(trifluoromethyl)pyrazin-2-yl]amino}cyclopentyl]benzamide (Example 37) from (1S,2S)-1-N-[5-(trifluoromethyl)pyrazin-2-yl]cyclopentane-1,2-diamine hydrochloride (Intermediate 14; 75 mg, 0.27 mmol) and 5-fluoro-2-(1H-1,2,3-triazol-1-yl)benzoic acid (Intermediate 9; 66 mg, 0.32 mmol) to afford the title compound.

$^1$H NMR (400 MHz, DCM-$d_2$) δ ppm 1.39-1.64 (m, 2H), 1.77-1.92 (m, 2H), 2.08-2.22 (m, 1H), 2.25-2.41 (m, 1H), 3.92-4.04 (m, 1H), 4.08-4.23 (m, 1H), 6.28-6.47 (m, 1H), 6.69-6.80 (m, 1H), 7.28-7.44 (m, 2H), 7.47-7.56 (m, 1H), 7.72 (d, J=1.01 Hz, 1H), 7.87 (d, J=1.01 Hz, 1H), 8.09 (s, 1H), 8.24 (s, 1H)

MS ES$^+$: 436

Example 42

5-Methyl-2-(1H-1,2,3-triazol-1-yl)-N-[(1S,2S)-2-{[5-(trifluoromethyl)pyrazin-2-yl]amino}cyclopentyl]benzamide

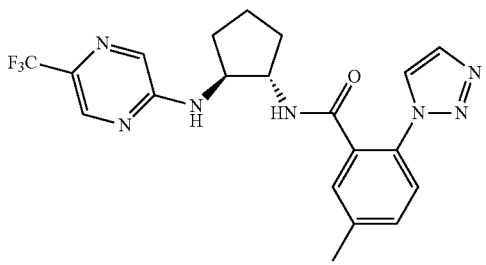 [SMILES: Cc1ccc(-n2ccnn2)c(C(=O)N[C@H]2CCC[C@@H]2Nc2cnc(C(F)(F)F)cn2)c1]

Prepared according to the procedure for 2-methoxy-5-methyl-N-[(1S,2S)-2-{[5-(trifluoromethyl)pyrazin-2-yl]amino}cyclopentyl]benzamide (Example 37) from (1S,2S)-1-N-[5-(trifluoromethyl)pyrazin-2-yl]cyclopentane-1,2-diamine hydrochloride (Intermediate 14; 75 mg, 0.27 mmol) and 5-methyl-2-(1H-1,2,3-triazol-1-yl)benzoic acid (CAS number 1149352-55-5; 65 mg, 0.32 mmol) to afford the title compound.

$^1$H NMR (400 MHz, DCM-$d_2$) δ ppm 1.42-1.65 (m, 2H), 1.76-1.91 (m, 2H), 2.07-2.19 (m, 1H), 2.27-2.40 (m, 1H), 3.89-4.05 (m, 1H), 4.09-4.28 (m, 1H), 6.55-6.78 (m, 2H), 7.34-7.41 (m, 1H), 7.43-7.49 (m, 2H), 7.70 (d, J=1.01 Hz, 1H), 7.86 (d, J=1.01 Hz, 1H), 8.13 (s, 1H), 8.23 (s, 1H)

MS ES$^+$: 432

Example 43

3-(1H-Pyrazol-1-yl)-N-[(1S,2S)-2-{[5-(trifluoromethyl)pyrazin-2-yl]amino}cyclopentyl]pyridine-2-carboxamide

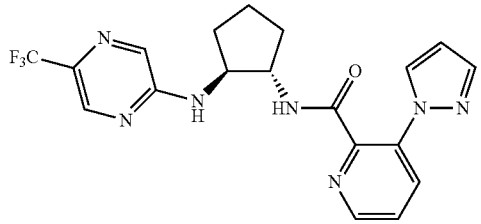 [SMILES: O=C(N[C@H]1CCC[C@@H]1Nc1cnc(C(F)(F)F)cn1)c1ncccc1-n1cccn1]

A solution of 3-bromo-N-[(1S,2S)-2-{[5-(trifluoromethyl)pyrazin-2-yl]amino}cyclopentyl]pyridine-2-carboxamide (Example 28; 100 mg, 0.23 mmol), 1H-pyrazole (CAS number 288-13-1; 32 mg, 0.47 mmol), cesium carbonate (151 mg, 0.47 mmol), copper (I) iodide (2.2 mg, 0.012 mmol) and trans-1-N,2-N-dimethylcyclohexane-1,2-diamine (1.7 mg, 0.012 mmol) in dry DMF (0.8 ml) was subjected to microwave irradiation at 120° C. for 1 hour. The reaction mixture was diluted with ethyl acetate and washed with water (×3) and brine, filtered through a hydrophobic frit and concentrated in vacuo. The resulting residue was purified by reverse phase preparative HPLC (eluted with acetonitrile/water containing 0.1% ammonia) to afford the title compound.

$^1$H NMR (400 MHz, DCME-$d_2$) δ ppm 1.42-1.59 (m, 1H), 1.59-1.77 (m, 1H), 1.77-1.93 (m, 2H), 2.10-2.31 (m, 1H), 2.31-2.48 (m, 1H), 3.94-4.18 (m, 1H), 4.19-4.35 (m, 1H), 6.21-6.36 (m, 1H), 6.37-6.43 (m, 1H), 7.51-7.58 (m, 1H), 7.61-7.67 (m, 1H), 7.71-7.75 (m, 1H), 7.84-7.88 (m, 1H), 7.90-7.96 (m, 1H), 7.97-8.07 (m, 1H), 8.25 (s, 1H), 8.49-8.59 (m, 1H)

MS ES$^+$: 418

Example 44

2-(5-Methyl-1,3,4-oxadiazol-2-yl)-N-[(1S,2S)-2-{[5-(trifluoromethyl)pyrazin-2-yl]amino}cyclopentyl]benzamide

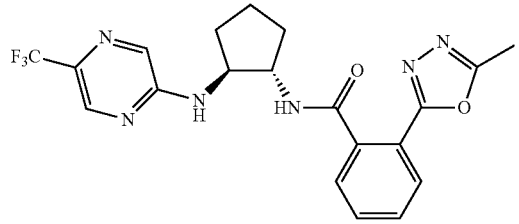 [SMILES: Cc1nnc(-c2ccccc2C(=O)N[C@H]2CCC[C@@H]2Nc2cnc(C(F)(F)F)cn2)o1]

Prepared according to the procedure for 2-methoxy-5-methyl-N-[(1S,2S)-2-{[5-(trifluoromethyl)pyrazin-2-yl]amino}cyclopentyl]benzamide (Example 37) from (1S,2S)-1-N-[5-(trifluoromethyl)pyrazin-2-yl]cyclopentane-1,2-diamine hydrochloride (Intermediate 14; 75 mg, 0.27 mmol) and 2-(5-methyl-1,3,4-oxadiazol-2-yl)benzoic acid (CAS number 898289-64-0; 75 mg, 0.37 mmol) except this was purified by column chromatography (silica, 40-100% ethyl acetate/petrol) to afford the title compound.

¹H NMR (400 MHz, DCM-d₂) δ ppm 1.53-1.69 (m, 2H), 1.80-1.94 (m, 2H), 2.23-2.34 (m, 1H), 2.37-2.47 (m, 1H), 2.50 (s, 3H), 3.98-4.14 (m, 1H), 4.26-4.40 (m, 1H), 6.53-6.74 (m, 1H), 6.78-6.90 (m, 1H), 7.48-7.55 (m, 1H), 7.55-7.61 (m, 2H), 7.80-7.90 (m, 1H), 8.12 (s, 1H), 8.15 (s, 1H)

MS ES⁺: 433

Example 45

2-(2H-1,2,3-Triazol-2-yl)-5-(trifluoromethyl)-N-[(1S,2S)-2-{[5-(trifluoromethyl)pyrazin-2-yl]amino}cyclopentyl]benzamide

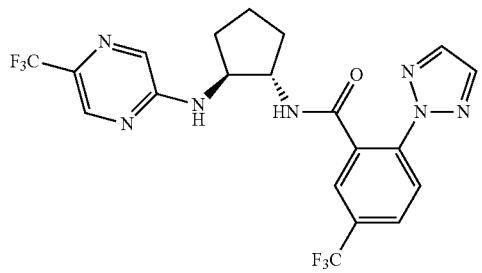 [SMILES: O=C(N[C@H]1CCC[C@@H]1Nc1cnc(C(F)(F)F)cn1)c1cc(C(F)(F)F)ccc1-n1nccn1]

Prepared according to the procedure for 2-methoxy-5-methyl-N-[(1S,2S)-2-{[5-(trifluoromethyl)pyrazin-2-yl]amino}cyclopentyl]benzamide (Example 37) from (1S,2S)-1-N-[5-(trifluoromethyl)pyrazin-2-yl]cyclopentane-1,2-diamine hydrochloride (Intermediate 14; 75 mg, 0.27 mmol) and 2-(2H-1,2,3-triazol-2-yl)-5-(trifluoromethyl)benzoic acid (Intermediate 37a; CAS number 1384066-81-2; 94 mg, 0.37 mmol) except this was purified by column chromatography (silica, 40-100% ethyl acetate/petrol) to afford the title compound.

¹H NMR (400 MHz, DCM-d₂) δ ppm 1.49-1.73 (m, 2H), 1.75-2.00 (m, 2H), 2.21-2.40 (m, 2H), 4.03-4.16 (m, 1H), 4.15-4.30 (m, 1H), 6.58-6.67 (m, 1H), 6.67-6.89 (m, 1H), 7.64-7.71 (m, 2H), 7.76-7.80 (m, 1H), 7.81-7.86 (m, 1H), 8.01-8.06 (m, 1H), 8.09 (s, 1H), 8.14 (s, 1H)

MS ES⁺: 486

Example 46

2-Fluoro-6-(1H-pyrazol-1-yl)-N-[(1S,2S)-2-{[5-(trifluoromethyl)pyrazin-2-yl]amino}cyclopentyl]benzamide

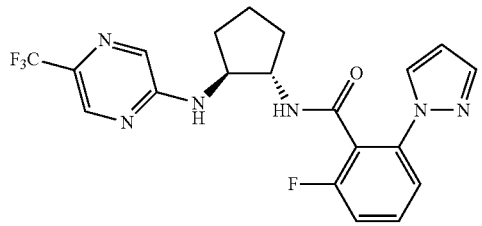 [SMILES: O=C(N[C@H]1CCC[C@@H]1Nc1cnc(C(F)(F)F)cn1)c1c(F)cccc1-n1cccn1]

Prepared according to the procedure for 2-methoxy-5-methyl-N-[(1S,2S)-2-{[5-(trifluoromethyl)pyrazin-2-yl]amino}cyclopentyl]benzamide (Example 37) from (1S,2S)-1-N-[5-(trifluoromethyl)pyrazin-2-yl]cyclopentane-1,2-diamine hydrochloride (Intermediate 14; 75 mg, 0.27 mmol) and 2-fluoro-6-(1H-pyrazol-1-yl)benzoic acid (CAS number 1521055-55-9; 75 mg, 0.37 mmol) except this was purified by column chromatography (silica, 40-100% ethyl acetate/petrol) to afford the title compound.

¹H NMR (400 MHz, DCM-d₂) δ ppm 1.41-1.59 (m, 2H), 1.73-1.93 (m, 2H), 2.12-2.38 (m, 2H), 3.93-4.04 (m, 1H), 4.16-4.27 (m, 1H), 6.24 (s, 1H), 6.52-6.60 (m, 1H), 7.10-7.18 (m, 1H), 7.29-7.35 (m, 1H), 7.42-7.53 (m, 2H), 7.72-7.76 (m, 1H), 8.01 (s, 1H), 8.16 (s, 1H)

MS ES⁺: 435

Example 47

5-Fluoro-2-(1H-pyrazol-1-yl)-N-[(1S,2S)-2-{[5-(trifluoromethyl)pyrazin-2-yl]amino}cyclopentyl]benzamide

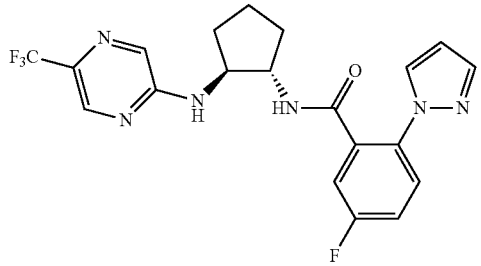

Prepared according to the procedure for 2-methoxy-5-methyl-N-[(1S,2S)-2-{[5-(trifluoromethyl)pyrazin-2-yl]amino}cyclopentyl]benzamide (Example 37) from (1S,2S)-1-N-[5-(trifluoromethyl)pyrazin-2-yl]cyclopentane-1,2-diamine hydrochloride (Intermediate 14; 75 mg, 0.27 mmol) and 5-fluoro-2-(1H-pyrazol-1-yl)benzoic acid (CAS number 1152964-04-9; 75 mg, 0.37 mmol) except this was purified by column chromatography (silica, 40-100% ethyl acetate/petrol) to afford the title compound.

¹H NMR (400 MHz, DCM-d₂) δ ppm 1.30-1.58 (m, 2H), 1.68-1.90 (m, 2H), 1.97-2.11 (m, 1H), 2.22-2.36 (m, 1H), 3.70-3.81 (m, 1H), 4.08-4.21 (m, 1H), 6.31-6.39 (m, 2H), 6.73-6.81 (m, 1H), 7.21-7.30 (m, 1H), 7.36-7.42 (m, 1H), 7.42-7.49 (m, 1H), 7.61 (s, 2H), 7.99 (s, 1H), 8.23 (s, 1H)

MS ES⁺: 435

Example 48

5-Methyl-2-(1H-pyrazol-1-yl)-N-[(1S,2S)-2-{[5-(trifluoromethyl)pyrazin-2-yl]amino}cyclopentyl]benzamide

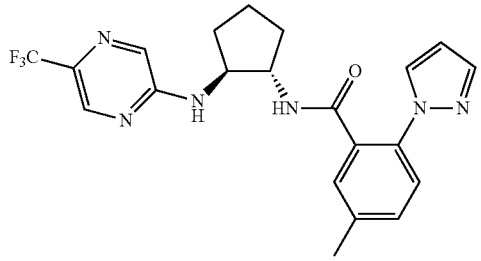 [SMILES: Cc1ccc(-n2cccn2)c(C(=O)N[C@H]2CCC[C@@H]2Nc2cnc(C(F)(F)F)cn2)c1]

Prepared according to the procedure for 2-methoxy-5-methyl-N-[(1S,2S)-2-{[5-(trifluoromethyl)pyrazin-2-yl]amino}cyclopentyl]benzamide (Example 37) from (1S,2S)-1-N-[5-(trifluoromethyl)pyrazin-2-yl]cyclopentane-1,2-diamine hydrochloride (Intermediate 14; 75 mg, 0.27 mmol) and 5-methyl-2-(1H-pyrazol-1-yl)benzoic acid (CAS number 1214622-46-4; 74 mg, 0.37 mmol) except this was purified by column chromatography (silica, 40-100% ethyl acetate/petrol) to afford the title compound.

$^1$H NMR (400 MHz, DCM-d$_2$) δ ppm 1.37-1.51 (m, 1H), 1.53-1.70 (m, 1H), 1.71-1.95 (m, 2H), 2.01-2.13 (m, 1H), 2.26-2.38 (m, 1H), 2.47 (s, 3H), 3.75-3.86 (m, 1H), 4.13-4.25 (m, 1H), 6.36-6.41 (m, 1H), 6.75-6.81 (m, 1H), 7.27-7.34 (m, 1H), 7.37-7.42 (m, 1H), 7.55-7.60 (m, 1H), 7.62-7.68 (m, 2H), 8.16-8.20 (m, 1H), 8.24 (s, 1H)

MS ES$^+$: 431

Example 49

2-Bromo-6-methoxy-N-[(1S,2S)-2-{[5-(trifluoromethyl)pyrazin-2-yl]amino}cyclopentyl]benzamide

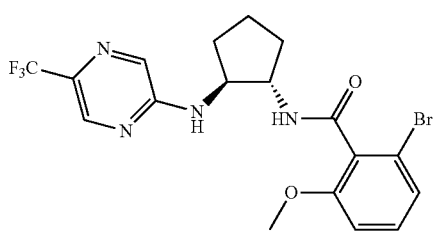 [SMILES: COc1cccc(Br)c1C(=O)N[C@H]1CCC[C@@H]1Nc1cnc(C(F)(F)F)cn1]

Prepared according to the procedure for 2-methoxy-5-methyl-N-[(1S,2S)-2-{[5-(trifluoromethyl)pyrazin-2-yl]amino}cyclopentyl]benzamide (Example 37) from (1S,2S)-1-N-[5-(trifluoromethyl)pyrazin-2-yl]cyclopentane-1,2-diamine hydrochloride (Intermediate 14; 250 mg, 0.88 mmol) and 2-bromo-6-methoxybenzoic acid (CAS number 31786-45-5; 245 mg, 1.06 mmol) except this was purified by column chromatography (silica, 0-100% ethyl acetate/petrol) to afford the title compound.

$^1$H NMR (400 MHz, DCM-d$_2$) δ ppm 1.55-1.74 (m, 2H), 1.80-2.00 (m, 2H), 2.19-2.43 (m, 2H), 3.69 (s, 3H), 4.14-4.27 (m, 1H), 4.30-4.41 (m, 1H), 6.33-6.39 (m, 1H), 6.84-6.91 (m, 1H), 7.11-7.17 (m, 1H), 7.18-7.26 (m, 1H), 8.16 (s, 1H), 8.23-8.27 (m, 1H)

MS ES$^+$: 559

Example 50

2-Methoxy-6-(1H-pyrazol-1-yl)-N-[(1S,2S)-2-{[5-(trifluoromethyl)pyrazin-2-yl]amino}cyclopentyl]benzamide

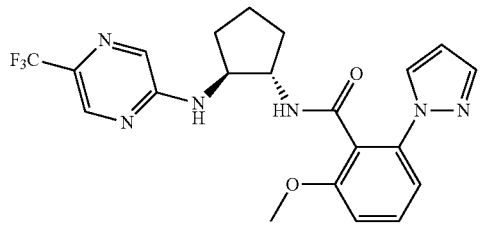 [SMILES: COc1cccc(-n2cccn2)c1C(=O)N[C@H]1CCC[C@@H]1Nc1cnc(C(F)(F)F)cn1]

Prepared according to the procedure for 3-(1H-pyrazol-1-yl)-N-[(1S,2S)-2-{[5-(trifluoromethyl)pyrazin-2-yl]amino}cyclopentyl]pyridine-2-carboxamide (Example 43) from 2-bromo-6-methoxy-N-[(1S,2S)-2-{[5-(trifluoromethyl)pyrazin-2-yl]amino}cyclopentyl]benzamide (Example 49; 100 mg, 0.218 mmol) and 1H-pyrazole (30 mg, 0.435 mmol) to afford the title compound.

$^1$H NMR (400 MHz, DCM-d$_2$) δ ppm 1.34-1.59 (m, 2H), 1.69-1.90 (m, 2H), 2.04-2.18 (m, 1H), 2.24-2.39 (m, 1H), 3.75 (s, 3H), 3.81-3.93 (m, 1H), 4.14-4.28 (m, 1H), 6.12-6.18 (m, 1H), 6.28-6.37 (m, 2H), 6.89-6.99 (m, 1H), 7.06-7.13 (m, 1H), 7.37-7.48 (m, 2H), 7.68-7.73 (m, 1H), 7.89 (s, 1H), 8.21 (s, 1H)

MS ES$^+$: 447

Example 51

3-(Piperidin-1-yl)-N-[(1S,2S)-2-{[5-(trifluoromethyl)pyrazin-2-yl]amino}cyclopentyl]pyridine-2-carboxamide

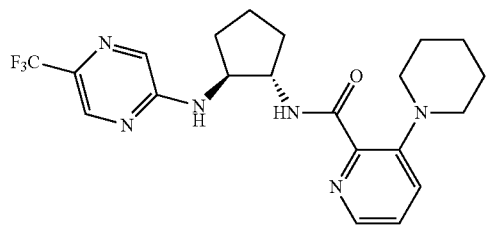 [SMILES: O=C(N[C@H]1CCC[C@@H]1Nc1cnc(C(F)(F)F)cn1)c1ncccc1N1CCCCC1]

A solution of (1S,2S)-1-N-[5-(trifluoromethyl)pyrazin-2-yl]cyclopentane-1,2-diamine hydrochloride (Intermediate 14; 75 mg, 0.27 mmol), 3-(piperidin-1-yl)pyridine-2-carboxylic acid (CAS number 898289-01-5; 66 mg, 0.32 mmol), 3H-[1,2,3]triazolo[4,5-b]pyridin-3-ol (54 mg, 0.40 mmol), EDC (76 mg, 0.40 mmol) and triethylamine (0.111 ml, 0.80 mmol) in DCM (1 ml) was stirred at room temperature overnight. The reaction was partitioned between DCM and a saturated solution of sodium bicarbonate, filtered through a hydrophobic frit and concentrated in vacuo. The resulting residue was purified by column chromatography (silica, 40-100% ethyl acetate/petrol) and then further purified by reverse phase preparative HPLC (eluted with acetonitrile/water containing 0.1% ammonia) to afford the title compound.

$^1$H NMR (400 MHz, DCM-d$_2$) δ ppm 1.46-1.63 (m, 2H), 1.65-1.79 (m, 6H), 1.83-1.96 (m, 2H), 2.17-2.32 (m, 1H), 2.41-2.56 (m, 1H), 2.88-3.05 (m, 4H), 3.91-4.05 (m, 1H), 4.35-4.52 (m, 1H), 6.85 (br. s., 1H), 7.27-7.37 (m, 1H), 7.44-7.54 (m, 1H), 7.94 (s, 1H), 8.17-8.27 (m, 2H), 8.86-8.95 (m, 1H)

MS ES$^+$: 435

Example 52

5-Chloro-2-(2H-1,2,3-triazol-2-yl)-N-[(1S,2S)-2-{[5-(trifluoromethyl)pyrazin-2-yl]amino}cyclopentyl]benzamide

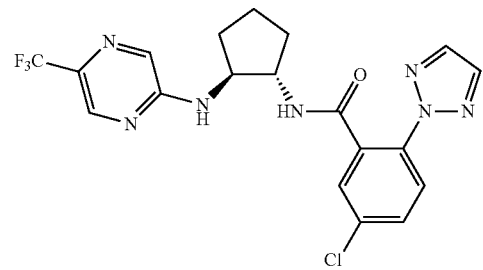 [SMILES: O=C(N[C@H]1CCC[C@@H]1Nc1cnc(C(F)(F)F)cn1)c1cc(Cl)ccc1-n1nccn1]

Prepared according to the procedure for 3-(piperidin-1-yl)-N-[(1S,2S)-2-{[5-(trifluoromethyl)pyrazin-2-yl]amino}cyclopentyl]pyridine-2-carboxamide (Example 51) from (1S,2S)-1-N-[5-(trifluoromethyl)pyrazin-2-yl]cyclopentane-1,2-diamine hydrochloride (Intermediate 14; 500 mg, 1.77 mmol) and 5-chloro-2-(2H-1,2,3-triazol-2-yl)benzoic acid (Intermediate 38a; CAS number 1293284-54-4; 396 mg, 1.77 mmol) except this was purified only by column chromatography (silica, 40-100% ethyl acetate/petrol) to afford the title compound.

$^1$H NMR (400 MHz, DCM-d$_2$) δ ppm 1.41-1.66 (m, 2H), 1.69-1.94 (m, 2H), 2.15-2.28 (m, 1H), 2.28-2.41 (m, 1H), 3.89-4.05 (m, 1H), 4.12-4.27 (m, 1H), 6.43-6.53 (m, 2H), 7.49-7.58 (m, 2H), 7.61-7.67 (m, 2H), 7.73-7.80 (m, 1H), 8.00 (s, 1H), 8.19 (s, 1H)

MS ES$^+$: 452

Example 53

3-Fluoro-2-(2H-1,2,3-triazol-2-yl)-N-[(1S,2S)-2-{[5-(trifluoromethyl)pyrazin-2-yl]amino}cyclopentyl]benzamide

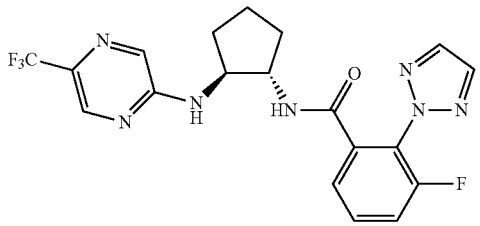 [SMILES: O=C(N[C@H]1CCC[C@@H]1Nc1cnc(C(F)(F)F)cn1)c1cccc(F)c1-n1nccn1]

Prepared according to the procedure for 2-methoxy-5-methyl-N-[(1S,2S)-2-{[5-(trifluoromethyl)pyrazin-2-yl]amino}cyclopentyl]benzamide (Example 37) from (1S,2S)-1-N-[5-(trifluoromethyl)pyrazin-2-yl]cyclopentane-1,2-diamine hydrochloride (Intermediate 14; 126 mg, 0.45 mmol) and 3-fluoro-2-(2H-1,2,3-triazol-2-yl)benzoic acid (CAS number 1293284-51-1; 111 mg, 0.54 mmol) except this was purified by column chromatography (silica, 40-100% ethyl acetate/petrol) to afford the title compound.

$^1$H NMR (400 MHz, DMSO-d$_6$) δ ppm 1.41-1.56 (m, 2H), 1.60-1.73 (m, 2H), 1.88-2.08 (m, 2H), 4.06-4.09 (m, 1H), 4.15-4.24 (m, 1H), 7.72-7.78 (m, 1H), 7.82-7.86 (m, 1H), 7.86-7.92 (m, 1H), 7.94-8.08 (m, 3H), 8.31 (s, 1H), 8.39-8.43 (m, 1H), 8.67-8.75 (m, 1H)

MS ES$^+$: 436

Example 54

2-(1H-1,2,3-Triazol-1-yl)-5-(trifluoromethyl)-N-[(1S,2S)-2-{[5-(trifluoromethyl)pyrazin-2-yl]amino}cyclopentyl]benzamide

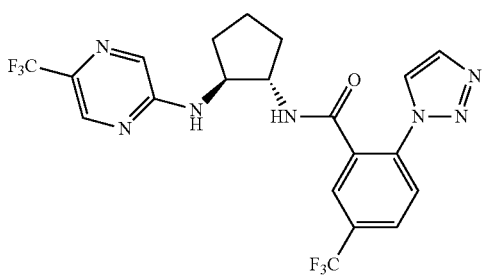 [SMILES: O=C(N[C@H]1CCC[C@@H]1Nc1cnc(C(F)(F)F)cn1)c1cc(C(F)(F)F)ccc1-n1ccnn1]

Prepared according to the procedure for 2-methoxy-5-methyl-N-[(1S,2S)-2-{[5-(trifluoromethyl)pyrazin-2-yl]amino}cyclopentyl]benzamide (Example 37) from (1S,2S)-1-N-[5-(trifluoromethyl)pyrazin-2-yl]cyclopentane-1,2-diamine hydrochloride (Intermediate 14; 126 mg, 0.45 mmol) and 2-(1H-1,2,3-triazol-1-yl)-5-(trifluoromethyl)benzoic acid (Intermediate 37b; 138 mg, 0.54 mmol) except this was purified by column chromatography (silica, 40-100% ethyl acetate/petrol) to afford the title compound.

$^1$H NMR (400 MHz, DMSO-d$_6$) δ ppm 1.36-1.52 (m, 2H), 1.58-1.72 (m, 2H), 1.86-2.09 (m, 2H), 3.93-4.07 (m, 1H), 4.07-4.16 (m, 1H), 7.33-7.39 (m, 1H), 7.53-7.72 (m, 2H), 7.87-8.03 (m, 4H), 8.37 (s, 1H), 8.45-8.53 (m, 1H)

MS ES$^+$: 486

Example 55

5-Chloro-2-(1H-1,2,3-triazol-1-yl)-N-[(1S,2S)-2-{[5-(trifluoromethyl)pyrazin-2-yl]amino}cyclopentyl]benzamide

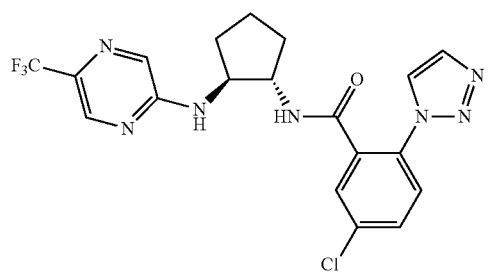

Prepared according to the procedure for 2-methoxy-5-methyl-N-[(1S,2S)-2-{[5-(trifluoromethyl)pyrazin-2-yl]amino}cyclopentyl]benzamide (Example 37) from (1S,2S)-1-N-[5-(trifluoromethyl)pyrazin-2-yl]cyclopentane-1,2-diamine hydrochloride (Intermediate 14; 126 mg, 0.45 mmol) and 5-chloro-2-(1H-1,2,3-triazol-1-yl)benzoic acid (Intermediate 38b; 120 mg, 0.54 mmol) except this was purified by column chromatography (silica, 40-100% ethyl acetate/petrol) to afford the title compound.

$^1$H NMR (400 MHz, DMSO-d$_6$) δ ppm 1.39-1.52 (m, 2H), 1.59-1.72 (m, 2H), 1.86-2.13 (m, 2H), 3.99-4.10 (m, 1H), 4.10-4.22 (m, 1H), 7.54 (d, J=2.40 Hz, 1H), 7.63-7.69 (m, 1H), 7.73 (d, J=2.40 Hz, 1H), 7.79 (d, J=1.01 Hz, 1H), 7.90-8.05 (m, 2H), 8.31 (d, J=1.01 Hz, 1H), 8.35 (s, 1H), 8.61-8.66 (m, 1H).

MS ES$^+$: 452

Example 56

2,3-Difluoro-6-(2H-1,2,3-triazol-2-yl)-N-[(1S,2S)-2-{[5-(trifluoromethyl)pyrazin-2-yl]amino}cyclopentyl]benzamide

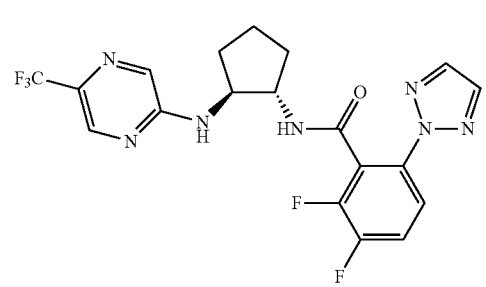 [SMILES: O=C(N[C@H]1CCC[C@@H]1Nc1cnc(C(F)(F)F)cn1)c1c(-n2nccn2)ccc(F)c1F]

Prepared according to the procedure for 2-methoxy-5-methyl-N-[(1S,2S)-2-{[5-(trifluoromethyl)pyrazin-2-yl]amino}cyclopentyl]benzamide (Example 37) from (1S,2S)-1-N-[5-(trifluoromethyl)pyrazin-2-yl]cyclopentane-1,2-diamine hydrochloride (Intermediate 14; 126 mg, 0.45 mmol) and 2,3-difluoro-6-(2H-1,2,3-triazol-2-yl)benzoic acid (Intermediate 39a; 120 mg, 0.535 mmol) except this was purified by column chromatography (silica, 40-100% ethyl acetate/petrol) and then further purified by reverse phase preparative HPLC (eluted with acetonitrile/water containing 0.1% ammonia) to afford the title compound.

$^1$H NMR (400 MHz, DCM-$d_2$) δ ppm 1.50-1.67 (m, 2H), 1.78-1.96 (m, 2H), 2.22-2.40 (m, 2H), 4.03-4.15 (m, 1H), 4.19-4.31 (m, 1H), 6.09-6.37 (m, 1H), 6.61-6.79 (m, 1H), 7.30-7.42 (m, 1H), 7.56 (s, 2H), 7.66-7.73 (m, 1H), 7.96 (s, 1H), 8.13 (s, 1H)

MS ES$^+$: 454

Example 57

5-Cyclopropyl-2-(2H-1,2,3-triazol-2-yl)-N-[(1S,2S)-2-{[5-(trifluoromethyl)pyrazin-2-yl]amino}cyclopentyl]benzamide

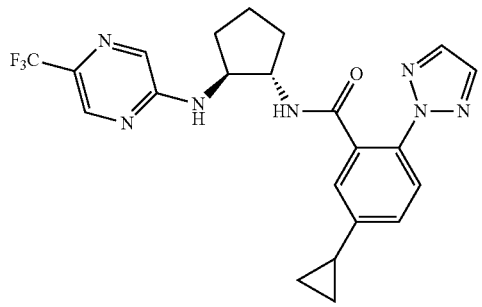 [SMILES: O=C(N[C@H]1CCC[C@@H]1Nc1cnc(C(F)(F)F)cn1)c1cc(C2CC2)ccc1-n1nccn1]

A solution of 5-chloro-2-(2H-1,2,3-triazol-2-yl)-N-[(1S,2S)-2-{[5-(trifluoromethyl)pyrazin-2-yl]amino}cyclopentyl]benzamide (Example 52; 100 mg, 0.22 mmol), cyclopropylboronic acid (CAS number 411235-57-9; 29 mg, 0.33 mmol), bis(triphenylphosphine)palladium(II) dichloride (3 mg, 4.43 µmol) and potassium carbonate (31 mg, 0.22 mmol) in 1,4-dioxane (1.3 ml) and water (0.13 ml) was sealed and degassed with nitrogen. The reaction was subjected to microwave irradiation at 130° C. for 30 minutes. To this was then added bis(di-tert-butyl(4-dimethylaminophenyl)phosphine)-dichloropalladium(II) (157 mg, 0.22 mmol) and the reaction was subjected to microwave irradiation at 130° C. for a further 1 hour. The reaction mixture was partitioned between ethyl acetate and water, washed with water and brine, filtered through a hydrophobic frit and concentrated in vacuo. The resulting residue was purified by reverse phase preparative HPLC (eluted with acetonitrile/water containing 0.1% ammonia) to afford the title compound.

$^1$H NMR (400 MHz, DCM-$d_2$) δ ppm 0.68-0.81 (m, 2H), 0.99-1.10 (m, 2H), 1.38-1.59 (m, 2H), 1.71-1.90 (m, 2H), 1.93-2.02 (m, 1H), 2.09-2.20 (m, 1H), 2.28-2.39 (m, 1H), 3.85-3.95 (m, 1H), 4.15-4.26 (m, 1H), 6.24-6.35 (m, 1H), 6.40-6.58 (m, 1H), 7.21-7.27 (m, 2H), 7.57-7.64 (m, 3H), 7.95 (s, 1H), 8.22 (s, 1H)

MS ES$^+$: 458

Example 58

3-(Trifluoromethoxy)-N-[(1S,2S)-2-{[5-(trifluoromethyl)pyrazin-2-yl]amino}cyclopentyl]pyridine-2-carboxamide

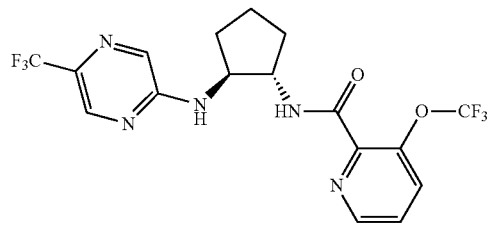 [SMILES: O=C(N[C@H]1CCC[C@@H]1Nc1cnc(C(F)(F)F)cn1)c1ncccc1OC(F)(F)F]

A solution of (1S,2S)-1-N-[5-(trifluoromethyl)pyrazin-2-yl]cyclopentane-1,2-diamine hydrochloride (Intermediate 14; 70 mg, 0.25 mmol), 3-(trifluoromethoxy)pyridine-2-carboxylic acid (CAS number 1221171-81-8; 86 mg, 0.42 mmol), EDC (71 mg, 0.37 mmol), 3H-[1,2,3]triazolo[4,5-b]pyridin-3-ol (51 mg, 0.37 mmol) and triethylamine (0.104 ml, 0.74 mmol) in DCM (1 ml) was stirred at room temperature overnight. The mixture was partitioned between ethyl acetate (25 ml) and water (10 ml). The organics were washed with water (2×10 ml) and brine (10 ml), dried over sodium sulfate and concentrated in vacuo. The resulting residue was purified by reverse phase chromatography (C18 silica, 0-100% water (with 0.05% ammonia)/acetonitrile) to afford the title compound.

$^1$H NMR (400 MHz, DMSO-$d_6$) δ ppm 1.46-1.82 (m, 4H), 2.01-2.19 (m, 2H), 4.15-4.42 (m, 2H), 7.64-7.74 (m, 1H), 7.88-8.13 (m, 3H), 8.29 (s, 1H), 8.55-8.67 (m, 1H), 8.74-8.87 (m, 1H)

MS ES$^+$: 436

Example 59

5-Chloro-2-(1H-pyrazol-1-yl)-N-[(1S,2S)-2-{[5-(trifluoromethyl)pyrazin-2-yl]amino}cyclopentyl]benzamide

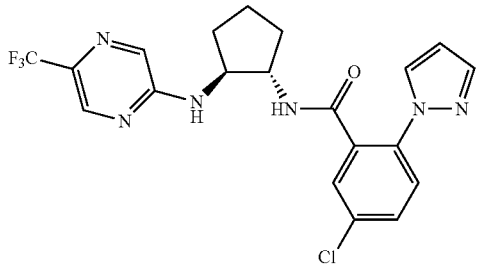

Prepared according to the procedure for 2-methoxy-5-methyl-N-[(1S,2S)-2-{[5-(trifluoromethyl)pyrazin-2-yl]amino}cyclopentyl]benzamide (Example 37) from (1S,2S)-1-N-[5-(trifluoromethyl)pyrazin-2-yl]cyclopentane-1,2-diamine hydrochloride (Intermediate 14; 75 mg, 0.27 mmol) and 5-chloro-2-(1H-pyrazol-1-yl)benzoic acid (CAS number 1214622-57-7; 120 mg, 0.54 mmol) except this was purified by column chromatography (silica, 0-100% ethyl acetate/petrol) to afford the title compound.

$^1$H NMR (400 MHz, DMSO-$d_6$) δ ppm 1.41-1.58 (m, 2H), 1.62-1.74 (m, 2H), 1.92-2.09 (m, 2H), 4.07-4.25 (m, 2H), 6.30-6.36 (m, 1H), 7.36-7.42 (m, 1H), 7.58-7.66 (m, 3H), 7.90-7.94 (m, 1H), 7.96-8.08 (m, 2H), 8.35 (s, 1H) and 8.52-8.60 (m, 1H).

MS ES+: 451

Example 60

3-Ethoxy-N-[(1S,2S)-2-{[5-(trifluoromethyl)pyrazin-2-yl]amino}cyclopentyl]pyridine-2-carboxamide

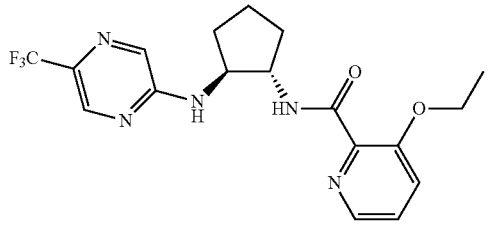 [SMILES: CCOc1cccnc1C(=O)N[C@H]1CCC[C@@H]1Nc1cnc(C(F)(F)F)cn1]

A solution of (1S,2S)-1-N-[5-(trifluoromethyl)pyrazin-2-yl]cyclopentane-1,2-diamine hydrochloride (Intermediate 14; 150 mg, 0.53 mmol), 3-ethoxypyridine-2-carboxylic acid (CAS number 103878-09-7; 106 mg, 0.64 mmol), EDC (153 mg, 0.80 mmol), 3H-[1,2,3]triazolo[4,5-b]pyridin-3-ol (108 mg, 0.80 mmol) and triethylamine (0.222 ml, 1.59 mmol) in DCM (1 ml) was stirred at room temperature over the weekend. The mixture was partitioned between ethyl acetate (50 ml) and water (20 ml). The organics were washed with water (2×20 ml) and brine (20 ml), dried over sodium sulfate and concentrated in vacuo. The resulting residue was purified by column chromatography (basic silica, 30-100% ethyl acetate/petrol) and then by reverse phase chromatography (C18 silica, 0-100% water (with 0.05% ammonia)/acetonitrile) to afford the title compound.

$^1$H NMR (400 MHz, DMSO-d$_6$) δ ppm 1.08-1.29 (m, 3H), 1.41-1.63 (m, 2H), 1.66-1.80 (m, 2H), 2.01-2.16 (m, 2H), 3.94-4.09 (m, 2H), 4.16-4.34 (m, 2H), 7.35-7.44 (m, 1H), 7.46-7.55 (m, 1H), 7.96-8.16 (m, 3H), 8.26-8.46 (m, 2H)

MS ES+: 396

Example 61

3,5-Difluoro-2-(2H-1,2,3-triazol-2-yl)-N-[(1S,2S)-2-{[5-(trifluoromethyl)pyrazin-2-yl]amino}cyclopentyl]benzamide

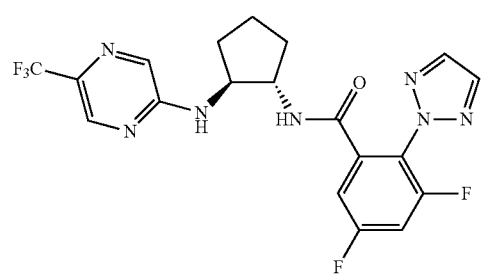 [SMILES: O=C(N[C@H]1CCC[C@@H]1Nc1cnc(C(F)(F)F)cn1)c1cc(F)cc(F)c1-n1nccn1]

Prepared according to the procedure for 3-(piperidin-1-yl)-N-[(1S,2S)-2-{[5-(trifluoromethyl)pyrazin-2-yl]amino}cyclopentyl]pyridine-2-carboxamide (Example 51) from (1S,2S)-1-N-[5-(trifluoromethyl)pyrazin-2-yl]cyclopentane-1,2-diamine hydrochloride (Intermediate 14; 75 mg, 0.27 mmol) and 3,5-difluoro-2-(2H-1,2,3-triazol-2-yl)benzoic acid (Intermediate 40a; 60 mg, 0.27 mmol) except this was purified only by column chromatography (silica, 40-100% ethyl acetate/petrol) to afford the title compound.

$^1$H NMR (400 MHz, DMSO-d$_6$) δ ppm 1.38-1.52 (m, 2H), 1.61-1.73 (m, 2H), 1.87-2.08 (m, 2H), 3.94-4.04 (m, 1H), 4.07-4.18 (m, 1H), 7.23-7.31 (m, 1H), 7.68-7.79 (m, 1H), 7.92 (d, J=7.70 Hz, 1H), 7.97-8.01 (m, 3H), 8.37 (s, 1H) and 8.57 (d, J=7.71 Hz, 1H)

MS ES+: 454

Example 62

2-(Trifluoromethyl)-N-[(1S,2S)-2-{[5-(trifluoromethyl)pyrazin-2-yl]amino}cyclopentyl]benzamide

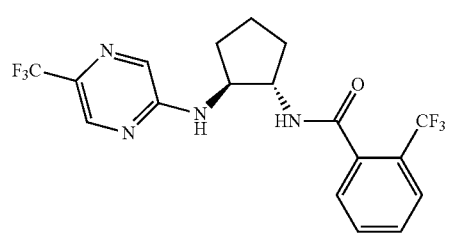 [SMILES: O=C(N[C@H]1CCC[C@@H]1Nc1cnc(C(F)(F)F)cn1)c1ccccc1C(F)(F)F]

To a solution of (1S,2S)-1-N-[5-(trifluoromethyl)pyrazin-2-yl]cyclopentane-1,2-diamine hydrochloride (Intermediate 14; 60 mg, 0.21 mmol) in DMF (3 ml) was added 2-(trifluoromethyl)benzoic acid (CAS number 433-97-6; 60 mg, 0.21 mmol), TBTU (0.082 g, 0.25 mmol) and DIPEA (0.1 g, 0.84 mmol) and the reaction was stirred at room temperature for 2 hours. The reaction was diluted with water (25 ml) and extracted with ethyl acetate (30 ml×3). The organics were washed with water (50 ml), brine (25 ml), dried over sodium sulfate and concentrated in vacuo. The resulting residue was purified by column chromatography (silica, 0-45% ethyl acetate/n-hexane) to afford the title compound.

$^1$H NMR (400 MHz, DMSO-d) δ ppm 1.23-1.62 (m, 2H), 1.69-1.76 (m, 2H), 2.01-2.33 (m, 2H), 4.21-4.24 (m, 2H), 7.39-7.41 (m, 1H), 7.62-75 (m, 3H), 8.03-8.07 (m, 2H), 8.35-8.39 (m, 1H), 8.61-8.63 (m, 1H)

MS ES+: 419

Example 63

3-Cyclopropyl-N-[(1S,2S)-2-{[5-(trifluoromethyl)pyrazin-2-yl]amino}cyclopentyl]pyridine-2-carboxamide

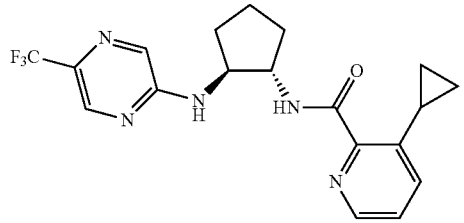 [SMILES: O=C(N[C@H]1CCC[C@@H]1Nc1cnc(C(F)(F)F)cn1)c1ncccc1C1CC1]

Prepared according to the procedure for 2-(trifluoromethyl)-N-[(1S,2S)-2-{[5-(trifluoromethyl)pyrazin-2-yl]amino}cyclopentyl]benzamide (Example 62) from (1S,2S)-1-N-[5-(trifluoromethyl)pyrazin-2-yl]cyclopentane-1,2- diamine hydrochloride (Intermediate 14; 75 mg, 0.30 mmol) and 3-cyclopropylpyridine-2-carboxylic acid (Intermediate 16; 50 mg, 0.31 mmol) to afford the title compound.

$^{1}$H NMR (400 MHz, DMSO-d) δ ppm 0.62-0.67 (m, 2H), 0.80-0.89 (m, 2H), 1.53-1.77 (m, 4H), 2.06-2.10 (m, 2H), 2.51-2.52 (m, 1H), 4.23-4.36 (m, 2H), 7.33-7.38 (m, 2H), 8.02-8.09 (m, 2H), 8.32-8.34 (m, 2H), 8.68-8.70 (m, 1H)

MS ES$^{+}$: 392

Example 64

3,6-Difluoro-2-(2H-1,2,3-triazol-2-yl)-N-[(1S,2S)-2-{[5-(trifluoromethyl)pyrazin-2-yl]amino}cyclopentyl]benzamide

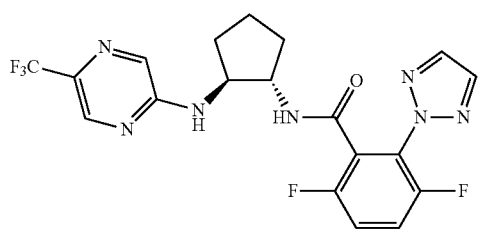 [SMILES: O=C(N[C@H]1CCC[C@@H]1Nc1cnc(C(F)(F)F)cn1)c1c(F)ccc(F)c1-n1nccn1]

Prepared according to the procedure for 2-(trifluoromethyl)-N-[(1S,2S)-2-{[5-(trifluoromethyl)pyrazin-2-yl]amino}cyclopentyl]benzamide (Example 62) from (1S,2S)-1-N-[5-(trifluoromethyl)pyrazin-2-yl]cyclopentane-1,2-diamine hydrochloride (Intermediate 14; 60 mg, 0.21 mmol) and 3,6-difluoro-2-(2H-1,2,3-triazol-2-yl)benzoic acid (Intermediate 17; 50 mg, 0.21 mmol) except this was purified by reverse phase preparative HPLC (eluted with acetonitrile/water containing 0.1% ammonia) to afford the title compound.

$^{1}$H NMR (400 MHz, DMSO-d) δ ppm 1.43-1.44 (m, 2H), 1.61-1.68 (m, 2H), 1.87-2.00 (m, 2H), 4.00-4.07 (m, 2H), 7.56-7.69 (m, 2H), 7.92-7.94 (m, 1H), 8.00-8.02 (m, 3H), 8.37 (s, 1H), 8.76-8.78 (m, 1H)

MS ES$^{+}$: 454

Example 65

2-(Difluoromethyl)-N-[(1S,2S)-2-{[5-(trifluoromethyl)pyrazin-2-yl]amino}cyclopentyl]benzamide

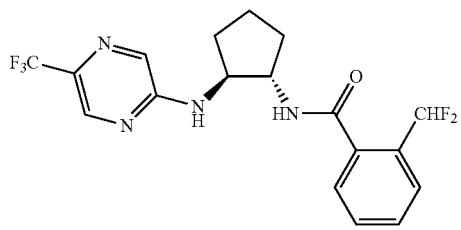 [SMILES: O=C(N[C@H]1CCC[C@@H]1Nc1cnc(C(F)(F)F)cn1)c1ccccc1C(F)F]

To a solution of (1S,2S)-1-N-[5-(trifluoromethyl)pyrazin-2-yl]cyclopentane-1,2-diamine hydrochloride (Intermediate 14; 100 mg, 0.35 mmol), 2-(difluoromethyl)benzoic acid (CAS number 799814-32-7; 61 mg, 0.35 mmol) and triethylamine (0.148 ml, 1.06 mmol) in DCM (2 ml) was added 1,3,5,2,4,6-trioxatriphosphorinane, 2,4,6-tripropyl-, 2,4,6-trioxide (CAS number 68957-94-8; 50% in ethyl acetate, 0.417 ml, 0.71 mmol). The reaction mixture was stirred at room temperature for 3 hours. To this was then added further 1,3,5,2,4,6-trioxatriphosphorinane, 2,4,6-tripropyl-, 2,4,6-trioxide (CAS number 68957-94-8; 50% in ethyl acetate, 0.417 ml, 0.71 mmol) and stirred at room temperature overnight. The reaction was partitioned between DCM and a saturated solution of sodium bicarbonate, filtered through a hydrophobic frit and concentrated in vacuo. The resulting residue was purified by column chromatography (silica, 0-100% ethyl acetate/petrol) and then triturated with diethyl ether to afford the title compound.

$^{1}$H NMR (400 MHz, DCM-d$_{2}$) δ ppm 1.62-1.74 (m, 2H), 1.84-2.01 (m, 2H), 2.30-2.50 (m, 2H), 4.12-4.28 (m, 1H), 4.28-4.40 (m, 1H), 6.06 (br. s., 1H), 6.64-6.86 (m, 1H), 7.09-7.39 (m, 1H), 7.46-7.51 (m, 1H), 7.52-7.58 (m, 1H), 7.58-7.65 (m, 1H), 7.71-7.80 (m, 1H), 8.03 (s, 1H), 8.25 (s, 1H)

MS ES$^{+}$: 401

Example 66

2-Cyclopropyl-6-fluoro-N-[(1S,2S)-2-{[5-(trifluoromethyl)pyrazin-2-yl]amino}cyclopentyl]benzamide

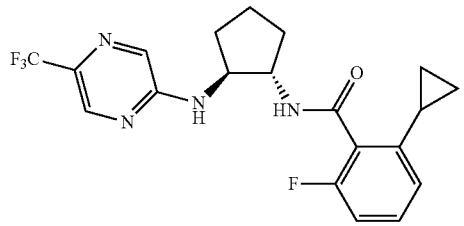 [SMILES: O=C(N[C@H]1CCC[C@@H]1Nc1cnc(C(F)(F)F)cn1)c1c(F)cccc1C1CC1]

Prepared according to the procedure for 2-(difluoromethyl)-N-[(1S,2S)-2-{[5-(trifluoromethyl)pyrazin-2-yl]amino}cyclopentyl]benzamide (Example 65) from (1S,2S)-1-N-[5-(trifluoromethyl)pyrazin-2-yl]cyclopentane-1,2-diamine hydrochloride (Intermediate 14; 100 mg, 0.35 mmol) and 2-cyclopropyl-6-fluorobenzoic acid (CAS number 1603213-26-8; 64 mg, 0.35 mmol) except to this was added EDC (68 mg, 0.354 mmol), 3H-[1,2,3]triazolo[4,5-b]pyridin-3-ol (48 mg, 0.35 mmol) and triethylamine (0.1 ml, 0.71 mmol) and the reaction was stirred at room temperature for a further 1 hour. The reaction mixture was partitioned between DCM and water, filtered through a hydrophobic frit and concentrated in vacuo. The resulting residue was purified by reverse phase preparative HPLC (eluted with acetonitrile/water containing 0.1% formic acid) and then triturated with heptane/diethyl ether to afford the title compound.

$^{1}$H NMR (400 MHz, DCM-d$_{2}$) δ ppm 0.55-0.69 (m, 2H), 0.70-0.80 (m, 1H), 0.81-0.91 (m, 1H), 1.58-1.69 (m, 2H), 1.83-1.94 (m, 3H), 2.24-2.43 (m, 2H), 4.06-4.23 (m, 1H), 4.33-4.50 (m, 1H), 6.10 (br. s., 1H), 6.38-6.40 (m, 1H), 6.64-6.69 (m, 1H), 6.82-6.91 (m, 1H), 7.23-7.27 (m, 1H), 7.97 (s, 1H), 8.20 (s, 1H)

MS ES$^{+}$: 409

Example 67

5-Methyl-2-(2H-1,2,3-triazol-2-yl)-N-[(1S,2S)-2-{[6-(trifluoromethyl)pyridin-3-yl]amino}cyclopentyl]benzamide

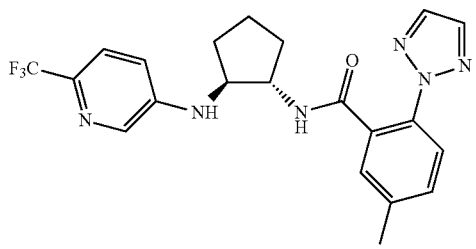 [SMILES: Cc1ccc(-n2nccn2)c(C(=O)N[C@H]2CCC[C@@H]2Nc2ccc(C(F)(F)F)nc2)c1]

N-[(1S,2S)-2-aminocyclopentyl]-5-methyl-2-(2H-1,2,3-triazol-2-yl)benzamide hydrochloride (Intermediate 7; 70 mg, 0.21 mmol), 5-bromo-2-(trifluoromethyl)pyridine (CAS number 436799-32-5; 73 mg, 0.32 mmol) and cesium carbonate (280 mg, 0.87 mmol) were suspended in toluene (3 ml). The reaction was degassed using nitrogen for 15 minutes. To this was then added BINAP (13 mg, 0.021 mmol) and tris(dibenzylideneacetone)dipalladium (0) (19 mg, 0.021 mmol) and the resulting reaction was heated to 100° C. overnight. The reaction mass was poured into water (20 ml) and the organics were extracted with ethyl acetate (3×20 ml). The combined organics were dried over sodium sulfate and concentrated in vacuo. This was then purified by reverse phase preparative HPLC (eluted with acetonitrile/water containing 0.1% ammonia) to afford the title compound.

$^1$H NMR (400 MHz, DMSO-d) δ ppm 1.48-1.54 (m, 2H), 1.69-1.75 (m, 2H), 1.88-2.03 (m, 2H), 2.38 (s, 3H), 3.73-3.77 (m, 1H), 3.98-4.04 (m, 1H), 6.64-6.66 (m, 1H), 7.21-7.24 (m, 2H), 7.40-7.43 (m, 1H), 7.49-7.51 (m, 1H), 7.66-7.68 (m, 1H), 8.00 (s, 2H), 8.16 (s, 1H), 8.41-8.43 (m, 1H)

MS ES$^+$: 431

Example 68

N-Cyclobutyl-2,6-dimethoxy-N-[(1S,2S)-2-{[5-(trifluoromethyl)pyridin-2-yl]amino}cyclopentyl]benzamide

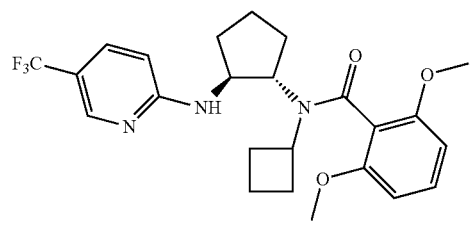 [SMILES: COc1cccc(OC)c1C(=O)N(C1CCC1)[C@H]1CCC[C@@H]1Nc1ccc(C(F)(F)F)cn1]

To a solution of N-[(1S,2S)-2-aminocyclopentyl]-N-cyclobutyl-2,6-dimethoxybenzamide hydrochloride (Intermediate 18; 200 mg, 0.56 mmol) in dry DMSO (1.9 ml) was added 2-chloro-5-(trifluoromethyl)pyridine (CAS number 52334-81-3; 153 mg, 0.85 mmol) and DIPEA (295 µl, 1.69 mmol). The reaction subjected to microwave irradiation at 150° C. for 2 hours and then was partitioned between ethyl acetate and water. The organics were washed with water and brine, dried over magnesium sulfate and concentrated in vacuo. This was then purified using column chromatography (silica, 0-100% ethyl acetate/petrol) and then further purified by reverse phase preparative HPLC (eluted with acetonitrile/water containing 0.1% ammonia) to afford the title compound.

$^1$H NMR (400 MHz, DMSO-d$_6$) δ ppm 1.19-1.36 (m, 1H), 1.39-1.95 (m, 7H), 1.96-2.20 (m, 3H), 2.88-3.10 (m, 1H), 3.42-3.54 (m, 3H), 3.59-3.74 (m, 3H), 3.76-3.99 (m, 2H), 4.35-5.12 (m, 1H), 6.41-6.79 (m, 3H), 7.21-7.29 (m, 1H), 7.30-7.38 (m, 1H), 7.54-7.65 (m, 1H) and 8.12-8.29 (m, 1H)

MS ES$^+$: 464

Example 69

2-Chloro-N-[(1S,2S)-2-{[5-(trifluoromethyl)pyridin-2-yl]amino}cyclopentyl]benzamide

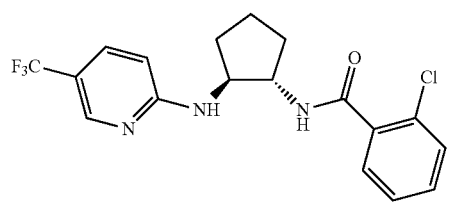 [SMILES: O=C(N[C@H]1CCC[C@@H]1Nc1ccc(C(F)(F)F)cn1)c1ccccc1Cl]

A solution of N-[(1S,2S)-2-aminocyclopentyl]-2-chlorobenzamide hydrochloride (Intermediate 19; 100 mg, 0.36 mmol), 2-chloro-5-(trifluoromethyl)pyridine (CAS number 52334-81-3; 79 mg, 0.44 mmol) and DIPEA (190 µl, 1.09 mmol) in dry DMSO (1.2 ml) was sealed and heated at 150° C. for 17 hours. The reaction mixture was filtered through cotton wool and purified by reverse phase preparative HPLC (eluted with acetonitrile/water containing 0.1% ammonia) to afford the title compound.

$^1$H NMR (400 MHz, DMSO-d$_6$) δ ppm 1.43-1.64 (m, 2H), 1.65-1.78 (m, 2H), 1.99-2.13 (m, 2H), 4.12-4.32 (m, 2H), 6.60-6.69 (m, 1H), 7.25-7.48 (m, 5H), 7.58-7.65 (m, 1H), 8.25 (s, 1H) and 8.44-8.54 (m, 1H).

MS ES$^+$: 384

Example 70

2-Chloro-N-[(1S,2S)-2-{[5-(trifluoromethyl)pyrimidin-2-yl]amino}cyclopentyl]benzamide

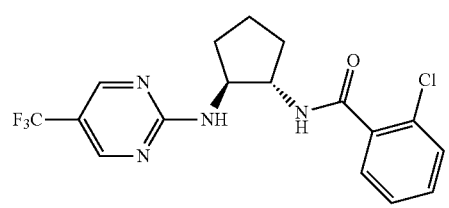 [SMILES: O=C(N[C@H]1CCC[C@@H]1Nc1ncc(C(F)(F)F)cn1)c1ccccc1Cl]

Prepared according to the procedure for 2-chloro-N-[(1S,2S)-2-{[5-(trifluoromethyl)pyridin-2-yl]amino}cyclopentyl]benzamide (Example 69) from N-[(1S,2S)-2-aminocyclopentyl]-2-chlorobenzamide hydrochloride (Intermediate 19; 100 mg, 0.363 mmol) and 2-chloro-5-(trifluoromethyl)pyrimidine (CAS number 69034-12-4; 80 mg, 0.436 mmol) to afford the title compound.

¹H NMR (400 MHz, DMSO-d₆) δ ppm 1.51-1.64 (m, 2H), 1.65-1.76 (m, 2H), 1.96-2.10 (m, 2H), 4.24-4.40 (m, 2H), 7.27-7.46 (m, 4H), 8.09-8.16 (m, 1H), 8.44-8.50 (m, 1H) and 8.58 (s, 2H)

MS ES⁺: 385

Example 71

2-Fluoro-6-methoxy-N-[(1S,2S)-2-{[5-(trifluoromethyl)pyridin-2-yl]amino}cyclopentyl]benzamide

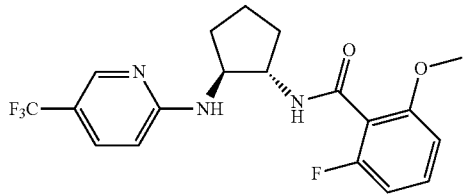 [SMILES: COc1cccc(F)c1C(=O)N[C@H]1CCC[C@@H]1Nc1ccc(C(F)(F)F)cn1]

Prepared according to the procedure for 2-chloro-N-[(1S,2S)-2-{[5-(trifluoromethyl)pyridin-2-yl]amino}cyclopentyl]benzamide (Example 69) from N-[(1S,2S)-2-aminocyclopentyl]-2-fluoro-6-methoxybenzamide hydrochloride (Intermediate 20; 50 mg, 0.17 mmol) and 2-chloro-5-(trifluoromethyl)pyridine (CAS number 52334-81-3; 38 mg, 0.21 mmol) to afford the title compound.

¹H NMR (400 MHz, DMSO-d₆) δ ppm 1.42-1.59 (m, 2H), 1.65-1.75 (m, 2H), 1.99-2.11 (m, 2H), 3.68 (s, 3H), 4.10-4.21 (m, 2H), 6.63-6.69 (m, 1H), 6.74-6.82 (m, 1H), 6.83-6.89 (m, 1H), 7.30-7.39 (m, 2H), 7.58-7.65 (m, 1H), 8.24 (s, 1H) and 8.40-8.47 (m, 1H)

MS ES⁺: 398

Example 72

2,6-Difluoro-N-[(1S,2S)-2-{[5-(trifluoromethyl)pyridin-2-yl]amino}cyclopentyl]benzamide

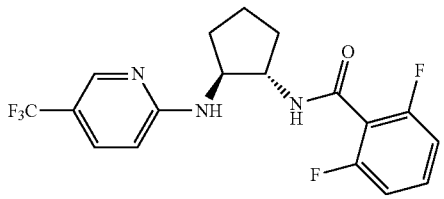 [SMILES: O=C(N[C@H]1CCC[C@@H]1Nc1ccc(C(F)(F)F)cn1)c1c(F)cccc1F]

Prepared according to the procedure for 2-chloro-N-[(1S,2S)-2-{[5-(trifluoromethyl)pyridin-2-yl]amino}cyclopentyl]benzamide (Example 69) from N-[(1S,2S)-2-amino cyclopentyl]-2,6-difluorobenzamide hydrochloride (Intermediate 21; 100 mg, 0.36 mmol) and 2-chloro-5-(trifluoromethyl)pyridine (CAS number 52334-81-3; 79 mg, 0.43 mmol) to afford the title compound.

¹H NMR (400 MHz, DMSO-d₆) δ ppm 1.42-1.58 (m, 2H), 1.65-1.76 (m, 2H), 2.01-2.13 (m, 2H), 4.12-4.25 (m, 2H), 6.61-6.67 (m, 1H), 7.07-7.15 (m, 2H), 7.38-7.43 (m, 1H), 7.44-7.52 (m, 1H), 7.59-7.64 (m, 1H), 8.25 (s, 1H) and 8.77-8.84 (m, 1H)

MS ES⁺: 386

Example 73

N-[(1S,2S)-2-{Methyl[5-(trifluoromethyl)pyrazin-2-yl]amino}cyclopentyl]-2-(2H-1,2,3-triazol-2-yl)benzamide

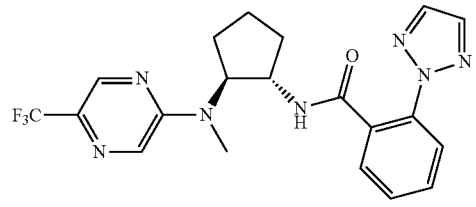 [SMILES: CN(c1cnc(C(F)(F)F)cn1)[C@H]1CCC[C@@H]1NC(=O)c1ccccc1-n1nccn1]

A solution of (1S,2S)-1-N-methyl-1-N-[5-(trifluoromethyl)pyrazin-2-yl]cyclopentane-1,2-diamine (Intermediate 22; 59 mg, 0.23 mmol), 2-(2H-1,2,3-triazol-2-yl)benzoic acid (CAS number 1001401-62-2; 51.5 mg, 0.27 mmol), EDC (65.2 mg, 0.34 mmol), 3H-[1,2,3]triazolo[4,5-b]pyridin-3-ol (52.4 mg, 0.34 mmol) and triethylamine (0.095 ml, 0.68 mmol) in DCM (2 ml) was stirred at room temperature for 18 hours. The reaction mixture was diluted with DCM (3 ml) and washed with HCl (aq, 1M, 2 ml) then a saturated solution of sodium bicarbonate (2 ml). The organics were filtered through a hydrophobic frit and concentrated in vacuo. The resulting residue was purified by reverse phase preparative HPLC (eluted with acetonitrile/water containing 0.1% ammonia) to afford the title compound.

¹H NMR (400 MHz, DMSO-d₆) δ ppm 1.47-1.61 (m, 1H), 1.66-1.78 (m, 3H), 1.83-2.03 (m, 2H), 3.03 (s, 3H), 4.32-4.48 (m, 1H), 4.69-4.86 (m, 1H), 7.15-7.24 (m, 1H), 7.39-7.48 (m, 1H), 7.53-7.61 (m, 1H), 7.65-7.76 (m, 1H), 7.90 (s, 2H), 8.29-8.39 (m, 2H), 8.41-8.49 (m, 1H)

MS ES⁺: 432

Example 74

5-Fluoro-N-[(1S,2S)-2-{methyl[5-(trifluoromethyl)pyrazin-2-yl]amino}cyclopentyl]-2-(2H-1,2,3-triazol-2-yl)benzamide

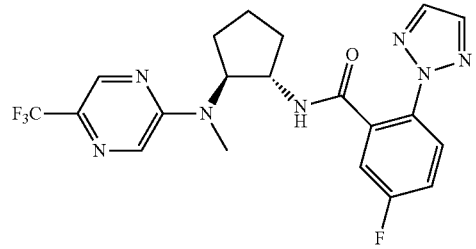 [SMILES: CN(c1cnc(C(F)(F)F)cn1)[C@H]1CCC[C@@H]1NC(=O)c1cc(F)ccc1-n1nccn1]

Prepared according to the procedure for N-[(1S,2S)-2-{methyl[5-(trifluoromethyl)pyrazin-2-yl]amino}cyclopentyl]-2-(2H-1,2,3-triazol-2-yl)benzamide (Example 73) from (1S,2S)-1-N-methyl-1-N-[5-(trifluoromethyl)pyrazin-2-yl]cyclopentane-1,2-diamine (Intermediate 22; 59 mg, 0.23 mmol) and 5-fluoro-2-(2H-1,2,3-triazol-2-yl)benzoic acid (Intermediate 8; 56 mg, 0.27 mmol) to afford the title compound.

¹H NMR (400 MHz, DMSO-d₆) δ ppm 1.48-1.61 (m, 1H), 1.64-1.78 (m, 3H), 1.81-2.03 (m, 2H), 3.31 (s, 3H), 4.29-4.45 (m, 1H), 4.70-4.88 (m, 1H), 6.95-7.03 (m, 1H), 7.37-7.48 (m, 1H), 7.70-7.80 (m, 1H), 7.90 (s, 2H), 8.28-8.34 (m, 1H), 8.41-8.50 (m, 2H)
MS ES⁺: 450

Example 75

2-Fluoro-N-[(1S,2S)-2-{methyl[5-(trifluoromethyl) pyrazin-2-yl]amino}cyclopentyl]-6-(2H-1,2,3-triazol-2-yl)benzamide

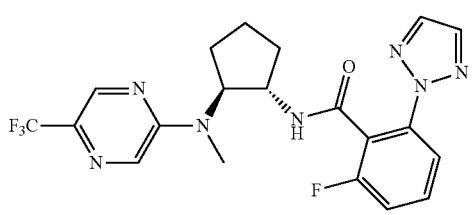 [SMILES: CN(c1cnc(C(F)(F)F)cn1)[C@H]1CCC[C@@H]1NC(=O)c1c(F)cccc1-n1nccn1]

Prepared according to the procedure for N-[(1S,2S)-2-{methyl[5-(trifluoromethyl)pyrazin-2-yl] amino}cyclopentyl]-2-(2H-1,2,3-triazol-2-yl)benzamide (Example 73) from (1S,2S)-1-N-methyl-1-N-[5-(trifluoromethyl)pyrazin-2-yl]cyclopentane-1,2-diamine (Intermediate 22; 59 mg, 0.23 mmol) and 2-fluoro-6-(2H-1,2,3-triazol-2-yl)benzoic acid (CAS number 1186050-58-7; 56 mg, 0.27 mmol) to afford the title compound.

¹H NMR (400 MHz, DMSO-d₆) δ ppm 1.43-1.57 (m, 1H), 1.63-1.81 (m, 3H), 1.85-1.94 (m, 1H), 1.96-2.07 (m, 1H), 3.07 (s, 3H), 4.39-4.52 (m, 1H), 4.66-4.83 (m, 1H), 7.25-7.36 (m, 1H), 7.53-7.64 (m, 1H), 7.66-7.72 (m, 1H), 7.95 (s, 2H), 8.33 (s, 1H), 8.43 (s, 1H), 8.56-8.59 (m, 1H)
MS ES⁺: 450

Example 76

N-[(1S,2S)-2-{[3-Methyl-5-(trifluoromethyl) pyrazin-2-yl]amino}cyclopentyl]-3-(2H-1,2,3-triazol-2-yl)pyridine-2-carboxamide

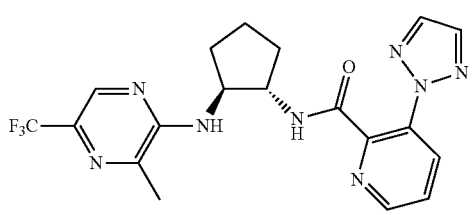 [SMILES: Cc1nc(C(F)(F)F)cnc1N[C@H]1CCC[C@@H]1NC(=O)c1ncccc1-n1nccn1]

A solution of (1S,2S)-1-N-methyl-1-N-[5-(trifluoromethyl)pyrazin-2-yl]cyclopentane-1,2-diamine hydrochloride (Intermediate 23; 60 mg, 0.20 mmol), 3-(2H-1,2,3-triazol-2-yl)pyridine-2-carboxylic acid (CAS number 1252907-86-0; 40 mg, 0.21 mmol), EDC (58 mg, 0.30 mmol), 3H-[1,2,3]triazolo[4,5-b]pyridin-3-ol (41 mg, 0.30 mmol) and triethylamine (0.085 ml, 0.61 mmol) in DCM (1 ml) was stirred at room temperature over the weekend. The reaction was concentrated in vacuo and was then purified by column chromatography (basic silica, 20 to 100% ethyl acetate/petrol) followed by column chromatography (silica, 0 to 100% ethyl acetate/petrol) to afford the title compound.

¹H NMR (400 MHz, DMSO-d6) δ ppm 1.39-1.84 (m, 4H), 1.95-2.24 (m, 2H), 2.31 (s, 3H), 4.17-4.44 (m, 2H), 7.14-7.23 (m, 1H), 7.66-7.75 (m, 1H), 7.88 (s, 2H), 8.17-8.33 (m, 2H), 8.62-8.70 (m, 1H), 8.71-8.81 (m, 1H)
MS ES⁺: 433

Example 77

N-[(1S,2S)-2-Methyl-2-{[5-(trifluoromethyl) pyrazin-2-yl]amino}cyclopentyl]-3-(2H-1,2,3-triazol-2-yl)pyridine-2-carboxamide

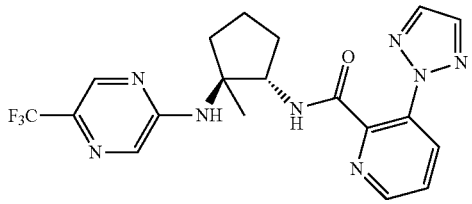 [SMILES: C[C@]1(Nc2cnc(C(F)(F)F)cn2)CCC[C@@H]1NC(=O)c1ncccc1-n1nccn1]

A solution of (1S,2S)-1-methyl-1-N-[5-(trifluoromethyl) pyrazin-2-yl]cyclopentane-1,2-diamine (Intermediate 25; 80 mg, 0.31 mmol), 3-(2H-1,2,3-triazol-2-yl)pyridine-2-carboxylic acid (CAS number 1252907-86-0; 70 mg, 0.37 mmol), EDC (177 mg, 0.92 mmol), 3H-[1,2,3]triazolo[4,5-b]pyridin-3-ol (126 mg, 0.922 mmol) and DIPEA (161 µl, 0.92 mmol) in dry DCM (1 ml) was stirred at room temperature overnight. The mixture was partitioned between ethyl acetate (20 ml) and water (10 ml). The organics were washed with water (2×10 ml), brine (10 ml), dried over sodium sulfate and concentrated in vacuo. The residue was purified by column chromatography (silica, 0 to 100% ethyl acetate/petrol) followed by a trituration in pentane/diethyl ether to afford the title compound. ¹H NMR (400 MHz, DCM-d₂) δ ppm 1.43 (s, 3H), 1.66-1.99 (m, 4H), 2.14-2.30 (m, 1H), 2.49-2.68 (m, 1H), 4.40-4.55 (m, 1H), 7.38-7.48 (m, 1H), 7.56 (br. s., 1H), 7.62-7.67 (m, 1H), 7.69 (br. s., 1H), 7.84 (s, 2H), 8.08-8.14 (m, 1H), 8.23 (br. s., 1H), 8.65-8.70 (m, 1H)
MS ES⁺: 433

Example 78

N-[(1S,2S)-2-{[3-Methyl-5-(trifluoromethyl) pyrazin-2-yl]amino}cyclopentyl]-2-(2H-1,2,3-triazol-2-yl)benzamide

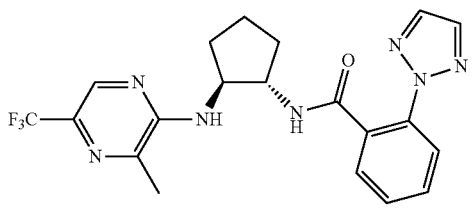

Prepared according to the procedure for N-[(1S,2S)-2-{[3-methyl-5-(trifluoromethyl)pyrazin-2-yl] amino}cyclopentyl]-3-(2H-1,2,3-triazol-2-yl)pyridine-2-carboxamide (Example 76) from (1S,2S)-1-N-methyl-1-N-[5-(trifluoromethyl)pyrazin-2-yl]cyclopentane-1,2-diamine hydrochloride (Intermediate 23; 60 mg, 0.20 mmol) and 2-(2H-1,2,3-triazol-2-yl)benzoic acid (CAS number 1001401-62-2; 40 mg, 0.21 mmol) except this was purified only by column chromatography (silica, 0 to 100% ethyl acetate/petrol) to afford the title compound.

¹H NMR (400 MHz, CHLOROFORM-d) δ ppm 1.36-1.61 (m, 2H), 1.79-1.93 (m, 2H), 2.04-2.20 (m, 1H), 2.38 (s, 3H), 2.49-2.60 (m, 1H), 3.76-3.88 (m, 1H), 4.36-4.48 (m, 1H), 6.04-6.17 (m, 1H), 6.66-6.70 (m, 1H), 7.43-7.52 (m, 3H), 7.53-7.64 (m, 2H), 7.77-7.82 (m, 1H), 8.20 (s, 1H)

MS ES⁺: 432

Example 79

N-[(1S,2S)-2-{[3-Methyl-5-(trifluoromethyl) pyrazin-2-yl]amino}cyclopentyl]-2-(pyrimidin-2-yl) benzamide

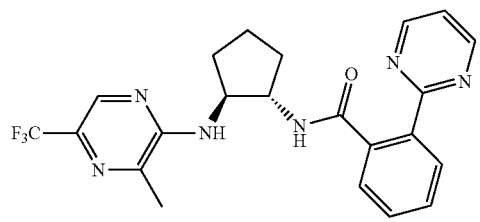 [SMILES: Cc1nc(C(F)(F)F)cnc1N[C@H]1CCC[C@@H]1NC(=O)c1ccccc1-c1ncccn1]

Prepared according to the procedure for N-[(1S,2S)-2-{[3-methyl-5-(trifluoromethyl)pyrazin-2-yl]amino} cyclopentyl]-3-(2H-1,2,3-triazol-2-yl)pyridine-2-carboxamide (Example 76) from (1S,2S)-1-N-methyl-1-N-[5-(trifluoromethyl)pyrazin-2-yl]cyclopentane-1,2-diamine hydrochloride (Intermediate 23; 60 mg, 0.20 mmol) and 2-(pyrimidin-2-yl) benzoic acid (CAS number 400892-62-8; 41 mg, 0.20 mmol) except this was purified only by column chromatography (silica, 0 to 100% ethyl acetate/petrol) to afford the title compound.

¹H NMR (400 MHz, DMSO-d6) δ ppm 1.34-1.77 (m, 4H), 1.93-2.06 (m, 1H), 2.09-2.27 (m, 4H), 4.08-4.22 (m, 1H), 4.25-4.39 (m, 1H), 7.18-7.26 (m, 1H), 7.29-7.42 (m, 2H), 7.44-7.59 (m, 2H), 7.89-7.99 (m, 1H), 8.28 (s, 1H), 8.39-8.48 (m, 1H), 8.57-8.63 (m, 2H)

MS ES⁺: 443

Example 80

5-Fluoro-N-[(1S,2S)-2-{[3-methyl-5-(trifluoromethyl)pyrazin-2-yl]amino}cyclopentyl]-2-(pyrimidin-2-yl)benzamide

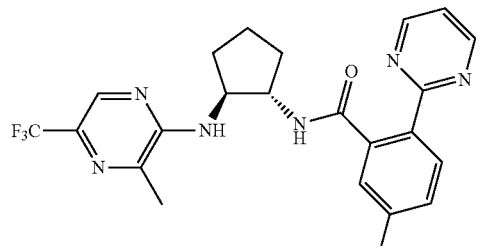

Prepared according to the procedure for N-[(1S,2S)-2-{ [3-methyl-5-(trifluoromethyl)pyrazin-2-yl]amino} cyclopentyl]-3-(2H-1,2,3-triazol-2-yl)pyridine-2-carboxamide (Example 76) from (1S,2S)-1-N-methyl-1-N-[5-(trifluoromethyl)pyrazin-2-yl]cyclopentane-1,2-diamine hydrochloride (Intermediate 23; 60 mg, 0.20 mmol) and 5-fluoro-2-(pyrimidin-2-yl)benzoic acid (CAS number 1293284-57-7; 41 mg, 0.20 mmol) except this was purified only by column chromatography (silica, 0 to 100% ethyl acetate/petrol) to afford the title compound.

¹H NMR (400 MHz, DMSO-d6) δ ppm 1.39-1.82 (m, 4H), 1.94-2.07 (m, 1H), 2.09-2.21 (m, 1H), 2.27 (s, 3H), 4.10-4.39 (m, 2H), 7.10-7.20 (m, 1H), 7.21-7.32 (m, 2H), 7.34-7.43 (m, 1H), 7.96-8.05 (m, 1H), 8.27 (s, 1H), 8.45-8.52 (m, 1H), 8.60-8.67 (m, 2H)

MS ES⁺: 461

Example 81

N-[(1S,2S)-2-Methyl-2-{[5-(trifluoromethyl) pyrazin-2-yl]amino}cyclopentyl]-2-(2H-1,2,3-triazol-2-yl)benzamide

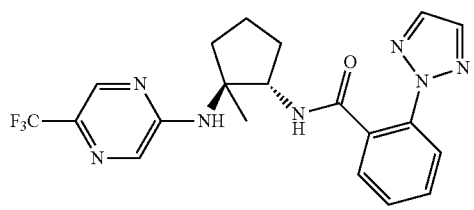 [SMILES: C[C@]1(Nc2cnc(C(F)(F)F)cn2)CCC[C@@H]1NC(=O)c1ccccc1-n1nccn1]

Prepared according to the procedure for N-[(1S,2S)-2-methyl-2-{[5-(trifluoromethyl)pyrazin-2-yl] amino}cyclopentyl]-3-(2H-1,2,3-triazol-2-yl)pyridine-2-carboxamide (Example 77) from (1S,2S)-1-methyl-1-N-[5-(trifluoromethyl)pyrazin-2-yl]cyclopentane-1,2-diamine (Intermediate 25; 510 mg, 1.96 mmol) and 2-(2H-1,2,3-triazol-2-yl)benzoic acid (CAS number 1001401-62-2; 445 mg, 2.35 mmol) except this was then partitioned between water (20 ml) and DCM (10 ml). The organics were washed with water (2×20 ml) and brine (20 ml), filtered through a hydrophobic frit and concentrated in vacuo. The residue was purified by column chromatography (silica, 0-100% ethyl acetate/petrol) followed by a trituration with diethyl ether and recrystallised from IPA/water to afford the title compound.

¹H NMR (400 MHz, DCM-d₂) δ ppm 1.38 (s, 3H), 1.42-1.53 (m, 1H), 1.71-2.00 (m, 3H), 2.02-2.13 (m, 1H), 2.57-2.66 (m, 1H), 4.44-4.52 (m, 1H), 6.17-6.24 (m, 1H), 7.54-7.59 (m, 1H), 7.64-7.72 (m, 3H), 7.74-7.77 (m, 1H), 7.80 (s, 2H), 7.83-7.88 (m, 1H) and 8.28 (s, 1H)

MS ES⁺: 432

Example 82

N-(2-Methyl-2-{[5-(trifluoromethyl)pyrazin-2-yl] amino}cyclopentyl)-2-(2H-1,2,3-triazol-2-yl)benzamide

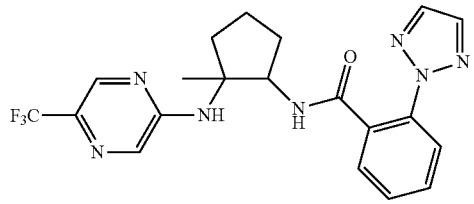 [SMILES: CC1(Nc2cnc(C(F)(F)F)cn2)CCCC1NC(=O)c1ccccc1-n1nccn1]

To a solution of N-(2-amino-2-methylcyclopentyl)-2-(2H-1,2,3-triazol-2-yl)benzamide hydrochloride (Intermediate 26; 287 mg, 1.01 mmol) in dry DMSO (3.4 ml) was added 2-chloro-5-(trifluoromethyl)pyrazine (CAS number 799557-87-2; 202 mg, 1.11 mmol) and DIPEA (527 μl, 3.02 mmol). The reaction was stirred at 140° C. for 1 hour and was then partitioned between ethyl acetate and water. The organics were washed with water, brine, filtered through a hydrophobic frit and concentrated in vacuo. This was purified by column chromatography (silica, 0-100% ethyl acetate/petrol then 0-20% methanol/ethyl acetate) and was then recrystallised from ethyl acetate to afford the title compound.

$^1$H NMR (400 MHz, DMSO-$d_6$) δ ppm 1.37 (s, 3H), 1.55-1.74 (m, 3H), 1.91-2.02 (m, 2H), 2.13-2.23 (m, 1H), 4.57-4.65 (m, 1H), 7.52-7.59 (m, 2H), 7.61-7.67 (m, 1H), 7.73 (s, 1H), 7.78-7.82 (m, 1H), 7.88 (s, 1H), 7.98 (s, 2H), 8.36 (s, 1H) and 8.53-8.59 (m, 1H)

MS ES$^+$: 432

Example 83

N-[(1R,2R)-2-Methyl-2-{[5-(trifluoromethyl) pyrazin-2-yl]amino}cyclopentyl]-2-(2H-1,2,3-triazol-2-yl)benzamide

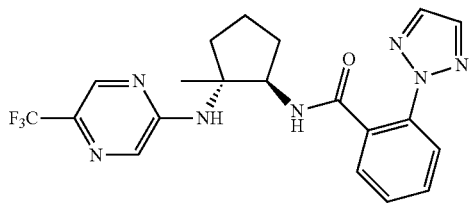 [SMILES: C[C@@]1(Nc2cnc(C(F)(F)F)cn2)CCC[C@H]1NC(=O)c1ccccc1-n1nccn1]

Prepared according to the procedure for N-(2-methyl-2-{[5-(trifluoromethyl)pyrazin-2-yl]amino}cyclopentyl)-2-(2H-1,2,3-triazol-2-yl)benzamide (Example 82) from N-(2-amino-2-methylcyclopentyl)-2-(2H-1,2,3-triazol-2-yl)benzamide hydrochloride (Intermediate 26; 287 mg, 1.01 mmol) and 2-chloro-5-(trifluoromethyl)pyrazine (CAS number 799557-87-2; 202 mg, 1.11 mmol) except this was then chirally separated using SFC (Waters prep30/MS system using 20% Ethanol, column AY) to afford the title compound.

$^1$H NMR (400 MHz, DMSO-$d_6$) δ ppm 1.56-1.75 (m, 4H), 1.92-2.03 (m, 4H), 2.14-2.24 (m, 1H), 4.56-4.66 (m, 1H), 7.52-7.59 (m, 2H), 7.61-7.68 (m, 1H), 7.75 (s, 1H), 7.79-7.83 (m, 1H), 7.88 (s, 1H), 7.99 (s, 2H), 8.37 (s, 1H), 8.55-8.62 (m, 1H)

MS ES$^+$: 432

Example 84

5-Fluoro-N-[(1S,2S)-2-methyl-2-{[5-(trifluoromethyl)pyrazin-2-yl]amino}cyclopentyl]-2-(2H-1,2,3-triazol-2-yl)benzamide

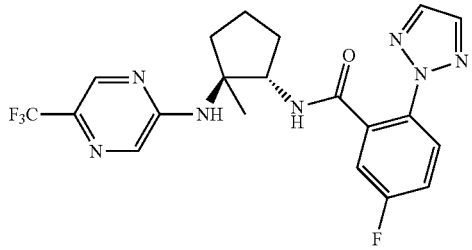 [SMILES: C[C@]1(Nc2cnc(C(F)(F)F)cn2)CCC[C@@H]1NC(=O)c1cc(F)ccc1-n1nccn1]

Prepared according to the procedure for N-[(1S,2S)-2-methyl-2-{[5-(trifluoromethyl)pyrazin-2-yl]amino}cyclopentyl]-3-(2H-1,2,3-triazol-2-yl)pyridine-2-carboxamide (Example 77) from (1S,2S)-1-methyl-1-N-[5-(trifluoromethyl)pyrazin-2-yl]cyclopentane-1,2-diamine (Intermediate 25; 80 mg, 0.31 mmol) and 5-fluoro-2-(2H-1,2,3-triazol-2-yl)benzoic acid (Intermediate 8; 76 mg, 0.37 mmol) except this was purified by column chromatography (0 to 50% ethyl acetate/petrol) followed by a trituration in pentane/diethyl ether to afford the title compound.

$^1$H NMR (400 MHz, DMSO-$d_6$) δ ppm 1.36 (s, 3H), 1.53-1.75 (m, 3H), 1.87-2.02 (m, 2H), 2.17-2.30 (m, 1H), 4.60-4.63 (m, 1H), 7.38-7.46 (m, 1H), 7.46-7.56 (m, 1H), 7.65 (s, 1H), 7.80-7.87 (m, 1H), 7.90 (s, 1H), 7.99 (s, 2H), 8.36 (s, 1H), 8.54-8.63 (m, 1H)

MS ES$^+$: 450

Example 85

N-[(1S,2S)-2-Methyl-2-{[5-(trifluoromethyl) pyrazin-2-yl]amino}cyclopentyl]-3-(1H-pyrazol-1-yl)pyridine-2-carboxamide

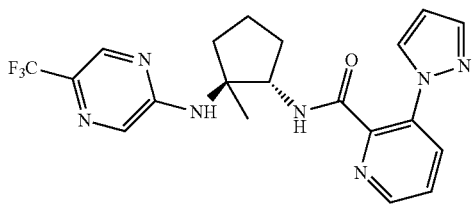 [SMILES: C[C@]1(Nc2cnc(C(F)(F)F)cn2)CCC[C@@H]1NC(=O)c1ncccc1-n1cccn1]

Prepared according to the procedure for N-[(1S,2S)-2-methyl-2-{[5-(trifluoromethyl)pyrazin-2-yl]amino}cyclopentyl]-3-(2H-1,2,3-triazol-2-yl)pyridine-2-carboxamide (Example 77) from (1S,2S)-1-methyl-1-N-[5-(trifluoromethyl)pyrazin-2-yl]cyclopentane-1,2-diamine (Intermediate 25; 80 mg, 0.31 mmol) and 3-(1H-pyrazol-1-yl)pyridine-2-carboxylic acid (CAS number 1521232-19-8; 70 mg, 0.37 mmol) except this was purified by column chromatography (silica, 50-100% ethyl acetate/petrol then 0-10% methanol/ethyl acetate) followed by reverse phase chromatography (C18 silica, 0-100% water (with 0.05% ammonia)/acetonitrile) to afford the title compound.

$^1$H NMR (400 MHz, DMSO-$d_6$) δ ppm 1.33 (s, 3H), 1.54-1.78 (m, 3H), 1.83-2.04 (m, 2H), 2.18-2.31 (m, 1H), 4.64-4.78 (m, 1H), 6.43-6.51 (m, 1H), 7.61-7.71 (m, 3H), 7.91 (s, 1H), 8.06-8.13 (m, 2H), 8.37 (s, 1H), 8.58-8.63 (m, 1H), 8.64-8.70 (m, 1H)

MS ES$^+$: 432

Example 86

3-Ethoxy-N-[(1S,2S)-2-methyl-2-{[5-(trifluoromethyl)pyrazin-2-yl]amino}cyclopentyl]pyridine-2-carboxamide

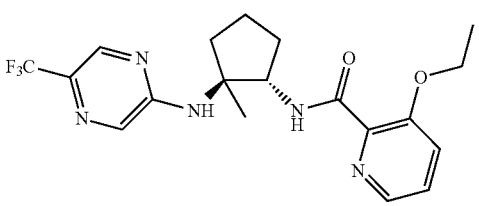 [SMILES: CCOc1cccnc1C(=O)N[C@H]1CCC[C@]1(C)Nc1cnc(C(F)(F)F)cn1]

Prepared according to the procedure for N-[(1S,2S)-2-methyl-2-{[5-(trifluoromethyl)pyrazin-2-yl]amino}cyclopentyl]-3-(2H-1,2,3-triazol-2-yl)pyridine-2-carboxamide (Example 77) from (1S,2S)-1-methyl-1-N-[5-(trifluoromethyl)pyrazin-2-yl]cyclopentane-1,2-diamine (Intermediate 25; 80 mg, 0.31 mmol) and 3-ethoxypyridine-2-carboxylic acid (CAS number 103878-09-7; 51 mg, 0.31 mmol) except this was purified by column chromatography (silica, 0-100% ethyl acetate/petrol) followed by reverse phase chromatography (C18 silica, 0-100% water (with 0.05% ammonia)/acetonitrile) to afford the title compound.

$^1$H NMR (400 MHz, DMSO-d6) δ ppm 1.24-1.34 (m, 3H), 1.40 (s, 3H), 1.54-1.78 (m, 3H), 1.85-1.96 (m, 1H), 2.00-2.11 (m, 1H), 2.22-2.36 (m, 1H), 4.05-4.14 (m, 2H), 4.69-4.77 (m, 1H), 7.41-7.47 (m, 1H), 7.52-7.58 (m, 1H), 7.82 (s, 1H), 8.01 (s, 1H), 8.12-8.17 (m, 1H), 8.30-8.46 (m, 2H)
MS ES+: 410

Example 87

2-Chloro-N-[(1S,2S)-2-methyl-2-{[5-(trifluoromethyl)pyrazin-2-yl]amino}cyclopentyl]-6-(2H-1,2,3-triazol-2-yl)benzamide

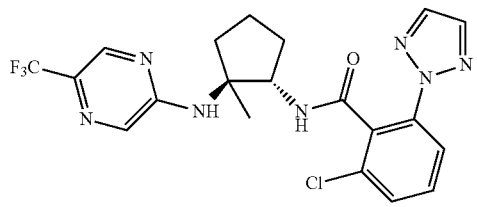 [SMILES: C[C@]1(Nc2cnc(C(F)(F)F)cn2)CCC[C@@H]1NC(=O)c1c(Cl)cccc1-n1nccn1]

Prepared according to the procedure for N-[(1S,2S)-2-methyl-2-{[5-(trifluoromethyl)pyrazin-2-yl]amino}cyclopentyl]-3-(2H-1,2,3-triazol-2-yl)pyridine-2-carboxamide (Example 77) from (1S,2S)-1-methyl-1-N-[5-(trifluoromethyl)pyrazin-2-yl]cyclopentane-1,2-diamine (Intermediate 25; 63 mg, 0.24 mmol) and 2-chloro-6-(2H-1,2,3-triazol-2-yl)benzoic acid (Intermediate 15; 65 mg, 0.29 mmol) except this was purified by column chromatography (silica, 0-30% ethyl acetate/petrol) followed by trituration with diethyl ether/pentane to afford the title compound.

$^1$H NMR (400 MHz, DCM-d2) δ ppm 1.43 (s, 3H), 1.44-1.57 (m, 1H), 1.68-2.18 (m, 4H), 2.52-2.67 (m, 1H), 4.45-4.58 (m, 1H), 6.06-6.16 (m, 1H), 7.47-7.56 (m, 2H), 7.75 (s, 2H), 7.83 (br. s., 1H), 7.89-8.01 (m, 1H), 8.25 (s, 1H)
MS ES+: 466

Example 88

2,6-Difluoro-N-[(1S,2S)-2-methyl-2-{[5-(trifluoromethyl)pyrazin-2-yl]amino}cyclopentyl]benzamide

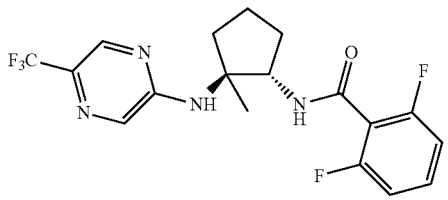 [SMILES: C[C@]1(Nc2cnc(C(F)(F)F)cn2)CCC[C@@H]1NC(=O)c1c(F)cccc1F]

Prepared according to the procedure for N-[(1S,2S)-2-methyl-2-{[5-(trifluoromethyl)pyrazin-2-yl]amino}cyclopentyl]-3-(2H-1,2,3-triazol-2-yl)pyridine-2-carboxamide (Example 77) from (1S,2S)-1-methyl-1-N-[5-(trifluoromethyl)pyrazin-2-yl]cyclopentane-1,2-diamine (Intermediate 25; 63 mg, 0.24 mmol) and 2,6-difluorobenzoic acid (CAS number 385-00-2; 46 mg, 0.29 mmol) except this was purified by column chromatography (silica, 0-20% ethyl acetate/petrol) followed by reverse phase chromatography (C18 silica, 0-100% water (with 0.05% ammonia)/acetonitrile) to afford the title compound.

$^1$H NMR (400 MHz, DMSO-d6) δ ppm 1.39 (s, 3H), 1.50-1.87 (m, 4H), 1.98-2.15 (m, 1H), 2.30-2.44 (m, 1H), 4.80-4.90 (m, 1H), 7.12-7.22 (m, 2H), 7.52 (s, 1H), 7.70 (s, 1H), 8.00-8.06 (m, 1H), 8.38 (s, 1H), 8.69-8.76 (m, 1H)
MS ES+: 401

Example 89

3-Cyclopropyl-N-[(1S,2S)-2-methyl-2-{[5-(trifluoromethyl)pyrazin-2-yl]amino}cyclopentyl]pyridine-2-carboxamide

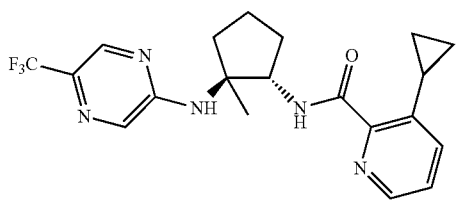 [SMILES: C[C@]1(Nc2cnc(C(F)(F)F)cn2)CCC[C@@H]1NC(=O)c1ncccc1C1CC1]

Prepared according to the procedure for N-[(1S,2S)-2-methyl-2-{[5-(trifluoromethyl)pyrazin-2-yl]amino}cyclopentyl]-3-(2H-1,2,3-triazol-2-yl)pyridine-2-carboxamide (Example 77) from (1S,2S)-1-methyl-1-N-[5-(trifluoromethyl)pyrazin-2-yl]cyclopentane-1,2-diamine (Intermediate 25; 48 mg, 0.15 mmol), 3-cyclopropylpyridine-2-carboxylic acid (Intermediate 16; 33 mg, 0.20 mmol) and triethylamine (0.077 ml, 0.55 mmol) except this was purified by column chromatography (silica, 0-50% ethyl acetate/petrol) followed by column chromatography (silica, 0-2.5% methanol/DCM) to afford the title compound.

$^1$H NMR (400 MHz, CHLOROFORM-d) δ ppm 0.58-0.80 (m, 2H), 1.05-1.17 (m, 2H), 1.39 (s, 3H), 1.61-2.08 (m, 4H), 2.12-2.24 (m, 1H), 2.63 (s, 1H), 3.28-3.43 (m, 1H), 4.46-4.59 (m, 1H), 7.31-7.37 (m, 2H), 7.78-7.89 (m, 2H), 8.23-8.33 (m, 2H), 8.33-8.38 (m, 1H)
MS ES[1]: 406

Example 90

N-[(1S,2S)-2-Methyl-2-{[5-(trifluoromethyl)pyrazin-2-yl]amino}cyclopentyl]-3-(trifluoromethoxy)pyridine-2-carboxamide

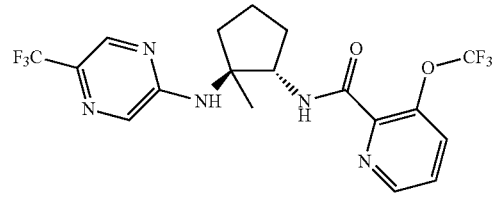 [SMILES: C[C@]1(Nc2cnc(C(F)(F)F)cn2)CCC[C@@H]1NC(=O)c1ncccc1OC(F)(F)F]

Prepared according to the procedure for N-[(1S,2S)-2-methyl-2-{[5-(trifluoromethyl)pyrazin-2-yl]amino}cyclopentyl]-3-(2H-1,2,3-triazol-2-yl)pyridine-2-carboxamide (Example 77) from (1S,2S)-1-methyl-1-N-[5-(trifluoromethyl)pyrazin-2-yl]cyclopentane-1,2-diamine (Intermediate 25; 48 mg, 0.15 mmol), 3-(trifluoromethoxy)pyridine-2-carboxylic acid (CAS number 1221171-81-8; 42 mg, 0.20 mmol) and triethylamine (0.077 ml, 0.55 mmol) except this was purified by column chromatography (silica, 0-50% ethyl acetate/petrol) to afford the title compound.

$^1$H NMR (400 MHz, CHLOROFORM-d) δ ppm 1.38 (s, 3H), 1.60-2.04 (m, 4H), 2.14-2.27 (m, 1H), 2.56-2.70 (m, 1H), 4.46-4.62 (m, 1H), 7.48-7.62 (m, 2H), 7.74-7.80 (m, 1H), 7.83-7.89 (m, 1H), 7.92-8.01 (m, 1H), 8.25 (s, 1H), 8.54-8.60 (m, 1H)

MS ES$^+$: 450

Example 91

N-[(1S,2S)-2-Methyl-2-{[5-(trifluoromethyl)pyrazin-2-yl]amino}cyclopentyl]-2-(pyrimidin-2-yl)benzamide

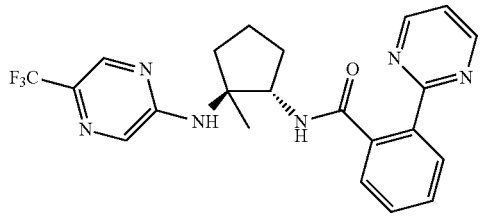 [SMILES: C[C@]1(Nc2cnc(C(F)(F)F)cn2)CCC[C@@H]1NC(=O)c1ccccc1-c1ncccn1]

Prepared according to the procedure for N-[(1S,2S)-2-methyl-2-{[5-(trifluoromethyl)pyrazin-2-yl]amino}cyclopentyl]-3-(2H-1,2,3-triazol-2-yl)pyridine-2-carboxamide (Example 77) from (1S,2S)-1-methyl-1-N-[5-(trifluoromethyl)pyrazin-2-yl]cyclopentane-1,2-diamine (Intermediate 25; 48 mg, 0.15 mmol), 2-(pyrimidin-2-yl)benzoic acid (CAS number 400892-62-8; 41 mg, 0.20 mmol) and triethylamine (0.077 ml, 0.55 mmol) except this was purified by column chromatography (silica, 0-100% ethyl acetate/petrol)) followed by reverse phase chromatography (C18 silica, 0-100% water (with 0.05% ammonia)/acetonitrile) to afford the title compound.

$^1$H NMR (400 MHz, CHLOROFORM-d) δ ppm 1.45 (s, 3H), 1.48-1.57 (m, 1H), 1.72-1.99 (m, 3H), 2.04-2.12 (m, 1H), 2.63-2.70 (m, 1H), 4.46-4.58 (m, 1H), 6.16-6.26 (m, 1H), 7.14-7.22 (m, 1H), 7.49-7.70 (m, 4H), 7.87 (s, 1H), 8.09-8.17 (m, 1H), 8.27 (s, 1H), 8.64-8.70 (m, 2H)

MS ES$^+$: 443

Example 92

5-Chloro-N-[(1S,2S)-2-methyl-2-{[5-(trifluoromethyl)pyrazin-2-yl]amino}cyclopentyl]-2-(2H-1,2,3-triazol-2-yl)benzamide

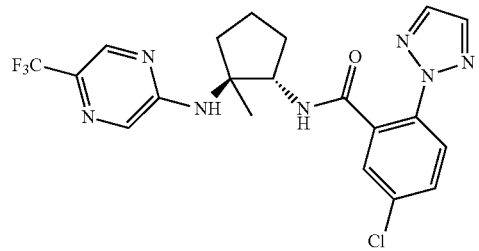 [SMILES: C[C@]1(Nc2cnc(C(F)(F)F)cn2)CCC[C@@H]1NC(=O)c1cc(Cl)ccc1-n1nccn1]

Prepared according to the procedure for N-[(1S,2S)-2-methyl-2-{[5-(trifluoromethyl)pyrazin-2-yl]amino}cyclopentyl]-3-(2H-1,2,3-triazol-2-yl)pyridine-2-carboxamide (Example 77) from (1S,2S)-1-methyl-1-N-[5-(trifluoromethyl)pyrazin-2-yl]cyclopentane-1,2-diamine (Intermediate 25; 90 mg, 0.35 mmol) and 5-chloro-2-(2H-1,2,3-triazol-2-yl)benzoic acid (Intermediate 38a; CAS number 1293284-54-4; 93 mg, 0.42 mmol) except this was purified by column chromatography (silica, 0-50% ethyl acetate/petrol) followed by recrystallisation from diethyl ether/pentane to afford the title compound.

$^1$H NMR (400 MHz, DMSO-d$_6$) δ ppm 1.37 (s, 3H), 1.51-1.77 (m, 3H), 1.86-2.04 (m, 2H), 2.19-2.31 (m, 1H), 4.63-4.66 (m, 1H), 7.57-7.76 (m, 3H), 7.81-7.88 (m, 1H), 7.91 (s, 1H), 8.03 (s, 2H), 8.37 (s, 1H), 8.58-8.68 (m, 1H)

MS ES$^+$: 466

Example 93

N-(2-Methyl-2-{[5-(trifluoromethyl)pyrimidin-2-yl]amino}cyclopentyl)-2-(2H-1,2,3-triazol-2-yl)benzamide

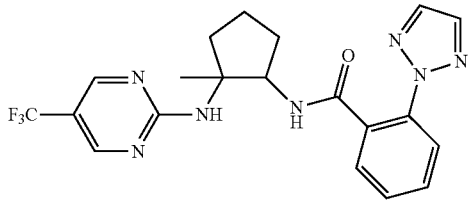 [SMILES: CC1(Nc2ncc(C(F)(F)F)cn2)CCCC1NC(=O)c1ccccc1-n1nccn1]

Prepared according to the procedure for N-(2-methyl-2-{[5-(trifluoromethyl)pyrazin-2-yl]amino}cyclopentyl)-2-(2H-1,2,3-triazol-2-yl)benzamide (Example 82) from N-(2-amino-2-methylcyclopentyl)-2-(2H-1,2,3-triazol-2-yl)benzamide hydrochloride (Intermediate 26; 200 mg, 0.70 mmol) and 2-chloro-5-(trifluoromethyl)pyrimidine (CAS number 69034-12-4; 141 mg, 0.77 mmol) except this was purified by column chromatography (silica, 0-100% ethyl acetate/petrol) followed by reverse phase chromatography (C18 silica, 0-100% water (with 0.05% ammonia)/acetonitrile) to afford the title compound.

$^1$H NMR (400 MHz, DMSO-d$_6$) δ ppm 1.33 (s, 3H), 1.58-1.74 (m, 3H), 1.84-2.01 (m, 2H), 2.25-2.34 (m, 1H), 4.42-4.51 (m, 1H), 7.52-7.59 (m, 2H), 7.62-7.68 (m, 1H), 7.81-7.85 (m, 1H), 7.90 (s, 1H), 7.95 (s, 2H), 8.54-8.66 (m, 2H) and 8.68-8.73 (m, 1H)

MS ES$^+$: 432

Example 94

N-(2-Methyl-2-{[5-(trifluoromethyl)pyrimidin-2-yl]amino}cyclopentyl)-2-(2H-1,2,3-triazol-2-yl)benzamide

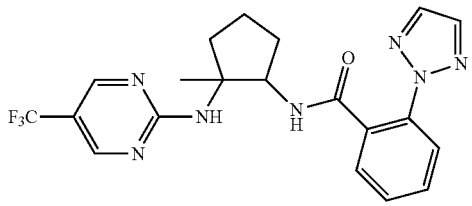

Prepared according to the procedure for N-(2-methyl-2-{[5-(trifluoromethyl)pyrimidin-2-yl]amino}cyclopentyl)-2-

(2H-1,2,3-triazol-2-yl)benzamide (Example 93) from N-(2-amino-2-methylcyclopentyl)-2-(2H-1,2,3-triazol-2-yl)benzamide hydrochloride (Intermediate 26; 200 mg, 0.70 mmol) and 2-chloro-5-(trifluoromethyl)pyrimidine (CAS number 69034-12-4; 141 mg, 0.77 mmol) except this was then chirally separated using SFC (acetonitrile with diethylamine modifier, column Lux A2) to afford the title compound as a single enantiomer.

$^1$H NMR (400 MHz, DMSO-$d_6$) δ ppm 1.34 (s, 3H), 1.58-1.77 (m, 3H), 1.84-2.03 (m, 2H), 2.25-2.36 (m, 1H), 4.42-4.53 (m, 1H), 7.50-7.61 (m, 2H), 7.62-7.70 (m, 1H), 7.81-7.85 (m, 1H), 7.91 (s, 1H), 7.96 (s, 2H), 8.54-8.67 (m, 2H), 8.68-8.73 (m, 1H)

MS ES$^+$: 432

Example 95

N-(2-Methyl-2-{[5-(trifluoromethyl)pyridin-2-yl]amino}cyclopentyl)-2-(2H-1,2,3-triazol-2-yl)benzamide

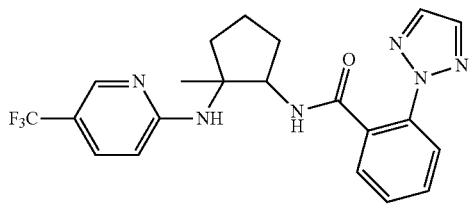

Prepared according to the procedure for N-(2-methyl-2-{[5-(trifluoromethyl)pyrazin-2-yl]amino}cyclopentyl)-2-(2H-1,2,3-triazol-2-yl)benzamide (Example 82) from N-(2-amino-2-methylcyclopentyl)-2-(2H-1,2,3-triazol-2-yl)benzamide hydrochloride (Intermediate 26; 95 mg, 0.30 mmol) and 2-chloro-5-(trifluoromethyl)pyridine (CAS number 52334-81-3; 100 mg, 0.55 mmol) except this was heated at 140° C. for 17 hours and then purified by column chromatography (basic silica, 0-100% ethyl acetate/petrol) to afford the title compound.

$^1$H NMR (400 MHz, DCM-$d_2$) δ ppm 1.34 (s, 3H), 1.37-1.51 (m, 1H), 1.68-1.90 (m, 2H), 1.90-2.00 (m, 1H), 2.02-2.14 (m, 1H), 2.39-2.52 (m, 1H), 4.37-4.47 (m, 1H), 6.19 (br. s., 1H), 6.34-6.55 (m, 1H), 6.92-7.23 (m, 1H), 7.44-7.56 (m, 2H), 7.57-7.69 (m, 2H), 7.76 (s, 2H), 7.78-7.84 (m, 1H), 8.24 (s, 1H)

MS ES$^+$: 431

Example 96

N-(2-Methyl-2-{[5-(trifluoromethoxy)pyridin-2-yl]amino}cyclopentyl)-2-(2H-1,2,3-triazol-2-yl)benzamide

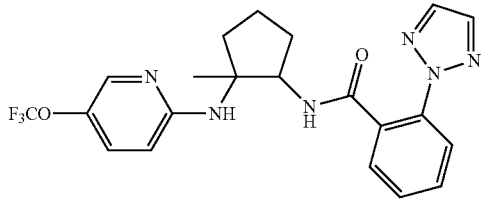 [SMILES: CC1(Nc2ccc(OC(F)(F)F)cn2)CCCC1NC(=O)c1ccccc1-n1nccn1]

A solution of N-(2-amino-2-methylcyclopentyl)-2-(2H-1,2,3-triazol-2-yl)benzamide hydrochloride (Intermediate 26; 150 mg, 0.47 mmol), 2-bromo-5-(trifluoromethoxy)pyridine (CAS number 888327-36-4; 118 mg, 0.49 mmol), BINAP (29 mg, 0.047 mmol), tris(dibenzylideneacetone)dipalladium(0) (21.34 mg, 0.023 mmol) and sodium tert-butoxide (63 mg, 0.65 mmol) in dry toluene (1.6 ml) was sealed, evacuated and purged with nitrogen. The reaction was heated at 140° C. for 17 hours and was then partitioned between ethyl acetate and water, washing with water, brine, dried over sodium sulfate and concentrated in vacuo. The residue was purified by column chromatography (silica, 0-70% ethyl acetate/petrol) to afford the title compound.

$^1$H NMR (400 MHz, DMSO-d6) δ ppm 1.31 (s, 3H), 1.45-1.78 (m, 3H), 1.80-2.14 (m, 3H), 4.39-4.50 (m, 1H), 6.39-6.47 (m, 1H), 6.78 (s, 1H), 7.35-7.44 (m, 1H), 7.49-7.59 (m, 2H), 7.59-7.70 (m, 1H), 7.77-7.85 (m, 1H), 7.92-8.02 (m, 3H), 8.47-8.58 (m, 1H)

MS ES$^+$: 447

Example 97

5-Chloro-2-(2H-1,2,3-triazol-2-yl)-N-[(1S,2S)-2-{[5-(trifluoromethyl)pyridin-2-yl]amino}cyclopentyl]benzamide

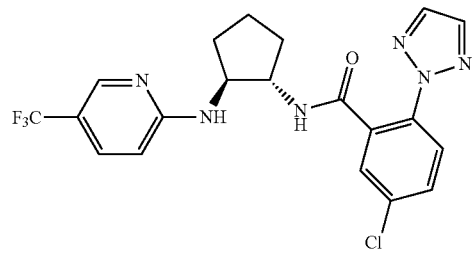 [SMILES: O=C(N[C@H]1CCC[C@@H]1Nc1ccc(C(F)(F)F)cn1)c1cc(Cl)ccc1-n1nccn1]

To a solution of (1S,2S)-1-N-[5-(trifluoromethyl)pyridin-2-yl]cyclopentane-1,2-diamine hydrochloride (Intermediate 1; 50 mg, 0.20 mmol) in DMF (3 ml) was added 5-chloro-2-(2H-1,2,3-triazol-2-yl)benzoic acid (Intermediate 38a; CAS number 1293284-54-4; 45 mg, 0.204 mmol), TBTU (78 mg, 0.245 mmol) and DIPEA (40 mg, 0.306 mmol). The reaction was stirred at room temperature for 2 hours and was then diluted with water (25 ml) and extracted with ethyl acetate (3×30 ml). The organics were washed with water (25 ml), brine (20 ml), dried over sodium sulfate and concentrated in vacuo. The residue was then purified by column chromatography (silica, 0-45% ethyl acetate/n-hexane) to afford the title compound.

$^1$H NMR (400 MHz, DMSO-d) δ ppm 1.50-1.60 (m, 4H), 1.66-2.08 (m, 2H), 4.03-4.10 (m, 1H), 4.18-4.22 (m, 1H), 6.65-6.67 (m, 1H), 7.33-7.35 (m, 1H), 7.43-7.44 (m, 1H) 7.62-7.70 (m, 2H) 7.80-7.82 (m, 1H), 7.99 (s, 2H), 8.29 (s, 1H), 8.53-8.55 (m, 1H)

MS ES$^+$: 451

Example 98

3-Fluoro-2-(2H-1,2,3-triazol-2-yl)-N-[(1S,2S)-2-{[5-(trifluoromethyl)pyridin-2-yl]amino}cyclopentyl]benzamide

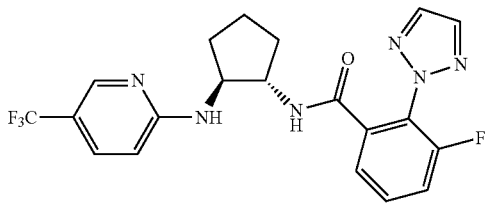 [SMILES: O=C(N[C@H]1CCC[C@@H]1Nc1ccc(C(F)(F)F)cn1)c1cccc(F)c1-n1nccn1]

Prepared according to the procedure for 5-chloro-2-(2H-1,2,3-triazol-2-yl)-N-[(1S,2S)-2-{[5-(trifluoromethyl)pyridin-2-yl]amino}cyclopentyl]benzamide (Example 97) from (1S,2S)-1-N-[5-(trifluoromethyl)pyridin-2-yl]cyclopentane-1,2-diamine hydrochloride (Intermediate 1; 50 mg, 0.20 mmol) and 3-fluoro-2-(2H-1,2,3-triazol-2-yl)benzoic acid (CAS number 1293284-51-1; 42 mg, 0.20 mmol) to afford the title compound.

$^1$H NMR (400 MHz, DMSO-d) δ ppm 1.41-1.44 (m, 2H), 1.61-1.68 (m, 2H), 1.89-2.03 (m, 2H), 3.93-3.96 (m, 1H), 4.02-4.06 (m, 1H), 6.59-6.62 (m, 1H) 7.31-7.36 (m, 2H) 7.59-7.68 (m, 3H), 8.01 (s, 2H), 8.28 (s, 1H), 8.49-8.51 (m, 1H)

MS ES$^+$: 435

Example 99

3,5-Difluoro-2-(2H-1,2,3-triazol-2-yl)-N-[(1S,2S)-2-{[5-(trifluoromethyl)pyridin-2-yl]amino}cyclopentyl]benzamide

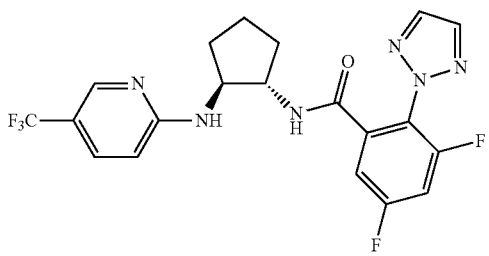 [SMILES: O=C(N[C@H]1CCC[C@@H]1Nc1ccc(C(F)(F)F)cn1)c1cc(F)cc(F)c1-n1nccn1]

Prepared according to the procedure for 5-chloro-2-(2H-1,2,3-triazol-2-yl)-N-[(1S,2S)-2-{[5-(trifluoromethyl)pyridin-2-yl]amino}cyclopentyl]benzamide (Example 97) from (1S,2S)-1-N-[5-(trifluoromethyl)pyridin-2-yl]cyclopentane-1,2-diamine hydrochloride (Intermediate 1; 50 mg, 0.20 mmol) and 3,5-difluoro-2-(2H-1,2,3-triazol-2-yl)benzoic acid (Intermediate 40a; 46 mg, 0.20 mmol) except this was purified by column chromatography (silica, 0-30% ethyl acetate/n-hexane) to afford the title compound.

$^1$H NMR (400 MHz, DMSO-d) δ ppm 1.41-1.48 (m, 2H), 1.61-1.69 (m, 2H), 1.88-1.93 (m, 2H), 3.91-3.96 (m, 1H), 4.04-4.08 (m, 1H), 7.58-7.61 (m, 1H), 7.24-7.31 (m, 2H) 7.62-7.64 (m, 1H) 7.72-7.77 (m, 1H), 8.02 (s, 2H), 8.28 (s, 1H), 8.56-8.58 (m, 1H)

MS ES$^+$: 453

Example 100

3-(2H-1,2,3-Triazol-2-yl)-N-[(1S,2S)-2-{[5-(trifluoromethyl)pyridin-2-yl]amino}cyclopentyl]pyridine-2-carboxamide

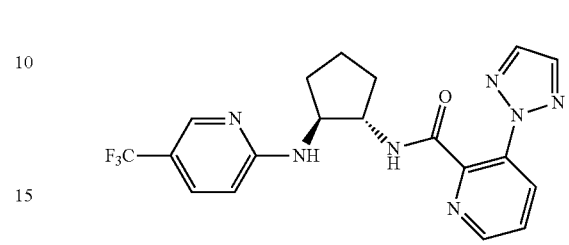

Prepared according to the procedure for 5-chloro-2-(2H-1,2,3-triazol-2-yl)-N-[(1S,2S)-2-{[5-(trifluoromethyl)pyridin-2-yl]amino}cyclopentyl]benzamide (Example 97) from (1S,2S)-1-N-[5-(trifluoromethyl)pyridin-2-yl]cyclopentane-1,2-diamine hydrochloride (Intermediate 1; 50 mg, 0.20 mmol) and 3-(2H-1,2,3-triazol-2-yl)pyridine-2-carboxylic acid (CAS number 1252907-86-0; 39 mg, 0.20 mmol) to afford the title compound.

$^1$H NMR (400 MHz, DMSO-d) δ ppm 1.46-1.77 (m, 4H), 2.01-2.09 (m, 2H), 4.07-4.21 (m, 2H), 6.65-6.67 (m, 1H), 7.38-7.40 (m, 1H), 7.62-7.65 (m, 1H), 7.71-7.73 (m, 1H), 8.04 (s, 2H), 8.23-8.28 (m, 2H), 8.66-8.68 (m, 1H), 8.68-8.76 (m, 1H)

MS ES$^+$: 418

Example 101

3-(1H-Pyrazol-1-yl)-N-[(1S,2S)-2-{[5-(trifluoromethyl)pyridin-2-yl]amino}cyclopentyl]pyridine-2-carboxamide

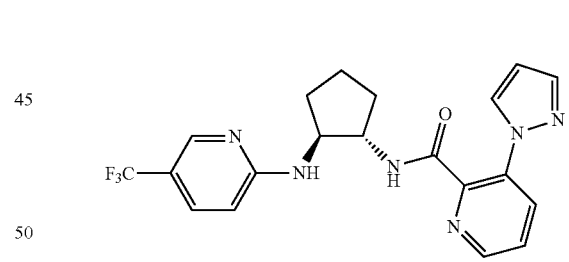

Prepared according to the procedure for 5-chloro-2-(2H-1,2,3-triazol-2-yl)-N-[(1S,2S)-2-{[5-(trifluoromethyl)pyridin-2-yl]amino}cyclopentyl]benzamide (Example 97) from (1S,2S)-1-N-[5-(trifluoromethyl)pyridin-2-yl]cyclopentane-1,2-diamine hydrochloride (Intermediate 1; 50 mg, 0.20 mmol) and 3-(1H-pyrazol-1-yl)pyridine-2-carboxylic acid (CAS number 1521232-19-8; 38 mg, 0.20 mmol) to afford the title compound.

$^1$H NMR (400 MHz, DMSO-d) δ ppm 1.41-1.71 (m, 4H), 1.99-2.05 (m, 2H), 4.11-4.23 (m, 2H), 6.35-6.36 (m, 1H), 6.64-6.66 (m, 1H), 7.42-7.44 (m, 1H), 7.63-7.68 (m, 3H), 7.96-7.96 (m, 1H), 8.08-8.10 (m, 1H), 8.27 (s, 1H), 8.57-8.58 (m, 1H), 8.80-8.82 (m, 1H)

MS ES$^+$: 417

Example 102

2-Fluoro-6-(2H-1,2,3-triazol-2-yl)-N-[(1S,2S)-2-{[5-(trifluoromethyl)pyridin-2-yl]amino}cyclopentyl]benzamide

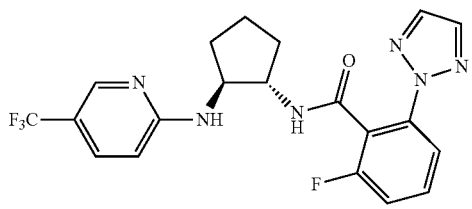 [SMILES: O=C(N[C@H]1CCC[C@@H]1Nc1ccc(C(F)(F)F)cn1)c1c(F)cccc1-n1nccn1]

To a solution of (1S,2S)-1-N-[5-(trifluoromethyl)pyridin-2-yl]cyclopentane-1,2-diamine hydrochloride (Intermediate 1; 1.09 g, 3.87 mmol) in DCM (13 ml) was added 2-fluoro-6-(2H-1,2,3-triazol-2-yl)benzoic acid (CAS number 1186050-58-7; 0.802 g, 3.87 mmol), DIPEA (2.027 ml, 11.61 mmol), 3H-[1,2,3]triazolo[4,5-b]pyridin-3-ol (0.579 g, 4.26 mmol) and EDC (0.816 g, 4.26 mmol). The reaction was stirred at room temperature for 17 hours and was then partitioned between DCM and a saturated solution of sodium bicarbonate, filtered through a hydrophobic frit and concentrated in vacuo. The residue was purified by column chromatography (basic silica, 0-100% ethyl acetate/petrol) and recrystallised from IPA to afford the title compound.

$^1$H NMR (400 MHz, DMSO-d$_6$) δ ppm 1.41-1.59 (m, 2H), 1.59-1.76 (m, 2H), 1.95-2.10 (m, 2H), 4.06-4.20 (m, 2H), 6.68 (d, J=8.8 Hz, 1H), 7.29-7.41 (m, 2H), 7.57-7.66 (m, 2H), 7.71-7.75 (m, 1H), 8.00 (s, 2H), 8.25-8.28 (m, 1H), 8.63 (d, J=6.8 Hz, 1H)

MS ES$^+$: 435

Example 103

N-(2-{[3-Fluoro-5-(trifluoromethyl)pyridin-2-yl]amino}-2-methylcyclopentyl)-3-(2H-1,2,3-triazol-2-yl)pyridine-2-carboxamide

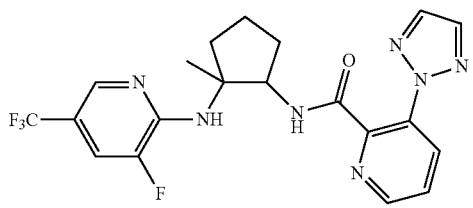 [SMILES: CC1(Nc2ncc(C(F)(F)F)cc2F)CCCC1NC(=O)c1ncccc1-n1nccn1]

A solution of 1-N-[3-fluoro-5-(trifluoromethyl)pyridin-2-yl]-1-methylcyclopentane-1,2-diamine (Intermediate 28; 57 mg, 0.21 mmol), 3-(2H-1,2,3-triazol-2-yl)pyridine-2-carboxylic acid (CAS number 1252907-86-0; 51 mg, 0.27 mmol), EDC (51 mg, 0.27 mmol), 3H-[1,2,3]triazolo[4,5-b]pyridin-3-ol (36 mg, 0.27 mmol) and triethylamine (0.086 ml, 0.62 mmol) in DCM (3 ml) was stirred at room temperature for 18 hours. The reaction was then diluted with DCM (20 ml) and a saturated solution of sodium bicarbonate (10 ml), filtered through a hydrophobic frit and concentrated in vacuo. The residue was purified by column chromatography (silica, 0-100% ethyl acetate/petrol) to afford the title compound.

$^1$H NMR (400 MHz, DCM-d$_2$) δ ppm 1.47 (s, 3H), 1.62-1.74 (m, 1H), 1.78-1.89 (m, 2H), 1.91-2.01 (m, 1H), 2.15-2.26 (m, 1H), 2.68-2.78 (m, 1H), 4.45-4.55 (m, 1H), 7.23-7.28 (m, 1H), 7.38 (br. s., 1H), 7.41-7.49 (m, 1H), 7.61-7.66 (m, 1H), 8.08-8.11 (m, 1H), 8.13 (s, 1H) and 8.65-8.70 (m, 1H).

MS ES$^+$: 450

Example 105

N-[(1S,2S)-2-{[3-Fluoro-5-(trifluoromethyl)pyridin-2-yl]amino}cyclopentyl]-2-(2H-1,2,3-triazol-2-yl)benzamide

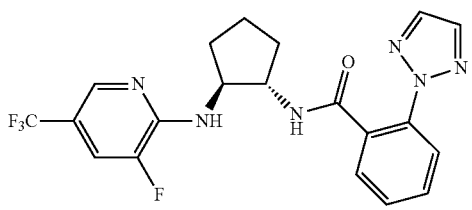

A solution of N-[(1S,2S)-2-aminocyclopentyl]-2-(2H-1,2,3-triazol-2-yl)benzamide hydrochloride (Intermediate 4; 100 mg, 0.33 mmol), 2,3-difluoro-5-(trifluoromethyl)pyridine (CAS number 89402-42-6; 65 mg, 0.36 mmol) and DIPEA (42 mg, 0.33 mmol) in dry DMSO (1.1 ml) was subjected to microwave irradiation at 140° C. for 1 hour. The reaction was filtered through cotton wool before being purified by reverse phase preparative HPLC (eluted with acetonitrile/water containing 0.1% ammonia) to afford the title compound.

$^1$H NMR (300 MHz, DMSO-d$_6$) δ ppm 1.41-1.77 (m, 4H), 1.91-2.15 (m, 2H), 4.17-4.40 (m, 2H), 7.32-7.44 (m, 2H), 7.44-7.54 (m, 1H), 7.54-7.66 (m, 1H), 7.68-7.81 (m, 2H), 7.82-7.92 (m, 2H), 8.14-8.22 (m, 1H), 8.35-8.46 (m, 1H)

MS ES$^+$: 435

Example 106

N-[(1S,2S)-2-{[3-Chloro-5-(trifluoromethyl)pyridin-2-yl]amino}cyclopentyl]-2-(2H-1,2,3-triazol-2-yl)benzamide

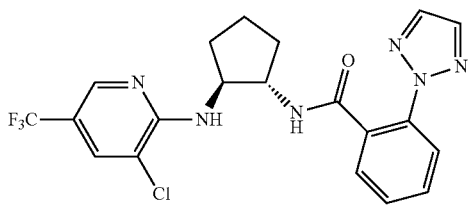 [SMILES: O=C(N[C@H]1CCC[C@@H]1Nc1ncc(C(F)(F)F)cc1F)c1ccccc1-n1nccn1]

Prepared according to the procedure for N-[(1S,2S)-2-{[3-fluoro-5-(trifluoromethyl)pyridin-2-yl]amino}cyclopentyl]-2-(2H-1,2,3-triazol-2-yl)benzamide (Example 105) from N-[(1S,2S)-2-amino cyclopentyl]-2-(2H-1,2,3-triazol-2-yl)benzamide hydrochloride (Intermediate 4; 100 mg, 0.33 mmol) and 3-chloro-2-fluoro-5-(trifluoromethyl)pyridine (CAS number 72537-17-8; 71 mg, 0.36 mmol) except this was then further purified using column chromatography (basic silica, 0-100% ethyl acetate/petrol) to afford the title compound.

$^1$H NMR (400 MHz, DMSO-d$_6$) δ ppm 1.46-1.63 (m, 2H), 1.63-1.77 (m, 2H), 1.91-2.05 (m, 1H), 2.11-2.23 (m, 1H), 4.15-4.25 (m, 1H), 4.26-4.39 (m, 1H), 7.17-7.20 (m, 1H), 7.38-7.45 (m, 1H), 7.46-7.52 (m, 1H), 7.56-7.64 (m, 1H), 7.77 (d, J=7.6 Hz, 1H), 7.82 (s, 2H), 7.95-7.99 (m, 1H), 8.32-8.37 (m, 1H), 8.48 (d, J=7.6 Hz, 1H)
MS ES+: 451

Example 107

N-[(1S,2S)-2-{[3-Bromo-5-(trifluoromethyl)pyridin-2-yl]amino}cyclopentyl]-2-(2H-1,2,3-triazol-2-yl)benzamide

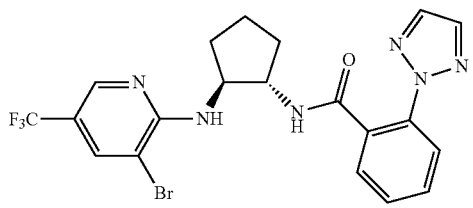 [SMILES: O=C(N[C@H]1CCC[C@@H]1Nc1ncc(C(F)(F)F)cc1Br)c1ccccc1-n1nccn1]

Prepared according to the procedure for N-[(1S,2S)-2-{[3-fluoro-5-(trifluoromethyl)pyridin-2-yl]amino}cyclopentyl]-2-(2H-1,2,3-triazol-2-yl)benzamide (Example 105) from N-[(1S,2S)-2-aminocyclopentyl]-2-(2H-1,2,3-triazol-2-yl)benzamide hydrochloride (Intermediate 4; 100 mg, 0.33 mmol) and 3-bromo-2-chloro-5-(trifluoromethyl)pyridine (CAS number 71701-92-3; 93 mg, 0.36 mmol) to afford the title compound.
$^1$H NMR (400 MHz, DMSO-d$_6$) δ ppm 1.40-1.62 (m, 2H), 1.62-1.78 (m, 2H), 1.91-2.03 (m, 1H), 2.14-2.27 (m, 1H), 4.08-4.19 (m, 1H), 4.27-4.39 (m, 1H), 7.01-7.03 (m, 1H), 7.39-7.45 (m, 1H), 7.46-7.52 (m, 1H), 7.57-7.65 (m, 1H), 7.75-7.79 (m, 1H), 7.81 (s, 2H), 8.08-8.12 (m, 1H), 8.36-8.40 (m, 1H), 8.47-8.50 (m, 1H)
MS ES+: 495, 497

Example 108

N-[(1S,2S)-2-{[3-Methyl-5-(trifluoromethyl)pyridin-2-yl]amino}cyclopentyl]-2-(2H-1,2,3-triazol-2-yl)benzamide

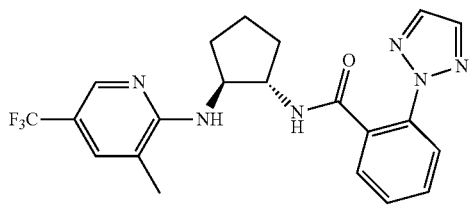

A mixture of N-[(1S,2S)-2-{[3-bromo-5-(trifluoromethyl)pyridin-2-yl]amino}cyclopentyl]-2-(2H-1,2,3-triazol-2-yl)benzamide (Example 107; 67 mg, 0.14 mmol), methylboronic acid (CAS number 13061-96-6; 24 mg, 0.41 mmol), tetrakis(triphenylphosphine)palladium (16 mg, 0.014 mmol) and potassium carbonate (aq. 2 M, 271 µl, 0.54 mmol) in 1,4-dioxane (450 µl) was sealed, evacuated and purged with nitrogen and then subjected to microwave irradiation at 140° C. for 30 minutes. The reaction was partitioned between ethyl acetate and water, washing with water, brine, dried over magnesium sulfate and concentrated in vacuo. This was then purified by reverse phase preparative HPLC (eluted with acetonitrile/water containing 0.1% ammonia) to afford the title compound.

$^1$H NMR (400 MHz, DMSO-d$_6$) δ ppm 1.38-1.51 (m, 1H), 1.52-1.62 (m, 1H), 1.63-1.76 (m, 2H), 1.91-2.03 (m, 1H), 2.05 (s, 3H), 2.14-2.27 (m, 1H), 4.06-4.18 (m, 1H), 4.21-4.33 (m, 1H), 6.60-6.64 (m, 1H), 7.37-7.45 (m, 1H), 7.45-7.55 (m, 2H), 7.57-7.65 (m, 1H), 7.71-7.80 (m, 3H), 8.19-8.22 (m, 1H), 8.49-8.52 (m, 1H)
MS ES+: 431

Example 109

N-[(1S,2S)-2-{[3-Cyclopropyl-5-(trifluoromethyl)pyrazin-2-yl]amino}cyclopentyl]-2-(2H-1,2,3-triazol-2-yl)benzamide

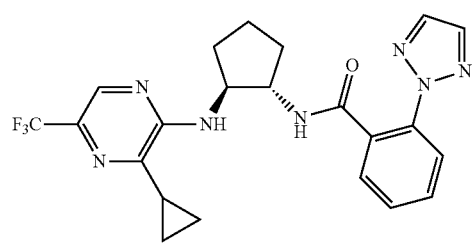 [SMILES: O=C(N[C@H]1CCC[C@@H]1Nc1ncc(C(F)(F)F)nc1C1CC1)c1ccccc1-n1nccn1]

A mixture of N-[(1S,2S)-2-{[3-chloro-5-(trifluoromethyl)pyrazin-2-yl]amino}cyclopentyl]-2-(2H-1,2,3-triazol-2-yl)benzamide (Intermediate 29; 170 mg, 0.38 mmol), cyclopropylboronic acid (CAS number 411235-57-9; 97 mg, 1.13 mmol), potassium carbonate (aq. 2 M, 752 µl, 1.51 mmol) and tetrakis(triphenylphosphine)palladium (44 mg, 0.038 mmol) in 1,4-dioxane (1.3 ml) was sealed, purged and evacuated with nitrogen and then subjected to microwave irradiation 120° C. for 1 hour. The reaction was partitioned between ethyl acetate and water, washed with water, brine, dried over magnesium sulfate and concentrated in vacuo. This was then purified by reverse phase preparative HPLC (eluted with acetonitrile/water containing 0.1% ammonia) to afford the title compound.
$^1$H NMR (400 MHz, DMSO-d$_6$) δ ppm 0.81-0.89 (m, 1H), 0.89-1.05 (m, 3H), 1.45-1.64 (m, 2H), 1.65-1.77 (m, 2H), 1.96-2.07 (m, 1H), 2.10-2.23 (m, 2H), 4.15-4.25 (m, 1H), 4.29-4.40 (m, 1H), 7.41-7.46 (m, 1H), 7.47-7.54 (m, 2H), 7.57-7.64 (m, 1H), 7.74-7.78 (m, 1H), 7.81 (s, 2H), 8.20 (s, 1H), 8.50-8.53 (m, 1H)
MS ES+: 458

Example 110

N-[(1S,2S)-2-{[3-(Propan-2-yl)-5-(trifluoromethyl)pyrazin-2-yl]amino}cyclopentyl]-2-(2H-1,2,3-triazol-2-yl)benzamide

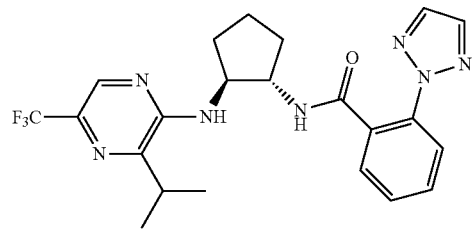 [SMILES: CC(C)c1nc(C(F)(F)F)cnc1N[C@H]1CCC[C@@H]1NC(=O)c1ccccc1-n1nccn1]

Prepared according to the procedure for N-[(1S,2S)-2-{[3-cyclopropyl-5-(trifluoromethyl)pyrazin-2-yl]amino}cyclopentyl]-2-(2H-1,2,3-triazol-2-yl)benzamide (Example 109) from N-[(1S,2S)-2-{[3-chloro-5-(trifluoromethyl)pyrazin-2-yl]amino}cyclopentyl]-2-(2H-1,2,3-triazol-2-yl)benzamide (Intermediate 29; 170 mg, 0.38 mmol) and 4,4,5,5-tetramethyl-2-(prop-1-en-2-yl)-1,3,2-dioxaborolane (CAS number 126726-62-3; 190 mg, 1.13 mmol) except this was then dissolved in methanol (1.4 ml) and to this was then added palladium on carbon (10% wt, 50% wet) (15 mg, 0.014 mmol) and the resulting mixture was stirred under a balloon of hydrogen gas for 2 hours. The reaction was filtered through diatomaceous earth (commercially sold under the trade mark "Celite") and concentrated in vacuo to afford the title compound.

$^1$H NMR (400 MHz, DMSO-d$_6$) δ ppm 1.11-1.15 (m, 3H), 1.14-1.17 (m, 3H), 1.42-1.63 (m, 2H), 1.63-1.77 (m, 2H), 1.93-2.05 (m, 1H), 2.10-2.22 (m, 1H), 3.11-3.22 (m, 1H), 4.14-4.26 (m, 1H), 4.30-4.41 (m, 1H), 7.27-7.29 (m, 1H), 7.36-7.43 (m, 1H), 7.44-7.52 (m, 1H), 7.56-7.65 (m, 1H), 7.73-7.82 (m, 3H), 8.27 (s, 1H), 8.48-8.51 (m, 1H)

MS ES$^+$: 460

Example 111

N-[(1S,2S)-2-{[3-Ethyl-5-(trifluoromethyl)pyrazin-2-yl]amino}cyclopentyl]-2-(2H-1,2,3-triazol-2-yl)benzamide

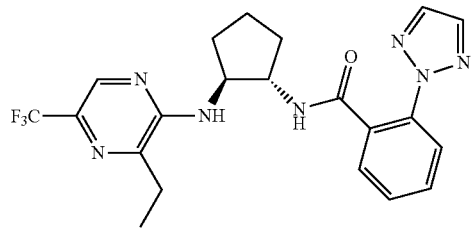 [SMILES: CCc1nc(C(F)(F)F)cnc1N[C@H]1CCC[C@@H]1NC(=O)c1ccccc1-n1nccn1]

Prepared according to the procedure for N-[(1S,2S)-2-{[3-cyclopropyl-5-(trifluoromethyl)pyrazin-2-yl]amino}cyclopentyl]-2-(2H-1,2,3-triazol-2-yl)benzamide (Example 109) from N-[(1S,2S)-2-{[3-chloro-5-(trifluoromethyl)pyrazin-2-yl]amino}cyclopentyl]-2-(2H-1,2,3-triazol-2-yl)benzamide (Intermediate 29; 170 mg, 0.38 mmol) and 2-ethenyl-4,4,5,5-tetramethyl-1,3,2-dioxaborolane (CAS number 75927-49-0; 174 mg, 1.13 mmol) except this was then dissolved in methanol (1.4 ml) and to this was then added palladium on carbon (10% wt, 50% wet) (15 mg, 0.014 mmol) and the resulting mixture was stirred under a balloon of hydrogen gas for 2 hours. The reaction was filtered through diatomaceous earth (commercially sold under the trade mark "Celite") and concentrated in vacuo to afford the title compound.

$^1$H NMR (400 MHz, DMSO-d$_6$) δ ppm 1.15-1.19 (m, 3H), 1.42-1.65 (m, 2H), 1.64-1.77 (m, 2H), 1.93-2.05 (m, 1H), 2.10-2.22 (m, 1H), 2.55-2.70 (m, 2H), 4.12-4.23 (m, 1H), 4.28-4.40 (m, 1H), 7.21-7.25 (m, 1H), 7.40-7.45 (m, 1H), 7.46-7.53 (m, 1H), 7.57-7.65 (m, 1H), 7.72-7.80 (m, 3H), 8.28 (s, 1H), 8.51-8.55 (m, 1H)

MS ES$^+$: 446

Example 112

N-[(1S,2S)-2-[(5-Cyclopropylpyrazin-2-yl)amino]cyclopentyl]-2-(2H-1,2,3-triazol-2-yl)benzamide

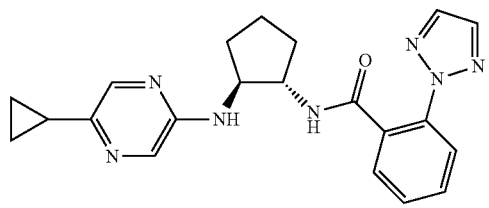 [SMILES: O=C(N[C@H]1CCC[C@@H]1Nc1cnc(C2CC2)cn1)c1ccccc1-n1nccn1]

A mixture of N-[(1S,2S)-2-[(5-bromopyrazin-2-yl)amino]cyclopentyl]-2-(2H-1,2,3-triazol-2-yl)benzamide and N-[(1S,2S)-2-[(5-chloropyrazin-2-yl)amino]cyclopentyl]-2-(2H-1,2,3-triazol-2-yl)benzamide (Intermediate 30a and 30b; 100 mg, 0.23 mmol), cyclopropylboronic acid (CAS number 411235-57-9; 60 mg, 0.70 mmol), sodium carbonate (aq. 2 M, 350 µl, 0.70 mmol) and tetrakis(triphenylphosphine)palladium (27 mg, 0.023 mmol) in 1,4-dioxane (778 µl) was sealed, purged and evacuated with nitrogen and then subjected to microwave irradiation at 100° C. for 1 hour. To this was then added further cyclopropylboronic acid (CAS number 411235-57-9; 60 mg, 0.70 mmol) and tetrakis(triphenylphosphine)palladium (27 mg, 0.023 mmol). The reaction was sealed, purged and evacuated with nitrogen and again subjected to microwave irradiation at 140° C. for 20 minutes. The reaction was partitioned between ethyl acetate and water, washed with water, brine, dried over magnesium sulfate and concentrated in vacuo. The resulting residue was purified by column chromatography (silica, 0-100% ethyl acetate/petrol) and then purified by reverse phase preparative HPLC (eluted with acetonitrile/water containing 0.1% formic acid) and further purified by column chromatography (basic silica, 0-100% ethyl acetate/petrol) to afford the title compound.

$^1$H NMR (400 MHz, DCM-d$_2$) δ ppm 0.77-0.92 (m, 4H), 1.40-1.60 (m, 2H), 1.68-1.94 (m, 3H), 2.14-2.29 (m, 2H), 3.80-3.91 (m, 1H), 3.99-4.10 (m, 1H), 6.65-6.73 (m, 1H), 7.43-7.59 (m, 4H), 7.64 (s, 2H), 7.68-7.72 (m, 1H), 7.74-7.78 (m, 1H) and 7.84 (br. s., 1H).

MS ES$^+$: 390

Example 113

N-[(1S,2S)-2-{[5-(Propan-2-yl)pyrazin-2-yl]amino}cyclopentyl]-2-(2H-1,2,3-triazol-2-yl)benzamide

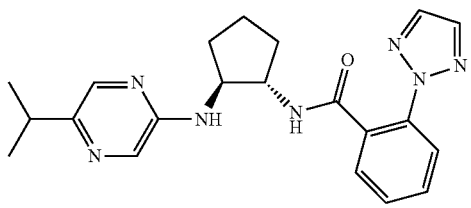 [SMILES: CC(C)c1cnc(N[C@H]2CCC[C@@H]2NC(=O)c2ccccc2-n2nccn2)cn1]

Prepared according to the procedure for N-[(1S,2S)-2-[(5-cyclopropylpyrazin-2-yl)amino]cyclopentyl]-2-(2H-1,2,3-triazol-2-yl)benzamide (Example 112) from N-[(1S,2S)-2-[(5-bromopyrazin-2-yl)amino]cyclopentyl]-2-(2H-1,2,3- triazol-2-yl)benzamide and N-[(1S,2S)-2-[(5-chloropyrazin-2-yl)amino]cyclopentyl]-2-(2H-1,2,3-triazol-2-yl) benzamide (Intermediate 30a and 30b; 100 mg, 0.23 mmol) and 4,4,5,5-tetramethyl-2-(prop-1-en-2-yl)-1,3,2-dioxaborolane (CAS number 126726-62-3; 165 mg, 0.98 mmol) except this was purified only by column chromatography (silica, 0-100% ethyl acetate/petrol) and then was dissolved in ethanol (2.5 ml). To this was then added palladium on carbon (10% wt, 50% wet) (26 mg, 0.025 mmol) and the resulting mixture was stirred under a balloon of hydrogen gas for 2 hours. The reaction was filtered through diatomaceous earth (commercially sold under the trade mark "Celite") and concentrated in vacuo. This was purified by column chromatography (basic silica, 0-100% ethyl acetate/petrol) to afford the title compound.

$^1$H NMR (400 MHz, DMSO-d$_6$) δ ppm 1.13-1.20 (m, 6H), 1.37-1.57 (m, 2H), 1.58-1.72 (m, 2H), 1.93-2.07 (m, 2H), 2.81-2.91 (m, 1H), 3.95-4.09 (m, 2H), 6.72-6.78 (m, 1H), 7.40-7.44 (m, 1H), 7.46-7.51 (m, 1H), 7.57-7.62 (m, 1H), 7.75-7.78 (m, 1H), 7.80-7.82 (m, 1H), 7.92-7.93 (m, 1H), 7.94 (s, 2H), 8.35-8.39 (m, 1H).

MS ES$^+$: 392

Example 114

N-[(1S,2S)-2-[(5-Ethylpyrazin-2-yl)amino]cyclopentyl]-2-(2H-1,2,3-triazol-2-yl)benzamide

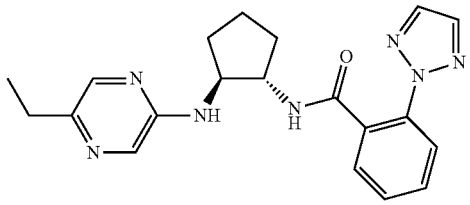 [SMILES: CCc1cnc(N[C@H]2CCC[C@@H]2NC(=O)c2ccccc2-n2nccn2)cn1]

Prepared according to the procedure for N-[(1S,2S)-2-[(5-cyclopropylpyrazin-2-yl)amino]cyclopentyl]-2-(2H-1,2,3-triazol-2-yl)benzamide (Example 112) from N-[(1S,2S)-2-[(5-bromopyrazin-2-yl)amino]cyclopentyl]-2-(2H-1,2,3-triazol-2-yl)benzamide and N-[(1S,2S)-2-[(5-chloropyrazin-2-yl)amino]cyclopentyl]-2-(2H-1,2,3-triazol-2-yl) benzamide (Intermediate 30a and 30b; 100 mg, 0.23 mmol) and 2-ethenyl-4,4,5,5-tetramethyl-1,3,2-dioxaborolane (CAS number 75927-49-0; 151 mg, 0.98 mmol) except this was purified only by column chromatography (silica, 0-100% ethyl acetate/petrol) and then was dissolved in ethanol (1.4 ml). To this was then added palladium on carbon (10% wt, 50% wet) (15 mg, 0.014 mmol) and the resulting mixture was stirred under a balloon of hydrogen gas for 2 hours. The reaction was filtered through diatomaceous earth (commercially sold under the trade mark "Celite") and concentrated in vacuo. This was purified by column chromatography (basic silica, 0-100% ethyl acetate/petrol) to afford the title compound.

$^1$H NMR (400 MHz, DCM-d$_2$) δ ppm 1.17-1.25 (m, 3H), 1.42-1.67 (m, 2H), 1.68-1.94 (m, 3H), 2.15-2.29 (m, 2H), 2.59-2.68 (m, 2H), 3.95 (br. s., 1H), 4.02-4.13 (m, 1H), 6.77 (br. s., 1H), 7.43-7.69 (m, 6H), 7.74-7.80 (m, 1H) and 8.07 (br. s., 1H).

MS ES$^+$: 378

Example 115

2-(2H-1,2,3-Triazol-2-yl)-N-[(1S,2S)-2-{[5-(trifluoromethoxy)pyridin-2-yl]amino}cyclopentyl]benzamide

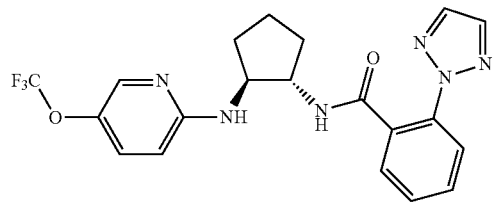 [SMILES: O=C(N[C@H]1CCC[C@@H]1Nc1ccc(OC(F)(F)F)cn1)c1ccccc1-n1nccn1]

A mixture of N-[(1S,2S)-2-aminocyclopentyl]-2-(2H-1,2,3-triazol-2-yl)benzamide hydrochloride (Intermediate 4; 75 mg, 0.24 mmol), 2-bromo-5-(trifluoromethoxy)pyridine (CAS number 888327-36-4; 59 mg, 0.24 mmol), BINAP (15 mg, 0.024 mmol), tris(dibenzylideneacetone)dipalladium(0) (11 mg, 0.012 mmol) and sodium tert-butoxide (33 mg, 0.34 mmol) in dry toluene (2.4 ml) was sealed, evacuated and purged with nitrogen and heated at 110° C. for 17 hours. The reaction was partitioned between ethyl acetate and water, washing with water, brine, filtered through a hydrophobic frit and concentrated in vacuo. The residue was purified by column chromatography (silica, 0-100% ethyl acetate/petrol) to afford the title compound.

$^1$H NMR (400 MHz, DMSO-d$_6$) δ ppm 1.37-1.58 (m, 2H), 1.59-1.73 (m, 2H), 1.92-2.08 (m, 2H), 3.96-4.08 (m, 2H), 6.58-6.65 (m, 1H), 6.81-6.90 (m, 1H), 7.40-7.46 (m, 2H), 7.46-7.53 (m, 1H), 7.56-7.65 (m, 1H), 7.74-7.81 (m, 1H), 7.93-8.01 (m, 3H), 8.33-8.42 (m, 1H)

MS ES$^+$: 433

Example 117

5-Chloro-2-(2H-1,2,3-triazol-2-yl)-N-[(1S,2S)-2-{[5-(trifluoromethoxy)pyridin-2-yl]amino}cyclopentyl]benzamide

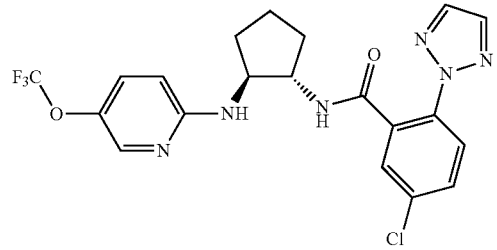 [SMILES: O=C(N[C@H]1CCC[C@@H]1Nc1ccc(OC(F)(F)F)cn1)c1cc(Cl)ccc1-n1nccn1]

A solution of N-[(1S,2S)-2-aminocyclopentyl]-5-chloro-2-(2H-1,2,3-triazol-2-yl)benzamide hydrochloride (Intermediate 31; 120 mg, 0.35 mmol), 2-bromo-5-(trifluoromethoxy) pyridine (CAS number 888327-36-4; 127 mg, 0.53 mmol) and potassium tert-butoxide (118 mg, 1.05 mmol) in toluene (10 ml) was degassed under a nitrogen atmosphere for 15 minutes. To this was then added BINAP (22 mg, 0.035 mmol) and tris(dibenzylideneacetone)dipalladium(0) (32 mg, 0.035 mmol) and the reaction mixture was again degassed for 15 minutes. The reaction mixture was heated at 120° C. for 15 hours and then was diluted with water, filtered through diatomaceous earth (commercially sold under the trade mark "Celite") and extracted with ethyl acetate. The organics were washed with water, brine, dried over sodium sulfate and concentrated in vacuo. The crude product was purified by column chromatography (silica, 0-2.5% methanol/DCM) to afford the title compound.

¹H NMR (400 MHz, DMSO-d) δ ppm 1.42-1.57 (m, 2H), 1.64-1.67 (m, 2H), 1.96-2.04 (m, 2H), 4.00-4.07 (m, 2H), 6.60-6.63 (m, 1H), 6.91-6.92 (m, 1H), 7.44-7.48 (m, 2H), 7.67-7.70 (m, 1H), 7.81-7.83 (m, 1H), 7.99-8.01 (m, 3H), 8.56-8.57 (m, 1H)

MS ES⁺: 468

Example 118

N-[(1S,2S)-2-[(5-Bromopyridin-2-yl)amino]cyclopentyl]-2-(2H-1,2,3-triazol-2-yl)benzamide

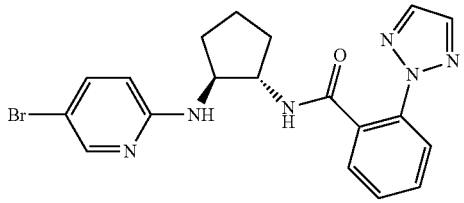 [SMILES: O=C(N[C@H]1CCC[C@@H]1Nc1ccc(Br)cn1)c1ccccc1-n1nccn1]

A mixture of N-[(1S,2S)-2-aminocyclopentyl]-2-(2H-1,2,3-triazol-2-yl)benzamide hydrochloride (Intermediate 4; 300 mg, 0.98 mmol), 5-bromo-2-chloropyridine (CAS number 53939-30-3; 225 mg, 1.17 mmol), sodium tert-butoxide (150 mg, 1.56 mmol), BINAP (24 mg, 0.039 mmol) and tris(dibenzylideneacetone)dipalladium(0) (18 mg, 0.019 mmol) in toluene (4 ml) was heated at 85° C. overnight. The mixture was partitioned between ethyl acetate (10 ml) and water (10 ml). The aqueous layer was further extracted ici with ethyl acetate (3×20 ml). The combined organics were washed with water (2×20 ml), filtered through a hydrophobic frit and concentrated in vacuo. The crude product was purified by column chromatography (silica, 0-100% ethyl acetate/petrol) to afford the title compound.

¹H NMR (300 MHz, DCM-d₂) δ ppm 1.40-1.52 (m, 2H), 1.66-1.88 (m, 2H), 2.08-2.30 (m, 2H), 3.72-3.90 (m, 1H), 3.94-4.12 (m, 1H), 5.00-5.19 (m, 1H), 6.34-6.45 (m, 1H), 6.59-6.79 (m, 1H), 7.39-7.61 (m, 4H), 7.66 (s, 2H), 7.73-7.79 (m, 1H), 7.92-7.96 (m, 1H).

MS ES⁺: 427, 429

Example 119

N-[(1S,2S)-2-[(5-Bromo-3-methoxypyridin-2-yl)amino]cyclopentyl]-2-(2H-1,2,3-triazol-2-yl)benzamide

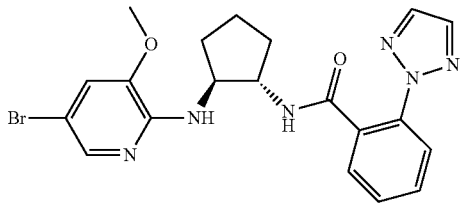 [SMILES: COc1cc(Br)cnc1N[C@H]1CCC[C@@H]1NC(=O)c1ccccc1-n1nccn1]

Prepared according to the procedure for N-[(1S,2S)-2-[(5-bromopyridin-2-yl)amino]cyclopentyl]-2-(2H-1,2,3-triazol-2-yl)benzamide (Example 118) from N-[(1S,2S)-2-aminocyclopentyl]-2-(2H-1,2,3-triazol-2-yl)benzamide hydrochloride (Intermediate 4; 300 mg, 0.98 mmol) and 5-bromo-2-chloro-3-methoxypyridine (CAS number 286947-03-3; 260 mg, 1.17 mmol) except after heating overnight, to this was then added further 5-bromo-2-chloro-3-methoxypyridine (CAS number 286947-03-3; 260 mg, 1.17 mmol), sodium tert-butoxide (150 mg, 1.56 mmol), BINAP (24 mg, 0.039 mmol) and tris(dibenzylideneacetone)dipalladium(0) (18 mg, 0.019 mmol) and the reaction was heated at 100° C. for 3 hours. The mixture was partitioned between ethyl acetate (10 ml) and water (10 ml). The aqueous layer was further extracted with ethyl acetate (3×10 ml). The combined organics were washed with brine, filtered through a hydrophobic frit and concentrated in vacuo. The crude product was purified by column chromatography (silica, 0-100% ethyl acetate/petrol) to afford the title compound.

¹H NMR (400 MHz, DCM-d₂) δ ppm 1.43-1.52 (m, 1H), 1.55-1.60 (m, 1H), 1.73-1.84 (m, 2H), 2.12-2.23 (m, 1H), 2.29-2.40 (m, 1H), 3.82 (s, 3H), 3.84-3.94 (m, 1H), 3.97-4.09 (m, 1H), 5.23-5.30 (m, 1H), 6.90-6.94 (m, 1H), 7.25-7.35 (m, 1H), 7.41-7.49 (m, 3H), 7.51-7.59 (m, 1H), 7.65 (s, 2H), 7.73-7.78 (m, 1H)

MS ES⁺: 457, 459

Example 121

2-(2H-1,2,3-Triazol-2-yl)-N-[(1S,2S)-2-{[4-(trifluoromethyl)pyridin-2-yl]amino}cyclopentyl]benzamide

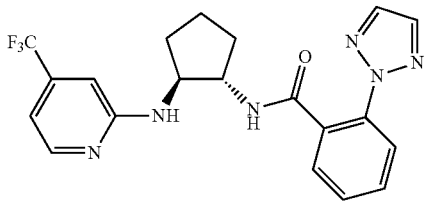 [SMILES: O=C(N[C@H]1CCC[C@@H]1Nc1cc(C(F)(F)F)ccn1)c1ccccc1-n1nccn1]

Prepared according to the procedure for N-[(1S,2S)-2-[(5-bromopyridin-2-yl)amino]cyclopentyl]-2-(2H-1,2,3-triazol-2-yl)benzamide (Example 118) from N-[(1S,2S)-2-aminocyclopentyl]-2-(2H-1,2,3-triazol-2-yl)benzamide hydrochloride (Intermediate 4; 200 mg, 0.65 mmol) and 2-bromo-4-(trifluoromethyl)pyridine (CAS number 175205-81-9; 147 mg, 0.650 mmol) except this was heated to 140° C. for 17 hours to afford the title compound.

¹H NMR (300 MHz, DMSO-d₆) δ ppm 1.38-1.59 (m, 2H), 1.60-1.73 (m, 2H), 1.92-2.10 (m, 2H), 3.96-4.15 (m, 2H), 6.71 (d, J=5.20 Hz, 1H), 6.85 (s, 1H), 7.03-7.11 (m, 1H), 7.39-7.54 (m, 2H), 7.55-7.64 (m, 1H), 7.73-7.80 (m, 1H), 7.94 (s, 2H), 8.17 (d, J=5.20 Hz, 1H), 8.33-8.43 (m, 1H)

MS ES⁺: 417

Example 122

N-[(1S,2S)-2-{[3-Chloro-5-(trifluoromethyl)pyridin-2-yl]amino}cyclopentyl]-3-(2H-1,2,3-triazol-2-yl)pyridine-2-carboxamide

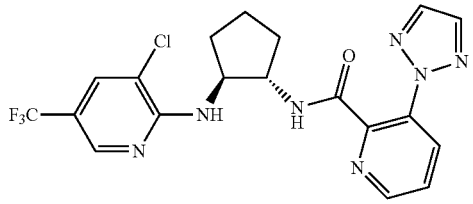

A solution of (1S,2S)-1-N-[3-chloro-5-(trifluoromethyl)pyridin-2-yl]cyclopentane-1,2-diamine hydrochloride (Intermediate 33; 100 mg, 0.32 mmol), 3-(2H-1,2,3-triazol-2-yl)pyridine-2-carboxylic acid (CAS number 1252907-86-0; 66 mg, 0.35 mmol), EDC (91 mg, 0.47 mmol), 3H-[1,2,3]triazolo[4,5-b]pyridin-3-ol (65 mg, 0.47 mmol) and triethylamine (0.132 ml, 0.95 mmol) in DCM (1 ml) was stirred at room temperature overnight. The reaction was partitioned between water (5 ml) and DCM (5 ml), filtered through a hydrophobic frit and concentrated in vacuo. The resulting residue was purified by column chromatography (silica, 0-100% ethyl acetate/petrol) to afford the title compound.

$^1$H NMR (400 MHz, DCM-$d_2$) δ ppm 1.49-1.73 (m, 2H), 1.80-1.91 (m, 2H), 2.26-2.44 (m, 2H), 4.11-4.21 (m, 1H), 4.26-4.37 (m, 1H), 6.04-6.12 (m, 1H), 7.54-7.60 (m, 1H), 7.61-7.64 (m, 1H), 7.76 (s, 2H), 7.97-8.02 (m, 1H), 8.07-8.14 (m, 1H), 8.21-8.25 (m, 1H), 8.62-8.66 (m, 1H)

MS ES$^+$: 452

Example 123

N-[(1S,2S)-2-{[3-Fluoro-5-(trifluoromethyl)pyridin-2-yl]amino}cyclopentyl]-3-(2H-1,2,3-triazol-2-yl)pyridine-2-carboxamide

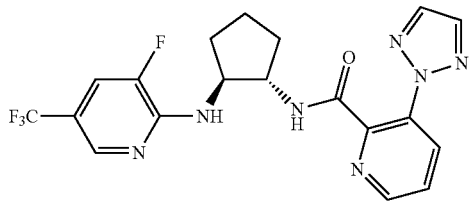 [SMILES: O=C(N[C@H]1CCC[C@@H]1Nc1ncc(C(F)(F)F)cc1F)c1ncccc1-n1nccn1]

Prepared according to the procedure for N-[(1S,2S)-2-{ [3-chloro-5-(trifluoromethyl)pyridin-2-yl]amino} cyclopentyl]-3-(2H-1,2,3-triazol-2-yl)pyridine-2-carboxamide (Example 122) from (1S,2S)-1-N-[3-fluoro-5-(trifluoromethyl)pyridin-2-yl]cyclopentane-1,2-diamine hydrochloride (Intermediate 34; 100 mg, 0.33 mmol) and 3-(2H-1,2,3-triazol-2-yl)pyridine-2-carboxylic acid (CAS number 1252907-86-0; 66 mg, 0.35 mmol) to afford the title compound.

$^1$H NMR (400 MHz, DCM-$d_2$) δ ppm 1.48-1.73 (m, 2H), 1.77-1.93 (m, 2H), 2.23-2.47 (m, 2H), 4.11-4.21 (m, 1H), 4.26-4.35 (m, 1H), 5.75-5.84 (m, 1H), 7.27-7.34 (m, 1H), 7.55-7.62 (m, 1H), 7.77 (s, 2H), 7.97-8.03 (m, 1H), 8.03-8.09 (m, 1H), 8.12 (s, 1H), 8.61-8.66 (m, 1H)

MS ES$^+$: 436

Example 124

N-[(1S,2S)-2-{[3-Methyl-5-(trifluoromethyl)pyridin-2-yl]amino}cyclopentyl]-3-(2H-1,2,3-triazol-2-yl)pyridine-2-carboxamide

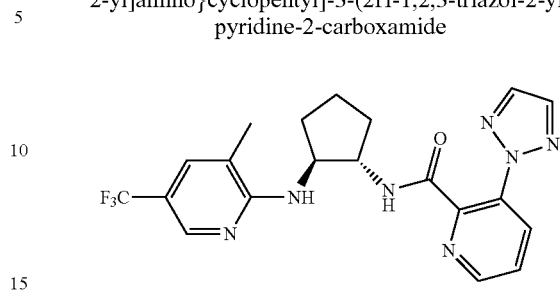

Prepared according to the procedure for N-[(1S,2S)-2-{ [3-chloro-5-(trifluoromethyl)pyridin-2-yl]amino} cyclopentyl]-3-(2H-1,2,3-triazol-2-yl)pyridine-2-carboxamide (Example 122) from (1S,2S)-1-N-[3-methyl-5-(trifluoromethyl)pyridin-2-yl]cyclopentane-1,2-diamine hydrochloride (Intermediate 35; 100 mg, 0.34 mmol) and 3-(2H-1,2,3-triazol-2-yl)pyridine-2-carboxylic acid (CAS number 1252907-86-0; 71 mg, 0.37 mmol) to afford the title compound.

$^1$H NMR (400 MHz, DMSO-$d_6$) δ ppm 1.34-1.55 (m, 1H), 1.57-1.79 (m, 3H), 1.94-2.10 (m, 4H), 2.15-2.28 (m, 1H), 4.15-4.37 (m, 2H), 6.52-6.65 (m, 1H), 7.42-7.58 (m, 1H), 7.67-7.78 (m, 1H), 7.87 (s, 2H), 8.15-8.31 (m, 2H), 8.60-8.72 (m, 1H), 8.77-8.89 (m, 1H)

MS ES$^+$: 432

Example 125

N-[(1S,2S)-2-{[3-Ethyl-5-(trifluoromethyl)pyrazin-2-yl]amino}cyclopentyl]-3-(2H-1,2,3-triazol-2-yl)pyridine-2-carboxamide

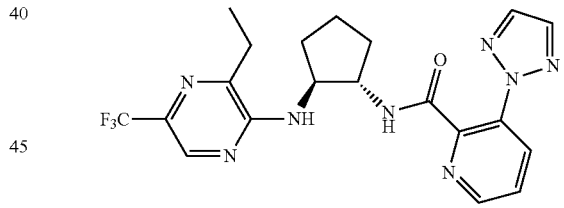

Prepared according to the procedure for N-[(1S,2S)-2-{ [3-chloro-5-(trifluoromethyl)pyridin-2-yl]amino} cyclopentyl]-3-(2H-1,2,3-triazol-2-yl)pyridine-2-carboxamide (Example 122) from (1S,2S)-1-N-[3-ethyl-5-(trifluoromethyl)pyrazin-2-yl]cyclopentane-1,2-diamine hydrochloride (Intermediate 41; 266 mg, 0.86 mmol) and 3-(2H-1,2,3-triazol-2-yl)pyridine-2-carboxylic acid (CAS number 1252907-86-0; 179 mg, 0.94 mmol) except this was further purified by reverse phase chromatography (C18 silica, 5-100% water (with 0.05% ammonia)/acetonitrile) to afford the title compound.

$^1$H NMR (400 MHz, DCM-$d_2$) δ ppm 1.20-1.27 (m, 3H), 1.39-1.52 (m, 1H), 1.63-1.76 (m, 1H), 1.81-1.92 (m, 2H), 2.18-2.29 (m, 1H), 2.42-2.59 (m, 3H), 4.00-4.11 (m, 1H), 4.26-4.37 (m, 1H), 6.38-6.47 (m, 1H), 7.55-7.61 (m, 1H), 7.70 (s, 2H), 7.75-7.83 (m, 1H), 7.97-8.02 (m, 1H), 8.15 (s, 1H), 8.61-8.67 (m, 1H).

MS ES$^+$: 447

Example 126

N-(4,4-Difluoro-2-{[5-(trifluoromethyl)pyrazin-2-yl]amino}cyclopentyl)-2-(2H-1,2,3-triazol-2-yl)benzamide

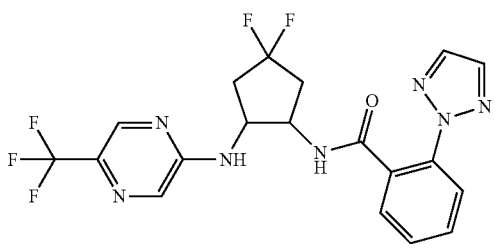 [SMILES: O=C(NC1CC(F)(F)CC1Nc1cnc(C(F)(F)F)cn1)c1ccccc1-n1nccn1]

A microwave vial was charged with N-(2-amino-4,4-difluorocyclopentyl)-2-(2H-1,2,3-triazol-2-yl)benzamide hydrochloride (Intermediate 42; 65 mg, 0.19 mmol), 2-chloro-5-(trifluoromethyl)pyrazine (CAS number 799557-87-2; 38 mg, 0.21 mmol) and DIPEA (99 µl, 0.57 mmol) in dry DMSO (630 µl). The reaction was subjected to microwave irradiation at 140° C. for 30 minutes. The reaction was partitioned between ethyl acetate and water. The organics were washed with water and brine, dried over magnesium sulfate, filtered and concentrated in vacuo. The crude material was purified by column chromatography (basic silica, 0-100% ethyl acetate/petrol) to afford the title compound.

$^1$H NMR (400 MHz, DMSO-d$_6$) δ ppm 2.00-2.22 (m, 2H), 2.56-2.76 (m, 2H), 4.35-4.53 (m, 2H), 7.38-7.42 (m, 1H), 7.47-7.52 (m, 1H), 7.59-7.65 (m, 1H), 7.76-7.81 (m, 1H), 7.93 (s, 2H), 8.05-8.08 (m, 1H), 8.16-8.25 (m, 1H), 8.40 (s, 1H), 8.62-8.69 (m, 1H).

MS ES$^+$: 454

Example 127

N-(4,4-Difluoro-2-{[5-(trifluoromethyl)pyrimidin-2-yl]amino}cyclopentyl)-2-(2H-1,2,3-triazol-2-yl)benzamide

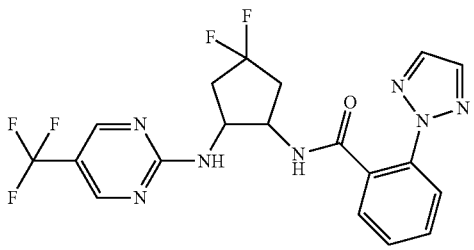

To a solution of N-(2-amino-4,4-difluorocyclopentyl)-2-(2H-1,2,3-triazol-2-yl)benzamide hydrochloride (Intermediate 42; 120 mg, 0.39 mmol) in dry DMSO (1.2 ml) was added 2-chloro-5-(trifluoromethyl)pyrimidine (CAS number 69034-12-4; 70 mg, 0.384 mmol) and DIPEA (183 µl, 1.047 mmol). The reaction mixture was heated in a sealed vial at 140° C. for 17 hours then partitioned between ethyl acetate and water. The organics were washed with water, filtered through a hydrophobic frit and concentrated in vacuo. The crude material was purified by column chromatography (basic silica, 0-100% ethyl acetate/petrol) then was chirally separated using SFC (Waters prep30/MS system using 20% Isopropanol, Daicel AD 10 mm id×250 mm long columns at 30 ml/min, 40° C. and 100 bar) to afford the title compound as a single enantiomer.

$^1$H NMR (400 MHz, DMSO-d$_6$) δ ppm 2.06-2.25 (m, 2H), 2.56-2.70 (m, 2H), 4.42-4.59 (m, 2H), 7.36-7.42 (m, 1H), 7.46-7.52 (m, 1H), 7.58-7.65 (m, 1H), 7.76-7.81 (m, 1H), 7.93 (s, 2H), 8.20-8.24 (m, 1H), 8.60-8.70 (m, 3H)

MS ES$^+$: 454

Example 128

N-(4,4-Difluoro-2-{[5-(trifluoromethyl)pyridin-2-yl]amino}cyclopentyl)-2-(2H-1,2,3-triazol-2-yl)benzamide

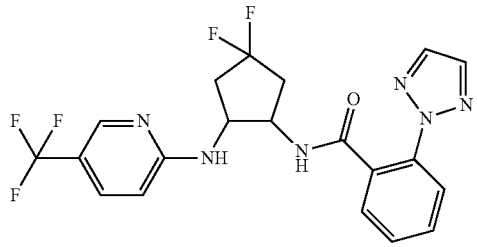 [SMILES: O=C(NC1CC(F)(F)CC1Nc1ccc(C(F)(F)F)cn1)c1ccccc1-n1nccn1]

To a solution of N-(2-amino-4,4-difluorocyclopentyl)-2-(2H-1,2,3-triazol-2-yl)benzamide hydrochloride (Intermediate 42; 120 mg, 0.349 mmol) in dry DMSO (1.2 ml) was added 2-chloro-5-(trifluoromethyl)pyridine (CAS number 52334-81-3; 70 mg, 0.38 mmol) and DIPEA (183 µl, 1.05 mmol). The reaction mixture was heated in a sealed vial at 140° C. for 17 hours then partitioned between ethyl acetate and water. The organics were washed with water, filtered through a hydrophobic frit and concentrated in vacuo. The crude material was purified by column chromatography (basic silica, 0-100% ethyl acetate in petrol) and then was chirally separated using SFC (Waters prep30/MS system using 10% Ethanol, Daicel AD 10 mm id×250 mm long columns at 30 ml/min, 40° C. and 100 bar) to afford the title compound as a single enantiomer.

$^1$H NMR (400 MHz, DCM-d$_2$) δ ppm 2.02-2.23 (m, 2H), 2.73-2.94 (m, 2H), 4.23-4.39 (m, 2H), 5.90 (br. s, 1H), 6.56-6.63 (m, 1H), 6.84-6.96 (m, 1H), 7.42-7.53 (m, 2H), 7.53-7.67 (m, 4H), 7.78-7.83 (m, 1H), 8.21 (s, 1H)

MS ES$^+$: 453

Example 129

N-(4,4-Difluoro-2-{[5-(trifluoromethyl)pyridin-2-yl]amino}cyclopentyl)-2-(2H-1,2,3-triazol-2-yl)benzamide

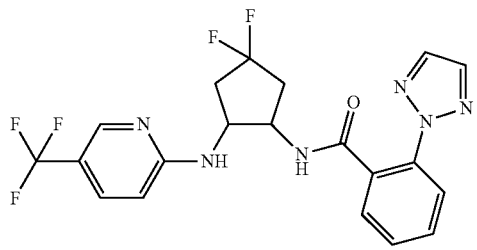 [SMILES: O=C(NC1CC(F)(F)CC1Nc1ccc(C(F)(F)F)cn1)c1ccccc1-n1nccn1]

Prepared according to the procedure for N-(4,4-difluoro-2-{[5-(trifluoromethyl)pyridin-2-yl]amino}cyclopentyl)-2-(2H-1,2,3-triazol-2-yl)benzamide (Example 128) from N-(2-amino-4,4-difluorocyclopentyl)-2-(2H-1,2,3-triazol-2-yl)benzamide hydrochloride (Intermediate 42; 120 mg, 0.349 mmol) and 2-chloro-5-(trifluoromethyl)pyridine (CAS number 52334-81-3; 70 mg, 0.38 mmol) and this was then chirally separated using SFC to afford the title compound as a single enantiomer.

$^1$H NMR (400 MHz, DCM-d$_2$) δ ppm 2.01-2.22 (m, 2H), 2.74-2.92 (m, 2H), 4.25-4.39 (m, 2H), 6.06 (br. s, 1H), 6.54-6.65 (m, 1H), 6.81-6.94 (m, 1H), 7.42-7.53 (m, 2H), 7.54-7.67 (m, 4H), 7.77-7.83 (m, 1H), 8.20 (s, 1H)

MS ES$^+$: 453

Example 130

N-(4,4-Difluoro-2-{[5-(trifluoromethyl)pyrazin-2-yl]amino}cyclopentyl)-2-(2H-1,2,3-triazol-2-yl)benzamide

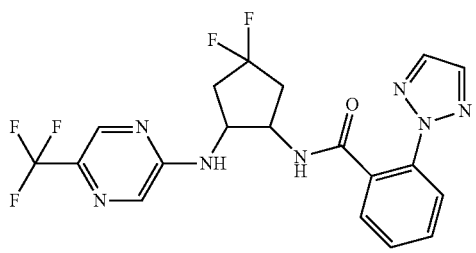 [SMILES: O=C(NC1CC(F)(F)CC1Nc1cnc(C(F)(F)F)cn1)c1ccccc1-n1nccn1]

Method 1:
Prepared according to the procedure for N-(4,4-difluoro-2-{[5-(trifluoromethyl)pyrazin-2-yl]amino}cyclopentyl)-2-(2H-1,2,3-triazol-2-yl)benzamide (Example 126) from N-(2-amino-4,4-difluorocyclopentyl)-2-(2H-1,2,3-triazol-2-yl)benzamide hydrochloride (Intermediate 42; 65 mg, 0.19 mmol) and 2-chloro-5-(trifluoromethyl)pyrazine (CAS number 799557-87-2; 38 mg, 0.21 mmol) and this was then chirally separated using SFC (Waters prep30/MS system using 16% Isopropanol, Phenomenex Lux-C-4 10 mm id×250 mm long columns at 30 ml/min, 40° C. and 100 bar) to afford the title compound as a single enantiomer.

$^1$H NMR (400 MHz, DMSO-d$_6$) δ ppm 1.98-2.27 (m, 2H), 2.58-2.78 (m, 2H), 4.32-4.57 (m, 2H), 7.36-7.45 (m, 1H), 7.46-7.54 (m, 1H), 7.58-7.69 (m, 1H), 7.75-7.84 (m, 1H), 7.94 (s, 2H), 8.03-8.12 (m, 1H), 8.16-8.29 (m, 1H), 8.41 (s, 1H), 8.67 (s, 1H)

MS ES$^+$: 454

Method 2:
To a mixture of 4,4-difluoro-1-N-[5-(trifluoromethyl)pyrazin-2-yl]cyclopentane-1,2-diamine (Intermediate 45; 35 mg, 0.12 mmol) in dry DCM (400 μl) was added 2-(2H-1,2,3-triazol-2-yl)benzoic acid (CAS number 1001401-62-2; 28 mg, 0.15 mmol), EDC (71 mg, 0.37 mmol), 3H-[1,2,3]triazolo[4,5-b]pyridin-3-ol (51 mg, 0.38 mmol) and DIPEA (65 μl, 0.37 mmol). The reaction was stirred at room temperature for 72 hours then partitioned between ethyl acetate and water. The organics were washed with water and brine, dried over sodium sulfate, filtered and concentrated in vacuo. The crude material was purified by column chromatography (silica, 0-100% ethyl acetate in petrol) then this was then chirally separated using SFC (Waters prep30/MS system using 16% Isopropanol, Phenomenex Lux-C-4 10 mm id×250 mm long columns at 30 ml/min, 40° C. and 100 bar) to afford the title compound as a single enantiomer.

$^1$H NMR (400 MHz, DMSO-d$_6$) δ ppm 1.98-2.27 (m, 2H), 2.58-2.78 (m, 2H), 4.32-4.57 (m, 2H), 7.36-7.45 (m, 1H), 7.46-7.54 (m, 1H), 7.58-7.69 (m, 1H), 7.75-7.84 (m, 1H), 7.94 (s, 2H), 8.03-8.12 (m, 1H), 8.16-8.29 (m, 1H), 8.41 (s, 1H), 8.67 (s, 1H)

MS ES$^+$: 454

Example 131

N-[(1S,2S)-4,4-Difluoro-2-{[5-(trifluoromethoxy)pyridin-2-yl]amino}cyclopentyl]-2-(2H-1,2,3-triazol-2-yl)benzamide

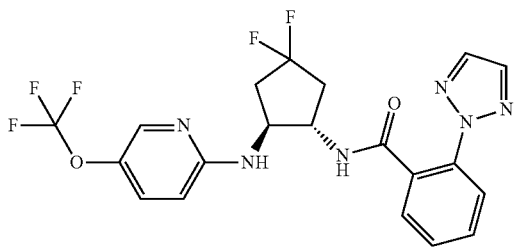 [SMILES: O=C(N[C@H]1CC(F)(F)C[C@@H]1Nc1ccc(OC(F)(F)F)cn1)c1ccccc1-n1nccn1]

To a solution of N-[(1S,2S)-2-amino-4,4-difluorocyclopentyl]-2-(2H-1,2,3-triazol-2-yl)benzamide (Intermediate 46; 50 mg, 0.16 mmol) in dry toluene (1.6 ml) was added 2-bromo-5-(trifluoromethoxy)pyridine (CAS number 888327-36-4; 40 mg, 0.17 mmol), BINAP (10 mg, 0.016 mmol), tris(dibenzylideneacetone)dipalladium(0) (8 mg, 8.74 μmol) and sodium tert-butoxide (22 mg, 0.23 mmol). The reaction was placed under an atmosphere of nitrogen, sealed and heated at 120° C. for 17 hours then partitioned between ethyl acetate and water. The organics were washed with water and brine, dried over sodium sulfate, filtered and concentrated in vacuo. The crude material was purified by column chromatography (silica, 10-70% ethyl acetate/petrol) to afford the title compound.

$^1$H NMR (400 MHz, DMSO-d6) δ ppm 1.87-2.22 (m, 2H), 2.53-2.78 (m, 2H), 4.23-4.43 (m, 2H), 6.52-6.66 (m, 1H), 7.07-7.16 (m, 1H), 7.34-7.41 (m, 1H), 7.45-7.53 (m, 2H), 7.57-7.64 (m, 1H), 7.77-7.82 (m, 1H), 7.95 (s, 2H), 8.00-8.06 (m, 1H), 8.58-8.66 (m, 1H)

MS ES$^+$: 469

Example 132

N-[(1S,2S)-4,4-Difluoro-2-{[3-fluoro-5-(trifluoromethyl)pyridin-2-yl]amino}cyclopentyl]-2-(2H-1,2,3-triazol-2-yl)benzamide

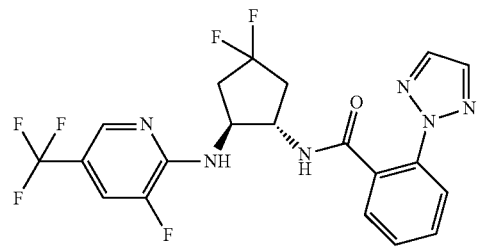 [SMILES: O=C(N[C@H]1CC(F)(F)C[C@@H]1Nc1ncc(C(F)(F)F)cc1F)c1ccccc1-n1nccn1]

A microwave vial was charged with N-[(1S,2S)-2-amino-4,4-difluorocyclopentyl]-2-(2H-1,2,3-triazol-2-yl)benzamide (Intermediate 46; 50 mg, 0.15 mmol), 2,3-difluoro-5-(trifluoromethyl)pyridine (CAS number 89402-42-6; 29 mg, 0.16 mmol) and DIPEA (26 µl, 0.15 mmol) in dry DMSO (485 µl). The reaction mixture was subjected to microwave irradiation at 120° C. for 30 minutes then partitioned between ethyl acetate and water. The organics were washed with water and brine, dried over sodium sulfate, filtered and concentrated in vacuo. The crude material was purified by column chromatography (silica, 0-60% ethyl acetate/petrol) to afford the title compound.

¹H NMR (400 MHz, DMSO-d6) δ ppm 2.06-2.28 (m, 2H), 2.53-2.76 (m, 2H), 4.46-4.69 (m, 2H), 7.32-7.38 (m, 1H), 7.42-7.51 (m, 1H), 7.55-7.65 (m, 2H), 7.74-7.85 (m, 2H), 7.89 (s, 2H), 8.21 (s, 1H), 8.60-8.68 (m, 1H)

MS ES⁺: 471

Example 135

2-(5-Ethoxypyrimidin-2-yl)-N-[(1S,2S)-2-{[5-(trifluoromethyl)pyrazin-2-yl]amino}cyclopentyl]benzamide

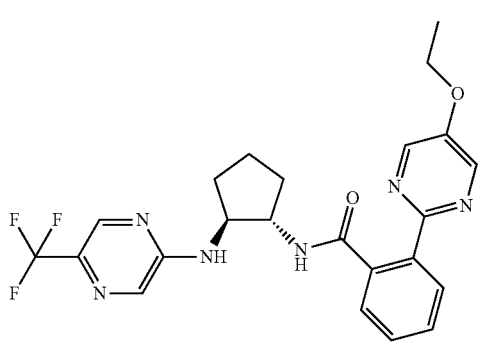 [SMILES: CCOc1cnc(-c2ccccc2C(=O)N[C@H]2CCC[C@@H]2Nc2cnc(C(F)(F)F)cn2)nc1]

A solution of (1S,2S)-1-N-[5-(trifluoromethyl)pyrazin-2-yl]cyclopentane-1,2-diamine hydrochloride (Intermediate 14; 116 mg, 0.41 mmol), 2-(5-ethoxypyrimidin-2-yl)benzoic acid (Intermediate 47; 100 mg, 0.41 mmol), 3H-[1,2,3]triazolo[4,5-b]pyridin-3-ol (84 mg, 0.61 mmol), EDC (118 mg, 0.61 mmol) and triethylamine (0.171 ml, 1.23 mmol) in dry DCM (4 ml) was stirred at room temperature for 4 hours. The reaction was partitioned between DCM and water, filtered through a hydrophobic frit and concentrated in vacuo. The crude product was purified by reverse phase preparative HPLC (eluted with acetonitrile/water with 0.1% ammonia) and then by reverse phase preparative HPLC (eluted with acetonitrile/water containing 0.1% formic acid) to afford the title compound.

¹H NMR (400 MHz, DCM-d2) δ ppm 1.40-1.43 (m, 3H), 1.46-1.91 (m, 4H), 2.14-2.23 (m, 1H), 2.35-2.44 (m, 1H), 3.86-4.06 (m, 3H), 4.25-4.34 (m, 1H), 6.38-6.42 (m, 1H), 6.67-6.72 (m, 1H), 7.40-7.55 (m, 3H), 7.83-7.87 (m, 1H), 7.98-8.02 (m, 1H), 8.16-8.25 (m, 3H)

MS ES⁺: 473

Example 136

2-Fluoro-6-methoxy-N-[(1S,2S)-2-{[5-(trifluoromethyl)pyrazin-2-yl]amino}cyclopentyl]benzamide

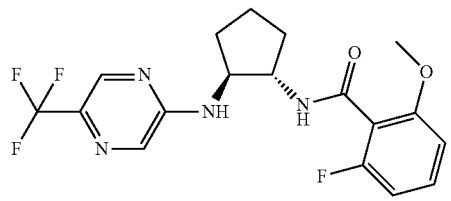 [SMILES: COc1cccc(F)c1C(=O)N[C@H]1CCC[C@@H]1Nc1cnc(C(F)(F)F)cn1]

A solution of (1S,2S)-1-N-[5-(trifluoromethyl)pyrazin-2-yl]cyclopentane-1,2-diamine hydrochloride (Intermediate 14; 14 mg, 0.05 mmol), 2-fluoro-6-methoxybenzoic acid (CAS number 137654-21-8; 8.5 mg, 0.05 mmol), TOTU (20 mg, 0.06 mmol) and 4-methylmorpholine (0.008 ml, 0.075 mmol) in DMF (0.25 ml) was stirred at room temperature for 1 hour. The reaction was then diluted with methanol and concentrated in vacuo. The resulting residue was purified by reverse phase preparative HPLC (eluted with acetonitrile/water with 0.1% ammonia) to afford the title compound.

¹H NMR (400 MHz, DCM-d2) δ ppm 1.51-1.67 (m, 2H), 1.82-1.95 (m, 2H), 2.20-2.32 (m, 1H), 2.32-2.43 (m, 1H), 3.70 (s, 3H), 4.05-4.17 (m, 1H), 4.28-4.45 (m, 1H), 6.20 (br. s., 1H), 6.35-6.53 (m, 1H), 6.66-6.76 (m, 2H), 7.24-7.36 (m, 1H), 7.98 (s, 1H), 8.21 (s, 1H)

MS ES⁺: 399

Example 137

N-[(1S,2S)-2-{[3-Methyl-5-(trifluoromethyl)pyridin-2-yl]amino}cyclopentyl]-3-(pyrimidin-2-yl)pyridine-2-carboxamide

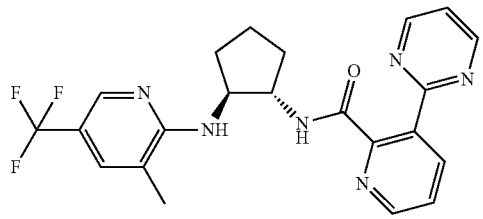 [SMILES: Cc1cc(C(F)(F)F)cnc1N[C@H]1CCC[C@@H]1NC(=O)c1ncccc1-c1ncccn1]

To a solution of 3-(pyrimidin-2-yl)pyridine-2-carboxylic acid (CAS number 1228431-21-7; 155 mg, 0.77 mmol), DIPEA (0.27 ml, 1.54 mmol) and (1S,2S)-1-N-[3-methyl-5-(trifluoromethyl)pyridin-2-yl]cyclopentane-1,2-diamine hydrochloride (Intermediate 35; 200 mg, 0.68 mmol) in DCM (3 ml) and acetonitrile (5 ml) was added HATU (293 mg, 0.77 mmol). The reaction was stirred at room temperature for 16 hours and then concentrated in vacuo. The residue was purified by reverse phase column chromatography (C18 silica, 0-100% water (0.1% formic acid)/acetonitrile) and then by reverse phase column chromatography (C18 silica, 5-95% water (0.05% ammonia)/acetonitrile) to afford the title compound.

¹H NMR (400 MHz, DMSO-d6) δ ppm 1.41-1.55 (m, 1H), 1.59-1.77 (m, 3H), 1.99 (s, 3H), 2.00-2.11 (m, 1H), 2.13-2.27 (m, 1H), 4.12-4.35 (m, 2H), 6.60-6.68 (m, 1H), 7.31-7.38 (m, 1H), 7.47-7.53 (m, 1H), 7.59-7.67 (m, 1H), 8.15-8.26 (m, 2H), 8.62-8.71 (m, 3H), 8.78-8.86 (m, 1H)
MS ES+: 443

Example 138

N-[(1S,2S)-2-{[3-Fluoro-5-(trifluoromethyl)pyridin-2-yl]amino}cyclopentyl]-2-(pyrimidin-2-yl)benzamide

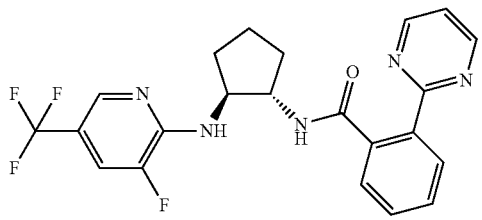 [SMILES: O=C(N[C@H]1CCC[C@@H]1Nc1ncc(C(F)(F)F)cc1F)c1ccccc1-c1ncccn1]

Prepared according to the procedure for 2-(5-Ethoxypyrimidin-2-yl)-N-[(1S,2S)-2-{[5-(trifluoromethyl)pyrazin-2-yl]amino}cyclopentyl]benzamide (Example 135) from (1S,2S)-1-N-[3-fluoro-5-(trifluoromethyl)pyridin-2-yl] cyclopentane-1,2-diamine hydrochloride (Intermediate 34: 263 mg, 1.00 mmol) and 2-(pyrimidin-2-yl)benzoic acid (CAS number 400892-62-8; 200 mg, 1.00 mmol) except after the reaction was complete it was concentrated in vacuo and the residue was purified by column chromatography (silica, 0-50% ethyl acetate/petrol) and then was purified by reverse phase column chromatography (C18 silica, 0-100% water (0.05% ammonia)/methanol) and triturated with DCM/petrol. The product was further purified by reverse phase column chromatography (C18 silica, 0-100% water (0.1% ammonia)/acetonitrile to afford the title compound.

$^1$H NMR (400 MHz, CHLOROFORM-d) δ ppm 1.49-1.66 (m, 2H), 1.73-1.92 (m, 2H), 2.29-2.48 (m, 2H), 4.09-4.30 (m, 2H), 5.80-5.97 (m, 1H), 6.68-6.80 (m, 1H), 6.99-7.11 (m, 1H), 7.28-7.33 (m, 1H), 7.40-7.58 (m, 3H), 7.95-8.03 (m, 1H), 8.03-8.10 (m, 1H), 8.54-8.65 (m, 2H)
MS ES+: 446

Example 139

5-Fluoro-N-[(1S,2S)-2-{[3-fluoro-5-(trifluoromethyl)pyridin-2-yl]amino}cyclopentyl]-2-(pyrimidin-2-yl)benzamide

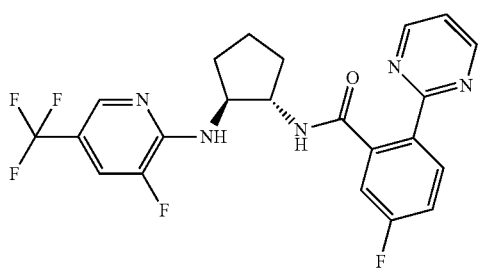 [SMILES: O=C(N[C@H]1CCC[C@@H]1Nc1ncc(C(F)(F)F)cc1F)c1cc(F)ccc1-c1ncccn1]

Prepared according to the procedure for 2-(5-Ethoxypyrimidin-2-yl)-N-[(1S,2S)-2-{[5-(trifluoromethyl)pyrazin-2-yl]amino}cyclopentyl]benzamide (Example 135) from (1S,2S)-1-N-[3-fluoro-5-(trifluoromethyl)pyridin-2-yl] cyclopentane-1,2-diamine hydrochloride (Intermediate 34: 200 mg, 0.76 mmol) and 5-fluoro-2-(pyrimidin-2-yl)benzoic acid (CAS number 1293284-57-7; 166 mg, 0.76 mmol) except after the reaction was complete it was concentrated in vacuo and the residue was purified by reverse phase column chromatography (C18 silica, 0-100% water (0.05% ammonia)/methanol), then by column chromatography (silica, 0-50% ethyl acetate/petrol) and then triturated with DCM/petrol to afford the title compound.

$^1$H NMR (400 MHz, CHLOROFORM-d) δ ppm 1.50-1.66 (m, 2H), 1.77-1.94 (m, 2H), 2.27-2.46 (m, 2H), 4.05-4.23 (m, 2H), 5.64-5.81 (m, 1H), 6.89-6.98 (m, 1H), 7.02-7.07 (m, 1H), 7.11-7.17 (m, 1H), 7.18-7.24 (m, 1H), 7.24-7.30 (m, 1H), 7.94-8.00 (m, 1H), 8.09-8.17 (m, 1H), 8.56-8.62 (m, 2H)
MS ES+: 464

Example 140

N-[(1S,2S)-2-{[3-Fluoro-5-(trifluoromethyl)pyridin-2-yl]amino}cyclopentyl]-2-(3-methyl-1,2,4-oxadiazol-5-yl)benzamide

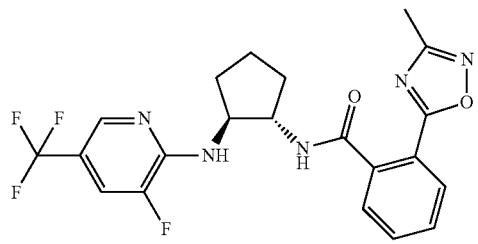 [SMILES: Cc1noc(-c2ccccc2C(=O)N[C@H]2CCC[C@@H]2Nc2ncc(C(F)(F)F)cc2F)n1]

Prepared according to the procedure for 2-(5-Ethoxypyrimidin-2-yl)-N-[(1S,2S)-2-{[5-(trifluoromethyl)pyrazin-2-yl]amino}cyclopentyl]benzamide (Example 135) from (1S,2S)-1-N-[3-fluoro-5-(trifluoromethyl)pyridin-2-yl] cyclopentane-1,2-diamine hydrochloride (Intermediate 34: 450 mg, 1.71 mmol) and 2-(3-methyl-1,2,4-oxadiazol-5-yl) benzoic acid (CAS number 475105-77-2; 349 mg, 1.71 mmol) except after the reaction was complete it was partitioned between DCM and a saturated solution of sodium bicarbonate, filtered through a hydrophobic frit. The organics were loaded directly on to a cation/anion mixed mode cartridge, eluted with DCM and concentrated in vacuo. The resulting residue was purified by column chromatography (silica, 0-100% ethyl acetate/petrol) and then purified by reverse phase column chromatography (C18 silica, 0-100% water (0.05% ammonia)/acetonitrile) to afford the title compound.

$^1$H NMR (400 MHz, DCM-d2) δ ppm 1.57-1.72 (m, 2H), 1.82-1.94 (m, 2H), 2.27-2.46 (m, 5H), 4.10-4.37 (m, 2H), 5.69-5.82 (m, 1H), 7.18-7.27 (m, 1H), 7.28-7.37 (m, 1H), 7.40-7.50 (m, 1H), 7.53-7.64 (m, 2H), 7.88-8.00 (m, 2H)
MS ES+: 450

Example 141

2-(3-Methyl-1,2,4-oxadiazol-5-yl)-N-[(1S,2S)-2-{[3-methyl-5-(trifluoromethyl)pyrazin-2-yl]amino}cyclopentyl]benzamide

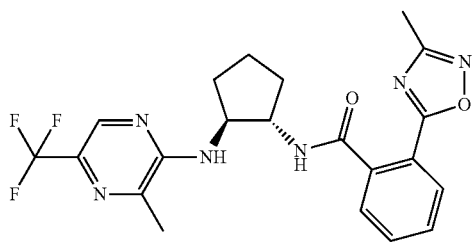 [SMILES: Cc1noc(-c2ccccc2C(=O)N[C@H]2CCC[C@@H]2Nc2ncc(C(F)(F)F)nc2C)n1]

Prepared according to the procedure for 2-(5-Ethoxypyrimidin-2-yl)-N-[(1S,2S)-2-{[5-(trifluoromethyl)pyrazin-2-yl]amino}cyclopentyl]benzamide (Example 135) from (1S,2S)-1-N-methyl-1-N-[5-(trifluoromethyl)pyrazin-2-yl]cyclopentane-1,2-diamine hydrochloride (Intermediate 23; 452 mg, 1.74 mmol) and 2-(3-methyl-1,2,4-oxadiazol-5-yl)benzoic acid (CAS number 475105-77-2; 355 mg, 1.74 mmol) except after the reaction was complete it was partitioned between DCM and a saturated solution of sodium bicarbonate, filtered through a hydrophobic frit. The organics were loaded directly on to a cation/anion mixed mode cartridge, eluted with DCM and concentrated in vacuo. The resulting residue was purified by column chromatography (silica, 0-100% ethyl acetate/petrol) and then recrystallised from MTBE/heptane to afford the title compound.

$^1$H NMR (400 MHz, CHLOROFORM-d) δ ppm 1.48-1.70 (m, 2H), 1.82-1.95 (m, 2H), 2.24 (s, 3H), 2.26-2.37 (m, 1H), 2.42 (s, 3H), 2.49-2.62 (m, 1H), 3.98-4.12 (m, 1H), 4.38-4.52 (m, 1H), 6.43-6.52 (m, 1H), 6.65-6.74 (m, 1H), 7.50-7.65 (m, 3H), 7.97-8.05 (m, 1H), 8.12 (s, 1H)

MS ES$^+$: 447

Example 142

N-[(1S,2S)-2-{[3-Cyclopropyl-5-(trifluoromethyl)pyrazin-2-yl]amino}cyclopentyl]-3-(2H-1,2,3-triazol-2-yl)pyridine-2-carboxamide

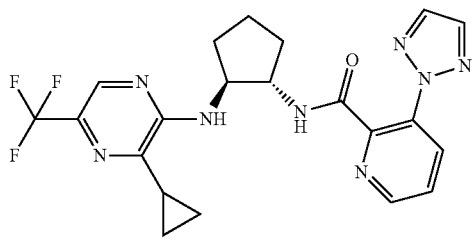 [SMILES: O=C(N[C@H]1CCC[C@@H]1Nc1ncc(C(F)(F)F)nc1C1CC1)c1ncccc1-n1nccn1]

Prepared according to the procedure for 2-(5-Ethoxypyrimidin-2-yl)-N-[(1S,2S)-2-{[5-(trifluoromethyl)pyrazin-2-yl]amino}cyclopentyl]benzamide (Example 135) from (1S,2S)-1-N-[3-cyclopropyl-5-(trifluoromethyl)pyrazin-2-yl]cyclopentane-1,2-diamine hydrochloride (Intermediate 48; 105 mg, 0.33 mmol) and 3-(2H-1,2,3-triazol-2-yl)pyridine-2-carboxylic acid (CAS number 1252907-86-0; 74 mg, 0.39 mmol) except after work-up, the organics were loaded directly on to a cation/anion mixed mode cartridge, eluted with DCM, then methanol and 2M ammonia in methanol and concentrated in vacuo. The resulting residue was purified by column chromatography (silica, 0-100% ethyl acetate/petrol) to afford the title compound.

$^1$H NMR (400 MHz, DMSO-d$_6$) δ ppm 0.79-1.05 (m, 4H), 1.45-1.80 (m, 4H), 2.00-2.24 (m, 3H), 4.24-4.43 (m, 2H), 7.48-7.54 (m, 1H), 7.68-7.73 (m, 1H), 7.90 (s, 2H), 8.18-8.21 (m, 1H), 8.22-8.26 (m, 1H), 8.65-8.69 (m, 1H), 8.72-8.83 (m, 1H)

MS ES$^+$: 459

Example 143

N-[(1S,2S)-2-{[3-Cyclopropyl-5-(trifluoromethyl)pyrazin-2-yl]amino}cyclopentyl]-3-(pyrimidin-2-yl)pyridine-2-carboxamide

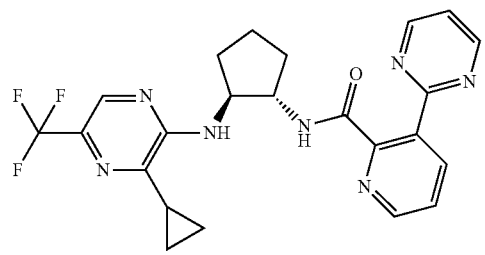 [SMILES: O=C(N[C@H]1CCC[C@@H]1Nc1ncc(C(F)(F)F)nc1C1CC1)c1ncccc1-c1ncccn1]

Prepared according to the procedure for 2-(5-Ethoxypyrimidin-2-yl)-N-[(1S,2S)-2-{[5-(trifluoromethyl)pyrazin-2-yl]amino}cyclopentyl]benzamide (Example 135) from (1S,2S)-1-N-[3-cyclopropyl-5-(trifluoromethyl)pyrazin-2-yl]cyclopentane-1,2-diamine hydrochloride (Intermediate 48; 105 mg, 0.33 mmol) and 3-(pyrimidin-2-yl)pyridine-2-carboxylic acid (CAS number 1228431-21-7; 79 mg, 0.39 mmol) except after work-up, the organics were loaded directly on to a cation/anion mixed mode cartridge, eluted with DCM, then methanol and 2M ammonia in methanol and concentrated in vacuo. The resulting residue was purified by column chromatography (silica, 0-100% ethyl acetate/petrol) to afford the title compound.

$^1$H NMR (400 MHz, DMSO-d$_6$) δ ppm 0.81-1.03 (m, 4H), 1.47-1.59 (m, 1H), 1.63-1.79 (m, 3H), 2.02-2.15 (m, 2H), 2.16-2.26 (m, 1H), 4.28-4.39 (m, 2H), 7.34-7.38 (m, 1H), 7.53-7.59 (m, 1H), 7.61-7.66 (m, 1H), 8.19-8.21 (m, 1H), 8.22-8.26 (m, 1H), 8.64-8.68 (m, 1H), 8.68-8.71 (m, 2H), 8.72-8.77 (m, 1H)

MS ES$^+$: 470

Example 144

N-[(1S,2S)-2-Methyl-2-{[5-(trifluoromethyl)pyrazin-2-yl]amino}cyclopentyl]-3-(pyrimidin-2-yl)pyridine-2-carboxamide

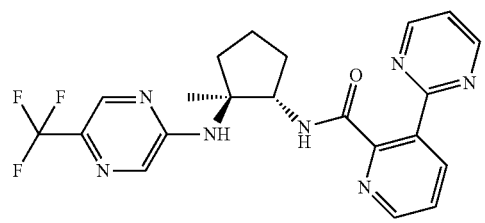 [SMILES: C[C@]1(Nc2cnc(C(F)(F)F)cn2)CCC[C@@H]1NC(=O)c1ncccc1-c1ncccn1]

A solution of (1S,2S)-1-methyl-1-N-[5-(trifluoromethyl)pyrazin-2-yl]cyclopentane-1,2-diamine (Intermediate 25; 50 mg, 0.192 mmol), 3-(pyrimidin-2-yl)pyridine-2-carboxylic acid (CAS number 1228431-21-7; 46 mg, 0.231 mmol), triethylamine (80 ul, 0.576 mmol), 3H-[1,2,3]triazolo[4,5-b]pyridin-3-ol (34 mg, 0.250 mmol) and EDC (48 mg, 0.250 mmol) in DCM (5 ml) was stirred at room temperature for 18 hours. The reaction was partitioned between DCM (20 ml) and a saturated solution of sodium bicarbonate (10 ml). The aqueous layer was further extracted with DCM (20 ml) and the combined organics were filtered through a hydrophobic frit and concentrated in vacuo. The resulting residue was purified by column chromatography (silica, 0-100% ethyl acetate/petrol) to afford the title compound.

$^1$H NMR (400 MHz, DCM-d$_2$) δ ppm 1.42 (s, 3H), 1.64-1.99 (m, 4H), 2.13-2.23 (m, 1H), 2.52-2.60 (m, 1H), 4.41-4.49 (m, 1H), 7.30-7.34 (m, 1H), 7.55-7.67 (m, 4H), 8.08-8.12 (m, 1H), 8.22 (s, 1H), 8.64-8.67 (m, 1H), 8.73-8.76 (m, 2H)

MS ES$^+$: 444

Example 145

2-(3-Methyl-1,2,4-oxadiazol-5-yl)-N-[(1S,2S)-2-methyl-2-{[5-(trifluoromethyl)pyrazin-2-yl]amino}cyclopentyl]benzamide

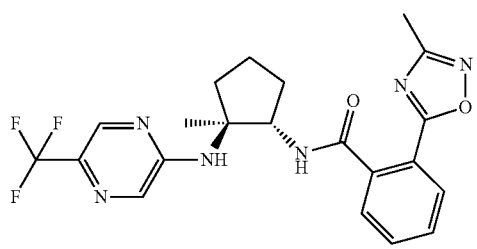 [SMILES: Cc1noc(-c2ccccc2C(=O)N[C@H]2CCC[C@]2(C)Nc2cnc(C(F)(F)F)cn2)n1]

Prepared according to the procedure for N-[(1S,2S)-2-methyl-2-{[5-(trifluoromethyl)pyrazin-2-yl]amino}cyclopentyl]-3-(pyrimidin-2-yl)pyridine-2-carboxamide (Example 144) from (1S,2S)-1-methyl-1-N-[5-(trifluoromethyl)pyrazin-2-yl]cyclopentane-1,2-diamine (Intermediate 25; 190 mg, 0.73 mmol) and 2-(3-methyl-1,2,4-oxadiazol-5-yl)benzoic acid (CAS number 475105-77-2; 179 mg, 0.88 mmol). After work-up, the crude material was loaded directly on to a cation/anion mixed mode cartridge, eluted with DCM and concentrated in vacuo. This was then recrystallised from MTBE to afford the title compound.

$^1$H NMR (400 MHz, DCM-d$_2$) δ ppm 1.41 (s, 3H), 1.50-1.63 (m, 1H), 1.72-2.04 (m, 3H), 2.10-2.24 (m, 1H), 2.31 (s, 3H), 2.56-2.66 (m, 1H), 4.46-4.65 (m, 1H), 6.34-6.52 (m, 1H), 7.59-7.74 (m, 4H), 7.82 (br. s., 1H), 8.01-8.09 (m, 1H), 8.21-8.31 (m, 1H)

MS ES$^+$: 447

Example 146

N-(2-{[3-Fluoro-5-(trifluoromethyl)pyridin-2-yl]amino}-2-methylcyclopentyl)-3-(pyrimidin-2-yl)pyridine-2-carboxamide

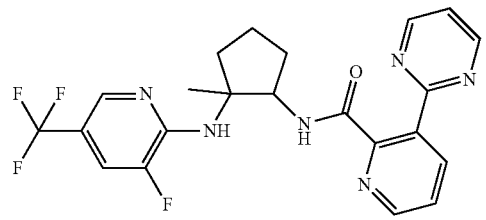 [SMILES: CC1(Nc2ncc(C(F)(F)F)cc2F)CCCC1NC(=O)c1ncccc1-c1ncccn1]

To a solution of 1-N-[3-fluoro-5-(trifluoromethyl)pyridin-2-yl]-1-methylcyclopentane-1,2-diamine (Intermediate 28; 0.225 g, 0.81 mmol) and 4-methylmorpholine (0.134 ml, 1.217 mmol) in acetonitrile (5 ml) was added TOTU (0.399 g, 1.23 mmol) and 3-(pyrimidin-2-yl)pyridine-2-carboxylic acid (CAS number 1228431-21-7; 0.163 g, 0.81 mmol). The reaction was stirred at room temperature for 1 hour and then was diluted with DCM and washed with brine. The organics were dried over magnesium sulfate, concentrated in vacuo and purified by SCX chromatography (2M ammonia in methanol). The resulting residue was purified by column chromatography (silica, 0-10% methanol/DCM) and further purified by reverse phase chromatography (C18 silica, 5-95% water (0.05% ammonia)/acetonitrile) to afford the title compound.

$^1$H NMR (400 MHz, DMSO-d$_6$) δ ppm 1.45 (s, 3H), 1.65-1.98 (m, 5H), 2.52-2.59 (m, 1H), 4.38-4.48 (m, 1H), 7.36-7.41 (m, 1H), 7.64-7.70 (m, 2H), 7.78-7.83 (m, 1H), 8.19 (s, 1H), 8.34-8.39 (m, 1H), 8.67-8.73 (m, 3H), 8.94-9.00 (m, 1H)

MS ES$^+$: 461

Example 147

N-[(1S,2S)-2-{[3-Fluoro-5-(trifluoromethyl)pyridin-2-yl]amino}cyclopentyl]-3-(pyrimidin-2-yl)pyridine-2-carboxamide

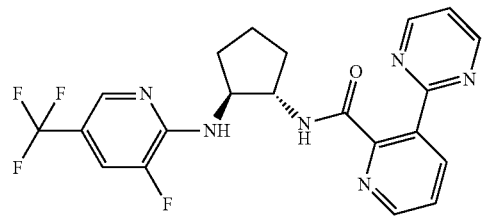 [SMILES: O=C(N[C@H]1CCC[C@@H]1Nc1ncc(C(F)(F)F)cc1F)c1ncccc1-c1ncccn1]

A solution of (1S,2S)-1-N-[3-fluoro-5-(trifluoromethyl)pyridin-2-yl]cyclopentane-1,2-diamine hydrochloride (Intermediate 34; 379 mg, 1.44 mmol), 3-(pyrimidin-2-yl)pyridine-2-carboxylic acid (CAS number 1228431-21-7; 290 mg, 1.44 mmol), 3H-[1,2,3]triazolo[4,5-b]pyridin-3-ol (34 mg, 0.250 mmol) (294 mg, 2.16 mmol), EDC (415 mg, 2.16 mmol) and triethylamine (0.604 ml, 4.32 mmol) in DCM (1 ml) was stirred at room temperature for 16 hours. The reaction was added partitioned between DCM and as saturated solution of sodium bicarbonate. The organics were filtered through a hydrophobic frit and loaded directly on to a cation/ anion mixed mode cartridge, eluted with DCM and concentrated in vacuo. The resulting residue was purified by reverse phase chromatography (C18 silica, 0-100% water (0.1% ammonia)/acetonitrile) to afford the title compound.

¹H NMR (400 MHz, DCM-d2) δ ppm 1.42-1.74 (m, 2H), 1.76-1.94 (m, 2H), 2.21-2.33 (m, 1H), 2.33-2.49 (m, 1H), 4.06-4.34 (m, 2H), 5.93 (br. s., 1H), 7.18-7.34 (m, 2H), 7.47-7.58 (m, 1H), 7.94-8.04 (m, 1H), 8.11-8.31 (m, 2H), 8.57-8.67 (m, 1H), 8.66-8.76 (m, 2H).

MS ES⁺: 447

Example 148

N-[(1S,2S)-2-{[3-Chloro-5-(trifluoromethyl)pyridin-2-yl]amino}cyclopentyl]-3-(pyrimidin-2-yl)pyridine-2-carboxamide

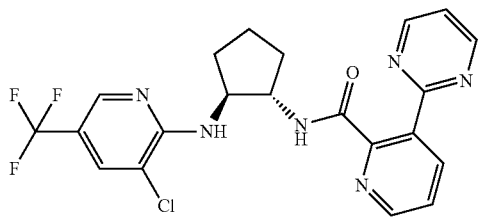 [SMILES: O=C(N[C@H]1CCC[C@@H]1Nc1ncc(C(F)(F)F)cc1Cl)c1ncccc1-c1ncccn1]

A solution of (1S,2S)-1-N-[3-chloro-5-(trifluoromethyl)pyridin-2-yl]cyclopentane-1,2-diamine hydrochloride (Intermediate 33; 327 mg, 1.03 mmol), 3-(pyrimidin-2-yl)pyridine-2-carboxylic acid (CAS number 1228431-21-7; 250 mg, 1.24 mmol), 3H-[1,2,3]triazolo[4,5-b]pyridin-3-ol (211 mg, 1.55 mmol), EDC (297 mg, 1.55 mmol) and triethylamine (0.432 ml, 3.10 mmol) in DCM (4 ml) was stirred at room temperature for 18 hours. The reaction was partitioned between DCM (10 ml) and water (10 ml), filtered through a hydrophobic frit and concentrated in vacuo. The resulting residue was purified by column chromatography (0-100% ethyl acetate/petrol) and was then by reverse phase chromatography (C18 silica, 5-95% water (0.05% ammonia)/acetonitrile) to afford the title compound.

¹H NMR (400 MHz, DMSO-d₆) δ ppm 1.44-1.57 (m, 1H), 1.63-1.78 (m, 3H), 1.95-2.10 (m, 1H), 2.14-2.27 (m, 1H), 4.27-4.36 (m, 2H), 7.21-7.25 (m, 1H), 7.36-7.40 (m, 1H), 7.61-7.66 (m, 1H), 7.95-7.97 (m, 1H), 8.21-8.24 (m, 1H), 8.34-8.37 (m, 1H), 8.64-8.67 (m, 1H), 8.69-8.72 (m, 3H)

MS ES⁺: 463, 465

Example 149

N-[(1S,2S)-2-{[3-Ethyl-5-(trifluoromethyl)pyrazin-2-yl]amino}cyclopentyl]-2-(3-methyl-1,2,4-oxadiazol-5-yl)benzamide

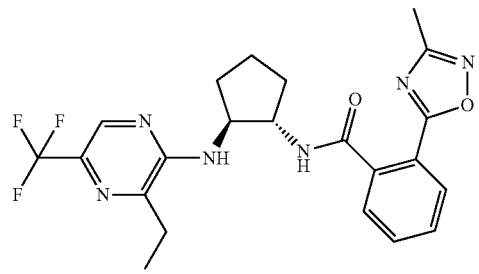 [SMILES: CCc1nc(C(F)(F)F)cnc1N[C@H]1CCC[C@@H]1NC(=O)c1ccccc1-c1nc(C)no1]

A solution of (1S,2S)-1-N-[3-ethyl-5-(trifluoromethyl)pyrazin-2-yl]cyclopentane-1,2-diamine hydrochloride (Intermediate 41; 450 mg, 1.64 mmol), 2-(3-methyl-1,2,4-oxadiazol-5-yl)benzoic acid (CAS number 475105-77-2; 335 mg, 1.64 mmol), 3H-[1,2,3]triazolo[4,5-b]pyridin-3-ol (335 mg, 2.46 mmol), EDC (472 mg, 2.46 mmol) and triethylamine (0.687 ml, 4.92 mmol) in DCM (5 ml) was stirred at room temperature for 16 hours. The reaction was partitioned between DCM and a saturated solution of sodium bicarbonate, filtered through a hydrophobic frit and loaded directly on to a cation/anion mixed mode cartridge, eluted with DCM and concentrated in vacuo. The resulting residue was purified by reverse phase chromatography (C18 silica, 0-100% water (0.1% ammonia)/acetonitrile) and recrystalised from MTBE/heptane to afford the title compound.

¹H NMR—(400 MHz, METHANOL-d4) δ ppm 1.25-1.32 (m, 3H), 1.55-1.96 (m, 4H), 2.14-2.28 (m, 4H), 2.32-2.44 (m, 1H), 2.64-2.75 (m, 2H), 4.23-4.34 (m, 1H), 4.40-4.51 (m, 1H), 7.45-7.51 (m, 1H), 7.61-7.71 (m, 2H), 7.99-8.06 (m, 1H), 8.11 (s, 1H).

MS ES⁺: 461

Example 150

N-[(1S,2S)-2-{[3-Ethyl-5-(trifluoromethyl)pyrazin-2-yl]amino}cyclopentyl]-3-(pyrimidin-2-yl)pyridine-2-carboxamide

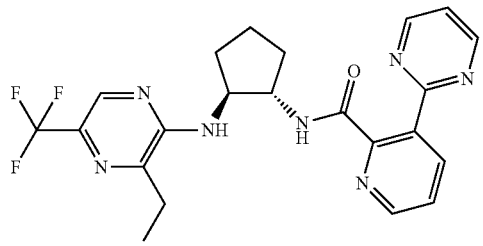 [SMILES: CCc1nc(C(F)(F)F)cnc1N[C@H]1CCC[C@@H]1NC(=O)c1ncccc1-c1ncccn1]

Prepared according to the procedure for N-[(1S,2S)-2-{[3-ethyl-5-(trifluoromethyl)pyrazin-2-yl]amino}cyclopentyl]-2-(3-methyl-1,2,4-oxadiazol-5-yl)benzamide (Example 149) from (1S,2S)-1-N-[3-ethyl-5-(trifluoromethyl)pyrazin-2-yl]cyclopentane-1,2-diamine hydrochloride (Intermediate 41; 450 mg, 1.64 mmol) and 3-(pyrimidin-2-yl)pyridine-2-carboxylic acid (CAS number 1228431-21-7; 330 mg, 1.64 mmol) to afford the title compound.

¹H NMR—(400 MHz, METHANOL-d4) δ ppm 1.18-1.28 (m, 3H), 1.54-1.95 (m, 4H), 2.17-2.30 (m, 1H), 2.32-2.45 (m, 1H), 2.49-2.70 (m, 2H), 4.23-4.42 (m, 2H), 7.29-7.36 (m, 1H), 7.62-7.71 (m, 1H), 8.17 (s, 1H), 8.28-8.35 (m, 1H), 8.62-8.75 (m, 3H).

MS ES⁺: 458

Example 151

N-[(1S,2S)-2-{[3-Ethyl-5-(trifluoromethyl)pyrazin-2-yl]amino}cyclopentyl]-2-(pyrimidin-2-yl)benzamide

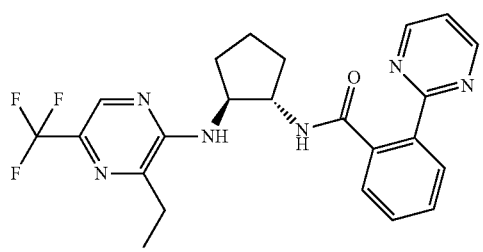 [SMILES: CCc1nc(C(F)(F)F)cnc1N[C@H]1CCC[C@@H]1NC(=O)c1ccccc1-c1ncccn1]

Prepared according to the procedure for N-[(1S,2S)-2-{[3-ethyl-5-(trifluoromethyl)pyrazin-2-yl]amino}cyclopentyl]-2-(3-methyl-1,2,4-oxadiazol-5-yl)benzamide (Example 149) from (1S,2S)-1-N-[3-ethyl-5-(trifluoromethyl)pyrazin-2-yl]cyclopentane-1,2-diamine hydrochloride (Intermediate 41; 450 mg 1.64 mmol) and 2-(pyrimidin-2-yl)benzoic acid (CAS number 400892-62-8; 328 mg, 1.64 mmol) to afford the title compound.

¹H NMR (400 MHz, METHANOL-d4) δ ppm 1.19-1.29 (m, 3H), 1.52-1.96 (m, 4H), 2.12-2.23 (m, 1H), 2.29-2.44 (m, 1H), 2.47-2.71 (m, 2H), 4.16-4.28 (m, 1H), 4.28-4.42 (m, 1H), 7.11-7.20 (m, 1H), 7.40-7.47 (m, 1H), 7.50-7.64 (m, 2H), 8.00-8.06 (m, 1H), 8.14 (s, 1H), 8.50-8.59 (m, 2H).

MS ES⁺: 457

Example 153

N-(2-Methyl-2-{[5-(trifluoromethyl)pyrimidin-2-yl]amino}cyclopentyl)-3-(pyrimidin-2-yl)pyridine-2-carboxamide

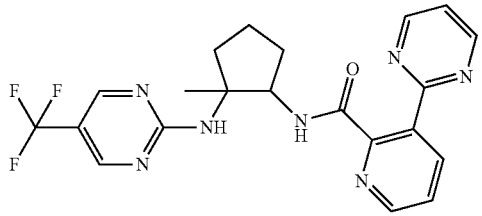

A solution of 3-(pyrimidin-2-yl)pyridine-2-carboxylic acid (CAS number 1228431-21-7; 80 mg, 0.40 mmol), 1-methyl-1-N-[5-(trifluoromethyl)pyrimidin-2-yl]cyclopentane-1,2-diamine (Intermediate 50; 103 mg, 0.40 mmol), 3H-[1,2,3]triazolo[4,5-b]pyridin-3-ol (81 mg, 0.60 mmol), EDC (114 mg, 0.60 mmol) and DIPEA (0.208 ml, 1.19 mmol) in DCM (4 ml) was stirred at room temperature for 4 days. The reaction was diluted with DCM (5 ml) and a saturated solution of sodium bicarbonate (5 ml), filtered through a hydrophobic frit and concentrated in vacuo. The crude product was purified by reverse phase chromatography (C18 silica, 5-95% water (0.05% ammonia)/acetonitrile) to afford the title compound.

¹H NMR (400 MHz, DMSO-d₆) δ ppm 1.40 (s, 3H), 1.61-1.84 (m, 3H), 1.87-2.00 (m, 2H), 2.29-2.42 (m, 1H), 4.43-4.54 (m, 1H), 7.38-7.43 (m, 1H), 7.63-7.69 (m, 1H), 7.99 (s, 1H), 8.34-8.39 (m, 1H), 8.51-8.66 (m, 2H), 8.68-8.71 (m, 1H), 8.72-8.75 (m, 2H), 8.80-8.86 (m, 1H)

MS ES⁺: 444

Example 154

N-(2-Methyl-2-{[5-(trifluoromethyl)pyrimidin-2-yl]amino}cyclopentyl)-3-(2H-1,2,3-triazol-2-yl)pyridine-2-carboxamide

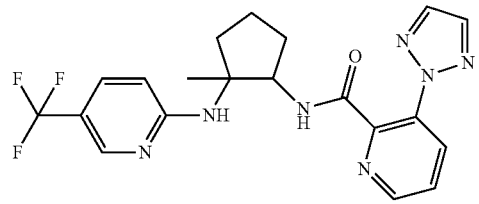

Prepared according to the procedure for N-(2-methyl-2-{[5-(trifluoromethyl)pyrimidin-2-yl]amino}cyclopentyl)-3-(pyrimidin-2-yl)pyridine-2-carboxamide (Example 153) from 1-methyl-1-N-[5-(trifluoromethyl)pyrimidin-2-yl]cyclopentane-1,2-diamine (Intermediate 50; 150 mg, 0.58 mmol) and 3-(2H-1,2,3-triazol-2-yl)pyridine-2-carboxylic acid (CAS number 1252907-86-0; 110 mg, 0.58 mmol) and then triturated with heptane to afford the title compound.

¹H NMR (400 MHz, DMSO-d₆) δ ppm 1.36 (s, 3H), 1.62-1.79 (m, 3H), 1.88-2.05 (m, 2H), 2.24-2.35 (m, 1H), 4.47-4.58 (m, 1H), 7.72-7.76 (m, 1H), 7.83 (s, 1H), 8.04 (s, 2H), 8.30-8.34 (m, 1H), 8.53-8.67 (m, 2H), 8.68-8.72 (m, 1H), 8.86-8.92 (m, 1H)

MS ES⁺: 433

Example 155

N-(2-Methyl-2-{[5-(trifluoromethyl)pyridin-2-yl]amino}cyclopentyl)-3-(2H-1,2,3-triazol-2-yl)pyridine-2-carboxamide

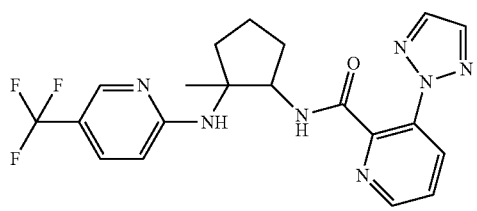 [SMILES: CC1(Nc2ccc(C(F)(F)F)cn2)CCCC1NC(=O)c1ncccc1-n1nccn1]

Prepared according to the procedure for N-(2-methyl-2-{[5-(trifluoromethyl)pyrimidin-2-yl]amino}cyclopentyl)-3-(pyrimidin-2-yl)pyridine-2-carboxamide (Example 153) from 1-methyl-1-N-[5-(trifluoromethyl)pyridin-2-yl]cyclopentane-1,2-diamine (Intermediate 51; 85 mg, 0.33 mmol), 3-(2H-1,2,3-triazol-2-yl)pyridine-2-carboxylic acid (CAS number 1252907-86-0; 75 mg, 0.33 mmol) and triethylamine (0.14 ml, 0.98 mmol) except this was then recrystallised from diisopropyl ether/pentane and then triturated with diethyl ether to afford the title compound.

¹H NMR (400 MHz, DCM-d₂) δ ppm 1.44 (s, 3H), 1.59-1.73 (m, 1H), 1.74-2.05 (m, 3H), 2.13-2.27 (m, 1H), 2.49 (br. s., 1H), 4.43-4.52 (m, 1H), 6.33 (br. s., 1H), 6.85 (br. s., 1H), 7.39-7.52 (m, 2H), 7.60-7.66 (m, 1H), 7.84 (s, 2H), 8.07-8.12 (m, 1H), 8.25 (br. s., 1H), 8.65-8.70 (m, 1H)

MS ES⁺: 432

Example 156

N-(2-Methyl-2-{[5-(trifluoromethyl)pyridin-2-yl]amino}cyclopentyl)-3-(pyrimidin-2-yl)pyridine-2-carboxamide

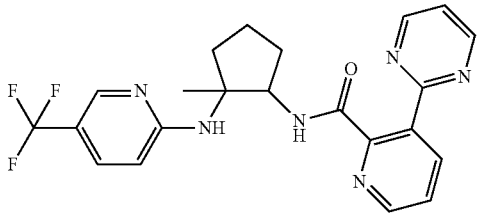 [SMILES: CC1(Nc2ccc(C(F)(F)F)cn2)CCCC1NC(=O)c1ncccc1-c1ncccn1]

Prepared according to the procedure for N-(2-methyl-2-{[5-(trifluoromethyl)pyrimidin-2-yl]amino}cyclopentyl)-3-(pyrimidin-2-yl)pyridine-2-carboxamide (Example 153) from 1-methyl-1-N-[5-(trifluoromethyl)pyridin-2-yl]cyclopentane-1,2-diamine (Intermediate 51; 91 mg, 0.35 mmol), 3-(pyrimidin-2-yl)pyridine-2-carboxylic acid (CAS number 1228431-21-7; 85 mg, 0.42 mmol) and triethylamine (0.147 ml, 1.06 mmol) except after work-up the organics were loaded directly on to a cation/anion mixed mode cartridge, eluted with DCM then with 2M ammonia in methanol and concentrated in vacuo. The resulting residue was purified by reverse phase chromatography (C18 silica, 5-100% water (0.05% ammonia)/acetonitrile) then recrystallised from MTBE/heptane to afford the title compound.

$^1$H NMR (400 MHz, DCM-$d_2$) δ ppm 1.44 (s, 3H), 1.60-1.74 (m, 1H), 1.75-2.02 (m, 3H), 2.12-2.23 (m, 1H), 2.47-2.58 (m, 1H), 4.38-4.48 (m, 1H), 6.23 (br. s., 1H), 6.97 (br. s., 1H), 7.24-7.29 (m, 1H), 7.40-7.47 (m, 1H), 7.53-7.60 (m, 2H), 8.08-8.12 (m, 1H), 8.25 (br. s., 1H), 8.63-8.66 (m, 1H), 8.71-8.75 (m, 2H)

MS ES$^+$: 443

Example 157

N-[(1S,2S)-2-{[5-(Difluoromethoxy)pyridin-2-yl]amino}-4,4-difluorocyclopentyl]-2-(2H-1,2,3-triazol-2-yl)benzamide

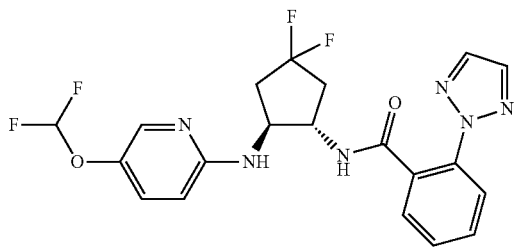 [SMILES: O=C(N[C@H]1CC(F)(F)C[C@@H]1Nc1ccc(OC(F)F)cn1)c1ccccc1-n1nccn1]

To a solution of N-[(1S,2S)-2-amino-4,4-difluorocyclopentyl]-2-(2H-1,2,3-triazol-2-yl)benzamide (Intermediate 46; 100 mg, 0.33 mmol) in dry toluene (3 ml) was added 2-bromo-5-(difluoromethoxy)pyridine (CAS number 845827-14-7; 89 mg, 0.33 mmol), BINAP (20 mg, 0.033 mmol), tris(dibenzylideneacetone)dipalladium(0) (15 mg, 0.016 mmol) and sodium tert-butoxide (44 mg, 0.46 mmol). The reaction was placed under an atmosphere of nitrogen, sealed and heated at 110° C. for 2.5 hours then filtered through a thiol cartridge, eluting with ethyl acetate and water. The filtrate was diluted with further ethyl acetate and water and then partitioned. The organics were washed with water, dried over magnesium sulfate, filtered and concentrated in vacuo. The crude material was purified by column chromatography (silica, 0-100% ethyl acetate/petrol) then triturated with heptane and diethyl ether to afford the title compound.

$^1$H NMR (400 MHz, DCM-$d_2$) δ ppm 1.88-2.23 (m, 2H), 2.71-2.95 (m, 2H), 4.07-4.32 (m, 2H), 6.19-6.69 (m, 2H), 7.12-7.20 (m, 1H), 7.23-7.31 (m, 1H), 7.43-7.53 (m, 2H), 7.55-7.61 (m, 1H), 7.64 (s, 2H), 7.75-7.82 (m, 2H)

MS ES$^+$: 451

Example 158

N-[(1S,2S)-2-{[3-Ethyl-5-(trifluoromethyl)pyrazin-2-yl]amino}cyclopentyl]-5-fluoro-2-(pyrimidin-2-yl)benzamide

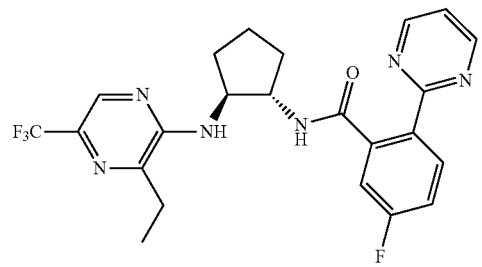 [SMILES: CCc1nc(C(F)(F)F)cnc1N[C@H]1CCC[C@@H]1NC(=O)c1cc(F)ccc1-c1ncccn1]

To a solution of 5-fluoro-2-(pyrimidin-2-yl)benzoic acid (CAS number 1293284-57-7; 53 mg, 0.24 mmol), 3H-[1,2,3]triazolo[4,5-b]pyridin-3-ol (33 mg, 0.24 mmol), EDC (46.3 mg, 0.241 mmol) and triethylamine (0.067 ml, 0.48 mmol) in DCM (5 ml) was added (1S,2S)-1-N-[3-ethyl-5-(trifluoromethyl)pyrazin-2-yl]cyclopentane-1,2-diamine hydrochloride (Intermediate 41; 50 mg, 0.161 mmol). The reaction mixture was stirred at room temperature for 88 hours and then partitioned between DCM and a saturated solution of sodium bicarbonate, passing through a hydrophobic frit. The organics were loaded directly on to a cation/anion mixed mode cartridge, eluted with DCM and concentrated in vacuo. This was then purified by reverse phase chromatography (C18 silica, 0-100% acetonitrile/water with 0.1% ammonia). The resulting aqueous was concentrated in vacuo and extracted with DCM. The organics were concentrated in vacuo to afford the title compound.

$^1$H NMR (400 MHz, METHANOL-$d_4$) δ ppm 1.18-1.29 (m, 3H), 1.55-1.73 (m, 2H), 1.77-1.90 (m, 2H), 2.07-2.26 (m, 1H), 2.29-2.41 (m, 1H), 2.45-2.72 (m, 2H), 4.16-4.42 (m, 2H), 6.99-7.05 (m, 1H), 7.08-7.20 (m, 2H), 7.22-7.36 (m, 1H), 8.03-8.18 (m, 2H), 8.42-8.57 (m, 2H)

MS ES$^+$: 475

Example 159

N-[(1S,2S)-2-{[3-Methyl-5-(trifluoromethyl)pyrazin-2-yl]amino}cyclopentyl]-3-(pyrimidin-2-yl)pyridine-2-carboxamide

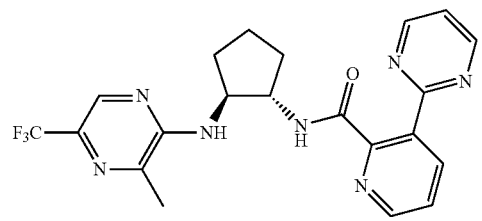 [SMILES: Cc1nc(C(F)(F)F)cnc1N[C@H]1CCC[C@@H]1NC(=O)c1ncccc1-c1ncccn1]

To a solution of (1S,2S)-1-N-methyl-1-N-[5-(trifluoromethyl)pyrazin-2-yl]cyclopentane-1,2-diamine hydrochloride (Intermediate 23; 100 mg, 0.34 mmol) in DCM (1.2 ml) was added 3-(pyrimidin-2-yl)pyridine-2-carboxylic acid (CAS number 1228431-21-7; 81 mg, 0.40 mmol), 3H-[1,2,3]triazolo[4,5-b]pyridin-3-ol (69 mg, 0.51 mmol), EDC (97 mg, 0.51 mmol) and triethylamine (0.14 ml, 1.01 mmol). The reaction was stirred at room temperature for 18 hours and then partitioned between water and DCM, passing through a hydrophobic frit. The organics were concentrated in vacuo and then purified by column chromatography (0-100% ethyl acetate/petrol) to afford the title compound.

$^1$H NMR (400 MHz, DCM-$d_2$) δ ppm 1.42-1.54 (m, 1H), 1.72-1.85 (m, 1H), 1.86-1.97 (m, 2H), 2.20 (s, 3H), 2.21-2.31 (m, 1H), 2.52-2.64 (m, 1H), 3.95-4.09 (m, 1H), 4.26-4.42 (m, 1H), 6.66-6.76 (m, 1H), 7.24-7.31 (m, 1H), 7.52-7.62 (m, 1H), 7.98-8.08 (m, 2H), 8.21 (s, 1H), 8.64-8.72 (m, 3H)

MS ES$^+$: 444

Example 160

2-(5-Methyl-1,3,4-oxadiazol-2-yl)-N-[(1S,2S)-2-methyl-2-{[5-(trifluoromethyl)pyrazin-2-yl]amino}cyclopentyl]benzamide

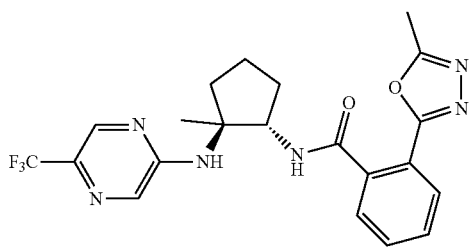 [SMILES: Cc1nnc(-c2ccccc2C(=O)N[C@H]2CCC[C@]2(C)Nc2cnc(C(F)(F)F)cn2)o1]

A solution of 2-(5-methyl-1,3,4-oxadiazol-2-yl)benzoic acid (CAS number 898289-64-0; 82 mg, 0.40 mmol), (1S,2S)-1-methyl-1-N-[5-(trifluoromethyl)pyrazin-2-yl]cyclopentane-1,2-diamine (Intermediate 25; 80 mg, 0.31 mmol), 3H-[1,2,3]triazolo[4,5-b]pyridin-3-ol (54 mg, 0.40 mmol), EDC (77 mg, 0.40 mmol) and triethylamine (0.13 ml, 0.92 mmol) in DCM (3 ml) was stirred at room temperature for 72 hours. The reaction was diluted with DCM and washed with a saturated solution of sodium bicarbonate, passing through a hydrophobic frit and concentrated in vacuo. The crude product was purified by reverse phase chromatography (C18 silica, 5-100% acetonitrile/water with 0.05% ammonia) to afford the title compound.

$^1$H NMR (400 MHz, DCM-$d_2$) δ ppm 1.36 (s, 3H), 1.51-1.65 (m, 1H), 1.71-1.92 (m, 2H), 1.94-2.05 (m, 1H), 2.10-2.20 (m, 1H), 2.49-2.53 (m, 3H), 2.55-2.65 (m, 1H), 4.55-4.64 (m, 1H), 6.46-6.58 (m, 1H), 7.51 (br. s., 1H), 7.59-7.67 (m, 3H), 7.90-7.95 (m, 1H), 7.96-7.99 (m, 1H), 8.23 (s, 1H)

MS ES$^+$: 447

3. Biological Efficacy of Compounds of the Invention

Orexin antagonist activity was determined by measuring changes in intracellular calcium levels using a $Ca^{2+}$ sensitive fluorescent dye. The changes in fluorescent signal were monitored by Fluorescent Imaging Plate Reader (FLIPR™) technology available from Molecular Devices, LLC, U.S.A. Orexin mediated increases in intracellular $Ca^{2+}$ concentration were readily detected upon activation with orexin-A. Twenty-four hours prior to the assay, RBL-2H3 cells stably expressing either human orexin receptor 1 or human orexin receptor 2 were seeded in cell culture medium in black, clear-bottom 384-well plates (commercially available from Corning Inc., U.S.A.) and grown overnight at 37° C., 5% $CO_2$. On the day of the assay, cell culture media was removed and cells were loaded with Calcium 5 Dye (commercially sold by Molecular Devices, LLC, U.S.A.) for 1 hour at 37° C., 5% $CO_2$. Test compounds (at 10 point half log concentration response curves from 10 μM) were added to cells for 15 minutes prior to the addition of orexin-A to all wells, to achieve a final concentration that produces approximately an 80% maximal response. The $IC_{50}$ values were determined from ten point concentration response curves. Curves were generated using the average of two wells for each data point. The results obtained are shown in the table below.

| Results | | |
|---|---|---|
| Example Number | Human Orexin1R $IC_{50}$ (nM) | Human Orexin2R $IC_{50}$ (nM) |
| 1 | 240 | >10,000 |
| 2 | 870 | >10,000 |
| 3 | 58 | >10,000 |
| 4 | 520 | >10,000 |
| 5 | 270 | >10,000 |
| 6 | 51 | >10,000 |
| 7 | 51 | >10,000 |
| 8 | 110 | >10,000 |
| 9 | 340 | >10,000 |
| 10 | 59 | >10,000 |
| 11 | 170 | >10,000 |
| 12 | 65 | >10,000 |
| 13 | 99 | >10,000 |
| 14 | 89 | >10,000 |
| 15 | 49 | >10,000 |
| 16 | 54 | >10,000 |
| 17 | 53 | >10,000 |
| 18 | 57 | >10,000 |
| 19 | 757 | 6105 |
| 20 | 875 | >10,000 |
| 21 | 576 | 6421 |
| 22 | 665 | 6160 |
| 23 | 792 | 3800 |
| 24 | 766 | >10,000 |
| 25 | 472 | >10,000 |
| 26 | 622 | >10,000 |
| 27 | 726 | 2000 |
| 28 | 776 | >10,000 |
| 29 | 279 | >10,000 |
| 30 | 370 | >10,000 |
| 31 | 122 | >10,000 |
| 32 | 32 | >10,000 |
| 33 | 890 | >10,000 |
| 34 | 523 | >10,000 |
| 35 | 693 | >10,000 |
| 36 | 207 | >10,000 |
| 37 | 340 | >10,000 |
| 38 | 49 | >10,000 |
| 39 | 81 | >10,000 |
| 40 | 35 | >10,000 |
| 41 | 644 | >10,000 |
| 42 | 261 | >10,000 |
| 43 | 289 | >10,000 |
| 44 | 199 | >10,000 |
| 45 | 241 | >10,000 |
| 46 | 172 | >10,000 |
| 47 | 445 | >10,000 |
| 48 | 88 | >10,000 |
| 49 | 367 | >10,000 |
| 50 | 80 | >10,000 |
| 51 | 301 | >10,000 |
| 52 | 69 | >10,000 |
| 53 | 93 | >10,000 |
| 54 | 950 | >10,000 |
| 55 | 761 | >10,000 |
| 56 | 166 | >10,000 |
| 57 | 38 | >10,000 |
| 58 | 934 | >10,000 |
| 59 | 161 | >10,000 |
| 60 | 852 | >10,000 |
| 61 | 321 | >10,000 |

-continued

| Example Number | Human Orexin1R IC$_{50}$ (nM) | Human Orexin2R IC$_{50}$ (nM) |
|---|---|---|
| 62 | 457 | >10,000 |
| 63 | 450 | >10,000 |
| 64 | 57 | >10,000 |
| 65 | 797 | >10,000 |
| 66 | 180 | >10,000 |
| 67 | 891 | >10,000 |
| 68 | 297 | 1610 |
| 69 | 321 | >10,000 |
| 70 | 678 | >10,000 |
| 71 | 722 | 7600 |
| 72 | 479 | >10,000 |
| 73 | 248 | >10,000 |
| 74 | 308 | >10,000 |
| 75 | 279 | >10,000 |
| 76 | 33 | >10,000 |
| 77 | 12 | >10,000 |
| 78 | 19 | >10,000 |
| 79 | 35 | >10,000 |
| 80 | 35 | >10,000 |
| 81 | 7 | >10,000 |
| 82 | 21 | 7541 |
| 83 | 2500 | 1400 |
| 84 | 22 | >10,000 |
| 85 | 18 | >10,000 |
| 86 | 129 | >10,000 |
| 87 | 8 | >10,000 |
| 88 | 166 | >10,000 |
| 89 | 140 | >10,000 |
| 90 | 68 | >10,000 |
| 91 | 6 | >10,000 |
| 92 | 8 | 5569 |
| 93 | 35 | >10,000 |
| 94 | 28 | >10,000 |
| 95 | 19 | 1067 |
| 96 | 86 | 1356 |
| 97 | 122 | >10,000 |
| 98 | 160 | >10,000 |
| 99 | 153 | >10,000 |
| 100 | 128 | >10,000 |
| 101 | 310 | >10,000 |
| 102 | 46 | >10,000 |
| 103 | 8 | 7897 |
| 105 | 39 | >10,000 |
| 106 | 29 | >10,000 |
| 107 | 27 | >10,000 |
| 108 | 24 | >10,000 |
| 109 | 21 | >10,000 |
| 110 | 43 | 3549 |
| 111 | 34 | >10,000 |
| 112 | 476 | >10,000 |
| 113 | 67 | >10,000 |
| 114 | 997 | >10,000 |
| 115 | 175 | >10,000 |
| 117 | 406 | >10,000 |
| 118 | 368 | >10,000 |
| 119 | 22 | 7800 |
| 121 | 822 | >10,000 |
| 122 | 32 | >10,000 |
| 123 | 18 | >10,000 |
| 124 | 21 | >10,000 |
| 125 | 14 | >10,000 |
| 126 | 119 | >10,000 |
| 127 | 68 | >10,000 |
| 128 | 33 | >10,000 |
| 129 | 633 | 8753 |
| 130 | 77 | >10,000 |
| 131 | 39 | >10,000 |
| 132 | 12 | >10,000 |
| 135 | 94 | >10,000 |
| 136 | 830 | >10,000 |
| 137 | 34 | >10,000 |
| 138 | 30 | >10,000 |
| 139 | 32 | >10,000 |
| 140 | 35 | >10,000 |
| 141 | 62 | >10,000 |
| 142 | 12 | 8827 |
| 143 | 49 | >10,000 |
| 144 | 13 | >10,000 |
| 145 | 11 | >10,000 |
| 146 | 7 | >10,000 |
| 147 | 24 | >10,000 |
| 148 | 19 | >10,000 |
| 149 | 25 | >10,000 |
| 150 | 43 | >10,000 |
| 151 | 29 | >10,000 |
| 153 | 66 | >10,000 |
| 154 | 42 | >10,000 |
| 155 | 8 | >10,000 |
| 156 | 11 | >10,000 |
| 157 | 236 | >10,000 |
| 158 | 5 | >10,000 |
| 159 | 25 | >10,000 |
| 160 | 29 | >10,000 |

The invention claimed is:

1. A compound of formula

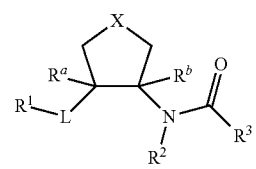

(I)

wherein
R$^1$ represents a 5- or 6-membered heteroaryl group optionally substituted by at least one substituent selected from halogen, cyano, hydroxyl, C$_3$-C$_6$ cycloalkyl, C$_1$-C$_3$ alkyl, C$_1$-C$_3$ alkoxy, C$_1$-C$_3$ alkoxycarbonyl, C$_1$-C$_3$ alkoxycarbonylamino, C$_1$-C$_3$ haloalkyl, C$_1$-C$_3$ haloalkoxy, —NR$^4$R$^5$, C$_3$-C$_6$ cycloalkylamino, C$_1$-C$_3$ alkylcarbonyloxy, C$_1$-C$_3$ alkylcarbonylamino, sulphonamido, C$_1$-C$_3$ alkylsulphonyl, C$_1$-C$_3$ alkylsulphonylamino and —C(O)NR$^6$R$^7$;

L represents a bond, CH$_2$, O or NR$^{12}$;

R$^a$ represents a hydrogen atom or a C$_1$-C$_3$ alkyl or C$_1$-C$_3$ haloalkyl group;

R$^b$ represents a hydrogen atom or a C$_1$-C$_3$ alkyl or C$_1$-C$_3$ haloalkyl group;

X represents CH$_2$, CHF or CF$_2$;

R$^2$ represents a hydrogen atom or a C$_1$-C$_6$ alkyl or C$_3$-C$_6$ cycloalkyl group;

R$^3$ represents a phenyl group or a 5- or 6-membered heteroaryl group, all optionally substituted by at least one substituent independently selected from halogen, hydroxyl, cyano, C$_1$-C$_3$ alkyl, C$_1$-C$_3$ haloalkyl, C$_1$-C$_3$ hydroxyalkyl, C$_1$-C$_3$ alkoxy, C$_1$-C$_3$ haloalkoxy, C$_2$-C$_4$ alkenyl, C$_1$-C$_3$ alkylcarbonyloxy, C$_1$-C$_3$ alkoxycarbonyl, —NR$^8$R$^9$, —C(O)NR$^{10}$R$^{11}$, C$_3$-C$_6$ cycloalkyl, C$_3$-C$_6$ cycloalkyloxy, C$_3$-C$_6$ cycloalkylmethyl or a 5- or 6-membered heteroaryl group, the heteroaryl group itself being optionally substituted by at least one substituent independently selected from C$_1$-C$_6$ alkyl, C$_1$-C$_6$ alkoxy and C$_1$-C$_6$ haloalkoxy;

R$^4$ and R$^5$ each independently represent a hydrogen atom or a C$_1$-C$_3$ alkyl or C$_3$-C$_6$ cycloalkyl group, or R$^4$ and R$^5$ may together with the nitrogen atom to which they are attached form a 4- to 7-membered saturated heterocyclic ring optionally substituted by at least one substituent independently selected from halogen, hydroxyl and $C_1$-$C_3$ alkoxy;

$R^6$ and $R^7$ each independently represent a hydrogen atom or a $C_1$-$C_3$ alkyl or $C_3$-$C_6$ cycloalkyl group, or $R^6$ and $R^7$ may together with the nitrogen atom to which they are attached form a 4- to 7-membered saturated heterocyclic ring optionally substituted by at least one substituent independently selected from halogen and hydroxyl;

$R^8$ and $R^9$ each independently represent a hydrogen atom or a $C_1$-$C_3$ alkyl or $C_3$-$C_6$ cycloalkyl group, or $R^8$ and $R^9$ may together with the nitrogen atom to which they are attached form a 4- to 7-membered saturated heterocyclic ring optionally substituted by at least one substituent independently selected from halogen, hydroxyl and $C_1$-$C_3$ alkoxy;

$R^{10}$ and $R^{11}$ each independently represent a hydrogen atom or a $C_1$-$C_3$ alkyl or $C_3$-$C_6$ cycloalkyl group, or $R^{10}$ and $R^{11}$ may together with the nitrogen atom to which they are attached form a 4- to 7-membered saturated heterocyclic ring optionally substituted by at least one substituent independently selected from halogen and hydroxyl; and $R^{12}$ represents a hydrogen atom, methyl group or a $C_2$-$C_3$ alkylene chain that links to $R^1$ to form a 5- or 6-membered ring;

or a pharmaceutically acceptable salt thereof.

2. A compound according to claim 1, wherein $R^1$ represents a 5- or 6-membered heteroaryl group containing one or two ring heteroatoms independently selected from nitrogen, oxygen and sulphur, the heteroaryl group being optionally substituted by one or two substituents independently selected from halogen, $C_1$-$C_3$ alkyl and $C_1$-$C_3$ haloalkyl.

3. A compound according to claim 1, wherein $R^1$ represents a 5- or 6-membered heteroaryl group selected from pyridinyl, pyrimidinyl and pyrazinyl, all optionally substituted as defined in claim 1.

4. A compound according to claim 3, wherein $R^1$ represents a group selected from:
(i) 4-(trifluoromethyl)pyridin-2-yl,
(ii) 5-(trifluoromethyl)pyridin-2-yl,
(iii) 5-(trifluoromethoxy)pyridin-2-yl,
(iv) 6-(trifluoromethyl)pyridin-2-yl,
(v) 6-(trifluoromethyl)pyridin-3-yl,
(vi) 5-chloropyridin-2-yl,
(vii) 5-bromopyridin-2-yl,
(viii) 3-fluoro-5-(trifluoromethyl)pyridin-2-yl,
(ix) 3-chloro-5-(trifluoromethyl)pyridin-2-yl,
(x) 3-bromo-5-(trifluoromethyl)pyridin-2-yl,
(xi) 5-bromo-3-methoxypyridin-2-yl,
(xii) 3-methyl-5-(trifluoromethyl)pyridin-2-yl,
(xiii) 5-(trifluoromethyl)pyrimidin-2-yl,
(xiv) 5-ethylpyrimidin-2-yl,
(xv) 5-(trifluoromethyl)pyrazin-2-yl,
(xvi) 5-chloropyrazin-2-yl,
(xvii) 5-(ethyl)pyrazin-2-yl,
(xviii) 5-(cyclopropyl)pyrazin-2-yl,
(xix) 5-(isopropyl)pyrazin-2-yl,
(xx) 3-methyl-5-(trifluoromethyl)pyrazin-2-yl,
(xxi) 3-ethyl-5-(trifluoromethyl)pyrazin-2-yl,
(xxii) 3-cyclopropyl-5-(trifluoromethyl)pyrazin-2-yl, and
(xxiii) 3-isopropyl-5-(trifluoromethyl)pyrazin-2-yl.

5. A compound according to claim 1, wherein X represents $CH_2$.

6. A compound according to claim 1, wherein L represents NH.

7. A compound according to claim 1, wherein $R^2$ represents a hydrogen atom.

8. A compound according to claim 1, wherein $R^3$ represents a 5- or 6-membered heteroaryl group selected from pyridinyl, pyrimidinyl and pyrazinyl, all optionally substituted as defined in claim 1.

9. A compound according to claim 1, wherein $R^3$ represents a phenyl group optionally substituted by at least one substituent independently selected from fluorine, chlorine, $C_1$-$C_3$ alkyl, $C_1$-$C_3$ alkoxy or a 5- or 6-membered heteroaryl group, the heteroaryl group itself being optionally substituted by one or two substituents independently selected from $C_1$-$C_2$ alkyl, $C_1$-$C_2$ alkoxy and $C_1$-$C_2$ haloalkoxy.

10. A compound according to claim 1, wherein $R^3$ represents a group selected from:
(i) 2-fluorophenyl,
(ii) 2-chlorophenyl,
(iii) 2-methylphenyl,
(iv) 2-cyclopropylphenyl,
(v) 2-methoxyphenyl,
(vi) 2-ethoxyphenyl,
(vii) 2-(difluoromethoxy)phenyl,
(viii) 3-methylphenyl,
(ix) 3-methoxyphenyl,
(x) 2,6-difluorophenyl,
(xi) 2,6-dichlorophenyl,
(xii) 2,6-dimethoxyphenyl,
(xiii) 2,6-diethoxyphenyl,
(xiv) 2-ethoxy-5-methylphenyl,
(xv) 2,5-dimethoxyphenyl,
(xvi) 2-fluoro-6-methoxyphenyl,
(xvii) 5-fluoro-2-methoxyphenyl,
(xviii) 3-fluoro-2-methoxyphenyl,
(xix) 2-(1H-1,2,4-triazol-1-yl)phenyl,
(xx) 2-(2H-1,2,3-triazol-2-yl)phenyl,
(xxi) 5-methyl-2-(1H-1,2,3-triazol-1-yl)phenyl,
(xxii) 5-methyl-2-(2H-1,2,3-triazol-2-yl)phenyl,
(xxiii) 5-fluoro-2-(1H-1,2,3-triazol-1-yl)phenyl,
(xxiv) 5-fluoro-2-(2H-1,2,3-triazol-2-yl)phenyl,
(xxv) 2-(3-methyl-1,2,4-oxadiazol-5-yl)phenyl,
(xxvi) 2-(pyrimidin-2-yl)phenyl,
(xxvii) 5-fluoro-2-(pyrimidin-2-yl)phenyl,
(xxviii) 2-(1H-pyrazol-1-yl)phenyl,
(xxix) 2-(1H-imidazol-1-yl)phenyl,
(xxx) 2-(1H-1,2,3-triazol-1-yl)phenyl,
(xxxi) 2-(pyrimidin-2-yl)-5-fluorophenyl,
(xxxii) 2-fluoro-6-(2H-1,2,3-triazol-2-yl)phenyl,
(xxxiii) 2-methoxy-5-methylphenyl,
(xxxiv) 2-chloro-6-(2H-1,2,3-triazol-2-yl)phenyl,
(xxxv) 2-(5-methyl-1,3,4-oxadiazol-2-yl)phenyl,
(xxxvi) 5-trifluoromethyl-2-(2H-1,2,3-triazol-2-yl)phenyl,
(xxxvii) 2-fluoro-6-(pyrazol-1-yl)phenyl,
(xxxviii) 5-fluoro-2-(pyrazol-1-yl)phenyl,
(xxxix) 5-methyl-2-(pyrazol-1-yl)phenyl,
(xl) 2-bromo-6-methoxyphenyl,
(xli) 2-methoxy-6-(pyrazol-1-yl)phenyl,
(xlii) 5-chloro-2-(2H-1,2,3-triazol-2-yl)phenyl,
(xliii) 3-fluoro-2-(2H-1,2,3-triazol-2-yl)phenyl,
(xliv) 5-trifluoromethyl-2-(1H-1,2,3-triazol-1-yl)phenyl,
(xlv) 5-chloro-2-(1H-1,2,3-triazol-1-yl)phenyl,
(xlvi) 2,3-difluoro-6-(2H-1,2,3-triazol-2-yl)phenyl,
(xlvii) 5-cyclopropyl-2-(2H-1,2,3-triazol-2-yl)phenyl,
(xlviii) 5-chloro-2-(pyrazol-1-yl)phenyl,
(xlix) 3,5-difluoro-2-(2H-1,2,3-triazol-2-yl)phenyl, (l) 2-(difluoromethyl)phenyl,
(li) 2-(trifluoromethyl)phenyl,
(lii) 3,6-difluoro-2-(2H-1,2,3-triazol-2-yl)phenyl,
(liii) 2-cyclopropyl-6-fluorophenyl,
(liv) 2-(5-ethoxypyrimidin-2-yl)phenyl,
(lv) 3-(pyrimidin-2-yl)pyridin-2-yl,
(lvi) 3-ethoxy-6-methylpyridin-2-yl,
(lvii) 3-(pyrazol-1-yl)pyridin-2-yl,
(lviii) 3-(piperidin-1-yl)pyridin-2-yl,
(lix) 3-(trifluoromethoxy)pyridin-2-yl,
(lx) 3-(ethoxy)pyridin-2-yl,
(lxi) 3-(cyclopropyl)pyridin-2-yl,
(lxii) 3-chloropyridin-2-yl,
(lxiii) 3-bromopyridin-2-yl,
(lxiv) 3-methoxypyridin-2-yl,
(lxv) 3-(propan-2-yloxy)pyridin-2-yl,
(lxvi) 6-bromo-3-methoxypyridin-2-yl,
(lxvii) 3-methoxy-6-methylpyridin-2-yl, and
(lxviii) 3-(2H-1,2,3-triazol-2-yl)pyridin-2-yl.

11. A compound of formula (I) as defined in claim 1 selected from the group consisting of:

2,6-Dimethoxy-N-[(1S,2S)-2-{[5-(trifluoromethyl)pyridin-2-yl]amino}cyclopentyl]benzamide;
2,6-Dimethoxy-N-[(1S,2S)-2-{[5-(trifluoromethyl)pyrimidin-2-yl]amino}cyclopentyl]benzamide;
5-Methyl-2-(2H-1,2,3-triazol-2-yl)-N-[(1S,2S)-2-{[5-(trifluoromethyl)pyrimidin-2-yl]amino}cyclopentyl]benzamide;
N-[(1S,2S)-2-[(5-Ethylpyrimidin-2-yl)amino]cyclopentyl]-5-methyl-2-(2H-1,2,3-triazol-2-yl)benzamide;
N-[(1S,2S)-2-[(5-Chloropyridin-2-yl)amino]cyclopentyl]-5-methyl-2-(2H-1,2,3-triazol-2-yl)benzamide;
5-Methyl-2-(2H-1,2,3-triazol-2-yl)-N-[(1S,2S)-2-{[5-(trifluoromethyl)pyridin-2-yl]amino}cyclopentyl]benzamide;
5-Methyl-2-(2H-1,2,3-triazol-2-yl)-N-[(1S,2S)-2-{[5-(trifluoromethyl)pyrazin-2-yl]amino}cyclopentyl]benzamide;
2-(3-Methyl-1,2,4-oxadiazol-5-yl)-N-[(1S,2S)-2-{[5-(trifluoromethyl)pyridin-2-yl]amino}cyclopentyl]benzamide;
N-[(1S,2S)-2-[(5-Chloropyrazin-2-yl)amino]cyclopentyl]-5-methyl-2-(2H-1,2,3-triazol-2-yl)benzamide;
5-Fluoro-2-(2H-1,2,3-triazol-2-yl)-N-[(1S,2S)-2-{[5-(trifluoromethyl)pyridin-2-yl]amino}cyclopentyl]benzamide;
2-(1H-Pyrazol-1-yl)-N-[(1S,2S)-2-{[5-(trifluoromethyl)pyridin-2-yl]amino}cyclopentyl]benzamide;
2-(2H-1,2,3-Triazol-2-yl)-N-[(1S,2S)-2-{[5-(trifluoromethyl)pyridin-2-yl]amino}cyclopentyl]benzamide;
2-(Pyrimidin-2-yl)-N-[(1S,2S)-2-{[5-(trifluoromethyl)pyridin-2-yl]amino}cyclopentyl]benzamide;
5-Fluoro-2-(pyrimidin-2-yl)-N-[(1S,2S)-2-{[5-(trifluoromethyl)pyridin-2-yl]amino}cyclopentyl]benzamide;
2-(3-Methyl-1,2,4-oxadiazol-5-yl)-N-[(1S,2S)-2-{[5-(trifluoromethyl)pyrazin-2-yl]amino}cyclopentyl]benzamide;
2-(3-Methyl-1,2,4-oxadiazol-5-yl)-N-[(1S,2S)-2-{[5-(trifluoromethyl)pyrimidin-2-yl]amino}cyclopentyl]benzamide;
2-(2H-1,2,3-Triazol-2-yl)-N-[(1S,2S)-2-{[5-(trifluoromethyl)pyrazin-2-yl]amino}cyclopentyl]benzamide;
2-(2H-1,2,3-Triazol-2-yl)-N-[(1S,2S)-2-{[5-(trifluoromethyl)pyrimidin-2-yl]amino}cyclopentyl]benzamide;
2-(2H-1,2,3-Triazol-2-yl)-N-[(1S,2R)-2-{[5-(trifluoromethyl)pyrazin-2-yl]oxy}cyclopentyl]benzamide;
2-(2H-1,2,3-Triazol-2-yl)-N-[(1S,2S)-2-{[4-(trifluoromethyl)pyridin-2-yl]oxy}cyclopentyl]benzamide;
2,6-Dimethoxy-N-[(1S,2S)-2-{[4-(trifluoromethyl)pyridin-2-yl]oxy}cyclopentyl]benzamide;
2-(2H-1,2,3-Triazol-2-yl)-N-(2-{[4-(trifluoromethyl)pyridin-2-yl]methyl}cyclopentyl)benzamide;
2-(2H-1,2,3-Triazol-2-yl)-N-(2-{[5-(trifluoromethyl)pyridin-2-yl]methyl}cyclopentyl)benzamide;
5-Methyl-2-(2H-1,2,3-triazol-2-yl)-N-(2-{[5-(trifluoromethyl)pyridin-2-yl]methyl}cyclopentyl)benzamide;
2,6-Dimethoxy-N-[(1S,2S)-2-{[6-(trifluoromethyl)pyridin-2-yl]amino}cyclopentyl]benzamide;
3-Bromo-N-[(1S,2S)-2-{[5-(trifluoromethyl)pyrazin-2-yl]amino}cyclopentyl]pyridine-2-carboxamide;
2-Ethoxy-5-methyl-N-[(1S,2S)-2-{[5-(trifluoromethyl)pyrazin-2-yl]amino}cyclopentyl]benzamide;
3-Ethoxy-6-methyl-N-[(1S,2S)-2-{[5-(trifluoromethyl)pyrazin-2-yl]amino}cyclopentyl]pyridine-2-carboxamide;
2-(1H-Pyrazol-1-yl)-N-[(1S,2S)-2-{[5-(trifluoromethyl)pyrazin-2-yl]amino}cyclopentyl]benzamide;
2-Fluoro-6-(2H-1,2,3-triazol-2-yl)-N-[(1S,2S)-2-{[5-(trifluoromethyl)pyrazin-2-yl]amino}cyclopentyl]benzamide;
2,6-Difluoro-N-[(1S,2S)-2-{[5-(trifluoromethyl)pyrazin-2-yl]amino}cyclopentyl]benzamide;
2,6-Dimethoxy-N-[(1S,2S)-2-{[5-(trifluoromethyl)pyrazin-2-yl]amino}cyclopentyl]benzamide;
2-(1H-1,2,3-Triazol-1-yl)-N-[(1S,2S)-2-{[5-(trifluoromethyl)pyrazin-2-yl]amino}cyclopentyl]benzamide;
5-Fluoro-2-(2H-1,2,3-triazol-2-yl)-N-[(1S,2S)-2-{[5-(trifluoromethyl)pyrazin-2-yl]amino}cyclopentyl]benzamide;
2-Methoxy-5-methyl-N-[(1S,2S)-2-{[5-(trifluoromethyl)pyrazin-2-yl]amino}cyclopentyl]benzamide;
2-(Pyrimidin-2-yl)-N-[(1S,2S)-2-{[5-(trifluoromethyl)pyrazin-2-yl]amino}cyclopentyl]benzamide;
5-Fluoro-2-(pyrimidin-2-yl)-N-[(1S,2S)-2-{[5-(trifluoromethyl)pyrazin-2-yl]amino}cyclopentyl]benzamide;
2-Chloro-6-(2H-1,2,3-triazol-2-yl)-N-[(1S,2S)-2-{[5-(trifluoromethyl)pyrazin-2-yl]amino}cyclopentyl]benzamide;
5-Fluoro-2-(1H-1,2,3-triazol-1-yl)-N-[(1S,2S)-2-{[5-(trifluoromethyl)pyrazin-2-yl]amino}cyclopentyl]benzamide;
5-Methyl-2-(1H-1,2,3-triazol-1-yl)-N-[(1S,2S)-2-{[5-(trifluoromethyl)pyrazin-2-yl]amino}cyclopentyl]benzamide;
3-(1H-Pyrazol-1-yl)-N-[(1S,2S)-2-{[5-(trifluoromethyl)pyrazin-2-yl]amino}cyclopentyl]pyridine-2-carboxamide;
2-(5-Methyl-1,3,4-oxadiazol-2-yl)-N-[(1S,2S)-2-{[5-(trifluoromethyl)pyrazin-2-yl]amino}cyclopentyl]benzamide;
2-(2H-1,2,3-Triazol-2-yl)-5-(trifluoromethyl)-N-[(1S,2S)-2-{[5-(trifluoromethyl)pyrazin-2-yl]amino}cyclopentyl]benzamide;
2-Fluoro-6-(1H-pyrazol-1-yl)-N-[(1S,2S)-2-{[5-(trifluoromethyl)pyrazin-2-yl]amino}cyclopentyl]benzamide;
5-Fluoro-2-(1H-pyrazol-1-yl)-N-[(1S,2S)-2-{[5-(trifluoromethyl)pyrazin-2-yl]amino}cyclopentyl]benzamide;
5-Methyl-2-(1H-pyrazol-1-yl)-N-[(1S,2S)-2-{[5-(trifluoromethyl)pyrazin-2-yl]amino}cyclopentyl]benzamide;
2-Bromo-6-methoxy-N-[(1S,2S)-2-{[5-(trifluoromethyl)pyrazin-2-yl]amino}cyclopentyl]benzamide;

2-Methoxy-6-(1H-pyrazol-1-yl)-N-[(1S,2S)-2-{[5-(trifluoromethyl)pyrazin-2-yl]amino}cyclopentyl]benzamide;
3-(Piperidin-1-yl)-N-[(1S,2S)-2-{[5-(trifluoromethyl)pyrazin-2-yl]amino}cyclopentyl]pyridine-2-carboxamide;
5-Chloro-2-(2H-1,2,3-triazol-2-yl)-N-[(1S,2S)-2-{[5-(trifluoromethyl)pyrazin-2-yl]amino}cyclopentyl]benzamide;
3-Fluoro-2-(2H-1,2,3-triazol-2-yl)-N-[(1S,2S)-2-{[5-(trifluoromethyl)pyrazin-2-yl]amino}cyclopentyl]benzamide;
2-(1H-1,2,3-Triazol-1-yl)-5-(trifluoromethyl)-N-[(1S,2S)-2-{[5-(trifluoromethyl)pyrazin-2-yl]amino}cyclopentyl]benzamide;
5-Chloro-2-(1H-1,2,3-triazol-1-yl)-N-[(1S,2S)-2-{[5-(trifluoromethyl)pyrazin-2-yl]amino}cyclopentyl]benzamide;
2,3-Difluoro-6-(2H-1,2,3-triazol-2-yl)-N-[(1S,2S)-2-{[5-(trifluoromethyl)pyrazin-2-yl]amino}cyclopentyl]benzamide;
5-Cyclopropyl-2-(2H-1,2,3-triazol-2-yl)-N-[(1S,2S)-2-{[5-(trifluoromethyl)pyrazin-2-yl]amino}cyclopentyl]benzamide;
3-(Trifluoromethoxy)-N-[(1S,2S)-2-{[5-(trifluoromethyl)pyrazin-2-yl]amino}cyclopentyl]pyridine-2-carboxamide;
5-Chloro-2-(1H-pyrazol-1-yl)-N-[(1S,2S)-2-{[5-(trifluoromethyl)pyrazin-2-yl]amino}cyclopentyl]benzamide;
3-Ethoxy-N-[(1S,2S)-2-{[5-(trifluoromethyl)pyrazin-2-yl]amino}cyclopentyl]pyridine-2-carboxamide;
3,5-Difluoro-2-(2H-1,2,3-triazol-2-yl)-N-[(1S,2S)-2-{[5-(trifluoromethyl)pyrazin-2-yl]amino}cyclopentyl]benzamide;
2-(Trifluoromethyl)-N-[(1S,2S)-2-{[5-(trifluoromethyl)pyrazin-2-yl]amino}cyclopentyl]benzamide;
3-Cyclopropyl-N-[(1S,2S)-2-{[5-(trifluoromethyl)pyrazin-2-yl]amino}cyclopentyl]pyridine-2-carboxamide;
3,6-Difluoro-2-(2H-1,2,3-triazol-2-yl)-N-[(1S,2S)-2-{[5-(trifluoromethyl)pyrazin-2-yl]amino}cyclopentyl]benzamide;
2-(Difluoromethyl)-N-[(1S,2S)-2-{[5-(trifluoromethyl)pyrazin-2-yl]amino}cyclopentyl]benzamide;
2-Cyclopropyl-6-fluoro-N-[(1S,2S)-2-{[5-(trifluoromethyl)pyrazin-2-yl]amino}cyclopentyl]benzamide;
5-Methyl-2-(2H-1,2,3-triazol-2-yl)-N-[(1S,2S)-2-{[6-(trifluoromethyl)pyridin-3-yl]amino}cyclopentyl]benzamide;
N-Cyclobutyl-2,6-dimethoxy-N-[(1S,2S)-2-{[5-(trifluoromethyl)pyridin-2-yl]amino}cyclopentyl]benzamide;
2-Chloro-N-[(1S,2S)-2-{[5-(trifluoromethyl)pyridin-2-yl]amino}cyclopentyl]benzamide;
2-Chloro-N-[(1S,2S)-2-{[5-(trifluoromethyl)pyrimidin-2-yl]amino}cyclopentyl]benzamide;
2-Fluoro-6-methoxy-N-[(1S,2S)-2-{[5-(trifluoromethyl)pyridin-2-yl]amino}cyclopentyl]benzamide;
2,6-Difluoro-N-[(1S,2S)-2-{[5-(trifluoromethyl)pyridin-2-yl]amino}cyclopentyl]benzamide;
N-[(1S,2S)-2-{Methyl[5-(trifluoromethyl)pyrazin-2-yl]amino}cyclopentyl]-2-(2H-1,2,3-triazol-2-yl)benzamide;
5-Fluoro-N-[(1S,2S)-2-{methyl[5-(trifluoromethyl)pyrazin-2-yl]amino}cyclopentyl]-2-(2H-1,2,3-triazol-2-yl)benzamide;
2-Fluoro-N-[(1S,2S)-2-{methyl[5-(trifluoromethyl)pyrazin-2-yl]amino}cyclopentyl]-6-(2H-1,2,3-triazol-2-yl)benzamide;
N-[(1S,2S)-2-{[3-Methyl-5-(trifluoromethyl)pyrazin-2-yl]amino}cyclopentyl]-3-(2H-1,2,3-triazol-2-yl)pyridine-2-carboxamide;
N-[(1S,2S)-2-Methyl-2-{[5-(trifluoromethyl)pyrazin-2-yl]amino}cyclopentyl]-3-(2H-1,2,3-triazol-2-yl)pyridine-2-carboxamide;
N-[(1S,2S)-2-{[3-Methyl-5-(trifluoromethyl)pyrazin-2-yl]amino}cyclopentyl]-2-(2H-1,2,3-triazol-2-yl)benzamide;
N-[(1S,2S)-2-{[3-Methyl-5-(trifluoromethyl)pyrazin-2-yl]amino}cyclopentyl]-2-(pyrimidin-2-yl)benzamide;
5-Fluoro-N-[(1S,2S)-2-{[3-methyl-5-(trifluoromethyl)pyrazin-2-yl]amino}cyclopentyl]-2-(pyrimidin-2-yl)benzamide;
N-[(1S,2S)-2-Methyl-2-{[5-(trifluoromethyl)pyrazin-2-yl]amino}cyclopentyl]-2-(2H-1,2,3-triazol-2-yl)benzamide;
N-(2-Methyl-2-{[5-(trifluoromethyl)pyrazin-2-yl]amino}cyclopentyl)-2-(2H-1,2,3-triazol-2-yl)benzamide;
N-[(1R,2R)-2-Methyl-2-{[5-(trifluoromethyl)pyrazin-2-yl]amino}cyclopentyl]-2-(2H-1,2,3-triazol-2-yl)benzamide;
5-Fluoro-N-[(1S,2S)-2-methyl-2-{[5-(trifluoromethyl)pyrazin-2-yl]amino}cyclopentyl]-2-(2H-1,2,3-triazol-2-yl)benzamide;
N-[(1S,2S)-2-Methyl-2-{[5-(trifluoromethyl)pyrazin-2-yl]amino}cyclopentyl]-3-(1H-pyrazol-1-yl)pyridine-2-carboxamide;
3-Ethoxy-N-[(1S,2S)-2-methyl-2-{[5-(trifluoromethyl)pyrazin-2-yl]amino}cyclopentyl]pyridine-2-carboxamide,
2-Chloro-N-[(1S,2S)-2-methyl-2-{[5-(trifluoromethyl)pyrazin-2-yl]amino}cyclopentyl]-6-(2H-1,2,3-triazol-2-yl)benzamide;
2,6-Difluoro-N-[(1S,2S)-2-methyl-2-{[5-(trifluoromethyl)pyrazin-2-yl]amino}cyclopentyl]benzamide;
3-Cyclopropyl-N-[(1S,2S)-2-methyl-2-{[5-(trifluoromethyl)pyrazin-2-yl]amino}cyclopentyl]pyridine-2-carboxamide;
N-[(1S,2S)-2-Methyl-2-{[5-(trifluoromethyl)pyrazin-2-yl]amino}cyclopentyl]-3-(trifluoromethoxy)pyridine-2-carboxamide;
N-[(1S,2S)-2-Methyl-2-{[5-(trifluoromethyl)pyrazin-2-yl]amino}cyclopentyl]-2-(pyrimidin-2-yl)benzamide;
5-Chloro-N-[(1S,2S)-2-methyl-2-{[5-(trifluoromethyl)pyrazin-2-yl]amino}cyclopentyl]-2-(2H-1,2,3-triazol-2-yl)benzamide;
N-(2-Methyl-2-{[5-(trifluoromethyl)pyrimidin-2-yl]amino}cyclopentyl)-2-(2H-1,2,3-triazol-2-yl)benzamide;
N-(2-Methyl-2-{[5-(trifluoromethyl)pyridin-2-yl]amino}cyclopentyl)-2-(2H-1,2,3-triazol-2-yl)benzamide;
N-(2-Methyl-2-{[5-(trifluoromethoxy)pyridin-2-yl]amino}cyclopentyl)-2-(2H-1,2,3-triazol-2-yl)benzamide;
5-Chloro-2-(2H-1,2,3-triazol-2-yl)-N-[(1S,2S)-2-{[5-(trifluoromethyl)pyridin-2-yl]amino}cyclopentyl]benzamide;
3-Fluoro-2-(2H-1,2,3-triazol-2-yl)-N-[(1S,2S)-2-{[5-(trifluoromethyl)pyridin-2-yl]amino}cyclopentyl]benzamide;

3,5-Difluoro-2-(2H-1,2,3-triazol-2-yl)-N-[(1S,2S)-2-{[5-(trifluoromethyl)pyridin-2-yl]amino}cyclopentyl]benzamide;
3-(2H-1,2,3-Triazol-2-yl)-N-[(1S,2S)-2-{[5-(trifluoromethyl)pyridin-2-yl]amino}cyclopentyl]pyridine-2-carboxamide;
3-(1H-Pyrazol-1-yl)-N-[(1S,2S)-2-{[5-(trifluoromethyl)pyridin-2-yl]amino}cyclopentyl]pyridine-2-carboxamide;
2-Fluoro-6-(2H-1,2,3-triazol-2-yl)-N-[(1S,2S)-2-{[5-(trifluoromethyl)pyridin-2-yl]amino}cyclopentyl]benzamide;
N-(2-{[3-Fluoro-5-(trifluoromethyl)pyridin-2-yl]amino}-2-methylcyclopentyl)-3-(2H-1,2,3-triazol-2-yl)pyridine-2-carboxamide;
N-[(1S,2S)-2-{[3-Fluoro-5-(trifluoromethyl)pyridin-2-yl]amino}cyclopentyl]-2-(2H-1,2,3-triazol-2-yl)benzamide;
N-[(1S,2S)-2-{[3-Chloro-5-(trifluoromethyl)pyridin-2-yl]amino}cyclopentyl]-2-(2H-1,2,3-triazol-2-yl)benzamide;
N-[(1S,2S)-2-{[3-Bromo-5-(trifluoromethyl)pyridin-2-yl]amino}cyclopentyl]-2-(2H-1,2,3-triazol-2-yl)benzamide;
N-[(1S,2S)-2-{[3-Methyl-5-(trifluoromethyl)pyridin-2-yl]amino}cyclopentyl]-2-(2H-1,2,3-triazol-2-yl)benzamide;
N-[(1S,2S)-2-{[3-Cyclopropyl-5-(trifluoromethyl)pyrazin-2-yl]amino}cyclopentyl]-2-(2H-1,2,3-triazol-2-yl)benzamide;
N-[(1S,2S)-2-{[3-(Propan-2-yl)-5-(trifluoromethyl)pyrazin-2-yl]amino}cyclopentyl]-2-(2H-1,2,3-triazol-2-yl)benzamide;
N-[(1S,2S)-2-{[3-Ethyl-5-(trifluoromethyl)pyrazin-2-yl]amino}cyclopentyl]-2-(2H-1,2,3-triazol-2-yl)benzamide;
N-[(1S,2S)-2-[(5-Cyclopropylpyrazin-2-yl)amino]cyclopentyl]-2-(2H-1,2,3-triazol-2-yl)benzamide;
N-[(1S,2S)-2-{[5-(Propan-2-yl)pyrazin-2-yl]amino}cyclopentyl]-2-(2H-1,2,3-triazol-2-yl)benzamide;
N-[(1S,2S)-2-[(5-Ethylpyrazin-2-yl)amino]cyclopentyl]-2-(2H-1,2,3-triazol-2-yl)benzamide;
2-(2H-1,2,3-Triazol-2-yl)-N-[(1S,2S)-2-{[5-(trifluoromethoxy)pyridin-2-yl]amino}cyclopentyl]benzamide;
5-Chloro-2-(2H-1,2,3-triazol-2-yl)-N-[(1S,2S)-2-{[5-(trifluoromethoxy)pyridin-2-yl]amino}cyclopentyl]benzamide;
N-[(1S,2S)-2-[(5-Bromopyridin-2-yl)amino]cyclopentyl]-2-(2H-1,2,3-triazol-2-yl)benzamide;
N-[(1S,2S)-2-[(5-Bromo-3-methoxypyridin-2-yl)amino]cyclopentyl]-2-(2H-1,2,3-triazol-2-yl)benzamide;
2-(2H-1,2,3-Triazol-2-yl)-N-[(1S,2S)-2-{[4-(trifluoromethyl)pyridin-2-yl]amino}cyclopentyl]benzamide;
N-[(1S,2S)-2-{[3-Chloro-5-(trifluoromethyl)pyridin-2-yl]amino}cyclopentyl]-3-(2H-1,2,3-triazol-2-yl)pyridine-2-carboxamide;
N-[(1S,2S)-2-{[3-Fluoro-5-(trifluoromethyl)pyridin-2-yl]amino}cyclopentyl]-3-(2H-1,2,3-triazol-2-yl)pyridine-2-carboxamide;
N-[(1S,2S)-2-{[3-Methyl-5-(trifluoromethyl)pyridin-2-yl]amino}cyclopentyl]-3-(2H-1,2,3-triazol-2-yl)pyridine-2-carboxamide;
N-[(1S,2S)-2-{[3-Ethyl-5-(trifluoromethyl)pyrazin-2-yl]amino}cyclopentyl]-3-(2H-1,2,3-triazol-2-yl)pyridine-2-carboxamide;
N-(4,4-Difluoro-2-{[5-(trifluoromethyl)pyrazin-2-yl]amino}cyclopentyl)-2-(2H-1,2,3-triazol-2-yl)benzamide;
N-(4,4-Difluoro-2-{[5-(trifluoromethyl)pyrimidin-2-yl]amino}cyclopentyl)-2-(2H-1,2,3-triazol-2-yl)benzamide;
N-(4,4-Difluoro-2-{[5-(trifluoromethyl)pyridin-2-yl]amino}cyclopentyl)-2-(2H-1,2,3-triazol-2-yl)benzamide;
N-[(1S,2S)-4,4-Difluoro-2-{[5-(trifluoromethoxy)pyridin-2-yl]amino}cyclopentyl]-2-(2H-1,2,3-triazol-2-yl)benzamide;
N-[(1S,2S)-4,4-Difluoro-2-{[3-fluoro-5-(trifluoromethyl)pyridin-2-yl]amino}cyclopentyl]-2-(2H-1,2,3-triazol-2-yl)benzamide;
2-(5-Ethoxypyrimidin-2-yl)-N-[(1S,2S)-2-{[5-(trifluoromethyl)pyrazin-2-yl]amino}cyclopentyl]benzamide;
2-Fluoro-6-methoxy-N-[(1S,2S)-2-{[5-(trifluoromethyl)pyrazin-2-yl]amino}cyclopentyl]benzamide;
N-[(1S,2S)-2-{[3-Methyl-5-(trifluoromethyl)pyridin-2-yl]amino}cyclopentyl]-3-(pyrimidin-2-yl)pyridine-2-carboxamide;
N-[(1S,2S)-2-{[3-Fluoro-5-(trifluoromethyl)pyridin-2-yl]amino}cyclopentyl]-2-(pyrimidin-2-yl)benzamide;
5-Fluoro-N-[(1S,2S)-2-{[3-fluoro-5-(trifluoromethyl)pyridin-2-yl]amino}cyclopentyl]-2-(pyrimidin-2-yl)benzamide;
N-[(1S,2S)-2-{[3-Fluoro-5-(trifluoromethyl)pyridin-2-yl]amino}cyclopentyl]-2-(3-methyl-1,2,4-oxadiazol-5-yl)benzamide;
2-(3-Methyl-1,2,4-oxadiazol-5-yl)-N-[(1S,2S)-2-{[3-methyl-5-(trifluoromethyl)pyrazin-2-yl]amino}cyclopentyl]benzamide;
N-[(1S,2S)-2-{[3-Cyclopropyl-5-(trifluoromethyl)pyrazin-2-yl]amino}cyclopentyl]-3-(2H-1,2,3-triazol-2-yl)pyridine-2-carboxamide;
N-[(1S,2S)-2-{[3-Cyclopropyl-5-(trifluoromethyl)pyrazin-2-yl]amino}cyclopentyl]-3-(pyrimidin-2-yl)pyridine-2-carboxamide;
N-[(1S,2S)-2-Methyl-2-{[5-(trifluoromethyl)pyrazin-2-yl]amino}cyclopentyl]-3-(pyrimidin-2-yl)pyridine-2-carboxamide;
2-(3-Methyl-1,2,4-oxadiazol-5-yl)-N-[(1S,2S)-2-methyl-2-{[5-(trifluoromethyl)pyrazin-2-yl]amino}cyclopentyl]benzamide;
N-(2-{[3-Fluoro-5-(trifluoromethyl)pyridin-2-yl]amino}-2-methylcyclopentyl)-3-(pyrimidin-2-yl)pyridine-2-carboxamide;
N-[(1S,2S)-2-{[3-Fluoro-5-(trifluoromethyl)pyridin-2-yl]amino}cyclopentyl]-3-(pyrimidin-2-yl)pyridine-2-carboxamide;
N-[(1S,2S)-2-{[3-Chloro-5-(trifluoromethyl)pyridin-2-yl]amino}cyclopentyl]-3-(pyrimidin-2-yl)pyridine-2-carboxamide;
N-[(1S,2S)-2-{[3-Ethyl-5-(trifluoromethyl)pyrazin-2-yl]amino}cyclopentyl]-2-(3-methyl-1,2,4-oxadiazol-5-yl)benzamide;
N-[(1S,2S)-2-{[3-Ethyl-5-(trifluoromethyl)pyrazin-2-yl]amino}cyclopentyl]-3-(pyrimidin-2-yl)pyridine-2-carboxamide;
N-[(1S,2S)-2-{[3-Ethyl-5-(trifluoromethyl)pyrazin-2-yl]amino}cyclopentyl]-2-(pyrimidin-2-yl)benzamide;
N-(2-Methyl-2-{[5-(trifluoromethyl)pyrimidin-2-yl]amino}cyclopentyl)-3-(pyrimidin-2-yl)pyridine-2-carboxamide;

N-(2-Methyl-2-{[5-(trifluoromethyl)pyrimidin-2-yl]amino}cyclopentyl)-3-(2H-1,2,3-triazol-2-yl)pyridine-2-carboxamide;

N-(2-Methyl-2-{[5-(trifluoromethyl)pyridin-2-yl]amino}cyclopentyl)-3-(2H-1,2,3-triazol-2-yl)pyridine-2-carboxamide;

N-(2-Methyl-2-{[5-(trifluoromethyl)pyridin-2-yl]amino}cyclopentyl)-3-(pyrimidin-2-yl)pyridine-2-carboxamide;

N-[(1S,2S)-2-{[5-(Difluoromethoxy)pyridin-2-yl]amino}-4,4-difluorocyclopentyl]-2-(2H-1,2,3-triazol-2-yl)benzamide;

N-[(1S,2S)-2-{[3-Ethyl-5-(trifluoromethyl)pyrazin-2-yl]amino}cyclopentyl]-5-fluoro-2-(pyrimidin-2-yl)benzamide;

N-[(1S,2S)-2-{[3-Methyl-5-(trifluoromethyl)pyrazin-2-yl]amino}cyclopentyl]-3-(pyrimidin-2-yl)pyridine-2-carboxamide;

2-(5-Methyl-1,3,4-oxadiazol-2-yl)-N-[(1S,2S)-2-methyl-2-{[5-(trifluoromethyl)pyrazin-2-yl]amino}cyclopentyl]benzamide;

enantiomers thereof and pharmaceutically acceptable salts of any of the foregoing.

12. A process for the preparation of a compound of formula (I) or a pharmaceutically acceptable salt thereof as defined in claim 1, which comprises (i) reacting a compound of formula

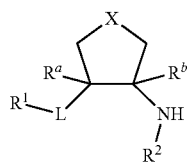

(II)

wherein L, X, $R^a$, $R^b$, $R^1$ and $R^2$ are as defined in formula (I), with a compound of formula

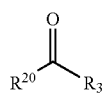

(III)

wherein $R^{20}$ represents a halogen atom or a hydroxyl group and $R^3$ is as defined in formula (I), or a salt thereof; or (ii) when L represents NH or N(CH$_3$), reacting a compound of formula

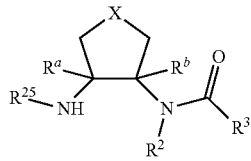

(IV)

wherein $R^{25}$ represents a hydrogen atom or methyl group and X, $R^a$, $R^b$, $R^2$ and $R^3$ are as defined in formula (I), with a compound of formula (V), $R^1$-LG$^1$, wherein LG$^1$ represents a leaving group and $R^1$ is as defined in formula (I);

and optionally thereafter carrying out one or more of the following procedures:
converting a compound of formula (I) into another compound of formula (I)
removing any protecting groups
forming a pharmaceutically acceptable salt.

13. A pharmaceutical composition comprising a compound of formula (I) or a pharmaceutically acceptable salt thereof as claimed in claim 1, in association with a pharmaceutically acceptable adjuvant, diluent or carrier, and optionally one or more other therapeutic agents.

14. A composition according to claim 13, wherein the one or more other therapeutic agents are selected from carbamazepine, olanzapine, quetiapine, verapamil, lamotrigine, oxcarbazepine, risperidone, aripiprazole, ziprasidone and lithium.

15. A compound of formula (I) or a pharmaceutically acceptable salt thereof as claimed in claim 1 for use in treating schizophrenia, schizophreniform disorder, schizoaffective disorder, cognitive disorders or pain.

16. A compound of formula (I) or a pharmaceutically acceptable salt thereof as claimed in claim 1 for use in treating post-traumatic stress disorder, panic disorders or addiction.

17. A compound of formula (I) as defined in claim 1, wherein the compound is N-[(1S,2S)-2-Methyl-2-{[5-(trifluoromethyl)pyrazin-2-yl]amino}cyclopentyl]-3-(2H-1,2,3-triazol-2-yl)pyridine-2-carboxamide, enantiomers thereof and pharmaceutically acceptable salts of any of the foregoing.

18. A compound of formula (I) as defined in claim 1, wherein the compound is N-[(1S,2S)-2-{[3-Ethyl-5-(trifluoromethyl)pyrazin-2-yl]amino}cyclopentyl]-3-(2H-1,2,3-triazol-2-yl)pyridine-2-carboxamide, enantiomers thereof and pharmaceutically acceptable salts of any of the foregoing.

19. A compound of formula (I) as defined in claim 1, wherein the compound is N-[(1S,2S)-2-Methyl-2-{[5-(trifluoromethyl)pyrazin-2-yl]amino}cyclopentyl]-3-(2H-1,2,3-triazol-2-yl)pyridine-2-carboxamide and pharmaceutically acceptable salts thereof.

20. A compound of formula (I) as defined in claim 1, wherein the compound is N-[(1S,2S)-2-{[3-Ethyl-5-(trifluoromethyl)pyrazin-2-yl]amino}cyclopentyl]-3-(2H-1,2,3-triazol-2-yl)pyridine-2-carboxamide and pharmaceutically acceptable salts thereof.

* * * * *